US011565000B2

(12) United States Patent
Schaffer et al.

(10) Patent No.: US 11,565,000 B2
(45) Date of Patent: Jan. 31, 2023

(54) ADENO-ASSOCIATED VIRUS VIRIONS WITH VARIANT CAPSID AND METHODS OF USE THEREOF

(71) Applicants: The Regents of the University of California, Oakland, CA (US); The Trustees of the University of Pennsylvania, Philadelphia, PA (US)

(72) Inventors: David V. Schaffer, Danville, CA (US); John G. Flannery, Berkeley, CA (US); William A. Beltran, Philadelphia, PA (US); Leah C. Byrne, San Francisco, CA (US); Meike Visel, El Cerrito, CA (US)

(73) Assignees: The Regents of the University of California, Oakland, CA (US); The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 17/842,553

(22) Filed: Jun. 16, 2022

(65) Prior Publication Data
US 2022/0331450 A1 Oct. 20, 2022

Related U.S. Application Data

(63) Continuation of application No. 16/315,032, filed as application No. PCT/US2017/044206 on Jul. 27, 2017.
(Continued)

(51) Int. Cl.
*A61K 48/00* (2006.01)
*A61K 9/00* (2006.01)
*C12N 7/00* (2006.01)

(52) U.S. Cl.
CPC ........ *A61K 48/0091* (2013.01); *A61K 9/0048* (2013.01); *A61K 48/0075* (2013.01);
(Continued)

(58) Field of Classification Search
None
See application file for complete search history.

(56) References Cited

U.S. PATENT DOCUMENTS

| 5,773,700 | A | 6/1998 | Grinsven et al. |
| 6,096,548 | A | 8/2000 | Stemmer |

(Continued)

FOREIGN PATENT DOCUMENTS

| AU | 2014331708 | 5/2016 |
| CA | 2379220 | 1/2001 |

(Continued)

OTHER PUBLICATIONS

Lee, at al.; "Adena-associated Virus (AAV) Vectors: Rational Design Strategies for Capsid Engineering"; Current Opinion in Biomedical Engineering; pp. 7:58-63 (2018).
(Continued)

*Primary Examiner* — Christopher M Babic
*Assistant Examiner* — Anjeanette Roberts
(74) *Attorney, Agent, or Firm* — Shweta Chandra; Bozicevic, Field & Francis LLP

(57) ABSTRACT

The present disclosure provides adeno-associated virus (AAV) virions with altered capsid protein, where the AAV virions exhibit greater infectivity of retinal cells compared to wild-type AAV. The present disclosure further provides methods of delivering a gene product to a retinal cell in an individual, and methods of treating ocular disease.

15 Claims, 27 Drawing Sheets

Specification includes a Sequence Listing.

Related U.S. Application Data

(60) Provisional application No. 62/368,929, filed on Jul. 29, 2016.

(52) U.S. Cl.
CPC ...... *C12N 7/00* (2013.01); *C12N 2750/14121* (2013.01); *C12N 2750/14122* (2013.01); *C12N 2750/14143* (2013.01); *C12N 2750/14145* (2013.01)

(56) References Cited

U.S. PATENT DOCUMENTS

| | | |
|---|---|---|
| 6,482,634 B1 | 11/2002 | Wilson et al. |
| 6,491,907 B1 | 12/2002 | Rabinowitz et al. |
| 6,596,539 B1 | 7/2003 | Stemmer et al. |
| 6,703,237 B2 | 3/2004 | Samulski et al. |
| 6,710,036 B2 | 3/2004 | Kurtzman et al. |
| 6,733,757 B2 | 5/2004 | Patel et al. |
| 6,855,314 B1 | 2/2005 | Chiorini et al. |
| 6,943,153 B1 | 9/2005 | Manning, Jr. et al. |
| 6,962,815 B2 | 11/2005 | Bartlett |
| 7,172,893 B2 | 2/2007 | Rabinowitz et al. |
| 7,252,997 B1 | 8/2007 | Hallek et al. |
| 7,254,489 B2 | 8/2007 | Mossel |
| 7,285,381 B1 | 10/2007 | Hallek et al. |
| 7,314,912 B1 | 1/2008 | Hallek et al. |
| 7,368,428 B2 | 5/2008 | Serrero |
| 7,427,396 B2 | 9/2008 | Arbetman et al. |
| 7,556,965 B2 | 7/2009 | Hallek et al. |
| 7,629,322 B2 | 12/2009 | Kleinschmidt et al. |
| 7,749,492 B2 | 7/2010 | Bartlett et al. |
| 7,968,340 B2 | 6/2011 | Hallek et al. |
| 8,524,446 B2 | 9/2013 | Gao et al. |
| 8,574,583 B2 | 11/2013 | Kay et al. |
| 8,632,764 B2 | 1/2014 | Xiao et al. |
| 8,663,624 B2 | 3/2014 | Schaffer et al. |
| 9,193,956 B2 | 11/2015 | Schaffer et al. |
| 9,233,131 B2 | 1/2016 | Schaffer et al. |
| 9,441,244 B2 | 9/2016 | Schaffer et al. |
| 9,457,103 B2 | 10/2016 | Schaffer et al. |
| 9,458,517 B2 | 10/2016 | Schaffer et al. |
| 9,587,282 B2 | 3/2017 | Schaffer et al. |
| 9,856,539 B2 | 1/2018 | Schaffer et al. |
| 10,046,016 B2 | 8/2018 | Schaffer et al. |
| 10,202,657 B2 | 2/2019 | Schaffer et al. |
| 10,214,566 B2 | 2/2019 | Schaffer et al. |
| 10,214,785 B2 | 2/2019 | Schaffer et al. |
| 11,021,519 B2 | 6/2021 | Chalberg et al. |
| 11,167,041 B2 | 11/2021 | Kim et al. |
| 2002/0136710 A1 | 9/2002 | Samulski et al. |
| 2002/0155610 A1 | 10/2002 | Colosi |
| 2002/0192823 A1 | 12/2002 | Bartlett |
| 2003/0138772 A1 | 7/2003 | Gao et al. |
| 2003/0143732 A1 | 7/2003 | Fosnaugh et al. |
| 2003/0171254 A1 | 9/2003 | Sasaki et al. |
| 2003/0228284 A1 | 12/2003 | McCown et al. |
| 2004/0180440 A1 | 9/2004 | Zolotukhin |
| 2005/0019927 A1 | 1/2005 | Hildinger et al. |
| 2005/0053922 A1 | 3/2005 | Schaffer |
| 2005/0089973 A1 | 4/2005 | Yocum et al. |
| 2005/0106558 A1 | 5/2005 | Perabo et al. |
| 2005/0148069 A1 | 7/2005 | Gage et al. |
| 2005/0220766 A1 | 10/2005 | Amalfitano et al. |
| 2005/0287122 A1 | 12/2005 | Bartlett et al. |
| 2006/0051333 A1 | 3/2006 | Arbetman et al. |
| 2006/0292117 A1 | 12/2006 | Loiler et al. |
| 2007/0020624 A1 | 1/2007 | Rubenfield et al. |
| 2007/0036760 A1 | 2/2007 | Wilson et al. |
| 2007/0172460 A1 | 7/2007 | Kleinschmidt et al. |
| 2007/0196338 A1 | 8/2007 | Samulski et al. |
| 2008/0269149 A1 | 10/2008 | Bowles et al. |
| 2009/0202490 A1 | 8/2009 | Schaffer et al. |
| 2010/0166729 A9 | 7/2010 | Madison et al. |
| 2010/0172871 A1 | 7/2010 | Flannery et al. |
| 2011/0104120 A1 | 5/2011 | Xiao et al. |
| 2011/0171262 A1 | 7/2011 | Bakker et al. |
| 2011/0236353 A1 | 9/2011 | Wilson et al. |
| 2012/0093772 A1 | 4/2012 | Horsager et al. |
| 2013/0323302 A1 | 12/2013 | Constable et al. |
| 2014/0242031 A1 | 8/2014 | Schaffer et al. |
| 2014/0294771 A1 | 10/2014 | Schaffer et al. |
| 2014/0364338 A1 | 12/2014 | Schaffer et al. |
| 2015/0118201 A1 | 4/2015 | Xiao et al. |
| 2015/0152142 A1 | 6/2015 | Asokan et al. |
| 2015/0225702 A1 | 8/2015 | Schaffer et al. |
| 2015/0232953 A1 | 8/2015 | Schaffer et al. |
| 2015/0315610 A1 | 11/2015 | Nishie et al. |
| 2016/0017295 A1 | 1/2016 | Schaffer et al. |
| 2016/0102324 A1 | 4/2016 | Duchateau et al. |
| 2016/0184394 A1 | 6/2016 | Schaffer et al. |
| 2016/0340393 A1 | 11/2016 | Schaffer et al. |
| 2016/0375151 A1 | 12/2016 | Schaffer et al. |
| 2016/0376323 A1 | 12/2016 | Schaffer et al. |
| 2017/0044504 A1 | 2/2017 | Schaffer et al. |
| 2017/0096683 A1 | 4/2017 | Scaria et al. |
| 2018/0066285 A1 | 3/2018 | Ojala et al. |
| 2018/0289757 A1 | 10/2018 | Schaffer et al. |
| 2019/0169237 A1 | 6/2019 | Schaffer et al. |
| 2019/0218627 A1 | 7/2019 | Schaffer et al. |
| 2019/0255192 A1 | 8/2019 | Kirn et al. |
| 2019/0300579 A1 | 10/2019 | Dudman et al. |
| 2021/0283274 A1 | 9/2021 | Schaffer et al. |

FOREIGN PATENT DOCUMENTS

| | | | |
|---|---|---|---|
| CN | 1325451 A | 12/2001 | |
| CN | 1826414 A | 8/2006 | |
| CN | 1966082 A | 5/2007 | |
| CN | 101484005 A | 7/2009 | |
| CN | 101532024 A | 9/2009 | |
| CN | 103561774 A | 2/2014 | |
| CN | 106232618 A | 10/2014 | |
| JP | 2002-518050 | 6/2002 | |
| JP | 2008-523813 A | 7/2008 | |
| WO | WO 1997/038723 | 10/1997 | |
| WO | WO 1999/067393 | 12/1999 | |
| WO | WO 2000/028004 | 5/2000 | |
| WO | WO 2001/070276 | 9/2001 | |
| WO | WO 2002/053703 | 7/2002 | |
| WO | WO 2003/018820 | 3/2003 | |
| WO | WO 2003/023032 | 3/2003 | |
| WO | WO 2003/054197 | 7/2003 | |
| WO | WO 2003/093436 | 11/2003 | |
| WO | WO 2004/108922 | 12/2004 | |
| WO | WO 2004/112727 | 12/2004 | |
| WO | WO 2005/005610 | 1/2005 | |
| WO | WO 2005/033321 | 4/2005 | |
| WO | WO 2006/066066 | 6/2006 | |
| WO | WO 2006/110689 | 10/2006 | |
| WO | WO 2007/120542 | 10/2007 | |
| WO | WO 2008/131951 | 11/2008 | |
| WO | WO 2009/137006 | 11/2009 | |
| WO | WO 2009/154452 | 12/2009 | |
| WO | WO 2010/093784 | 8/2010 | |
| WO | WO 2010/138263 | 12/2010 | |
| WO | WO 2011/117258 | 9/2011 | |
| WO | WO 2012/145601 | 10/2012 | |
| WO | WO-2012145601 A2 * | 10/2012 | ......... A61K 38/1709 |
| WO | WO 2013/029030 | 2/2013 | |
| WO | WO 2013/170078 | 11/2013 | |
| WO | WO 2013/173512 | 11/2013 | |
| WO | WO 2014/124282 | 8/2014 | |
| WO | WO2004/083441 | 9/2014 | |
| WO | WO 2014/194132 | 12/2014 | |
| WO | WO 2014/207190 | 12/2014 | |
| WO | WO 2015/048534 | 4/2015 | |
| WO | WO 2015/054653 | 4/2015 | |
| WO | WO2015/121501 | 8/2015 | |
| WO | WO 2015/142941 | 9/2015 | |
| WO | WO 2015/191693 | 12/2015 | |
| WO | WO2016/134375 | 8/2016 | |
| WO | WO 2016/141078 | 9/2016 | |
| WO | WO 2016/144892 | 9/2016 | |

(56) References Cited

FOREIGN PATENT DOCUMENTS

| WO | WO 2017/023724 | 2/2017 |
|---|---|---|
| WO | WO 2017/197355 | 11/2017 |
| WO | WO 2019/046069 | 3/2019 |

OTHER PUBLICATIONS

Office Action dated Mar. 29, 2022, Appl. No. 16/315,032, 43 pp.
Third-Party Submission dated Mar. 15, 2022, U.S. Appl. No. 16/315,032, 95 pp.
U.S. Appl. No. 17/842,530, filed Jun. 16, 2022, Schaffer et al.
U.S. Appl. No. 17/842,639, filed Jun. 16, 2022, Schaffer et al.
Co-pending U.S. Appl. No. 16/230,080, filed Dec. 21, 2018.
Co-pending U.S. Appl. No. 16/315,032, filed Jan. 3, 2019.
Co-pending U.S. Appl. No. 16/662,987, filed Oct. 24, 2019.
Adachi, et al.; "A New Recombinant Adeno-Associated Virus (AAV)-Based Random Peptide Display Library System: Infection-Defective AAV1.9-3 as a Novel Detargeted Platform for Vector Evolution"; Gene Therapy and Regulation; vol. 5, No. 1, pp. 31-55 (Oct. 2010).
Akiyama, et al.; "Intraocular Injection of an Aptamer that Binds PDGF-B: A Potential Treatment for Proliferative Retinopathies"; Journal of Cellular Physiology; vol. 207, pp. 407-412 (2006).
Ali, et al.; "Restoration of photoreceptor ultrastructure and function in retinal degeneration slow mice by gene therapy"; Nature Genetics; vol. 25, pp. 306-310 (Jul. 2000).
Allocca, et al.; "Novel adeno-associated virus serotypes efficiently transduce murine photoreceptors"; Journal of Virology; vol. 81, No. 20, pp. 11372-11380 (Oct. 2007).
Asokan, et al., "Reengineering a receptor footprint of adeno-associated virus enables selective and systemic gene transfer to muscle"; Nat Biotechnol; vol. 28, No. 1, pp. 79-82 (Jan. 2010).
Asuri, et al.; "Directed Evolution of Adena-associated Virus for Enhanced Gene Delivery and Gene Targeting in Human Pluripotent Stem Cells"; Molecular Therapy, vol. 20, No. 2, pp. 329-338 (Feb. 1, 2012).
Attached Score Report Result Per SEQ ID No. 17 per US2002/0192823 to Bartlett Published Dec. 19, 2002.
Bichsel, et al.; "Bacterial delivery of nuclear proteins into pluripotent and differentiated cells"; PLoS One; vol. 6, No. 1, pp. 1-9 (Jan. 2011).
Blacklow, et al.; "A Seroepidemiologic Study of Adenovirus-Associated Virus Infection in Infants and Children"; Am J Epidemiol.; vol. 94, No. 4, pp. 359-366 (Oct. 1971).
Boucas, et al.; "Engineering adeno-associated virus serotype 2-based targeting vectors using a new insertion site-position 453-and single point mutations"; J Gene Med.; vol. 11, No. 12, pp. 1103-1113 (Dec. 2009).
Buch, et al., "in Contrast to AAC-Mediated Cntf Expression, AAV-Mediated Gdnf Expression Enhances Gene Replacement Therapy in Rodent Models of Retinal Degeneration"; Molecular Therapy; vol. 14, No. 5, pp. 700-709 (Nov. 2006).
Buning, et al., "Receptor targeting of adeno-associated virus vectors"; Gene Therapy; vol. 10, pp. 1142-1151 (2003).
Chadderton, et al.; "Improved Retinal Function in a Mouse Model of Dominant Retinitis Pigmentosa Following AAV-delivered Gene Therapy"; Molecular Therapy; vol. 17, No. 4, pp. 593-599 (Apr. 2009).
Choi, et al.; "AAV Hybrid Serotypes: Improved Vectors for Gene Delivery."; Current Gene Therapy; vol. 5, No. 3, pp. 299-310 (Jun. 2005).
Cronin, et al.; "Efficient transduction and optogenetic stimulation of retinal bipolar cells by a synthetic adeno-associated virus capsid and promoter"; EMBO Molecular Medicine; 16 pages (2014).
Dalkara, et al.; "In Vivo—Directed Evolution of a New Adeno-Associated Virus for Therapeutic Outer Retinal Gene Delivery from the Vitreous"; Science Translational Medicine; vol. 5, Issue 187, 11 pages (Jun. 12, 2013).
Dalkara, et al.; "Developing Photoreceptor Targeted AAV Variant by Directed Evolution"; ARVO Annual Meeting Abstract Search and Program Planner; vol. 2011, pp. 4381 (May 2011).

Database Geneseq [Online] Oct. 16, 2008 (Oct. 16, 2008), "Modified Adena-associated virus (hu.44) capsid protein, VP1, hu.44R2.", retrieved from EBI accession No. GSP:AEL63853, Database accession No. AEL63853.
Database Geneseq [Online] Oct. 16, 2008 (Oct. 16, 2008), "Modified Adena-associated virus (hu.44) capsid protein, VP1, hu.44R3.", retrieved from EBI accession No. GSP:AEL63854, Database accession No. AEL63854.
Davidson, et al.; "Recombinant adeno-associated virus type 2, 4, and 5 vectors: transduction of variant cell types and regions in the mammalian central nervous system."; Proc Natl Acad Sci USA.; vol. 97, No. 7, pp. 3428-3432 (Mar. 28, 2000).
Day, et al.; "Advances in AAV Vector Development for Gene Therapy in the Retina"; Adv. Exp. Med. Biol.; vol. 801, pp. 687-693 (2014).
Den Dunnen, et al.; "Mutation nomenclature extensions and suggestions to describe complex mutations: a discussion."; Human Mutation; vol. 15, pp. 7-12 (2000).
Diprimio, et al.; "Surface loop dynamics in adeno-associated virus capsid assembly"; Journal of Virology; vol. 82, No. 11, pp. 5178-5189 (Jun. 2008).
Erles, et al.; "Update on the prevalence of serum antibodies (IgG and IgM) to adeno-associated virus (AAV)."; J Med Virol.; vol. 59, No. 3, pp. 406-411 (Nov. 1999).
Excoffon, et al.; "Directed evolution of adeno-associated virus to an infectious respiratory virus"; Proc Natl Acad Sci USA; vol. 106, No. 10, pp. 3865-3870 (Mar. 10, 2009).
Flotte, et al.; "Gene expression from adeno-associated virus vectors in airway epithelial cells"; Am J Respir Cell Mol Biol.; vol. 7, No. 3, pp. 349-356 (Sep. 1992).
Gen Bank accession No. AAZ79678; rat AAV1 VP3 capsid protein sequence downloaded from NCBI; downloaded on Nov. 3, 2008.
GenBank accession No. ABZ10812; AAV13 capsid protein sequence downloaded from NCBI; downloaded on Nov. 3, 2008.
Girod, et al.; "Genetic capsid modifications allow efficient re-targeting of adeno-associated virus type 2"; Nat. Med.; vol. 5, No. 9, pp. 1052-1056 (Sep. 1999).
Gray, et al.; "Directed Evolution of a Novel Adeno-associated Virus (AAV) Vector That Crosses the Seizure-compromised Blood-Brain Barrier (BBB)"; Molecular Therapy; vol. 18, No. 3, pp. 570-578 (2010).
Gregory-Evans, et al.; "Ex vivo Gene Therapy Using Intravitreal Injection of GDNF-secreting Mouse Embryonic Stem Cells in a Rat Model of Retinal Degeneration"; Molecular Vision; vol. 15, pp. 962-973 (May 13, 2009).
Grieger, et al.; "Separate basic region motifs within the adeno-associated virus capsid proteins are essential for infectivity and assembly"; Journal of Virology; vol. 80, No. 11, pp. 5199-5210 (2006).
Grifman, et al.; "Incorporation of tumor-targeting peptides into recombinant adeno-associated virus capsids"; Molecular Therapy; vol. 3, No. 6, pp. 964-975 (Jun. 2001).
Grimm, et al.; "In Vitro and In Vivo Gene Therapy Vector Evolution via Multispecies Interbreeding and Retargeting of Adeno-Associated Viruses"; Journal of Virology; vol. 82, No. 12, pp. 5887-5911 (Jun. 2008).
Halbert, et al.; "Repeat transduction in the mouse lung by using adeno-associated virus vectors with different serotypes." J. Virol.; vol. 74, No. 3, pp. 1524-1532 (Feb. 2000).
Hellstrom, et al.; "Cellular tropism and transduction properties of seven adeno-associated viral vector serotypes in adult retina after intravitreal injection"; Gene Therapy; vol. 16, pp. 521-532 (2009).
Hirsch, et al.; "Directed Evolution of the AAV Capsid for Human Embryonic Stem Cell Transduction"; Molecular Therapy; vol. 17, Supp. 1, S177- S178 (May 2009).
Huttner, et al "Genetic Modifications of the Adeno-Associated Virus Type 2 Capsid Reduce Affinity to Human Serum Antibodies and Overcome Potential Limitations of Neutralizing Antibodies for the Used in Human Gene Therapy"; Blood; vol. 100, No. 11, pp. Abstract No. 5548 (Nov. 16, 2002).

(56) References Cited

OTHER PUBLICATIONS

Huttner, et al.; "Genetic modifications of the adeno-associated virus type 2 capsid reduce the affinity and the neutralizing effects of human serum antibodies."; Gene Ther; vol. 10, pp. 2139-2147 (Dec. 2003).

Jang, et al.; "An evolved adeno-associated viral variant enhances gene delivery and gene targeting in neural stem cells"; Mol Ther.; vol. 19, No. 4, pp. 667-675 (Apr. 2011).

Jeune, et al.; "Pre-existing Anti-Adeno-Associated Virus Antibodies as a Challenge in AAV Gene Therapy"; Human Gene Therapy Methods; vol. 24, pp. 59-67 (Apr. 2013).

Karp, et al.; "An in vitro model of differentiated human airway epithelia, Methods for establishing primary cultures"; Methods Mol Biol.; vol. 188, pp. 115-137 (2002).

Kern, et al.; "Identification of a heparin-binding motif on adeno-associated virus type 2 capsids"; Journal of Virology; vol. 77, No. 20, pp. 11072-11081 (Oct. 2003).

Khabou, et al.; "Insight Into the Mechanisms of Enhanced Retinal Transduction by the Engineered AAV2 Capsid Variant -7m8"; Biotechnology and Bioengineering; vol. 113, No. 12, pp. 2712-2724 (Dec. 2016).

Khani, et al.; "AAV-Mediated Expression Targeting of Rod and Cone Photoreceptors with a Human Rhodopsin Kinase Promoter"; Investigative Ophthalmology & Visual Science; vol. 48, No. 9, pp. 3954-3961 (Sep. 2007).

Klimczak, et al.; "A Novel Adeno-Associated Viral Variant for Efficient and Selective Intravitreal Transduction of Rat Muller Cells"; PLoS ONE; vol. 4, No. 10, pp. 1-10 (Oct. 2009).

Klimczak; "Molecular Evolution of Adeno-associated Virus for Improved Retinal Gene Therapies"; Dissertation submitted in partial fulfillment of the requirements for the degree of Doctor of Philosophy in Molecular and Cell Biology in the Graduate Division of University of California, Berkeley; 116 pages (2010).

Koerber, et al.; "DNA Shuffling of Adeno-associated Virus Yields Functionally Diverse Viral Progeny"; Molecular Therapy; vol. 16, No. 10, pp. 1703-1709 (Oct. 2008).

Koerber, et al.; "Engineering of a Novel AAV Vector in a Human Airway Model System for Cystic Fibrosis Gene Therapy"; AIChE Annual Meeting Abstract, 3 pages (Nov. 29, 2008).

Koerber, et al.; "Molecular Evolution of Adeno-associated Virus for Enhanced Glial Gene Delivery", Molecular Therapy; vol. 17, No. 12, pp. 2088-2095 (Dec. 2009).

Kotterman, et al.; "Engineering adeno-associated viruses for clinical gene therapy"; Nat Rev Genet; vol. 15, No. 7, pp. 445-451 (Jul. 1, 2014).

Kotterman, et al.; "Enhanced selective gene delivery to neural stem cells in vivo by an adeno-associated viral variant"; Development; vol. 142, pp. 1885-1892 (2015).

Kwon, et al.; "Designer gene delivery vectors: molecular engineering and evolution of adeno-associated viral vectors for enhanced gene transfer"; Pharmaceutical Research; vol. 25, No. 3, pp. 489-499 (Mar. 2008).

Lai, et al.; "Long-term evaluation of AAV-mediated sFlt-1 gene therapy for ocular neovascularization in mice and monkeys"; Mol Ther.; vol. 12, No. 4, pp. 659-668 (Oct. 2005).

Li, et al.; "Engineering and Selection of Shuffled AAV Genomes: A New Strategy for Producing Targeted Biological Nanoparticles"; Molecular Therapy; vol. 16, No. 7, pp. 1252-1260 (Jul. 2008).

Li, et al.; "Generation of Novel AAV Variants by Directed Evolution for Improved CFTR Delivery to Human Ciliated Airway Epithelium"; Molecular Therapy; vol. 17, No. 12, pp. 2067-2077 (Dec. 2009).

Limberis, et al.; "Adeno-associated virus serotype 9 vectors transduce murine alveolar and nasal epithelia and can be readministered"; Proc Natl Acad Sci USA; vol. 103, No. 35, pp. 12993-12998 (Aug. 29, 2006).

Loiler, et al.; "Targeting recombinant adeno-associated virus vectors to enhance gene transfer to pancreatic islets and liver"; Gene Ther.; vol. 10, pp. 1551-1558 (2003).

Maguire, et al.; "Directed evolution of adeno-associated virus for glioma cell transduction"; J. Neurooncol.; vol. 96, pp. 337-347 (2010).

Maheshri, et al.; "Directed evolution of adeno-associated virus yields enhanced gene delivery vectors"; Nature Biotechnology; vol. 24, No. 2, pp. 198-204 (Feb. 2006).

McCullum, et al.; "Random Mutagenesis by Error-Prone PCR"; Methods Mol Biol.; vol. 634, pp. 103-109; doi: 10.1007/978-1-60761-652-8_7 (2010).

McGee, et al., "Glial Cell Line Derived Neurotrophic Factor Delays Photoreceptor in a Transgenic Rat Model of Retinitis Pigmentosa"; Molecular Therapy; vol. 4, No. 6, pp. 622-629 (Dec. 2001).

Michelfelder, et al.; "Successful Expansion but Not Complete Restriction of Tropism of Adeno-Associated Virus by In Vivo Biopanning of Random Virus Display Peptide Libraries"; PLoS One; vol. 4, No. 4, pp. 1-13 (Apr. 2009).

Michelfelder, et al.; "Vectors selected from adeno-associated viral display peptide libraries for leukemia cell-targeted cytotoxic gene therapy"; Experimental Hematology; vol. 35, pp. 1766-1776 (2007).

Mitchell, et al.; "AAV's anatomy: Roadmap for optimizing vectors for translational success"; Curr Gene Ther.; vol. 10, No. 5, pp. 319-340 (Oct. 2010).

Miyake, et al.; "Global gene transfer into the CNS across the BBB after neonatal systemic delivery of single-stranded AAV vectors"; Brain Research; vol. 1389, pp. 19-26 (2011).

Moskalenko, et al; "Epitope mapping of human anti-adeno-associated virus type 2 neutralizing antibodies: implications for gene therapy and virus structure."; J. Virol.; vol. 74, No. 4, pp. 1761-1766 (Feb. 2000).

Muller, et al.; "Random peptide libraries displayed on adeno-associated virus to select for targeted gene therapy vectors"; Nat Biotechnol; vol. 21, No. 9, pp. 1040-1046 (Sep. 2003).

Nguyen, et al; "Convection-enhanced delivery of AAV-2 combined with heparin increases TK gene transfer in the rat brain."; Neuroreport; vol. 12, No. 9, pp. 1961-1964 (Jul. 3, 2001).

Nicklin, et al.; "Efficient and selective AAV2-mediated gene transfer directed to human vascular endothelial cells"; Mol. Ther.; vol. 4, No. 2, pp. 174-181 (Aug. 2001).

Opie, et al.; "Identification of Amino Acid Residues in the Capsid Proteins of Adeno-Associated Virus Type 2 that Contribute to Heparan Sulfate Proteoglycan Binding"; Journal of Virology; vol. 77, No. 12, pp. 6995-7006 (Jun. 2003).

Ortolano, et al.; "Present and Future of Adeno Associated Virus Based Gene Therapy Approaches"; Recent Patents on Endocrine, Metabolic & Immune Drug Discovery; vol. 6, pp. 47-66 (2012).

Paddison, et al.; "Stable suppression of gene expression by RNAi in mammalian cells"; Proc. Nat'l Acad. Sci. USA; vol. 99, No. 3, pp. 1443-1448 (Feb. 5, 2002).

Padron, et al.; "Structure of adeno-associated virus type 4"; Journal of Virology; vol. 79, No. 8, pp. 5047-5058 (Apr. 2005).

Park, et al.; "Intravitreal delivery of AAV8 retinoschisin results in cell type-specific gene expression and retinal rescue in the Rs1-KO mouse"; Gene Therapy; vol. 16, pp. 916-926 (2009).

Pechan, et al; "Novel anti-VEGF chimeric molecules delivered by AAV vectors for inhibition of retinal neovascularization."; Gene. Ther.; vol. 16, No. 1, pp. 10-16 (Jan. 2009).

Perabo, et al.; "Combinatorial engineering of a gene therapy vector: directed evolution of adeno-associated virus"; The Journal of Gene Medicine; vol. 8, No. 2, pp. 155-162 (Feb. 2006).

Perabo, et al.; "Heparan Sulfate Proteoglycan Binding Properties of Adeno-Associated Virus Retargeting Mutants and Consequences for Their In Vivo Tropism"; Journal of Virology; vol. 80, No. 14, pp. 7265-7269 (Jul. 2006).

Perabo, et al.; "In Vitro Selection of Viral Vectors with Modified Tropism: The Adeno-associated Virus Display"; Molecular Therapy; vol. 8, No. 1, pp. 151-157 (Jul. 2003).

Petrs-Silva, et al.; "High-efficiency transduction of the mouse retina by tyrosine-mutant AAV serotype vectors"; Molecular Therapy; vol. 17, No. 3, pp. 463-471 (Mar. 2009).

Popa-Wagner, et al.; "Impact of VP1-Specific Protein Sequence Motifs on Adeno-Associated Virus Type 2 Intracellular Trafficking and Nuclear Entry"; Journal of Virology; vol. 86, No. 17, pp. 9163-9174 (Sep. 2012).

(56) References Cited

OTHER PUBLICATIONS

Rabinowitz, et al.; "Building a Better Vector: The Manipulation of AAV Virions"; Virology; vol. 278, pp. 301-308 (2000).
Rabinowitz, et al.; "Insertional mutagenesis of AAV2 capsid and the production of recombinant virus."; Virology; vol. 265, No. 2, pp. 274-285 (Dec. 20, 1999).
Rayaprolu, et al.; "Comparative Analysis of Adeno-Associated Virus Capsid Stability and Dynamics"; Journal of Virology; vol. 87, No. 24, pp. 13150-13160 (Dec. 2013).
Ried, et al.; "Adeno-associated virus capsids displaying immunoglobulin-binding domains permit antibody-mediated vector retargeting to specific cell surface receptors"; J. Virol.; vol. 76, No. 9, pp. 4559-4566 (May 2002).
Ryals, et al.; "Quantifying transduction efficiencies of unmodified and tyrosine capsid mutant AAV vectors in vitro using two ocular cell lines"; Mol Vision; vol. 17, pp. 1090-1102 (Apr. 2011).
Santiago-Ortiz, et al.; "AAV Ancestral Reconstruction Library Enables Selection of Broadly Infectious Viral Variants"; Gene. Ther.; vol. 22, No. 12, pp. 934-946 (Dec. 2015).
Schaffer, et al.; "Directed evolution of AAV vector mutants for enhanced gene delivery"; Abstracts of Papers American Chemical Society; vol. 227, Part 1, p. U214 (Mar. 2004).
Score result 33 for Arbetman et al WO2004112727-A2, Dec. 29, 2004.
Shao, et al.; "Gene Transfer to the Gastrointestinal Tract After Peroral Administration of Recombinant Adeno-associated Virus Type 2 Vectors"; Journal of Pediatric Gastroenterology and Nutrition; vol. 43, pp. 168-179 (Aug. 2006).
Shen, et al.; "Characterization of the relationship of AAV capsid domain swapping to liver transduction efficiency"; Mol Ther.; vol. 15, No. 11, pp. 1955-1962 (Aug. 28, 2007).
Shen, et al.; "Multiple Roles for Sialylated Glycans in Determining the Cardiopulmonary Tropism of Adeno-Associated Virus 4"; Journal of Virology; vol. 87, No. 24, pp. 13206-13213 (Dec. 2013).
Shi, et al.; "Capsid modifications overcome low heterogeneous expression of heparan sulfate proteoglycan that limits AAV2-mediated gene transfer and therapeutic efficacy in human ovarian carcinoma"; Gynecol. Oncol.; vol. 103, pp. 1054-1062 (2006).
Shi, et al.; "Insertional mutagenesis at positions 520 and 584 of adeno-associated virus type 2 (AAV2) capsid gene and generation of AAV2 vectors with eliminated heparin-binding ability and introduced novel tropism"; Hum. Gene Ther.; vol. 17, pp. 353-361 (Mar. 2006).
Shi, et al.; "RGD inclusion in VP3 provides adeno-associated virus type 2 (AAV2)-based vectors with a heparan sulfate-independent cell entry mechanism"; Mol. Ther.; vol. 7, No. 4, pp. 515-525 (Apr. 2003).
Shi, W. et al.; "Insertional Mutagenesis of the Adeno-Associated Virus Type 2 (AAV2) Capsid Gene and Generation of AAV2 Vectors Targeted to Alternative Cell-Surface Receptors"; Human Gene Therapy; vol. 12, pp. 1697-1711 (Sep. 20, 2001).
Sonntag, et al.; "Adeno-associated virus type 2 capsids with externalized VP1/VP2 trafficking domains are generated prior to passage through the cytoplasm and are maintained until uncoating occurs in the nucleus"; Journal of Virology; vol. 80, No. 22, pp. 11040-11054 (Nov. 2006).
Steinbach, et al.; "Assembly of adeno-associated virus type 2 capsids in vitro" J of Gen Virology; vol. 78, pp. 1453-1462 (1997).
Sullivan, et al.; "Rationally designed AAV2 and AAVrh8R capsids provide improved transduction in the retina and brain"; Gene Therapy; vol. 25, pp. 205-219 (2018).
Sun, et al.; "Immune responses to adeno-associated virus and its recombinant vectors"; Gene Therapy; vol. 10, pp. 964-976 (2003).
Surace, et al.; "Delivery of Adeno-Associated Virus Vectors to the Fetal Retina: Impact of Viral Capsid Proteins on Retinal Neuronal Progenitor Transduction"; Journal of Virology; vol. 77, No. 14, pp. 7957-7962 (Jul. 2003).

Takada, et al.; "Synaptic Pathology in Retinoschisis Knockout (Rs1$^{-/y}$) Mouse Retina and Modification by rAAV-Rs1 Gene Delivery"; Investigative Ophthalmology & Visual Science; vol. 49, No. 8, pp. 3677-3678 (Aug. 2008).
Tal; "Adeno-Associated Virus-Based Vectors in Gene Therapy"; Journal of Biomedical Science; vol. 7, No. 4, pp. 279-291 (Jul. 2000).
Tervo, et al.; "A Designer AAV Variant Permits Efficient Retrograde Access to Projection Neurons"; Neuron; vol. 92, pp. 372-382 (2016).
Tomar, et al.; "Use of Adeno-Associated Viral Vector for Delivery of Small Interfering RNA"; Oncogene; vol. 22, No. 36, pp. 5712-5715 (Aug. 28, 2003).
UniProtKB database: B4Y881_9VIRU; "Capsid protein VP1, adeno-associated virus"; 6 pages (Sep. 23, 2008).
Van Vliet, et al.; "Proteolytic mapping of the adeno-associated virus capsid"; Mol Ther.; vol. 14, No. 6, pp. 809-821 (Dec. 2006).
Venkatakrishnan, et al.; "Structure and Dynamics of Adeno-Associated Virus Serotype 1 VP1-Unique N-Terminal Domain and Its Role in Capsid Trafficking"; Journal of Virology; vol. 87, No. 9, pp. 4974-4984 (May 2013).
Watanabe, et al.; "Tropisms of AAV for Subretinal Delivery to the Neonatal Mouse Retina and Its Application for In Vivo Rescue of Developmental Photoreceptor Disorders"; PLoS ONE; vol. 8, No. 1, 12 pages (Jan. 15, 2013).
Waterkamp, et al.; "Isolation of targeted AAV2 vectors from novel virus display libraries"; J. Gene. Med.; vol. 8, pp. 1307-1319 (Sep. 6, 2006).
White, et al.; "Genetic Modification of Adeno-Associated Viral Vector Type 2 Capsid Enhances Gene Transfer Efficiency in Polarized Human Airway Epithelial Cells"; Human Gene Therapy; vol. 19, pp. 1407-1414 (Dec. 2008).
White, et al.; "Targeted gene delivery to vascular tissue in vivo by tropism-modified adeno-associated virus vectors"; Circulation; vol. 109, pp. 513-519 (Feb. 3, 2004).
Wickham, et al.; "Increased in vitro and in vivo gene transfer by adenovirus vectors containing chimeric fiber proteins"; Journal of Virology; vol. 71, No. 11, pp. 8221-8229 (Nov. 1997).
Willett, et al.; "Immunology of AAV-mediated gene transfer in the eye"; Frontiers in Immunology; vol. 4, No. 261, 8 pages (Aug. 2013).
Wobus, et al.; "Monoclonal antibodies against the adeno-associated virus type 2 (AAV-2) capsid: epitope mapping and identification of capsid domains involved in AAV-2-cell interaction and neutralization of AAV-2 infection."; J. Virol.; vol. 74, No. 19, pp. 9281-9293 (Oct. 2000).
Work, et al.; "Vascular bed-targeted in vivo gene delivery using tropism-modified adeno-associated viruses"; Mol. Ther.; vol. 13, No. 4, pp. 683-693 (Apr. 2006).
Wu, et al.; "Mutational analysis of the adeno-associated virus type 2 (AAV2) capsid gene and construction of AAV2 vectors with altered tropism"; Journal of Virology; vol. 74, No. 18, pp. 8635-8647 (Sep. 2000).
Wu, et al.; "$\alpha 2,3$ and $\alpha 2,6$ N-linked Sialic Acids Facilitate Efficient Binding and Transduction by Adeno-Associated Virus Types 1 and 6"; Journal of Virology; vol. 80, No. 18, pp. 9093-9103 (Sep. 2006).
Xiao, et al.; "Adenovirus-facilitated nuclear translocation of adeno-associated virus type 2"; Journal of Virology; vol. 76, No. 22, pp. 11505-11517 (Nov. 2002).
Xie, et al.; "The atomic structure of adeno-associated virus (AAV-2), a vector for human gene therapy"; PNAS; vol. 99, No. 16, pp. 10405-10410 (Aug. 6, 2002).
Yang, et al.; "A myocardium tropic adeno-associated virus (AAV) evolved by DNA shuffling and in vivo selection"; PNAS; vol. 106, No. 10, pp. 3946-3951 (Mar. 10, 2009).
Yang, et al.; "Directed Evolution of Adeno-Associated Virus (AAV) as Vector for Muscle Gene Therapy"; Methods in Molecular Biology; vol. 709, pp. 127-139 (2011).
Yu; "Current Approaches and Future Directions of Gene Therapy in Alzheimer's Disease"; Neurochemical Journal; vol. 5, No. 3, pp. 159-168 (2011).

(56) References Cited

OTHER PUBLICATIONS

Zabner, et al.; "Adeno-associated virus type 5 (AAV5) but not AAV2 binds to the apical surfaces of airway epithelia and facilitates gene transfer"; J Virol.; No. 74, No. 8, pp. 3852-3858 (Apr. 2000).

Zhao, et al.; "Molecular evolution by staggered extension process (StEP) in vitro recombination"; Nat Biotechnol; vol. 16, No. 3, pp. 258-261 (Mar. 1998).

Zincarelli, et al.; "Analysis of AAV Serotypes 1-9 Mediated Gene Expression and Tropism in Mice After Systemic Injection"; Molecular Therapy; vol. 16, No. 6, pp. 1073-1080 (Jun. 2008).

Zolotukhin, et al.; "Recombinant adeno-associated virus purification using novel methods improves infectious titer and yield"; Gene Therapy; vol. 6, pp. 973-985 (1999).

* cited by examiner

FIG. 4

| | | |
|---|---|---|
| AAV2 VP1 | 1 | MAADGYLPDWLEDTLSEGIRQWWKLKPGPPPKPAERHKDDSRGLVLPGYKYLGPFNGLD |
| AAV2 VP1 | 61 | KGEPVNEADAAALEHDKAYDRQLDSGDNPYLKYNHADAEFQERLKEDTSFGGNLGRAVFQ |
| AAV2 VP1 | 121 | AKKRVLEPLGIVEEPVKTAPGKKRPVEHSPVEPDSSSGTGKAGQQPARKRLNFGQTGDAD |
| AAV2 VP1 | 181 | SVPDPQPLGQPPAAPSGLGTNTMATGSGAPMADNNEGADGVGNSSGNWHCDSTWMGDRVI |
| AAV2 VP1 | 241 | TTSTRTWALPTYNNHLYKQISSQSGASNDNHYFGYSTPWGYFDFNRFHCHFSPRDWQRLI |
| AAV2 VP1 | 301 | NNNWGFRPKRLNFKLFNIQVKEVTQNDGTTTIANNLTSTVQVFTDSEYQLPYVLGSAHQG |
| AAV2 VP1 | 361 | CLPPFPADVFMVPQYGYLTLNNGSQAVGRSSFYCLEYFPSQMLRTGNNFTFSYTFEDVPF |
| AAV2 VP1 | 421 | HSSYAHSQSLDRLMNPLIDQYLYYLSRTNTPSGTTTQSRLQFSQAGASDIRDQSRNWLPG |
| AAV2 VP1 | 481 | PCYRQQRVSKTSADNNNSEYSWTGATKYHLNGRDSLVNPGPAMASHKDDEEKFFPQSGVL |
| AAV2 VP1 | 541 | IFGKQGSEKTNVDIEKVMITDEEEIRTTNPVATEQYGSVSTNLQRGNRQAATADVNTQGV |
| AAV2 VP1 | 601 | LPGMVWQDRDVYLQGPIWAKIPHTDGHFHPSPLMGGFGLKHPPPQILIKNTPVPANPSTT |
| AAV2 VP1 | 661 | FSAAKFASFITQYSTGQVSVEIEWELQKENSKRWNPEIQYTSNYNKSVNVDFTVDTNGVY |
| AAV2 VP1 | 721 | SEPRPIGTRYLTR (SEQ ID NO:1) |

FIG. 5

| | | | | |
|---|---|---|---|---|
| AAV-2 | 570 | PVATEQYGSVSTNLQRGNNRQAATADVNTQGVLPGMVWQDRDV | 611 | (SEQ ID NO:2) |
| AAV-1 | 571 | PVATERFGTVAVNFQSSTDPATGDVHAMGALPGMVWQDRDV | 612 | (SEQ ID NO:3) |
| AAV-5 | 560 | RVAYNVGGQMATNNQSSTTAPATGTYNLQEIVPGSVWMERDV | 601 | (SEQ ID NO:4) |
| AAV-6 | 571 | PVATERFGTVAVNLQSSTDPATGDVHVMGALPGMVWQDRDV | 612 | (SEQ ID NO:5) |
| AAV-7 | 572 | PVATEEYGIVSSNLQAANTAAQTQVVNNQGALPGMVWQNRDV | 613 | (SEQ ID NO:6) |
| AAV-8 | 573 | PVATEEYGIVADNLQQNTAPQIGTVNSQGALPGMVWQNRDV | 614 | (SEQ ID NO:7) |
| AAV-9 | 571 | PVATESYGQVATNHQSAQAQAQTGWVQNQGILPGMVWQDRDV | 612 | (SEQ ID NO:8) |
| AAV-10 | 573 | PVATEQYGVVADNLQQANTGPIVGNVNSQGALPGMVWQNRDV | 614 | (SEQ ID NO:9) |

FIG. 6A

```
AAV1     ---TFSYTFEEVPFHSSYAHSQSLDRLMNPLIDQYLYYLNRTQ-NQSGSAQNKDLLFSRGS   467
AAV6     ---TFSYTFEDVPFHSSYAHSQSLDRLMNPLIDQYLYYLNRTQ-NQSGSAQNKDLLFSRGS   467
AAV3     ---FSYTFEDVPFHSSYAHSQSLDRLMNPLIDQYLYYLNRTQGTTSGTTNQSRLLFSQAG    467
AAV2     ---FSYTFEDVPFHSSYAHSQSLDRLMNPLIDQYLYYLSRTN-TPSGTTTQSRLQFSQAG    466
AAV8     NFQFTYTFEDVPFHSSYAHSQSLDRLMNPLIDQYLYYLSRTQTT-GGTANTQTLGFSQGG    469
AAV8.1   NFQFTYTFEDVPFHSSYAHSQSLDRLMNPLIDQYLYYLSRTQTT-GGTANTQTLGFSQGG    469
AAV8 rh8 FQFSYTFEDVPFHSSYAHSQSLDRLMNPLIDQYLYYLSRTQTTGGTQTLAFSQAGFS       469
AAV10    NFEFSYTFEDVPFHSSYAHSQSLDRLMNPLIDQYLYYLSRTQST-GGTQGTQQLLFSQAG    469
AAV7     -FEFSYTFEDVPFHSSYAHSQSLDRLMNPLIDQYLYYLARTQSNPGGTAGNRELQFYQGG    469
AAV9     -FQFSYEFENVPFHSSYAHSQSLDRLMNPLIDQYLYYLSKTI--NGSGQNQQTLKFSVAG    467
AAV9.1   -FQFSYEFENVPFHSSYAHSQSLDRLMNPLIDQYLYYLSKTI--NGSGQNQQTLKFSVAG    467
AAV5     NFEFTYNFEEVPFHSSFAPSQNLFKLANPLVDQYLYRFVSTN-------NTGGVQFNKNL    453
                 *:.** ******:*****     *:.**:****:          *

AAV1     PAGMSVQPKNWLPGPCYRQQRVSKTKTDNNNSNFTWTGASKYNLNGRESIINPGTAMASH    527
AAV6     PAGMSVQPKNWLPGPCYRQQRVSKTKTDNNNSNFTWTGASKYNLNGRESIINPGTAMASH    527
AAV3     PQSMSLQARNWLPGPCYRQQRLSKTANDNNNSNFPWTAASKYHLNGRDSLVNPGPAMASH    527
AAV2     ASDIRDQSRNWLPGPCYRQQRVSKTSADNNNSEYSWTGATKYHLNGRDSLVNPGPAMASH    526
AAV8     PNTMANQAKNWLPGPCYRQQRVSTTTGQNNNSNFAWTAGTKYHLNGRNSLANPGIAMATH    529
AAV8.1   PNTMANQAKNWLPGPCYRQQRVSTTTGQNNNSNFAWTAGTKYHLNGRNSLANPGIAMATH    529
AAV8 rh8 S--MANQARNWVPGPCYRQQRVSTTTNQNNNNSNFAWTGAAKFKLNGRDSLMNPGVAMASH    527
AAV10    PANMSAQAKNWLPGPCYRQQRVSTTLSQNNNSNFAWTGATKYHLNGRDSLVNPGVAMATH    529
AAV7     PSTMAEQAKNWLPGPCFRQQRVSKTLDQNNNSNFAWTGATKYHLNGRDSLVNPGVAMATH    527
AAV9     PSNMAVQGRNYIPGPSYRQQRVSTVTQNNNSEFAWPGASSWALNGRNSLMNPGPAMASH    529
AAV9.1   PSNMAVQGRNYIPGPSYRQQRVSTVTQNNNSEFAWPGASSWALNGRNSLMNPGPAMASH    527
AAV5     AGRYANTYKNWFPGPMGRTQGWNLGSGVNRASVSAFATTNRMELEGASYQVPPQPNGMTN    513
               .  :*: ** *   .       :        *  :  *         *::
```

FIG. 6B

```
AAV1      KDDEDKFFPMSGVMIFGK--ESAGASNTALD-NVMITDEEEIKATNPVATERFGTVAVNF 584
AAV6      KDDKDKFFPMSGVMIFGK--ESAGASNTALD-NVMITDEEEIKATNPVATERFGTVAVNL 584
AAV3      KDDEEKFFPMHGNLIFGK--EGTTASNAELD-NVMITDEEEIRTTNPVATEQYGTVANNL 584
AAV2      KDDEEKFFPQSGVLIFGK--QGSEKTNVDIE-KVMITDEEEIRTTNPVATEQYGSVSTNL 583
AAV8      KDDEERFFPSNGILIFGK--QNAARDNADYS-DVMLTSEEEIKTTNPVATEEYGIVADNL 586
AAV8.1    KDDEERFFPSNGILIFGK--QNAARDNADYS-DVMLTSEEEIKTTNPVATEEYGIVADNL 586
AAV8 rh8  KDDDDRFFPSSGVLIFGK--QGAGNDGVDYS-QVLITDEEEIKATNPVATEEYGAVAINN 584
AAV10     KDDEERFFPSSGVLMFGK--QGAGRDNVDYS-SVMLTSEEEIKTTNPVATEQYGVVADNL 586
AAV7      KDDEDRFFPSSGVLIFGK--TGAT-NKTTLE-NVLMTNEEEIRPTNPVATEEYGIVSSNL 585
AAV9      KEGEDRFFPLSGSLIFGK--QGTGRDNVDAD-KVMITNEEEIKTTNPVATESYGQVATNH 584
AAV9.1    KEGEDRFFPLSGSLIFGK--QGTGRDNVDAD-KVMITNEEEIKTTNPVATESYGQVATNH 584
AAV5      NLQGSNTYALENTMIFNSQPANPGTTATYLEGNMLITSESETQPVNRVAYNVGGQMATNN 573
               * ::    *. :       ..* :.::* :.*:  .
                         ** ** *:.:*  . :

AAV1      QSSSTDPATGDVHAMGALPGMVWQDRDVYLQGPIWAKIPHTDGHFHPSPLMGGFGLKNPP 644
AAV6      QSSSTDPATGDVHVMGALPGMVWQDRDVYLQGPIWAKIPHTDGHFHPSPLMGGFGLKHPP 644
AAV3      QSSNTAPTTGTVNHQGALPGMVWQDRDVYLQGPIWAKIPHTDGHFHPSPLMGGFGLKHPP 644
AAV2      QRGNRQAATADVNTQGVLPGMVWQDRDVYLQGPIWAKIPHTDGNFHPSPLMGGFGLKHPP 643
AAV8      QQNTAPQIGTVNSQGALPGMVWQNRDVYLQGPIWAKIPHTDGNFHPSPLMGGFGLKHPP 646
AAV8.1    QGQNTAPQIGTVNSQGALPGMVWQNRDVYLQGPIWAKIPHTDGNFHPSPLMGGFGLKHPP 646
AAV8 rh8  QAANTQAQTGLVHNQGVIPGMVWQNRDVYLQGPIWAKIPHTDGNFHPSPLMGGFGLKHPP 644
AAV10     QQANTGPIVGNVNSQGALPGMVWQNRDVYLQGPIWAKIPHTDGNFHPSPLMGGFGLKHPP 646
AAV7      QAANTAAQTQVVNNQGALPGMVWQNRDVYLQGPIWAKIPHTDGNFHPSPLMGGFGLKHPP 645
AAV9      QSAQAQAQTGWVQNQGILPGMVWQDRDVYLQGPIWAKIPHTDGNFHPSPLMGGFGMKHPP 644
AAV9.1    QSGQAQAQTGWVQNQGILPGMVWQDRDVYLQGPIWAKIPHTDGNFHPSPLMGGFGMKHPP 644
AAV5      QSTTAPATGTYNLQEIVPGSVWMERDVYLQGPIWAKIPETGAHFHPSPAMGGFGLKHPP 633
           *          :    ** ** :*****************:**..****.****:**
```

FIG. 6C

| | | |
|---|---|---|
| AAV1 | PQILIK- 650 | (SEQ ID NO:35) |
| AAV6 | PQILIK- 650 | (SEQ ID NO:36) |
| AAV3 | PQIMIK- 650 | (SEQ ID NO:37) |
| AAV2 | PQILIKN 650 | (SEQ ID NO:38) |
| AAV8 | PQILIKN 653 | (SEQ ID NO:39) |
| AAV8.1 | PQILIKN 653 | (SEQ ID NO:40) |
| AAV8 rh8 | PQILIKN 651 | (SEQ ID NO:41) |
| AAV10 | PQILIKN 653 | (SEQ ID NO:42) |
| AAV7 | PQILIKN 652 | (SEQ ID NO:43) |
| AAV9 | PQILIK- 650 | (SEQ ID NO:44) |
| AAV9.1 | PQILIK- 650 | (SEQ ID NO:45) |
| AAV5 | PMMLIKN 640 | (SEQ ID NO:46) |
| | *  ::** | |

Retinoschisin-1
*Homo sapiens*

```
  1 msrkiegfll lllfgyeatl glsstedege dpwyqkackc dcqggpnalw sagatslsdci
 61 pecpyhkpig fesgevtpdg itcsnpeqyv gwysswtank arlnsqgfgc awlskfqdss
121 qwlqidlkei kvisgiitqg rcdidewmtk ysvqyrtder lnwiyykdqt gnnrvfygns
181 drtstvqnil rppiisrfir lipigwhvri airmeliecv skca (SEQ ID NO:10)
```

FIG. 7A

BDNF
*Homo sapiens*

```
  1 mtilfltmvi syfgcmkaap mkeanirqgg glaypgvrth gtlesvngpk agsrgltsla
 61 dtfehvieel ldedhkvrpn eennkdadly tsrvmissqv plepplifil eeyknyldaa
121 nmsmmvlrhs dparrgelsv cdsisewvta adkktavdms ggtvtvlekv pvskgqikqy
181 fyetkcnpmg ytkegcrgid krhwnsqcrt tqsyvraltm dskkrigwrf iridtscvct
241 itikrgr (SEQ ID NO:11)
```

RPE65
*Homo sapiens*

```
  1  msiqvehpag gykklfetve elsspltahv tgriplwltg sllrcgpglf evgsepfyhl
 61  fdgqallhkf dfkeghvtyh rfirtdayv ramtekrivi tefgtcafpd pcknifsrff
121  syfrgvevtd nalvnvypvg edyyactetn fitkinpeti etikqvdicn yvsvngatah
181  phiendgtvy nigncfgknf siaynivkip pigadkedpi skseivvqfp csdrfkpsyv
241  hsfgltpnyi vfvetpvkin lfkflsswsl wganymdcfe snetmgvwih iadkkrkkyi
301  nnkyrtspfn lfhhintyed ngfliivdicc wkgfefvyny lylanlrenw eevkknarka
361  pqpevrryvl pinidkadtg knlvtlpntt atailcsdet iwlepevifs gprqafefpq
421  inyqkycgkp ytyayglgln hfvpdrickl nvktketwvw qepdsypsep ifvshpdale
481  eddgvvlsvv vspgagqkpa yllilnakdl sevaraevei nipvtfhgif kks
                                                          (SEQ ID NO:12)
```

FIG. 7D

Peripherin-2
*Homo sapiens*

```
  1  mallkvkfdq kkrvklaqqi wlmnwfsvia giiifslglf lkielrkrsd vmnnseshfv
 61  pnsligmqvl scvfnslagk icydaldpak yarwkpwlkp ylaicvlfni iiflvaiccf
121  llrgslentl gqglkngmky yrdtdtpgrc fmkktidmlq iefkccgnng frdwfeiqwi
181  snryldfssk evkdriksnv dgrylvdgvp fsccnpsspr pciqyqitnn sahysydhqt
241  eelnlwvrgc raallsyyss lmnsmgvvtl liwlfevtit iglrylqtsl dgvsnpeese
301  sesgqwlier svpetwkafl esvkklqkgn qveaegadag qapeag           (SEQ ID NO:13)
```

FIG. 7E

Peripherin
*Homo sapiens*

```
  1 mshhpsgira gfsstsyrrt fgpppslspg afsyssssrf sssrllgsas pssvrlgsf
 61 rspragagal lripseridf smaealngef latrsnekqe lqeindrfan fiekvrfleg
121 qnaairgeis qargqepara dqlcqqeire lrreleilgr erdrvqverd glaediaalk
181 qrleeetrkr edaehnivlf rkdvddatis rielerkies lmdeiefikk iheeelrdlq
241 vsvesqqvqq veveatvkpe ltaalrdira qyesiaakni qeaeewyksk yadlsdaanr
301 nhealrqakq emnesrrqiq sltcevdgir gtnealirql releeqfaie aggyqagaar
361 leeelrqike emarhireyq ellnvkmaid ieiatyrkli egeesrisvp vhsfasinik
421 ttvpeveppq dshsrktvli ktietrngev vtesqkeqrs eldkssahsy (SEQ ID NO:14)
```

FIG. 7F

RPGR-interacting protein-1
*Homo sapiens*

```
   1  mshlvdptsg dipvrdidai plvlipaskgk nmktqpplsr mnreeledsf frlredhmlv
  61  kelswkqqde ikrlrttllr ltaagrdlrv aeeaaplset arrggkagwr qrlsmhqrpq
 121  mhrlgghfhc vgpasprraq prvqvghrql htagapvpek pkrgprdris ytappsfkeh
 181  atnenrgeva skpselvsgs nsiisfssvi smakpiglcm pnsahimasn tmqveeppks
 241  pekmwpkden feqrssleca qkaaelrasi kekvelirlk kliherasl vmtkaqltev
 301  qeayetilqk nqgilsaahe alikqvnelr aelkeeskka vsiksqledv silqmtlkef
 361  qervedleke rkllndnydk llesmldssd sssqphwsne liaeqlqqqv sqlqdqldae
 421  ledkrkvlle israkagned lkievtnilq khkqevellq naatisqppd rqsepathpa
 481  vlqentqiep sepknqeekk lsqvlnelqv shaettlele ktrdmliIqr kinvcyqeei
 541  eammtkadnd nrdhkekler ltrlldlknn rikqiegilr shdiptseql kdvaygtrpi
 601  slcietlpah gdedkvdisl lhqgenlfel hihqafltsa alaqagdtqp ttfctysfyd
 661  fethctpisv gpqplydfts qyvmetdslf ihylqeasar ldihqamase hstlaagwic
 721  fdrvletvek vhglatliga ggeefgvley wmrlrfpikp slqacnkrkk aqvylstdvi
 781  ggrkaqeeef rseswepqne lwieitkccg lrsrwlgtqp spyavyrfft fsdhdtailp
 841  asnnpyfrdg arfpvivtsd ldhylrreal sihvfdddedi epgsylgrar vpllpiakne
 901  sikgdfnitd paekpngsiq vqldwkfpyi ppesfikpea qtkgkdtkds skisseeka
 961  sfpsqdqmas pevpieaggy rskrkpphgg erkekehqvv sysrrkhgkr igvqgknrme
1021  ylslnilngn tpeqvnytew kfsetnsfig dgfknqheee emtlshsaik qkeplhpvnd
1081  kesseggsev seaqttdsdd vivppmsqky pkadsekmci eivslafype aevmsdenik
1141  qvyveykfyd iplsetetpv slrkpragee inhfhfskvid ldpqeggqrr rflfdmlngq
1201  dpdqghlkft vvsdpldeek keceevgyay iqlwqilesg rdileqeidi vspedlatpi
1261  grlkvslqaa avlhaiykem tedlifs (SEQ ID NO:15)
```

FIG. 7G

Rab escort protein-1

```
  1 madtlpsefd vivigtgipe siiaaacsrs grrvihvdsr syggnwasf sfsgiliswlk
 61 eygensdivs dspvwqdqil eneeaialsr kdktiqhvev fcyasqdlhe dveeagalqk
121 nhalvtsans teaadsaflp tedesistms cemlteqtps sdpenalevn qaevtgeken
181 hcddktcvps tsaedmsenv piaedtteqp kknritysqi ikegrrfnid lvskillysrg
241 liidlliksn vsryaefkni trilafregr veqvpcsrad vfnskqltmv ekrmimkflt
301 fcmeyekypd eykgyeeitf yeylktqklt pnlqyivmhs iamtsetass tidglkatkn
361 fihclgrygn tpflfplygq gelpqcfcrm cavfggiycl rhsvqclvvd kesrkckaii
421 dqfggriise hflvedsyfp enmcsrvqyr qisravlitd rsvlktdsdq qisiltvpae
481 epgtfavrvi elcsstmtcm kgtylvhltc tssktaredl esvvqklfvp ytemeieneq
541 vekpriiwal yfnmrdssdi srscyndlps nvyvcsgpdc glgndnavkq aetifqeicp
601 nedfcppppn pediildgds lqpeasessa ipeansetfk estnignlee sse
```

(SEQ ID NO:16)

FIG. 7H

212-amino acid isoform of RdCVF

```
  1 masifsgril irnnsdqdel dteaevsrri enrlvilffg agacpgcgaf vpilkdffvr
 61 ltdefyvlra aqlalvyvsq dsteeqqdlf lkdmpkkwlf lpfeddlrrd lgrqfsverl
121 pavvvikpdg dvltrdgade iqrlgtacfa nwqeaaevld rnfglpedie dqeprsitec
181 lrrhkyrvek aarggrdpgg gggeeggagg lf (SEQ ID NO:17)
```

FIG. 7I

156-amino acid isoform of RdCVF (isoform 1)

```
  1 mvdilgerhl vtckgatvea eaalqnkvva lyfaaarcap srdftpllcd fytalvaear
 61 rpapfevvfv sadgssqeml dfmrelhgaw laipfhdpyr helrkrynvt aipklivkq
121 ngevitnkgr kqirerglac fqdwveaadi fqnfsv (SEQ ID NO:18)
```

FIG. 7J

135-amino acid isoform of RdCVF (isoform 2)

```
  1 mvdilgerhl vtckgatvea eaalqnkvva lyfaaarcap srdftpllcd fytalvaear
 61 rpapfevvfv sadgssqeml dfmrelhgaw laipfhdpyr qrslallprl ecsgvilahc
121 nlcilgssds lalas (SEQ ID NO:19)
```

FIG. 7K

Rod cGMP-specific 3',5'-cyclic phosphodiesterase subunit alpha (PDE6α)
GenBank NP_00431

```
  1 mgevtaeeve kfldsnigfa kqyynlhyra klisdilgak eaavdfsnyh spssmeesei
 61 ifdilrdfqe niqtekciifn vmkklcfllq adrmslfmyr trngiaelat rlfnvhkdav
121 ledclvmpdg eivfpldmgi vghvahskki anvpnteede hfcdfvdilt eyktknilas
181 pimngkdvva iimavnkvdg shftkrdeei ilkyinfanl imkvyhlsyi hncetrrgqi
241 liwsgskvfe eitdierqfh kalytvrafl ncdrysvgli dmtkqkeffd vwpvimgevp
301 pysgprtpdg reinfykvid yilhgkedik vipnpppdhw alvsqipayv agngiicnim
361 napaedffaf qkepldesgw miknvlsmpi vnkkeeivgv atfynrkdgk pfdemdetim
421 esitqfigws vinpdtyesm nklenrkdif qdivkyhvkc dneeiqkilk trevygkepw
481 eceeeelaei lqaelpdadk yeinkfhfsd lpiteielvk cgiqmyyelk vvdkfhipqe
541 alvrfmysls kgyrkityhn wrhgfnvqqt mfslivtgki kryftdleal amvtaafchd
601 idhrgtnnly qmksgnplak lhgssilerh hlefgktllr desinifqnl nrrqhehaih
661 mmdiaiiatd lalyfkkrtm fqkivdqskt yeseqewtqy mmleqtrkei vmamnmtacd
721 lsaitkpwev qsqvalivaa efweggdler tvlqqnpipm mdrnkadelp klqvgfidfv
781 ctfvykefsr fheeitpmld gitnnrkewk aladeydakm kvqeekkqkq qsaksaaagn
841 qpggnpspgg attsksccig (SEQ ID NO:20)
```

FIG. 7L

Rod cGMP-specific 3',5'-cyclic phosphodiesterase subunit beta isoform 1 (PDE6β isoform 1)
GenBank NP_000274

```
  1  msiseeqars  fldqnpdfar  qyfgkkispe  nvaaacedgc  ppdcdsirdl  cqveestall
 61  elvqdmqesi  nmervvfkvl  rrictligad  rcslfmyrqr  ngvaeiatrl  fsvqpdsvle
121  dclvppdsei  vfpldigvvg  hvaqtkkmvn  vedvaecphf  ssfadeitdy  ktknmiatpi
181  mngkdvvavi  mavnklngpf  ftsededvfl  kylnfatlyl  kiyhlsylhn  cetrrgqvll
241  wsankvfeel  tdiergfhka  fytvrayinc  erysvgildm  tkekeffdvw  svlmgesqpy
301  sgprtpdgre  ivfykvidyi  lhgkeeikvi  ptpsadhwal  asglpsyvae  sgficnimna
361  sademfkfqe  gaiddsgwli  knvlsmpivn  kkeeivgvat  fynrkdgkpf  deqdevlmes
421  ltqflgwsvm  ntdtydkmnk  lenrkdiaqd  mvlyhvkccdr  deiqliiptr  arlgkepadc
481  dedelgeiik  eeipgpttfd  iyefhfsdle  cteldivkcg  iqmyyeigvv  rkfqippqevl
541  vrfifsiskg  yrrityhnwr  hgfnvaqtmf  tilmtgklks  yytdleafam  vtagichdid
601  hrgtnnlyqm  ksqnplaklh  gssilerhhl  efgkfiisee  tlniyqnlnr  rqhehvihlm
661  diaiiatdia  lyfkkramfq  kivdesknyq  dkkswweyls  lettrkeivm  ammmtacdls
721  aitkpwevqs  kvallvaaef  weggdiertv  idqqpipmmd  rnkaaelpkl  qvgfidfvct
781  fvykefsrfh  eeilpmfdrl  qnnrkewkal  adeyeakvka  leekeeeerv  aakkvgteic
841  nggpapksst  ccil  (SEQ ID NO:21)
```

FIG. 7M

Rod cGMP-specific 3',5'-cyclic phosphodiesterase subunit beta isoform 2 (PDE6β isoform 2) GenBank NP_001138763

```
  1 mslseegars fldqnpdfar qyfgkklspe nvaaacedgc ppdcdsirdl cqveestall
 61 elvqdmqesi nmervvfkvi rrictliqad rcslfmyrqr ngvaelatrl fsvqpdsvle
121 dclvppdsei vfpldigvvg hvaqtkkmvn vedvaecphf ssfadeitdy ktknmlatpi
181 mngkdvvavi mavnklngpf ftsededvfl kyinfatlyl kiyhlsylhn cetrrgqvll
241 wsankvfeel tdiergfhka fytvrayinc erysvglidm tkekeffdvw svlmgesqpy
301 sgprtpdgre ivfykvidyi lhgkeeikvi ptpsadhwal asglpsyvae sgficnimna
361 sademfkfqe galddsgwli knvlsmpivn kkeelvgvat fynrkdgkpf deqdevlmes
421 ltqflgwsvm ntdtydkmnk lenrkdiaqd mvlyhvkcdr deiqlliptr arlgkepadc
481 dedeigeilk eeipgpttfd iyefhfsdle cteldlvkcg iqmyyelgvv rkfqipqevl
541 vrflfsiskg yrrityhnwr hgfnvaqtmf tlimtgkiks yytdleafam vtagichdid
601 hrgtnnlyqm ksqnplakih gssilerhhl efgkflisee tiniyqnlnr rqhehvihlm
661 diailiatdla lyfkkramfq kivdesknyq dkkswveyis lettrkeivm amnmtacdls
721 aitkpwevqs kvallvaaef weggdlertv ldqgpipmmd rnkaaeipkl qvgfidfvct
781 fvykefsrfh eeilpmfdrl qnnrkewkal adeyeakvka leekeeeerv aakkgteicn
841 ggpapksstc cil (SEQ ID NO:22)
```

FIG. 7N

Rod cGMP-specific 3',5'-cyclic phosphodiesterase subunit beta isoform 3 (PDE6β isoform 3)
GenBank NP_001138764

```
  1 mtkekeffdv wsvlmgesqp ysgprtpdgr eivfykvidy ilhgkeeikv iptpsadhwa
 61 lasgipsyva esgficnimn asademfkfq egalddsgwi iknvlsmpiv nkkeeivgva
121 tfynrkdgkp fdeqdevlne sitqflgwsv mntdtydkmn klenirkdiaq dmvlyhvkcd
181 rdeiqlilpt rarlgkepad cdedelgeil vrflfsisk diyefhfsdi ecteldivkc
241 giqmyyelgv vrkfqipqev vrflfsisk gyrrityhnw rhgfnvagtm ftllmtgkik
301 syytdleafa mvtagichdi dhrgtnnlyq mksqnplaki hgssilerhh iefgkflise
361 etiniygnln rrqhehvihl mdialiatdi alyfkkramf qkivdeskny qdikkswveyi
421 slettrkeiv mammmtacdl saitkpwevq skvallvaae fweqgdlert vldqqpipmm
481 drnkaaelpk lqvgfidfvc tfvykefsrf heeilpmfdr lqnnrkewka ladeyeakvk
541 aleekeeeer vaakkvgtei cnggpapkss tccil (SEQ ID NO:23)
```

FIG. 7O

Cyclic nucleotide-gated cation channel alpha-3 isoform 1 (CNGA3 isoform 1)
GenBank NP_001289

```
  1 makintqysh psrthlkvt sdrdlnraen glsrahssse etssvlqpgi ametrgiads
 61 gqgsftgqgi arisrlifli rrwaarhvhh qdqgpdsfpd rfrgaelkev ssqesnaqan
121 vgsqepadrg rsawplakcn tntsnnteee kktkkkdaiv vdpssnlyyr witaialpvf
181 ynwyllicra cfdelqseyi miwlvldysa dvlyvldviv rartgfleqg lmvsdtnrlw
241 qhykttqfk ldvislvptd laylkvgtny pevrfnrlik fsrlfeffdr tetrtnypnm
301 frignlvlyi liihwnaci yfaiskfigf gtdswvypni sipehgrlsr kyiyslywst
361 ltittigetp ppvkdeeylf vvvdflvgvi ifativgnvg smismnasr aefqakidsi
421 kqymqfrkvt kdietrvirw fdyiwankkt vdekevlksi pdklkaeiai nvhldtlkkv
481 rifqdceagl lvelviklrp tvfspgdyic kkgdigkeny linegklavv addgvtqfvv
541 isdgsyfgei siinikgsks gnrrtanirs igysdlfcis kddlmealte ypeakkaiee
601 kgrqilmkdn lideelarag adpkdleekv eqigssldti qtrfarllae ynatqmkmkq
661 risqiesqvk gggdkpladg evpgdatkte dkqq (SEQ ID NO:24)
```

FIG. 7P

Cyclic nucleotide-gated cation channel alpha-3 isoform 2 (CNGA3 isoform 2)
GenBank NP_001073347

```
  1 makintqysh psrthlkvkt sdrdlnraen glsrahssse etssvlqpgi ametrglads
 61 gqgsftgqgi arlsrlifll rrwaarhvhh qdqgpdsfpd rfrgaelkev ssqesnaqan
121 vgsqepadrg rrkktkkkda ivvdpssnly yrwitaialp vfynwyllic racfdelqse
181 ylmlwlvidy sadvlyvidv ivrartgfle qglmvsdtnr lwqhykttq fkldvislvp
241 tdiaylkvgt nypevrfnrl ikfsrlfeff drtetrtnyp nmfrignlvl yliliihwna
301 ciyfaiskfi gfgtdswvyp nisipehgrl srkyiyslyw stltittige tpppvkdeey
361 lfvvvdfivg vlifativgn vgsmisnmna sraefqakid sikqymqfrk vtkdietrvi
421 rwfdylwank ktvdekevlk slpdklkaei ainvhidtlik kvrifqdcea gllvelviki
481 rptvfispgdy ickkgdigke myiinegkla vvaddgvtqf vvlsdgsyfg eisilnikgs
541 ksgnrrtani rsigysdlfc lskddlmeal teypeakkal eekgrqilmk dnlideelar
601 agadpkdlee kveqlgssld tlqtrfarli aeynatqmkm kqrisqlesq vkggdkpia
661 dgevpgdatk tedkqq (SEQ ID NO:25)
```

FIG. 7Q

Cyclic nucleotide-gated cation channel beta-3 (CNGB3)
GenBank NP_061971

```
  1 mfksltkvnk vkpigennen eqssrrneeg shpsnqsqqt taqeenkgee kslktkstpv
 61 tseephtniq dklskknssg dlttnpdpqn aaeptgtvpe qkemdpgkeg pnspqnkppa
121 apvineyada qihnlvkrmr qrtalykkkl vegdisspea spqtakptav ppvkesddkp
181 tehyyrliwf kvkkmpitey ikriklipnsi dsytdrlyll willvtiayn wnccfipirl
241 vfpyqtadni hywlladiic dilylydmif iqprlqfvrg gdiilvdsnel rkhyrtstkf
301 qldvasiipf dicylffgfn pmfranrmik ytsffefnhh lesimdkayi yrvirttgyi
361 lfilhinacv yywasnyegi gttrwvydge gneylrcyyw avrtlitigg lpepqtifei
421 vfqlnffsg vfvissligq mrdvigaata nqnyfracmd dtiaymnnys ipkivqkrvr
481 twyeytwdsq rmidesdlik tipttvqlai aidvnfsiis kvdlfkgcdt qmiydmllri
541 ksvylipgdf vckkgeigke myiikhgevq vlggpdgtkv ivtlkagsvf geisliaagg
601 gnrrtanvva hgfanlitld kktlqeilvh ypdserilmk karvlikqka ktaeatpprk
661 dlalifppke etpklfktil ggtgkaslar llkikreqaa qkkensegge eegkenedkq
721 kenedkqken edkgkenedk dkgrepeekp ldrpectasp iIaveeephsv rrtvlprgts
781 rqsilismap saeggeevit ievkekakq (SEQ ID NO:26)
```

FIG. 7R

Guanine nucleotide-binding protein G(t) subunit alpha-2 (GNAT2)
GenBank NP_005263

```
  1 mgsgasaedk eiakrskele kklqedadke aktvklilig agesgkstiv kqmkiihqdg
 61 yspeeclefk ailygnvlqs ilairamtt lgidyaepsc addgrqinnl adsieegtmp
121 pelvevirrl wkdggvqacf eraaeyqlnd sasyylnqie ritdpeylps eqdvirsrvk
181 ttgiietkfs vkdlnfrmfd vggqrserkk winchfegvtc iifcaalsay dmvleddev
241 nrmheslhlf nsicnhkffa atsivlifink kdlfeekikk vhlsicfpey dgnnsyddag
301 nyiksqfidl nmrkdvkeiy shmtcatdtq nvkfvfdavt diiikenikd cqlf
(SEQ ID NO:27)
```

FIG. 7S

RPGR – 815 amino acids
GenBank NP_000319

```
  1 mrepeelmpd sgavftfgks kfaennpgkf wfkndvpvhl scgdehsavv tgnnklymfg
 61 snnwgqlgig sksaiskptc vkalkpekvk laacgrnhtl vsteggnvya tggnneqqlg
121 lgdteerntf hvisfftseh kikqlsagsn tsaaltedgr lfmwgdnseg qiglknvsnv
181 cvpqqvtigk pvswiscgyy hsafvttdge lyvfgepeng kiglpnqllg nhrtpqlvse
241 ipekviqvac ggehtvvlte navytfgigq fgqlgigtfl fetsepkvie nirdqtisyi
301 scgenhtali tdiglmytfg dgrhgkiglg lenftnhfip tlcsnflrfi vklvacggch
361 mvvfaaphrg vakelefdei ndtclsvatf lpyssitsgn vlqrtisarm rrererspd
421 sfsmrrtlpp iegtlgisac flpnsvfprc sernlqesvl seqdimqpee pdylldemtk
481 eaeidnsstv esigettdil nmthimslns neksikispv qkqkkqgtig eltqdtalte
541 nddsdeyeem semkegkack qhvsqgifmt qpattieafs deeveipeek egaedskqng
601 ieeqeveane envkvhggrk ekteilsddl tdkaedhefs kteelkiedv deeinaenve
661 skkktvgdde svptgyhskt egaertndds saetiekkek anleeraice ynenpkgyml
721 ddadssslei lensettpsk dmkktkkifl fkrvpsinqk ivknnneplp eiksigdqii
781 lksdnkdadq nhmsqnhqni pptnterrsk sctii (SEQ ID NO:28)
```

FIG. 7T

RPGR – 646 amino acids
GenBank CAB54002

```
  1 mrepeelmpd sgavftfgks kfaennpgkf wfkndvpvhl scgdehsavv tgnnklymfg
 61 snnwgqlgig sksaiskptc vkalkpekvk laacgrnhtl vsteggnvya tggnneggqlg
121 lgdteerntf hvisfftseh kikglsagsn tsaaltedgr lfmwgdnseg qiglknvsnv
181 cvpqqvtigk pvswiscgyy hsafvttdge lyvfgepeng klglpnglig nhrtpqlvse
241 ipekviqvac ggehtvvite navytfglgq fgqlgigtfl fetsepkvie nirdqtisyi
301 scgenhtali tdiglmytfg dgrhgkiglg lenftnhfip tlcsnflrfi vklvacggch
361 mvvfaaphrg vakeiefdei ndtclsvatf lpyssitsgn vlqrtisarm rrerererspd
421 sfsmrrtlpp iegtlgisac flpnsvfprc sernlqesvl seqdimqpee pdylldemtk
481 eaeidnsstv esligettdil nmthimslns nekslkispv qkqkkqgtig eltqdtalite
541 nddsdeyeem semkegkack qhvsqgifmt qpattieafs deeveipeek egaedskgng
601 ieegeveane envkvhggrk ekteiisddl tdkaeysash sqivsv (SEQ ID NO:29)
```

FIG. 7U

RPGR – 1152 amino acids

```
   1  mrepeelmpd sgavftfgks kfaennpgkf wfkndvpvhi scgdehsavv tgnnklymfg
  61  snnwgqiglg sksaiskptc vkalkpekvk laacgrnhti vsteggnvya tggnneggqig
 121  igdteerntf hvisfftseh kikqisagsn tsaaltedgr lfmwgdnseg qigiknvsnv
 181  cvpqgvtigk pvswiscgyy hsafvttdge iyvfgepeng kiglpnqlig nhrtpqlvse
 241  ipekviqvac ggehtvvlte navytfglgq fgqigigtfi fetsepkvie nirdqtisyi
 301  scgenhtali tdiglmytfg dgrhgkiglg lenftnhfip ticsnflrfi vkivacggch
 361  mvvfaaphrg vakeiefdei ndtcisvatf lpyssitsgn vlqrtisarm rrerererspd
 421  sfsmrrtlpp iegtiglsac flpnsvfiprc serniqesvi seqdimqpee pdyildemtk
 481  eaeidnsstv eslgettdil nmthimslns neksiklspv qkqkkqgtig eltqdtaite
 541  nddsdeyeem semkegkack qhvsqgifmt qpattieafs deeveipeek egaedskgng
 601  ieeqeveane envkvhggrk ekteiisddi tdkaevsegk aksvgeaedg pegrgdgtce
 661  egssgaehwq deerekgekd kgrgemerpg egekelaeke ewkkrdgeeq eqkereqghq
 721  kernqemeeg geeehgegee kegegkeege geeveggeve eegkgereeee eegegeeeeg
 781  agkeekgeee gdqgegeeee tegrgeekee ggeveggeve egkgereeee eegegeeeeg
 841  egeeeegee eegegkgee egegegegeg egeeeegeeg eegegegee gegegegeeg
 901  egegeeegeg egeeegegk geeeeegeeg egeegegegee egegegegeg eegewegeee
 961  egegegeeeg egegegeeeg egeeeegeeg geeeegeeee eeegegeeeg gegeeegeeeg
1021  vegevegeeg egegeegeee eegeeerekeg eegeeerekeg eeeeeegkyq etgeeenerq
1081  dgeeykkvsk ikgsvkygkh ktyqkksvtn tqgngkeqrs kmpvqskril kngpsgskkf
1141  wnnvlphyle ik (SEQ ID NO:30)
```

FIG. 7V

RPGR – 1020 amino acids

```
  1 mrepeeimpd sgavftfgks kfaennpgkf wfkndvpvhl scgdehsavv tgnnklymfg
 61 snnwgqiglg sksaiskptc vkalkpekvk iaacgrnhtl vsteggnvya tggnneqqig
121 lgdteerntf hvisfftseh kikqlsagsn tsaaitedgr ifmwgdnseg qigiknvsnv
181 cvpqqvtigk pvswiscgyy hsafvttdge lyvfgepeng kiglpnqlig nhrtpqlvse
241 ipekviqvac ggehtvvlte navytfglgq fgqigigtfl fetsepkvie nirdqtisyi
301 scgenhtali tdigimytfg dgrhgkiglg ienftnhfip ticsnflrfi vklvacggch
361 mvvfaaphrg vakeiefdei ndtclsvatf lpyssitsgn vlqrtisarm rrererspd
421 sfsmrrtlpp iegtlgisac flpnsvfprc sernlqesvi seqdlmqpee pdylidemtk
481 eaeidnsstv eslgetttdil nmthimslns neksiklspv qkqkkqqtig eltqdtalte
541 nddsdeyeem semkegkack qhvsqgifmt qpattieafs deevqndtgq vgpqadtdge
601 giqkevyrhe nnngvdqlda keiekesdgg hsqkeseaee idseketkia eiagmkdlre
661 rekstkkmsp ffgnlpdrgm nteseenkdf vkkresckqd vifdseresv ekpdsymega
721 sesqgiadg fqqpeaiefs sgekeddeve tdqnirygrk lieqgneket kpiiisksmak
781 ydfkcdrlse ipeekegaed skgngieege veaneenvkv hggrkektei lsdditdkae
841 dhefskteel kledvdeein aenveskkkt vgddesvptg yhsktegaer ttpskdmkkt tnddssaeti
901 ekkekanlee raiceynenp kgymiddads ssleilense ttpskdmkkt kkififkrvp
961 singkivknn neplpeiksi gdqiilksdn kdadqnhmsq nhqnipptnt errsksctil
```

(SEQ ID NO:31)

FIG. 8A

*Streptococcus pyogenes* Cas9

```
   1  mdkkysigld  igtnsvgwav  itdeykvpsk  kfkvlgntdr  hsikknliga  llfdsgetae
  61  atrlkrtarr  rytrrknric  ylqeifsnem  akvddsffhr  leesflveed  kkherhpifg
 121  nivdevayhe  kyptiyhlrk  klvdstdkad  lrliylalah  mikfrghfli  egdlnpdnsd
 181  vdkifiqlvq  tynqlfeenp  inasgvdaka  ilsarlsksr  rlenliaqlp  gekknglfgn
 241  liaislgltp  nfksnfdlae  dakiqlskdt  ydddldnlla  qigdqyadlf  laaknlsdai
 301  llsdilrvnt  eitkapisas  mikrydehhq  ditllkalvr  qqlpekykei  ffdqskngya
 361  gyidggasqe  efykfikpil  ekmdgteell  vklnredllr  kqrtfdngsi  phqihlgelh
 421  ailrrqedfy  pflkdnreki  ekiltfripy  yvgplargns  rfawmtrkse  etitpwnfee
 481  vvdkgasaqs  fiermtnfdk  nlpnekvlpk  hsllyeyftv  yneltkvkyv  teqmrkpafl
 541  sgeqkkaivd  llfktnrkvt  vkqlkedyfk  kiecfdsvei  sgvedrfnas  lgtyhdllki
 601  ikdkdfldne  enediledlv  ltltlfedre  mieerlktya  hlfddkvmkq  lkrrrytgwg
 661  risrklingi  rdkqsgktil  dflksdgfan  rnfmqlihdd  sltfkedlqk  aqvsgqgdsl
 721  hehianlags  paikkgilqt  vkvvdeivkv  mgrhkpeniv  iemarenqtt  qkgqknsrer
 781  mkrieegike  lgsqilkehp  ventqlqnek  lylylyqngr  dmyvdqeldi  nrlsdydvdh
 841  ivpqsflkdd  sidnkvltrs  dknrgksdnv  pseevvkkmk  nywrqllnak  lltqrkfdnl
 901  tkaerggise  ldkagfikrq  lvetrqitkh  vaqildsrmn  tkydendkli  revkvitlks
 961  klvsdfrkdf  qfykvreinn  yhhahdayln  avvgtalikk  ypklesefvy  gdykvydvrk
1021  miakseqeig  katakyffys  nimnffktei  tlangeirkr  plietngetg  eivwdkgrdf
1081  atvrkvlsmp  qvnivkktev  qtggfskesi  lpkrnsdkli  arkkdwdpkk  yggfdsptva
1141  ysvivvakve  kgkskkliksv  keligitime  rssfeknpid  fleakgykev  kkdliiklpk
1201  yslfelengi  krmlasagel  qkgnelalps  kyvnflylas  hyeklkgspe  dneqkqlfve
1261  qhkhyldeii  eqisefskrv  iladanldkv  lsaynkhrdk  pireqaenii  hlfltlniga
1321  paafkyfdtt  idrkrytstk  evldatlihq  sitglyetri  dlsqiqqd  (SEQ ID NO:32)
```

FIG. 8B

*Staphylococcus aureus* Cas9

```
   1  mkrnyilgld  igitsvgygi  idyetrdvid  agvrlfkean  vennegrrsk  rgarrikrrr
  61  rhrigrvkkl  lfdynlltdh  selsginpye  arvkglsqkl  seeefsaall  hlakrrgvhn
 121  vneveedtgn  elstkeqisr  nskaleekyv  aelqlerlkk  dgevrgsinr  fktsdyvkea
 181  kqlikvqkay  hqldqsfidt  yidlletrrt  yyegpgegsp  fgwkdikewy  emlmghctyf
 241  peelrsvkya  ynadlynaln  dinnlvitrd  enekleyyek  fqlienvfkq  kkkptlkqla
 301  keilvneedi  kgyrvtstgk  peftnlkvyh  dikditarke  ilenaelldq  lakiltiyqs
 361  sediqeeltn  lnseltqeei  eqisnlkgyt  gthnlslkal  nlildelwht  ndnqlalfnr
 421  lklvpkkvdl  sqqkelpttl  vddfilspvv  krsflqslkv  inallkkygl  pndillelar
 481  eknskdaqkm  lnemqkrnrq  tnerleellr  ttgkenakyl  lekikihdmq  egkclyslea
 541  lpledllnnp  fnyevdhlip  rsvsfdnsfn  nkvlvkqeen  skkgnrtpfq  ylsssdskls
 601  yetfkkhlln  lakgkgrisk  tkkeylleer  dlnrfsvqkd  flnrnlvdtr  yatrglmnll
 661  rsyfrvnnld  vkvksinggf  tsflrrkwkf  kkernkgykh  haedallian  adflfkewkk
 721  ldkakkvmen  qmfeekqaes  mpelteqey  kelfltphql  khlkdfkdyk  yshrvdkkpn
 781  relindtlys  trkddkqntl  ivnnlnglyd  kdndklkkll  nkspeklmy  hhdpqtyqkl
 841  klimeqygde  knplykyyee  tgnyltkysk  kdngpvikkl  kyygnklnah  ldltddypns
 901  rnkvvklslk  pyrfdvylgn  gvykfvtvkn  ldvlkkenyy  evnskcyeea  kklkklsnqa
 961  eflasfynnd  llkngelyr  vlgvnndlln  rlevnmldlt  yreylenmnd  krppriikti
1022  asktgsikky  stdllgnlye  vkskkhpqll  kkg  (SEQ ID NO:33)
```

FIG. 8C

*Francisella tularensis* Cpf1

```
   1 msiyqefvnk yslsktlrfe lipqgktlen ikargliIdd ekrakdykka kqiidkyhqf
  61 fieeilssvc isedllqnys dvyfklkksd ddnlqkdfks akdtikkqis eyikdsekfk
 121 nlfnqnlida kkgqesdlil wlkqskdngi elfkansdit didealeiik sfkgwttyfk
 181 gfhenrknvy ssndiptsii yrivddnlpk flenkakyes lkdkapeain yeqikkdlae
 241 eltfdidykt sevnqrvfsl devfeianfn nylnqsgitk fntiiggkfv ngentkrkgi
 301 neyinlysqq indktlkkyk msvlfkqils dtesksfvid kleddsdvvt tmqsfyeqia
 361 afktveeksi ketlsllfdd lkaqkldlsk iyfkndkslt dlsqqvfddy svigtavley
 421 itqqiapknl dnpskkeqel iakktekaky lsletiklal eefnkhrdid kqcrfeeila
 481 nfaaipmifd eiaqnkdnla qisikyqnqg kkdllqasae ddvkaikdll dqtnnllhkl
 541 kifhisqsed kanildkdeh fylvfeecyf elanivplyn kirnyitqkp ysdekfklnf
 601 enstlangwd knkepdntai lfikddkyyl gvmnkknnki fddkaikenk gegykkivyk
 661 llpgankmlp kvffsaksik fynpsedilr irnhsthtkn gspqkgyekf efniedcrkf
 721 idfykqsisk hpewkdfgfr fsdtqrynsi defyrevenq gykltfenis esyidsvvnq
 781 gklylfqiyn kdfsayskgr pnlhtlywka lfdernlqdv vyklngeael fyrkqsipkk
 841 ithpakeaia nknkdnpkke svfeydlikd krftedkfff hcpitinfks sgankfndei
 901 nlllkekand vhilsidrge rhlayytlvd gkgniikqdt fniigndrmk tnyhdklaai
 961 ekdrdsarkd wkkinnikem kegylsqvvh eiaklvieyn aivvfedlnf gfkrgrfkve
1021 kqvyqklekm lieklnylvf kdnefdktgg vlrayqltap fetfkkmgkq tgiiyyvpag
1081 ftskicpvtg fvnqlypkye svsksqeffs kfdkicynld kgyfefsfdy knfgdkaakg
1141 kwtiasfgsr linfrnsdkn hnwdtrevyp tkelekllkd ysieyghgec ikaaicgesd
1201 kkffakltsv lntilqmrns ktgteldyli spvadvngnf fdsrqapknm pqdadangay
1261 higlkglmll griknnqegk klnlviknee yfefvqnrnn (SEQ ID NO:34)
```

ADENO-ASSOCIATED VIRUS VIRIONS WITH VARIANT CAPSID AND METHODS OF USE THEREOF

CROSS-REFERENCE

This application is continuation of U.S. application Ser. No. 16/315,032 filed Jan. 3, 2019, which application is a national stage filing under 35 U.S.C. § 371 of PCT/US2017/044206, filed Jul. 27, 2017, which claims the benefit of U.S. Provisional Patent Application No. 62/368,929, filed Jul. 29, 2016, which applications are incorporated herein by reference in their entirety.

STATEMENT REGARDING FEDERALLY SPONSORED RESEARCH

This invention was made with government support under Contract/Grant Nos. EY022975, EY018241 and EY006855 awarded by the National Institutes of Health. The government has certain rights in the invention.

INCORPORATION BY REFERENCE OF SEQUENCE LISTING PROVIDED AS A TEXT FILE

A Sequence Listing is provided herewith in a text file, BERK-335_SEQ_LISTING_ST25, created on Jan. 3, 2019 and having a size of 208,613 bytes. The contents of the text file are incorporated herein by reference in its entirety.

INTRODUCTION

Photoreceptors are the first neurons in the retina to receive and process visual information, converting visible electromagnetic radiation into hyperpolarized responses through phototransduction. The overwhelming majority of inherited retinal diseases result in the loss of these cells, either directly, such as in dominant mutations that affect rhodopsin protein folding, or indirectly, such as in recessive mutations that affect retinal recycling pathways in the retinal pigment epithelium (RPE).

Adeno-associated virus (AAV) belongs to the Parvoviridae family and Dependovirus genus, whose members require co-infection with a helper virus such as adenovirus to promote replication, and AAV establishes a latent infection in the absence of a helper. Virions are composed of a 25 nm icosahedral capsid encompassing a 4.9 kb single-stranded DNA genome with two open reading frames: rep and cap. The non-structural rep gene encodes four regulatory proteins essential for viral replication, whereas cap encodes three structural proteins (VP1-3) that assemble into a 60-mer capsid shell. This viral capsid mediates the ability of AAV vectors to overcome many of the biological barriers of viral transduction—including cell surface receptor binding, endocytosis, intracellular trafficking, and unpackaging in the nucleus.

SUMMARY

The present disclosure provides recombinant adeno-associated virus (AAV) virions with altered capsid protein, where the recombinant AAV (rAAV) virions exhibit greater infectivity of a retinal cell compared to wild-type AAV, and where the rAAV virions comprise a heterologous nucleic acid. The present disclosure further provides methods of delivering a gene product to a retinal cell in an individual, and methods of treating ocular disease. The present disclosure provides an rAAV virion, where the rAAV virion exhibits at least 5-fold increased localization to one or more of the inner nuclear layer, the outer nuclear layer, the photoreceptor layer, the ganglion cell layer, and the retinal pigment epithelium, compared to the extent of localization to the inner nuclear layer, the outer nuclear layer, the photoreceptor layer, the ganglion cell layer, or the retinal pigment epithelium, by an AAV virion comprising the corresponding parental AAV capsid protein.

BRIEF DESCRIPTION OF THE DRAWINGS

FIG. 4 provides an amino acid sequence of AAV2 capsid protein VP1. Amino acids 587 and 588 (NP) are in bold and underlined.

FIG. 5 provides amino acid sequences corresponding to amino acids 570-610 of AAV capsid protein VP1 of various AAV serotypes.

FIG. 6A-6C provide an alignment of amino acid sequences of AAV capsid protein loop IV (GH loop) regions. Insertion sites are shown in bold and underlining. AAV1: SEQ ID NO:35; AAV6: SEQ ID NO:36; AAV3: SEQ ID NO:37; AAV2: SEQ ID NO:38; AAV8: SEQ ID NO:39; AAV8.1: SEQ ID NO:40; AAV8 rh8: SEQ ID NO:41; AAV10: SEQ ID NO:42; AAV7: SEQ ID NO:43; AAV9: SEQ ID NO:44; AAV 9.1: SEQ ID NO:45; AAV5: SEQ ID NO:46.

FIG. 7A-7V provide amino acid sequences of exemplary heterologous gene products.

FIG. 8A-8C provide amino acid sequences of exemplary guide-RNA-directed endonucleases.

DEFINITIONS

Figure 1:
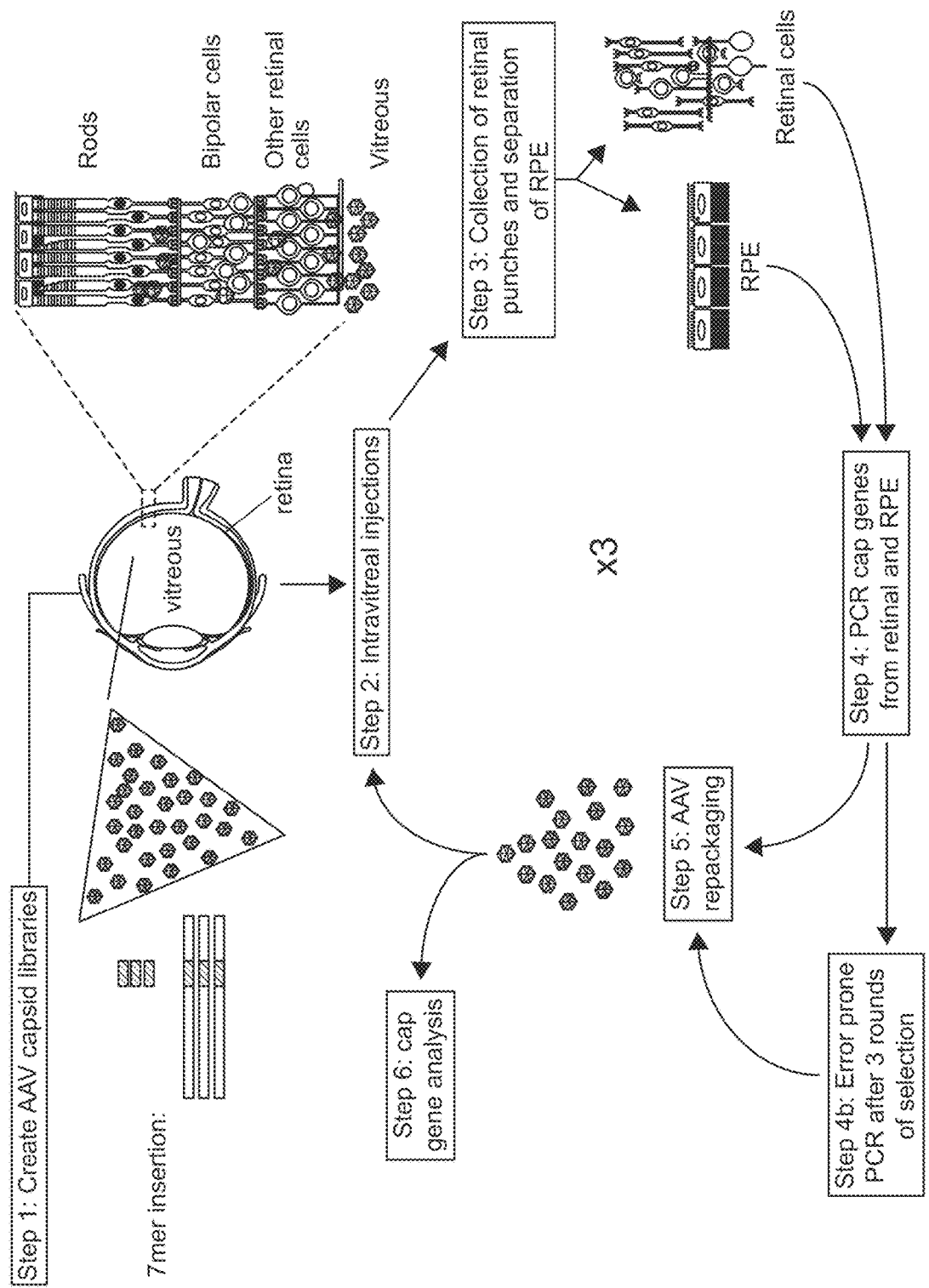
FIG. 1 is a schematic depiction of a directed evolution method used to develop AAV variants that exhibit increased infectivity of an ocular cell (e.g., a retinal cell), compared to the parental AAV.

The term "retinal cell" can refer herein to any of the cell types that comprise the retina, such as retinal ganglion cells; amacrine cells; horizontal cells; bipolar cells; photoreceptor cells including rods and cones; Müller glial cells; astrocytes (e.g., a retinal astrocyte); and retinal pigment epithelium.

"AAV" is an abbreviation for adeno-associated virus, and may be used to refer to the virus itself or derivatives thereof. The term covers all subtypes and both naturally occurring and recombinant forms, except where required otherwise. The abbreviation "rAAV" refers to recombinant adeno-associated virus, also referred to as a recombinant AAV vector (or "rAAV vector"). The term "AAV" includes AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), AAV type 9 (AAV-9), avian AAV, bovine AAV, canine AAV, equine AAV, primate AAV, non-primate AAV, and ovine AAV. "Primate AAV" refers to AAV isolated from a primate, "non-primate AAV" refers to AAV isolated from a non-primate mammal, "bovine AAV" refers to AAV isolated from a bovine mammal (e.g., a cow), etc.

An "rAAV vector" as used herein refers to an AAV vector comprising a polynucleotide sequence not of AAV origin (i.e., a polynucleotide heterologous to AAV), typically a sequence of interest for the genetic transformation of a cell. In general, the heterologous polynucleotide is flanked by at least one, and generally by two AAV inverted terminal repeat sequences (ITRs). The term rAAV vector encompasses both rAAV vector particles and rAAV vector plasmids.

An "AAV virus" or "AAV viral particle" or "rAAV vector particle" refers to a viral particle composed of at least one AAV capsid protein (typically by all of the capsid proteins of a wild-type AAV) and an encapsidated polynucleotide rAAV vector. If the particle comprises a heterologous polynucleotide (i.e. a polynucleotide other than a wild-type AAV genome, such as a transgene to be delivered to a mammalian cell), it is typically referred to as an "rAAV vector particle" or simply an "rAAV vector". Thus, production of rAAV particle necessarily includes production of rAAV vector, as such a vector is contained within an rAAV particle.

"Packaging" refers to a series of intracellular events that result in the assembly and encapsidation of an AAV particle.

AAV "rep" and "cap" genes refer to polynucleotide sequences encoding replication and encapsidation proteins of adeno-associated virus. AAV rep and cap are referred to herein as AAV "packaging genes."

A "helper virus" for AAV refers to a virus that allows AAV (e.g. wild-type AAV) to be replicated and packaged by a mammalian cell. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

"Helper virus function(s)" refers to function(s) encoded in a helper virus genome which allow AAV replication and packaging (in conjunction with other requirements for replication and packaging described herein). As described herein, "helper virus function" may be provided in a number of ways, including by providing helper virus or providing, for example, polynucleotide sequences encoding the requisite function(s) to a producer cell in trans.

An "infectious" virus or viral particle is one that comprises a polynucleotide component which it is capable of delivering into a cell for which the viral species is tropic. The term does not necessarily imply any replication capacity of the virus. As used herein, an "infectious" virus or viral particle is one that can access a target cell, can infect a target cell, and can express a heterologous nucleic acid in a target cell. Thus, "infectivity" refers to the ability of a viral particle to access a target cell, infect a target cell, and express a heterologous nucleic acid in a target cell. Infectivity can refer to in vitro infectivity or in vivo infectivity. Assays for counting infectious viral particles are described elsewhere in this disclosure and in the art. Viral infectivity can be expressed as the ratio of infectious viral particles to total viral particles. Total viral particles can be expressed as the number of viral genome (vg) copies. The ability of a viral particle to express a heterologous nucleic acid in a cell can be referred to as "transduction." The ability of a viral particle to express a heterologous nucleic acid in a cell can be assayed using a number of techniques, including assessment of a marker gene, such as a green fluorescent protein (GFP) assay (e.g., where the virus comprises a nucleotide sequence encoding GFP), where GFP is produced in a cell infected with the viral particle and is detected and/or measured; or the measurement of a produced protein, for example by an enzyme-linked immunosorbent assay (ELISA). Viral infectivity can be expressed as the ratio of infectious viral particles to total viral particles. Methods of determining the ratio of infectious viral particle to total viral particle are known in the art. See, e.g., Grainger et al. (2005) *Mol. Ther.* 11:S337 (describing a TCID50 infectious titer assay); and Zolotukhin et al. (1999) *Gene Ther.* 6:973.

A "replication-competent" virus (e.g. a replication-competent AAV) refers to a phenotypically wild-type virus that is infectious, and is also capable of being replicated in an infected cell (i.e. in the presence of a helper virus or helper virus functions). In the case of AAV, replication competence generally requires the presence of functional AAV packaging genes. In general, rAAV vectors as described herein are replication-incompetent in mammalian cells (especially in human cells) by virtue of the lack of one or more AAV packaging genes. Typically, such rAAV vectors lack any AAV packaging gene sequences in order to minimize the possibility that replication competent AAV are generated by recombination between AAV packaging genes and an incoming rAAV vector. In many embodiments, rAAV vector preparations as described herein are those which contain few if any replication competent AAV (rcAAV, also referred to as RCA) (e.g., less than about 1 rcAAV per $10^2$ rAAV particles, less than about 1 rcAAV per $10^4$ rAAV particles, less than about 1 rcAAV per $10^8$ rAAV particles, less than about 1 rcAAV per $10^{12}$ rAAV particles, or no rcAAV).

The term "polynucleotide" refers to a polymeric form of nucleotides of any length, including deoxyribonucleotides or ribonucleotides, or analogs thereof. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST/. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970)

Of interest is the BestFit program using the local homology algorithm of Smith Waterman (Advances in Applied Mathematics 2: 482-489 (1981) to determine sequence identity. The gap generation penalty will generally range from 1 to 5, usually 2 to 4 and in many embodiments will be 3. The gap extension penalty will generally range from about 0.01 to 0.20 and in many instances will be 0.10. The program has default parameters determined by the sequences inputted to be compared. Preferably, the sequence identity is determined using the default parameters determined by the program. This program is available also from Genetics Computing Group (GCG) package, from Madison, Wis., USA.

Another program of interest is the FastDB algorithm. FastDB is described in Current Methods in Sequence Comparison and Analysis, Macromolecule Sequencing and Synthesis, Selected Methods and Applications, pp. 127-149, 1988, Alan R. Liss, Inc. Percent sequence identity is calculated by FastDB based upon the following parameters:
  Mismatch Penalty: 1.00;
  Gap Penalty: 1.00;
  Gap Size Penalty: 0.33; and
  Joining Penalty: 30.0.

A "gene" refers to a polynucleotide containing at least one open reading frame that is capable of encoding a particular protein after being transcribed and translated.

The term "guide RNA", as used herein, refers to an RNA that comprises: i) an "activator" nucleotide sequence that binds to a guide RNA-directed endonuclease (e.g., a class 2 CRISPR/Cas endonuclease such as a type II, type V, or type VI CRISPR/Cas endonuclease) and activates the RNA-directed endonuclease; and ii) a "targeter" nucleotide sequence that comprises a nucleotide sequence that hybridizes with a target nucleic acid. The "activator" nucleotide sequence and the "targeter" nucleotide sequence can be on separate RNA molecules (e.g., a "dual-guide RNA"); or can be on the same RNA molecule (a "single-guide RNA").

A "small interfering" or "short interfering RNA" or siRNA is a RNA duplex of nucleotides that is targeted to a gene interest (a "target gene"). An "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length.

As used herein, the term "microRNA" refers to any type of interfering RNAs, including but not limited to, endogenous microRNAs and artificial microRNAs (e.g., synthetic miRNAs). Endogenous microRNAs are small RNAs naturally encoded in the genome which are capable of modulating the productive utilization of mRNA. An artificial microRNA can be any type of RNA sequence, other than endogenous microRNA, which is capable of modulating the activity of an mRNA. A microRNA sequence can be an RNA molecule composed of any one or more of these sequences. MicroRNA (or "miRNA") sequences have been described in publications such as Lim, et al., 2003, Genes & Development, 17, 991-1008, Lim et al., 2003, Science, 299, 1540, Lee and Ambrose, 2001, Science, 294, 862, Lau et al., 2001, Science 294, 858-861, Lagos-Quintana et al., 2002, Current Biology, 12, 735-739, Lagos-Quintana et al., 2001, Science, 294, 853-857, and Lagos-Quintana et al., 2003, RNA, 9, 175-179. Examples of microRNAs include any RNA that is a fragment of a larger RNA or is a miRNA, siRNA, stRNA, sncRNA, tncRNA, snoRNA, smRNA, shRNA, snRNA, or other small non-coding RNA. See, e.g., US Patent Applications 20050272923, 20050266552, 20050142581, and 20050075492. A "microRNA precursor" (or "pre-miRNA") refers to a nucleic acid having a stem-loop structure with a microRNA sequence incorporated therein. A "mature microRNA" (or "mature miRNA") includes a microRNA that has been cleaved from a microRNA precursor (a "pre-miRNA"), or that has been synthesized (e.g., synthesized in a laboratory by cell-free synthesis), and has a length of from about 19 nucleotides to about 27 nucleotides, e.g., a mature microRNA can have a length of 19 nt, 20 nt, 21 nt, 22 nt, 23 nt, 24 nt, 25 nt, 26 nt, or 27 nt. A mature microRNA can bind to a target mRNA and inhibit translation of the target mRNA.

"Recombinant," as applied to a polynucleotide means that the polynucleotide is the product of various combinations of cloning, restriction or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter.

"Operatively linked" or "operably linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

An "expression vector" is a vector comprising a region which encodes a polypeptide of interest, and is used for effecting the expression of the protein in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

"Heterologous" means derived from a genotypically distinct entity from that of the rest of the entity to which it is being compared. For example, a polynucleotide introduced by genetic engineering techniques into a plasmid or vector derived from a different species is a heterologous polynucleotide. A promoter removed from its native coding sequence and operatively linked to a coding sequence with which it is not naturally found linked is a heterologous promoter. Thus, for example, an rAAV that includes a heterologous nucleic acid encoding a heterologous gene product is an rAAV that includes a nucleic acid not normally included in a naturally-occurring, wild-type AAV, and the encoded heterologous gene product is a gene product not normally encoded by a naturally-occurring, wild-type AAV. As another example, a variant AAV capsid protein that comprises a heterologous peptide inserted into the GH loop of the capsid protein is a variant AAV capsid protein that includes an insertion of a peptide not normally included in a naturally-occurring, wild-type AAV.

The terms "genetic alteration" and "genetic modification" (and grammatical variants thereof), are used interchangeably herein to refer to a process wherein a genetic element (e.g., a polynucleotide) is introduced into a cell other than by mitosis or meiosis. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, or contacting with a polynucleotide-liposome complex. Genetic alteration may also be effected, for example, by transduction or infection with a DNA or RNA virus or viral vector. Generally, the genetic element is introduced into a chromosome or mini-chromosome in the cell; but any alteration that changes the phenotype and/or genotype of the cell and its progeny is included in this term.

A cell is said to be "stably" altered, transduced, genetically modified, or transformed with a genetic sequence if the sequence is available to perform its function during extended culture of the cell in vitro. Generally, such a cell is "heritably" altered (genetically modified) in that a genetic alteration is introduced which is also inheritable by progeny of the altered cell.

The terms "polypeptide," "peptide," and "protein" are used interchangeably herein to refer to polymers of amino acids of any length. The terms also encompass an amino acid polymer that has been modified; for example, disulfide bond formation, glycosylation, lipidation, phosphorylation, or conjugation with a labeling component. Polypeptides such as anti-angiogenic polypeptides, neuroprotective polypeptides, and the like, when discussed in the context of delivering a gene product to a mammalian subject, and compositions therefor, refer to the respective intact polypeptide, or any fragment or genetically engineered derivative thereof, which retains the desired biochemical function of the intact protein. Similarly, references to nucleic acids encoding anti-angiogenic polypeptides, nucleic acids encoding neuroprotective polypeptides, and other such nucleic acids for use in delivery of a gene product to a mammalian subject (which may be referred to as "transgenes" to be delivered to a recipient cell), include polynucleotides encoding the intact polypeptide or any fragment or genetically engineered derivative possessing the desired biochemical function.

An "isolated" plasmid, nucleic acid, vector, virus, virion, host cell, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this invention are increasingly more isolated. An isolated plasmid, nucleic acid, vector, virus, host cell, or other substance is in some embodiments purified, e.g., from about 80% to about 90% pure, at least about 90% pure, at least about 95% pure, at least about 98% pure, or at least about 99%, or more, pure.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease or at risk of acquiring the disease but has not yet been diagnosed as having it; (b) inhibiting the disease, i.e., arresting its development; and (c) relieving the disease, i.e., causing regression of the disease.

The terms "individual," "host," "subject," and "patient" are used interchangeably herein, and refer to a mammal, including, but not limited to, human and non-human primates, including simians and humans; mammalian sport animals (e.g., horses, camels, etc.); mammalian farm animals (e.g., sheep, goats, cows, etc.); mammalian pets (dogs, cats, etc.); and rodents (e.g., mice, rats, etc.). In some cases, the individual is a human.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an AAV capsid" includes a plurality of such capsids and reference to "the AAV virion" includes reference to one or more AAV virions and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides recombinant adeno-associated virus (AAV) virions with altered capsid protein, where the recombinant AAV (rAAV) virions exhibit greater infectivity of a retinal cell compared to wild-type AAV; and where the rAAV virions comprise a heterologous nucleic acid. The rAAV virions exhibit greater infectivity of a retinal cell, compared to the infectivity of a corresponding wild-type AAV for the retinal cell. The retinal cell can be a photoreceptor (e.g., rods; cones), a retinal ganglion cell (RGC), a Müller cell (a Müller glial cell), an astrocyte (e.g., a retinal astrocyte), a bipolar cell, an amacrine cell, a horizontal cell, or a retinal pigment epithelium (RPE) cell. The present disclosure further provides methods of delivering a gene product to a retinal cell in an individual, and methods of treating an ocular disease. The present disclosure provides an rAAV virion with an altered capsid protein, where the rAAV virion exhibits at least 5-fold increased localization to one or more of the inner nuclear layer, the outer nuclear layer, the photoreceptor layer, the ganglion cell layer, and the retinal pigment epithelium, compared to the extent of localization to the inner nuclear layer, the outer nuclear layer, the photoreceptor layer, the ganglion cell layer, or the retinal pigment epithelium, by an AAV virion comprising the corresponding parental AAV capsid protein; and where the rAAV virions comprise a heterologous nucleic acid.

Variant AAV Capsid Polypeptides

The present disclosure provides a variant AAV capsid protein. A variant AAV capsid protein of the present disclosure comprises an insertion of a heterologous peptide of from 5 amino acids to 20 amino acids in length in an insertion site in a surface-accessible (e.g., solvent-accessible) portion of a parental AAV capsid protein, such that the variant capsid protein, when present in an AAV virion, confers increased infectivity of a retinal cell compared to the infectivity of the retinal cell by an AAV virion comprising the corresponding parental AAV capsid protein. In other cases, the retinal cell is a Müller cell. Other retinal cells include amacrine cells, bipolar cells, and horizontal cells. An "insertion of from about 5 amino acids to about 20 amino acids" is also referred to herein as a "peptide insertion" (e.g., a heterologous peptide insertion). A "corresponding parental AAV capsid protein" refers to an AAV capsid protein of the same AAV serotype, without the peptide insertion. In many instances, the variant AAV capsid comprises a single heterologous peptide insert of from 5 amino acids to 20 amino acids (e.g., from 5 to 7, from 7 to 10, from 10 to 12, from 12 to 15, or from 15 to 20 amino acids) in length.

The insertion site is in the GH loop, or loop IV, of the AAV capsid protein, e.g., in a solvent-accessible portion of the GH loop, or loop IV, of the AAV capsid protein. For the GH loop/loop IV of AAV capsid, see, e.g., van Vliet et al. (2006) *Mol. Ther.* 14:809; Padron et al. (2005) *J. Virol.* 79:5047; and Shen et al. (2007) *Mol. Ther.* 15:1955. For example, the insertion site can be within amino acids 411-650 of an AAV capsid protein, as depicted in FIG. 6A-6C. For example, the insertion site can be within amino acids 570-611 of AAV2, within amino acids 571-612 of AAV1, within amino acids 560-601 of AAV5, within amino acids 571 to 612 of AAV6, within amino acids 572 to 613 of AAV7, within amino acids 573 to 614 of AAV8, within amino acids 571 to 612 of AAV9, or within amino acids 573 to 614 of AAV10, as depicted in FIG. 5. In some cases, the insertion site is between amino acids 588 and 589 of an AAV2 capsid protein, or a corresponding insertion site in an AAV of a different serotype. In some cases, the insertion site is between amino acids 587 and 588 of an AAV2 capsid protein, or a corresponding insertion site in an AAV of a different serotype.

In some cases, a heterologous peptide of from about 5 amino acids to about 20 amino acids (e.g., from 5 to 7, from 7 to 10, from 10 to 12, from 12 to 15, or from 15 to 20 amino acids) in length is inserted in an insertion site in the GH loop or loop IV of the capsid protein relative to a corresponding parental AAV capsid protein. For example, the insertion site can be between amino acids 587 and 588 of AAV2, or the corresponding positions of the capsid subunit of another AAV serotype. It should be noted that the insertion site 587/588 is based on an AAV2 capsid protein. A heterologous peptide of 5 amino acids to about 20 amino acids (e.g., from 5 to 7, from 7 to 10, from 10 to 12, from 12 to 15, or from 15 to 20 amino acids) in length can be inserted in a corresponding site in an AAV serotype other than AAV2 (e.g., AAV8, AAV9, etc.). Those skilled in the art would know, based on a comparison of the amino acid sequences of capsid proteins of various AAV serotypes, where an insertion site "corresponding to amino acids 587-588 of AAV2" would be in a capsid protein of any given AAV serotype. Sequences corresponding to amino acids 570-611 of capsid protein VP1 of AAV2 (see FIG. 4) in various AAV serotypes are shown in FIG. 5. See, e.g., GenBank Accession No. NP_049542 for AAV1; GenBank Accession No. AAD13756 for AAV5; GenBank Accession No. AAB95459 for AAV6; GenBank Accession No. YP_077178 for AAV7; GenBank Accession No. YP_077180 for AAV8; GenBank Accession No. AAS99264 for AAV9 and GenBank Accession No. AAT46337 for AAV10.

For example, the insertion site can be between amino acids 587 and 588 of AAV2, between amino acids 590 and 591 of AAV1, between amino acids 575 and 576 of AAV5, between amino acids 590 and 591 of AAV6, between amino acids 589 and 590 of AAV7, between amino acids 590 and 591 of AAV8, between amino acids 588 and 589 of AAV9, or between amino acids 588 and 589 of AAV10. The insertion sites are underlined in FIG. 5; the amino acid numbering is based on the numbering depicted in FIG. 5.

In some embodiments, a subject capsid protein includes a GH loop comprising an amino acid sequence having at least about 85%, at least about 90%, at least about 95%, at least about 98%, at least about 99%, or 100%, amino acid sequence identity to an amino acid sequence set forth in FIG. 6A-6C; and having an insertion of a heterologous peptide of from 5 to 20 amino acids (e.g., from 5 to 7, from 7 to 10, from 10 to 12, from 12 to 15, or from 15 to 20 amino acids) in length.

Insertion Peptides

As noted above, a heterologous peptide of from about 5 amino acids to about 20 amino acids in length is inserted into the GH loop of an AAV capsid. In some cases, the insertion peptide has a length of from 5 amino acids to 20 amino acids. In some cases, the insertion peptide has a length of from 7 amino acids to 15 amino acids. In some cases, the insertion peptide has a length of from 9 amino acids to 15 amino acids. In some cases, the insertion peptide has a length of from 9 amino acids to 12 amino acids. The insertion peptide has a length of 5 amino acids, 6 amino acids, 7 amino acids, 8 amino acids, 9 amino acids, 10 amino acids, 11 amino acids, 12 amino acids, 13 amino acids, 14 amino acids, 15 amino acids, 16 amino acids, 17 amino acids, 18 amino acids, 19 amino acids, or 20 amino acids. In some cases, the insertion peptide has a length of 7 amino acids. In some cases, the insertion peptide has a length of 8 amino acids. In some cases, the insertion peptide has a length of 9 amino acids. In some cases, the insertion peptide has a length of 10 amino acids. In some cases, the insertion peptide has a length of 11 amino acids. In some cases, the insertion peptide has a length of 12 amino acids. In some cases, the insertion peptide has a length of 13 amino acids. In some cases, the insertion peptide has a length of 14 amino acids. In some cases, the insertion peptide has a length of 15 amino acids.

The peptide insert is, in some cases, a peptide of Formula I:

$X_1X_2X_3X_4X_5X_6X_7X_8X_9X_{10}$, where:

$X_1$ is Leu, Ile, Pro, or Gln;
$X_2$ is Ala, Pro, Ser, Asp, Gly, Thr, or Val;
$X_3$ is Lys, His, Thr, Ile, Pro, Val, Arg, Ala, Asp, Glu, Asn, Gln, or Tyr;
$X_4$ (if present) is Gln, Asp, Ser, Gly, Thr, Ile, Asn, Glu, Lys, or Arg;
$X_5$ is Asp, Ser, Gln, Val, Thr, Gly, Ala, Asn, Lys, or Tyr;
$X_6$ is Thr, Ala, Gln, Ser, Glu, Pro, or Ile;
$X_7$ is Thr, Ser, Asn, Pro, Leu, Gln, Lys, Ala, or Cys;
$X_8$ is Lys, Ser, Arg, Thr, Ala, Glu, Ile, or Asn;
$X_9$ is Asn, Pro, Ser, Lys, His, Ile, Thr, or Ala; and
$X_{10}$ is Ala, Phe, Asp, Thr, Val, or Met.

Peptide inserts of Formula I include, but are not limited to, (1) LAKDATKNA (SEQ ID NO:47); (2) PAHQDTTKNA (SEQ ID NO:48); (3) LAHQDTTKNA (SEQ ID NO:49); (4) LATTSQNKPA (SEQ ID NO:50); (5) LAISDQTKHA (SEQ ID NO:51); (6) IARGVAPSSA (SEQ ID NO:52); (7) LAPDSTTRSA (SEQ ID NO:53); (8) LAKGTELKPA (SEQ ID NO:54); (9) LAIIDATKNA (SEQ ID NO:55); (10) LAVDGAQRSA (SEQ ID NO:56); (11) PAPQDTTKKA (SEQ ID NO:57); (12) LPHQDTTKNA (SEQ ID NO:58); (13) LAKDATKTIA (SEQ ID NO:59); (14) LAKQQSASTA (SEQ ID NO:60); (15) LAKSDQSKPA (SEQ ID NO:61); (16) LSHQDTTKNA (SEQ ID NO:62); (17) LAANQPSKPA (SEQ ID NO:63); (18) LAVSDSTKAA (SEQ ID NO:64); (19) LAAQGTAKKPA (SEQ ID NO:65); (20) LAPDQTTRNA (SEQ ID NO:66); (21) LAASDSTKAA (SEQ ID NO:67); (22) LAPQDTTKNA (SEQ ID NO:68); (23) LAKADETRPA (SEQ ID NO:69); (24) LAHQDTAKNA (SEQ ID NO:70); (25) LAHQDTKKNA (SEQ ID NO:71); (26) LAHQDTTKHA (SEQ ID NO:72); (27) LAHQDTTKKA (SEQ ID NO:73); (28) LAHQDTTRNA (SEQ ID NO:74); (29) LAHQDTTNA (SEQ ID NO:75); (30) LAHQGTTKNA (SEQ ID NO:76); (31) LAHQVTTKNA (SEQ ID NO:77); (32) LAISDQSKPA (SEQ ID NO:78); (33) LADATKTA (SEQ ID NO:79); (34) LAKDTTKNA (SEQ ID NO:80); (35) LAKSDQSRPA (SEQ ID NO:81); (36) LAPQDTKKNA (SEQ ID NO:82); (37) LATSDSTKAA (SEQ ID NO:83); (38) LAVDGSQRSA (SEQ ID NO:84); (39) LPISDQTKHA (SEQ ID NO:85); (40) LPKDATKTIA (SEQ ID NO:86); (41) LPPQDTTKNA (SEQ ID NO:87); (42) PAPQDTTKNA (SEQ ID NO:88); (43) QAHQDTTKNA (SEQ ID NO:89); (44) LAHETSPRPA (SEQ ID NO:90); (45) LAKSTSTAPA (SEQ ID NO:91); (46) LADQDTTKNA (SEQ ID NO:92); (47) LAESDQSKPA (SEQ ID NO:93); (48) LAHKDTTKNA (SEQ ID NO:94); (49) LAHKTQQKM (SEQ ID NO:95); (50) LAHQDTTENA (SEQ ID NO:96); (51) LAHQDTTINA (SEQ ID NO:97); (52) LAHQDTTKKT (SEQ ID NO:98); (53) LAHQDTTKND (SEQ ID NO:99); (54) LAHQDTTKNT (SEQ ID NO:100); (55) LAHQDTTKNV (SEQ ID NO:101); (56) LAHQDTTKTM (SEQ ID NO:102); (57) LAHQNTTKNA (SEQ ID NO:103); (58) LAHRDTTKNA (SEQ ID NO:104); (59) LAISDQTNHA (SEQ ID NO:105); (60) LAKQKSASTA (SEQ ID NO:106); (61) LAKSDQCKPA (SEQ ID NO:107); (62) LAKSDQSKPD (SEQ ID NO:108); (63) LAKSDQSNPA (SEQ ID NO:109); (64) LAKSYQSKPA (SEQ ID NO:110); (65) LANQDTTKNA (SEQ ID NO:111); (66) LAPQNTTKNA (SEQ ID NO:112); (67) LAPSSIQKPA (SEQ ID NO:113); (68) LAQQDTTKNA (SEQ ID NO:114); (69) LAYQDTTKNA (SEQ ID NO:115); (70) LDHQDTTKNA (SEQ ID NO:116); (71) LDHQDTTKSA (SEQ ID NO:117); (72) LGHQDTTKNA (SEQ ID NO:118); (73) LPHQDTTKND (SEQ ID NO:119); (74) LPHQDTTKNT (SEQ ID NO:120); (75) LPHQDTTNNA (SEQ ID NO:121); (76) LTHQDTTKNA (SEQ ID NO:122); (77) LTKDATKTIA (SEQ ID NO:123); (78) LTPQDTTKNA (SEQ ID NO:124); and (79) LVHQDTTKNA (SEQ ID NO:125).

The peptide insert is, in some cases, a peptide of Formula II:

$X_1X_2X_3X_4X_5X_6X_7X_8X_9X_{10}$, where:

$X_1$ is Leu, Ile, or Pro;
$X_2$ is Ala, Pro, or Ser;
$X_3$ is Lys, His, Thr, Ile, Pro, Val, Arg, or Ala;
$X_4$ (if present) is Gln, Asp, Ser, Gly, Thr, Ile, or Asn;
$X_5$ is Asp, Ser, Gln, Val, Thr, Gly, or Ala;
$X_6$ is Thr, Ala, Gln, Ser, Glu, or Pro;
$X_7$ is Thr, Ser, Asn, Pro, Leu, Gln, Lys, or Ala;
$X_8$ is Lys, Ser, Arg, or Thr;
$X_9$ is Asn, Pro, Ser, Lys, His, Ile, Thr, or Ala; and
$X_{10}$ is Ala.

Peptide inserts of Formula II include, but are not limited to, (1) LAKDATKNA (SEQ ID NO:47); (2) PAHQDTTKNA (SEQ ID NO:48); (3) LAHQDTTKNA (SEQ ID NO:49); (4) LATTSQNKPA (SEQ ID NO:50); (5) LAIS- DQTKHA (SEQ ID NO:51); (6) IARGVAPSSA (SEQ ID NO:52); (7) LAPDSTTRSA (SEQ ID NO:53); (8) LAKGTELKPA (SEQ ID NO:54); (9) LAIIDATKNA (SEQ ID NO:55); (10) LAVDGAQRSA (SEQ ID NO:56); (11) PAPQDTTKKA (SEQ ID NO:57); (12) LPHQDTTKNA (SEQ ID NO:58); (13) LAKDATKTIA (SEQ ID NO:59); (14) LAKQQSASTA (SEQ ID NO:60); (15) LAKSDQSKPA (SEQ ID NO:61); (16) LSHQDTTKNA (SEQ ID NO:62); (17) LAANQPSKPA (SEQ ID NO:63); (18) LAVSDSTKAA (SEQ ID NO:64); (19) LAAQGTAKKPA (SEQ ID NO:65); (20) LAPDQTTRNA (SEQ ID NO:66); (21) LAASDSTKAA (SEQ ID NO:67); (22) LAPQDTTKNA (SEQ ID NO:68); (23) LAKADE-TRPA (SEQ ID NO:69); (24) LAHQDTAKNA (SEQ ID NO:70); (25) LAHQDTKKNA (SEQ ID NO:71); (26) LAHQDTTKHA (SEQ ID NO:72); (27) LAHQDTTKKA (SEQ ID NO:73); (28) LAHQDTTRNA (SEQ ID NO:74); (29) LAHQDTTNA (SEQ ID NO:75); (30) LAHQGTTKNA (SEQ ID NO:76); (31) LAHQVTTKNA (SEQ ID NO:77); (32) LAISDQSKPA (SEQ ID NO:78); (33) LADATKTA (SEQ ID NO:79); (34) LAKDTTKNA (SEQ ID NO:80); (35) LAKSDQSRPA (SEQ ID NO:81); (36) LAPQDTTKKNA (SEQ ID NO:82); (37) LATSDSTKAA (SEQ ID NO:83); (38) LAVDGSQRSA (SEQ ID NO:84); (39) LPISDQTKHA (SEQ ID NO:85); (40) LPKDATKTIA (SEQ ID NO:86); (41) LPPQDTTKNA (SEQ ID NO:87); and (42) PAPQDTTKNA (SEQ ID NO:88).

Peptides of Formula II include, but are not limited to: (1) LAKDATKNA (SEQ ID NO:47); (2) PAHQDTTKNA (SEQ ID NO:48); (3) LAHQDTTKNA (SEQ ID NO:49); (4) LATTSQNKPA (SEQ ID NO:50); (5) LAISDQTKHA (SEQ ID NO:51); (6) IARGVAPSSA (SEQ ID NO:52); (7) LAPDSTTRSA (SEQ ID NO:53); (8) LAKGTELKPA (SEQ ID NO:54); (9) LAIIDATKNA (SEQ ID NO:55); (10) LAVDGAQRSA (SEQ ID NO:56); (11) PAPQDTTKKA (SEQ ID NO:57); (12) LPHQDTTKNA (SEQ ID NO:58); (13) LAKDATKTIA (SEQ ID NO:59); (14) LAKQQSASTA (SEQ ID NO:60); (15) LAKSDQSKPA (SEQ ID NO:61); (16) LSHQDTTKNA (SEQ ID NO:62); (17) LAANQPSKPA (SEQ ID NO:63); and (18) LAVSDSTKAA (SEQ ID NO:64). In some cases, the peptide insert is (1) LAKDATKNA (SEQ ID NO:47). In some cases, the peptide insert is (2) PAHQDTTKNA (SEQ ID NO:48). In some cases, the peptide insert is (3) LAHQDTTKNA (SEQ ID NO:49). In some cases, the peptide insert is (4) LATTSQNKPA (SEQ ID NO:50). In some cases, the peptide insert is (5) LAISDQTKHA (SEQ ID NO:51). In some cases, the peptide insert is (6) IARGVAPSSA (SEQ ID NO:52). In some cases, the peptide insert is (7) LAPDSTTRSA (SEQ ID NO:53). In some cases, the peptide insert is (8) LAKGTELKPA (SEQ ID NO:54). In some cases, the peptide insert is (9) LAIIDATKNA (SEQ ID NO:55). In some cases, the peptide insert is (10) LAVDGAQRSA (SEQ ID NO:56). In some cases, the peptide insert is (11) PAPQDTTKKA (SEQ ID NO:57). In some cases, the peptide insert is (12) LPHQDTTKNA (SEQ ID NO:58). In some cases, the peptide insert is (13) LAKDATKTIA (SEQ ID NO:59). In some cases, the peptide insert is (14) LAKQQSASTA (SEQ ID NO:60). In some cases, the peptide insert is (15) LAKSDQSKPA (SEQ ID NO:61). In some cases, the peptide insert is (16) LSHQDTTKNA (SEQ ID NO:62). In some cases, the peptide insert is (17) LAANQPSKPA (SEQ ID NO:63). In some cases, the peptide insert is (18) LAVSDSTKAA (SEQ ID NO:64).

The peptide insert is, in some cases, a peptide of Formula III:

$X_1X_2X_3X_4X_5X_6X_7X_8X_9X_{10}$, where:
$X_1$ is Leu, Ile, or Pro;
$X_2$ is Ala, Pro, or Ser;
$X_3$ is Lys, His, Thr, Ile, Pro, Val, Arg, or Ala;
$X_4$ (if present) is Gln, Asp, Ser, Gly, Thr, Ile, or Asn;
$X_5$ is Asp, Ser, Gln, Val, Thr, Gly, or Ala;
$X_6$ is Thr, Ala, Gln, Ser, Glu, or Pro;
$X_7$ is Thr, Ser, Asn, Pro, Leu, Gln, Lys, or Ala;
$X_8$ is Lys, Ser, Arg, or Thr;
$X_9$ is Asn, Pro, Ser, Lys, His, Ile, Thr, or Ala; and
$X_{10}$ is Ala, Thr, Asp Val, or Met.

Peptide inserts of Formula III include, but are not limited to, (1) LAKDATKNA (SEQ ID NO:47); (2) PAHQDTTKNA (SEQ ID NO:48); (3) LAHQDTTKNA (SEQ ID NO:49); (6) IARGVAPSSA (SEQ ID NO:52); (7) LAPDSTTRSA (SEQ ID NO:53); (8) LAKGTELKPA (SEQ ID NO:54); (9) LAIIDATKNA (SEQ ID NO:55); (10) LAVDGAQRSA (SEQ ID NO:56); (11) PAPQDTTKKA (SEQ ID NO:57); (12) LPHQDTTKNA (SEQ ID NO:58); (13) LAKDATKTIA (SEQ ID NO:59); (14) LAKQQSASTA (SEQ ID NO:60); (16) LSHQDTTKNA (SEQ ID NO:62); (17) LAANQPSKPA (SEQ ID NO:63); (18) LAVSDSTKAA (SEQ ID NO:64); (19) LAAQGTAKPA (SEQ ID NO:65); (20) LAPDQTTRNA (SEQ ID NO:66); (24) LAHQDTAKNA (SEQ ID NO:70); (25) LAHQDTKKNA (SEQ ID NO:71); (26) LAHQDTTKHA (SEQ ID NO:72); (27) LAHQDTTKKA (SEQ ID NO:73); (28) LAHQDTTRNA (SEQ ID NO:74); (29) LAHQDTTTNA (SEQ ID NO:75); (30) LAHQGTTKNA (SEQ ID NO:76); (21) LAASDSTKAA (SEQ ID NO:67); (22) LAPQDTTKNA (SEQ ID NO:68); (31) LAHQVTTKNA (SEQ ID NO:77); (33) LAKDATKTA (SEQ ID NO:79); (34) LAKDTTKNA (SEQ ID NO:80); (36) LAPQDTKKNA (SEQ ID NO:82); (37) LATSDSTKAA (SEQ ID NO:83); (38) LAVDGSQRSA (SEQ ID NO:84); (41) LPPQDTTKNA (SEQ ID NO:87); (42) PAPQDTTKNA (SEQ ID NO:88); (52) LAHQDTTKKT (SEQ ID NO:98); (53) LAHQDTTKND (SEQ ID NO:99); (54) LAHQDTTKNT (SEQ ID NO:100); (55) LAHQDTTKNV (SEQ ID NO:101); (56) LAHQDTTKTM (SEQ ID NO:102); (73) LPHQDTTKND (SEQ ID NO:119); and (74) LPHQDTTKNT (SEQ ID NO:120).

The peptide insert is, in some cases, a peptide of Formula IV:

$X_1X_2X_3X_4X_5X_6X_7X_8X_9X_{10}$, where:
$X_1$ is Leu;
$X_2$ is Ala;
$X_3$ is Lys, His, Thr, Ile, Pro, or Val;
$X_4$ (if present) is Gln, Asp, Ser, or Gly;
$X_5$ is Asp, Ser, or Gln;
$X_6$ is Thr, Ala, Gln, or Ser;
$X_7$ is Thr or Ser;
$X_8$ is Lys, Ser, or Arg;
$X_9$ is Asn, Pro, or Ser; and
$X_{10}$ is Ala.

Peptide inserts of Formula IV include, but are not limited to, (1) LAKDATKNA (SEQ ID NO:47); (3) LAHQDTTKNA (SEQ ID NO:49); (7) LAPDSTTRSA (SEQ ID NO:53); (15) LAKSDQSKPA (SEQ ID NO:61); (20) LAPDQTTRNA (SEQ ID NO:66); (22) LAPQDTTKNA (SEQ ID NO:68); (28) LAHQDTTRNA (SEQ ID NO:74); (32) LAISDQSKPA (SEQ ID NO:78); (34) LAKDTTKNA (SEQ ID NO:80); and (35) LAKSDQSRPA (SEQ ID NO:81).

The peptide insert is, in some cases, a peptide of Formula V:

$X_1X_2X_3X_4X_5X_6X_7X_8X_9X_{10}$, where:
$X_1$ is Leu;
$X_2$ is Ala;

X₃ is Lys or His;
X₄ (if present) is Gln, Asp, Ser, or Gly;
X₅ is Asp, Ser, or Gln;
X₆ is Thr, Ala, Gln, or Ser;
X₇ is Thr or Ser;
X₈ is Lys, Ser, or Arg;
X₉ is Asn, Pro, or Ser; and
X₁₀ is Ala.

Peptide inserts of Formula V include, but are not limited to, (1) LAKDATKNA (SEQ ID NO:47); (15) LAKSDQSKPA (SEQ ID NO:51); (34) LAKDTTKNA (SEQ ID NO:80); and (35) LAKSDQSRPA (SEQ ID NO:81).

The peptide insert is, in some cases, a peptide of Formula VI:
X₁X₂X₃X₄X₅X₆X₇X₈X₉X₁₀, where:
X₁ is Leu;
X₂ is Ala;
X₃ is Asn, Lys, Thr, Gln, Ser, Ile, or Leu;
X₄ is Ser, Ala, Thr, Glu, Gln, Gly, Lys, or Pro;
X₅ is Asp, Pro, Glu, Thr, Asn, or Arg;
X₆ is Ile, His, Thr, Gln, Asn, Tyr, Asp, or Glu;
X₇ is Gln, Thr, Asn, Ala, or Lys;
X₈ is Lys, Thr, Arg, or Asp;
X₉ is Pro, Asn, Thr, Arg, Lys, or Ser; and
X₁₀ is Ala.

Peptides of Formula VI include, but are not limited to: (80) LAKANQNTPA (SEQ ID NO:126); (81) LATTPITKPA (SEQ ID NO:127); (82) LATTPIAKPA (SEQ ID NO:128); (83) LAIEDHTKSA (SEQ ID NO:129); (84) LAQSEHQRPA (SEQ ID NO:130); (85) LAKSPNKDNA (SEQ ID NO:131); (86) LANQDYTKTA (SEQ ID NO:132); (87) LANSTDQTRA (SEQ ID NO:133); (88) LALGETTRPA (SEQ ID NO:134); (89) LANSTEQTRA (SEQ ID NO:135); (90) LAQADTTKNA (SEQ ID NO:136); (91) LASKDITKTA (SEQ ID NO:137); and (92) LASPRHNKKC (SEQ ID NO:138).

In some cases, the peptide insert is a peptide of Formula VII: LAHQDTTKX₁X₂X₃ (SEQ ID NO:148), where X₁ is Lys, Thr, Asn, or His; X₂ is Ala, Thr, Val, Ile, Met, or Asp; and X₃, if present, is Ala. Peptides of Formula VII include, but are not limited to: (26) LAHQDTTKHA (SEQ ID NO:72); (27) LAHQDTTKKA (SEQ ID NO:73); (52) LAHQDTTKKT (SEQ ID NO:98); (53) LAHQDTTKND (SEQ ID NO:99); (54) LAHQDTTKNT (SEQ ID NO:100); (55) LAHQDTTKNV (SEQ ID NO:101); (56) LAHQDTTKTM (SEQ ID NO:102); and (93) LAHQDTTKTIA (SEQ ID NO:139).

In some cases, the peptide insert is a peptide of Formula VIII: LAX₁QX₂TX₃X₄X₅X₆ (SEQ ID NO:149), where X₁ is Ala, Pro, Asp, or His; X₂ is Gly or Asp; X₃ is Ala, Thr, or Lys; X₄ is Asn, Glu, Lys, Arg, or Thr; X₅ is Leu, Asn, Lys, or Thr; and X₆, if present, is Ala, Thr, Asp, Val, or Met. Peptides of Formula VIII include, but are not limited to, (94) LAAQGTANL (SEQ ID NO:140); (22) LAPQDTTKNA (SEQ ID NO:68); (46) LADQDTTKNA (SEQ ID NO:92); (24) LAHQDTAKNA (SEQ ID NO:70); (25) LAHQDTKKNA (SEQ ID NO:71); (26) LAHQDTTKHA (SEQ ID NO:72); (27) LAHQDTTKKA (SEQ ID NO:73); (28) LAHQDTTRNA (SEQ ID NO:74); (29) LAHQDTTTNA (SEQ ID NO:75); (50) LAHQDTTENA (SEQ ID NO:96); (51) LAHQDTTINA (SEQ ID NO:97); (52) LAHQDTTKKT (SEQ ID NO:98); (53) LAHQDTTKND (SEQ ID NO:99); (54) LAHQDTTKNT (SEQ ID NO:100); (55) LAHQDTTKNV (SEQ ID NO:101); and (56) LAHQDTTKTM (SEQ ID NO:102).

In some cases, the peptide insert is a peptide of Formula IX: X₁AX₂X₃DX₄TKX₅A (SEQ ID NO:150), where X₁ is Val or Leu; X₂ is Ile, Val, His, or Asp; X₃ is Glu, Ser, Lys, or Gln; X₄ is His, Ser, or Thr; and X₅ is Ser, Ala, Asn, His, or Lys. Peptides of Formula IX include, but are not limited to, (95) VAIEDHTKSA (SEQ ID NO:141); (18) LAVSDSTKAA (SEQ ID NO:64); (46) LADQDTTKNA (SEQ ID NO:92); (48) LAHKDTTKNA (SEQ ID NO:94); (26) LAHQDTTKHA (SEQ ID NO:72); and (27) LAHQDTTKKA (SEQ ID NO:73).

In some cases, the peptide insert is a peptide of Formula X: X₁X₂X₃AX₄QX₅TX₆KNA (SEQ ID NO:151), where X₁, if present, is Leu; X₂, if present, is Ala; X₃ is Lys, Leu, or Pro; X₄ is Asn, His, Pro, or Tyr; X₅ is Asn, Gly, Val, or Asp; and X₆ is Pro or Thr. Peptides of Formula X include, but are not limited to, (96) LAKANQNTPKNA (SEQ ID NO:142); (57) LAHQNTTKNA (SEQ ID NO:103); (66) LAPQNTTKNA (SEQ ID NO:112); (69) LAYQDTTKNA (SEQ ID NO:115); (30) LAHQGTTKNA (SEQ ID NO:76); (31) LAHQVTTKNA (SEQ ID NO:77); and (42) PAPQDTTKNA (SEQ ID NO:88).

In some cases, the peptide insert is LAHQDTTKKX (SEQ ID NO:143), where X is any amino acid. In some cases, the peptide insert is LAHQDTTKKX (SEQ ID NO:143), where X is Ala, Thr, Asp, Val, or Met. In some cases, the peptide insert is (27) LAHQDTTKKA (SEQ ID NO:73). In some cases, the peptide insert is (52) LAHQDTTKKT (SEQ ID NO:98). In some cases, the peptide insert is LAHQDTTKKD (SEQ ID NO:144). In some cases, the peptide insert is LAHQDTTKKV (SEQ ID NO:145). In some cases, the peptide insert is LAHQDTTKKM (SEQ ID NO:146).

In some cases, the peptide insert is not (88) LALGETTRPA (SEQ ID NO:134). In some cases, the peptide insert is not LGETTRP (SEQ ID NO:147).

Suitable peptide inserts include, but are not limited to, (1) LAKDATKNA (SEQ ID NO:47); (2) PAHQDTTKNA (SEQ ID NO:48); (3) LAHQDTTKNA (SEQ ID NO:49); (4) LATTSQNKPA (SEQ ID NO:50); (5) LAISDQTKHA (SEQ ID NO:51); (6) IARGVAPSSA (SEQ ID NO:52); (7) LAPDSTTRSA (SEQ ID NO:53); (8) LAKGTELKPA (SEQ ID NO:54); (9) LAIIDATKNA (SEQ ID NO:55); (10) LAVDGAQRSA (SEQ ID NO:56); (11) PAPQDTTKKA (SEQ ID NO:57); (12) LPHQDTTKNA (SEQ ID NO:58); (13) LAKDATKTIA (SEQ ID NO:59); (14) LAKQQSASTA (SEQ ID NO:60); (15) LAKSDQSKPA (SEQ ID NO:61); (16) LSHQDTTKNA (SEQ ID NO:62); (17) LAANQPSKPA (SEQ ID NO:63); (18) LAVSDSTKAA (SEQ ID NO:64); (19) LAAQGTAKKPA (SEQ ID NO:65); (20) LAPDQTTRNA (SEQ ID NO:66); (21) LAASDSTKAA (SEQ ID NO:67); (22) LAPQDTTKNA (SEQ ID NO:68); (23) LAKADETRPA (SEQ ID NO:69); (24) LAHQDTAKNA (SEQ ID NO:70); (25) LAHQDTKKNA (SEQ ID NO:71); (26) LAHQDTTKHA (SEQ ID NO:72); (27) LAHQDTTKKA (SEQ ID NO:73); (28) LAHQDTTRNA (SEQ ID NO:74); (29) LAHQDTTNA (SEQ ID NO:75); (30) LAHQGTTKNA (SEQ ID NO:76); (31) LAHQVTTKNA (SEQ ID NO:77); (32) LAISDQSKPA (SEQ ID NO:78); (33) LADATKTA (SEQ ID NO:79); (34) LAKDTTKNA (SEQ ID NO:80); (35) LAKSDQSRPA (SEQ ID NO:81); (36) LAPQDTKKNA (SEQ ID NO:82); (37) LATSDSTKAA (SEQ ID NO:83); (38) LAVDGSQRSA (SEQ ID NO:84); (39) LPISDQTKHA (SEQ ID NO:85); (40) LPKDATKTIA (SEQ ID NO:86); (41) LPPQDTTKNA (SEQ ID NO:87); (42) PAPQDTTKNA (SEQ ID NO:88); (43) QAHQDTTKNA (SEQ ID NO:89); (44) LAHETSPRPA (SEQ ID NO:90); (45)

LAKSTSTAPA (SEQ ID NO:91); (46) LADQDTTKNA (SEQ ID NO:92); (47) LAESDQSKPA (SEQ ID NO:93); (48) LAHKDTTKNA (SEQ ID NO:94); (49) LAHKTQQKM (SEQ ID NO:95); (50) LAHQDTTENA (SEQ ID NO:96); (51) LAHQDTTINA (SEQ ID NO:97); (52) LAHQDTTKKT (SEQ ID NO:98); (53) LAHQDTTKND (SEQ ID NO:99); (54) LAHQDTTKNT (SEQ ID NO:100); (55) LAHQDTTKNV (SEQ ID NO:101); (56) LAHQDTTKTM (SEQ ID NO:102); (57) LAHQNTTKNA (SEQ ID NO:103); (58) LAHRDTTKNA (SEQ ID NO:104); (59) LAISDQTNHA (SEQ ID NO:105); (60) LAKQKSASTA (SEQ ID NO:106); (61) LAKSDQCKPA (SEQ ID NO:107); (62) LAKSDQSKPD (SEQ ID NO:108); (63) LAKSDQSNPA (SEQ ID NO:109); (64) LAKSYQSKPA (SEQ ID NO:110); (65) LANQDTTKNA (SEQ ID NO:111); (66) LAPQNTTKNA (SEQ ID NO:112); (67) LAPSSIQKPA (SEQ ID NO:113); (68) LAQQDTTKNA (SEQ ID NO:114); (69) LAYQDTTKNA (SEQ ID NO:115); (70) LDHQDTTKNA (SEQ ID NO:116); (71) LDHQDTTKSA (SEQ ID NO:117); (72) LGHQDTTKNA (SEQ ID NO:118); (73) LPHQDTTKND (SEQ ID NO:119); (74) LPHQDTTKNT (SEQ ID NO:120); (75) LPHQDTTNNA (SEQ ID NO:121); (76) LTHQDTTKNA (SEQ ID NO:122); (77) LTKDATKTIA (SEQ ID NO:123); (78) LTPQDTTKNA (SEQ ID NO:124); (79) LVHQDTTKNA (SEQ ID NO:125); (80) LAKANQNTPA (SEQ ID NO:126); (81) LATTPITKPA (SEQ ID NO:127); (82) LATTPIAKPA (SEQ ID NO:128); (83) LAIEDHTKSA (SEQ ID NO:129); (84) LAQSEHQRPA (SEQ ID NO:130); (85) LAKSPNKDNA (SEQ ID NO:131); (86) LANQDYTKTA (SEQ ID NO:132); (87) LANSTDQTRA (SEQ ID NO:133); (88) LALGETTRPA (SEQ ID NO:134); (89) LANSTEQTRA (SEQ ID NO:135); (90) LAQADTTKNA (SEQ ID NO:136); (91) LASKDITKTA (SEQ ID NO:137); (92) LASPRHNKKC (SEQ ID NO:138); (93) LAHQDTTKTIA (SEQ ID NO:139); (94) LAAQGTANL (SEQ ID NO:140); (95) VAIEDHTKSA (SEQ ID NO:141); and (96) LAKANQNTPKNA (SEQ ID NO:142).

In some cases, the peptide insert is (11) PAPQDTTKKA (SEQ ID NO:57). In some cases, the peptide insert is (7) LAPDSTTRSA (SEQ ID NO:53).

In some embodiments, a subject rAAV virion capsid does not include any other amino acid substitutions, insertions, or deletions, other than an insertion of from about 5 amino acids to about 20 amino acids (e.g., 5, 6, 7, 8, 9, 10, 11, 12, 13, 14, 15, 16, 17, 18, 19, or 20 amino acids; e.g., 9 amino acids, 10 amino acids, 11 amino acids, or 12 amino acids) in the GH loop or loop IV relative to a corresponding parental AAV capsid protein. In other embodiments, a subject rAAV virion capsid includes from 1 to about 25 amino acid insertions, deletions, or substitutions, compared to the parental AAV capsid protein, in addition to an insertion of from about 5 amino acids to about 20 amino acids (e.g., 5, 6, 7, 8, 9, 10, 11, 12, 13, 14, 15, 16, 17, 18, 19, or 20 amino acids; e.g., 9 amino acids, 10 amino acids, 11 amino acids, or 12 amino acids) in the GH loop or loop IV relative to a corresponding parental AAV capsid protein. For example, in some embodiments, a subject rAAV virion capsid includes from 1 to about 5, from about 5 to about 10, from about 10 to about 15, from about 15 to about 20, or from about 20 to about 25 amino acid insertions, deletions, or substitutions, compared to the parental AAV capsid protein, in addition to an insertion of from about 5 amino acids to about 20 amino acids (e.g., 5, 6, 7, 8, 9, 10, 11, 12, 13, 14, 15, 16, 17, 18, 19, or 20 amino acids; e.g., 9 amino acids, 10 amino acids, 11 amino acids, or 12 amino acids) in the GH loop or loop IV relative to a corresponding parental AAV capsid protein.

In some cases, a subject rAAV virion capsid does not include one, two, three, or four, of the following amino acid substitutions: Y273F, Y444F, Y500F, and Y730F.

In some cases, a subject variant capsid polypeptide comprises, in addition to an insertion peptide as described above, one, two, three, or four, of the following amino acid substitutions: Y273F, Y444F, Y500F, and Y730F.

In some cases, a subject rAAV virion capsid is a chimeric capsid, e.g., the capsid comprises a portion of an AAV capsid of a first AAV serotype and a portion of an AAV capsid of a second serotype; and comprises an insertion of from about 5 amino acids to about 20 amino acids (e.g., 5, 6, 7, 8, 9, 10, 11, 12, 13, 14, 15, 16, 17, 18, 19, or 20 amino acids; e.g., 9 amino acids, 10 amino acids, 11 amino acids, or 12 amino acids) in the GH loop or loop IV relative to a corresponding parental AAV capsid protein.

In some embodiments, a subject rAAV virion comprises a capsid protein comprising an amino acid sequence having at least about 85%, at least about 90%, at least about 95%, at least about 98%, or at least about 99%, amino acid sequence identity to the amino acid sequence provided in FIG. 4; and an insertion of from about 5 amino acids to about 20 amino acids (e.g., 5, 6, 7, 8, 9, 10, 11, 12, 13, 14, 15, 16, 17, 18, 19, or 20 amino acids; e.g., 9 amino acids, 10 amino acids, 11 amino acids, or 12 amino acids) in the GH loop or loop IV relative to a corresponding parental AAV capsid protein. In some embodiments, a subject rAAV virion comprises a capsid protein comprising an amino acid sequence having at least about 85%, at least about 90%, at least about 95%, at least about 98%, or at least about 99%, amino acid sequence identity to the amino acid sequence provided in FIG. 4; and an insertion of from about 5 amino acids to about 20 amino acids (e.g., 5, 6, 7, 8, 9, 10, 11, 12, 13, 14, 15, 16, 17, 18, 19, or 20 amino acids; e.g., 9 amino acids, 10 amino acids, 11 amino acids, or 12 amino acids) between amino acids 587 and 588 relative to the amino acid sequence depicted in FIG. 4, or at a corresponding site relative to a corresponding parental AAV capsid protein.

In some embodiments, a subject rAAV virion comprises a capsid protein that includes a GH loop comprising an amino acid sequence having at least about 85%, at least about 90%, at least about 95%, at least about 98%, at least about 99%, or 100%, amino acid sequence identity to an amino acid sequence set forth in FIG. 5, and comprising an insertion of from about 5 amino acids to about 20 amino acids (e.g., 5, 6, 7, 8, 9, 10, 11, 12, 13, 14, 15, 16, 17, 18, 19, or 20 amino acids; e.g., 9 amino acids, 10 amino acids, 11 amino acids, or 12 amino acids) between the bolded and underlined amino acids.

In some embodiments, a subject rAAV virion comprises a capsid protein comprising an amino acid sequence having at least about 85%, at least about 90%, at least about 95%, at least about 98%, or at least about 99%, amino acid sequence identity to any one of the amino acid sequences provided in FIG. 6A-6C; and an insertion of from about 5 amino acids to about 20 amino acids (e.g., 5, 6, 7, 8, 9, 10, 11, 12, 13, 14, 15, 16, 17, 18, 19, or 20 amino acids; e.g., 9 amino acids, 10 amino acids, 11 amino acids, or 12 amino acids) between amino acids 587 and 588 of AAV2, or at a corresponding site relative to another AAV genotype. In some cases, the corresponding insertion site is a site as indicated by bold text and underlining in FIG. 6B.

A subject rAAV virion exhibits at least 5-fold, at least 10-fold, at least 15-fold, at least 20-fold, at least 25-fold, at least 50-fold, or more than 50-fold, increased infectivity of a retinal cell, compared to the infectivity of the retinal cell by an AAV virion comprising the corresponding parental AAV capsid protein.

In some cases, a subject rAAV virion exhibits at least 5-fold, at least 10-fold, at least 15-fold, at least 20-fold, at least 25-fold, at least 50-fold, or more than 50-fold, increased infectivity of a retinal cell, when administered via intravitreal injection, compared to the infectivity of the retinal cell by an AAV virion comprising the corresponding parental AAV capsid protein, when administered via intravitreal injection.

In some embodiments, a subject rAAV virion exhibits at least 5-fold, at least 10-fold, at least 15-fold, at least 20-fold, at least 25-fold, at least 50-fold, or more than 50-fold, increased infectivity of a photoreceptor (rod or cone) cell, compared to the infectivity of the photoreceptor cell by an AAV virion comprising the corresponding parental AAV capsid protein.

In some embodiments, a subject rAAV virion exhibits at least 5-fold, at least 10-fold, at least 15-fold, at least 20-fold, at least 25-fold, at least 50-fold, or more than 50-fold, increased infectivity of a photoreceptor (rod or cone) cell, when administered via intravitreal injection, compared to the infectivity of the photoreceptor cell by an AAV virion comprising the corresponding parental AAV capsid protein, when administered via intravitreal injection.

In some embodiments, a subject rAAV virion exhibits at least 5-fold, at least 10-fold, at least 15-fold, at least 20-fold, at least 25-fold, at least 50-fold, or more than 50-fold, increased infectivity of an RGC, compared to the infectivity of the RGC by an AAV virion comprising the corresponding parental AAV capsid protein.

In some embodiments, a subject rAAV virion exhibits at least 5-fold, at least 10-fold, at least 15-fold, at least 20-fold, at least 25-fold, at least 50-fold, or more than 50-fold, increased infectivity of an RGC, when administered via intravitreal injection, compared to the infectivity of the RGC by an AAV virion comprising the corresponding parental AAV capsid protein, when administered via intravitreal injection.

In some embodiments, a subject rAAV virion exhibits at least 5-fold, at least 10-fold, at least 15-fold, at least 20-fold, at least 25-fold, at least 50-fold, or more than 50-fold, increased infectivity of an RPE cell, compared to the infectivity of the RPE cell by an AAV virion comprising the corresponding parental AAV capsid protein.

In some embodiments, a subject rAAV virion exhibits at least 5-fold, at least 10-fold, at least 15-fold, at least 20-fold, at least 25-fold, at least 50-fold, or more than 50-fold, increased infectivity of an RPE cell, when administered via intravitreal injection, compared to the infectivity of the RPE cell by an AAV virion comprising the corresponding parental AAV capsid protein, when administered via intravitreal injection.

In some embodiments, a subject rAAV virion exhibits at least 5-fold, at least 10-fold, at least 15-fold, at least 20-fold, at least 25-fold, at least 50-fold, or more than 50-fold, increased infectivity of a Müller cell, compared to the infectivity of the Müller cell by an AAV virion comprising the corresponding parental AAV capsid protein.

In some embodiments, a subject rAAV virion exhibits at least 5-fold, at least 10-fold, at least 15-fold, at least 20-fold, at least 25-fold, at least 50-fold, or more than 50-fold, increased infectivity of a Müller cell, when administered via intravitreal injection, compared to the infectivity of the Müller cell by an AAV virion comprising the corresponding parental AAV capsid protein, when administered via intravitreal injection.

In some embodiments, a subject rAAV virion exhibits at least 5-fold, at least 10-fold, at least 15-fold, at least 20-fold, at least 25-fold, at least 50-fold, or more than 50-fold, increased infectivity of a bipolar cell, compared to the infectivity of the bipolar cell by an AAV virion comprising the corresponding parental AAV capsid protein.

In some embodiments, a subject rAAV virion exhibits at least 5-fold, at least 10-fold, at least 15-fold, at least 20-fold, at least 25-fold, at least 50-fold, or more than 50-fold, increased infectivity of a bipolar cell, when administered via intravitreal injection, compared to the infectivity of the bipolar cell by an AAV virion comprising the corresponding parental AAV capsid protein, when administered via intravitreal injection.

In some embodiments, a subject rAAV virion exhibits at least 5-fold, at least 10-fold, at least 15-fold, at least 20-fold, at least 25-fold, at least 50-fold, or more than 50-fold, increased infectivity of an amacrine cell, compared to the infectivity of the amacrine cell by an AAV virion comprising the corresponding parental AAV capsid protein.

In some embodiments, a subject rAAV virion exhibits at least 5-fold, at least 10-fold, at least 15-fold, at least 20-fold, at least 25-fold, at least 50-fold, or more than 50-fold, increased infectivity of an amacrine cell, when administered via intravitreal injection, compared to the infectivity of the amacrine cell by an AAV virion comprising the corresponding parental AAV capsid protein, when administered via intravitreal injection.

In some embodiments, a subject rAAV virion exhibits at least 5-fold, at least 10-fold, at least 15-fold, at least 20-fold, at least 25-fold, at least 50-fold, or more than 50-fold, increased infectivity of a horizontal cell, compared to the infectivity of the horizontal cell by an AAV virion comprising the corresponding parental AAV capsid protein.

In some embodiments, a subject rAAV virion exhibits at least 5-fold, at least 10-fold, at least 15-fold, at least 20-fold, at least 25-fold, at least 50-fold, or more than 50-fold, increased infectivity of a horizontal cell, when administered via intravitreal injection, compared to the infectivity of the horizontal cell by an AAV virion comprising the corresponding parental AAV capsid protein, when administered via intravitreal injection.

In some embodiments, a subject rAAV virion exhibits at least 5-fold, at least 10-fold, at least 15-fold, at least 20-fold, at least 25-fold, at least 50-fold, or more than 50-fold, increased infectivity of a retinal astrocyte, compared to the infectivity of the retinal astrocyte by an AAV virion comprising the corresponding parental AAV capsid protein.

In some embodiments, a subject rAAV virion exhibits at least 5-fold, at least 10-fold, at least 15-fold, at least 20-fold, at least 25-fold, at least 50-fold, or more than 50-fold, increased infectivity of a retinal astrocyte, when administered via intravitreal injection, compared to the infectivity of the retinal astrocyte by an AAV virion comprising the corresponding parental AAV capsid protein, when administered via intravitreal injection.

In some cases, a subject rAAV virion exhibits at least 5-fold, at least 10-fold, at least 15-fold, at least 20-fold, at least 25-fold, at least 50-fold, or more than 50-fold, increased ability to cross the internal limiting membrane (ILM), compared to the ability of an AAV virion comprising the corresponding parental AAV capsid protein to cross the ILM.

In some cases, a subject rAAV virion exhibits at least 5-fold, at least 10-fold, at least 15-fold, at least 20-fold, at least 25-fold, at least 50-fold, or more than 50-fold, increased ability, when administered via intravitreal injection, to cross the ILM, compared to the ability of an AAV virion comprising the corresponding parental AAV capsid protein to cross the ILM when administered via intravitreal injection.

A subject rAAV virion can cross the ILM, and can also traverse cell layers, including Müller cells, amacrine cells, etc., to reach the photoreceptor cells and or RPE cells. For example, a subject rAAV virion, when administered via intravitreal injection, can cross the ILM, and can also traverse cell layers, including Müller cells, amacrine cells, etc., to reach the photoreceptor cells and or RPE cells.

In some cases, a subject rAAV virion, when injected intravitreally, exhibits at least 5-fold, at least 10-fold, at least 15-fold, at least 20-fold, at least 25-fold, at least 50-fold, or more than 50-fold, increased localization past the ILM, compared to the extent of localization past the ILM by an intravitreally injected control AAV virion comprising the corresponding parental AAV capsid protein. For example, in some cases, a subject rAAV virion, when injected intravitreally, exhibits at least 5-fold, at least 10-fold, at least 15-fold, at least 20-fold, at least 25-fold, at least 50-fold, or more than 50-fold, increased localization to the retinal pigment epithelium (RPE), compared to the extent of localization to the RPE layer by an intravitreally injected control AAV virion comprising the corresponding parental AAV capsid protein. As another example, in some cases, a subject rAAV virion, when injected intravitreally, exhibits at least 5-fold, at least 10-fold, at least 15-fold, at least 20-fold, at least 25-fold, at least 50-fold, or more than 50-fold, increased localization to the photoreceptor (PR) layer, compared to the extent of localization to the PR layer by an intravitreally injected control AAV virion comprising the corresponding parental AAV capsid protein. As another example, in some cases, a subject rAAV virion, when injected intravitreally, exhibits at least 5-fold, at least 10-fold, at least 15-fold, at least 20-fold, at least 25-fold, at least 50-fold, or more than 50-fold, increased localization to the inner nuclear layer, compared to the extent of localization to the inner nuclear layer by an intravitreally injected control AAV virion comprising the corresponding parental AAV capsid protein. As another example, in some cases, a subject rAAV virion, when injected intravitreally, exhibits at least 5-fold, at least 10-fold, at least 15-fold, at least 20-fold, at least 25-fold, at least 50-fold, or more than 50-fold, increased localization to the outer nuclear layer, compared to the extent of localization to the outer nuclear layer by an intravitreally injected control AAV virion comprising the corresponding parental AAV capsid protein. As another example, in some cases, a subject rAAV virion, when injected intravitreally, exhibits at least 5-fold, at least 10-fold, at least 15-fold, at least 20-fold, at least 25-fold, at least 50-fold, or more than 50-fold, increased localization to the ganglion cell layer, compared to the extent of localization to the ganglion cell layer by an intravitreally injected control AAV virion comprising the corresponding parental AAV capsid protein.

In some embodiments, a subject rAAV virion selectively infects a retinal cell, e.g., a subject rAAV virion infects a retinal cell with 10-fold, 15-fold, 20-fold, 25-fold, 50-fold, or more than 50-fold, specificity than a non-retinal cell, e.g., a cell outside the eye. For example, in some embodiments, a subject rAAV virion selectively infects retinal cell, e.g., a subject rAAV virion infects a photoreceptor cell with 10-fold, 15-fold, 20-fold, 25-fold, 50-fold, or more than 50-fold, specificity than a non-retinal cell, e.g., a cell outside the eye.

In some embodiments, a subject rAAV virion selectively infects a photoreceptor cell, e.g., a subject rAAV virion infects a photoreceptor cell with 10-fold, 15-fold, 20-fold, 25-fold, 50-fold, or more than 50-fold, specificity than a non-photoreceptor cell present in the eye, e.g., a retinal ganglion cell, a Müller cell, etc.

In some embodiments, a subject rAAV virion exhibits at least 10-fold, at least 15-fold, at least 20-fold, at least 25-fold, at least 50-fold, or more than 50-fold, increased infectivity of a photoreceptor cell, when administered via intravitreal injection, compared to the infectivity of the photoreceptor cell by an AAV virion comprising the corresponding parental AAV capsid protein, when administered via intravitreal injection.

Gene Products

A subject rAAV virion comprises a heterologous nucleic acid comprising a nucleotide sequence encoding a gene product (a heterologous gene product. In some cases, the gene product is a polypeptide. In some cases, the gene product is an RNA. Where the gene product is an RNA, in some cases, the RNA gene product encodes a polypeptide. In some cases, an rAAV virion of the present disclosure comprises a single heterologous nucleic acid comprising a nucleotide sequence encoding a single heterologous gene product. In some cases, an rAAV virion of the present disclosure comprises a single heterologous nucleic acid comprising a nucleotide sequence encoding two heterologous gene products. In some cases, an rAAV virion of the present disclosure comprises two heterologous nucleic acids, each comprising a nucleotide sequence encoding a heterologous gene product.

In some embodiments, the gene product is an interfering RNA. In some embodiments, the gene product is an aptamer. In some embodiments, the gene product is a polypeptide. In some embodiments, the gene product is a site-specific nuclease that provide for site-specific knock-down of gene function. In some embodiments, the gene product is an RNA-guided endonuclease that provides for modification of a target nucleic acid.

Interfering RNA

Where the gene product is an interfering RNA (RNAi), suitable RNAi include RNAi that decrease the level of an apoptotic or angiogenic factor in a cell. For example, an RNAi can be an shRNA or siRNA that reduces the level of a gene product that induces or promotes apoptosis in a cell. Genes whose gene products induce or promote apoptosis are referred to herein as "pro-apoptotic genes" and the products of those genes (mRNA; protein) are referred to as "pro-apoptotic gene products." Pro-apoptotic gene products include, e.g., Bax, Bid, Bak, and Bad gene products. See, e.g., U.S. Pat. No. 7,846,730.

Interfering RNAs could also be against an angiogenic product, for example vascular endothelial growth factor (VEGF) (e.g., Cand5; see, e.g., U.S. Patent Publication No. 2011/0143400; U.S. Patent Publication No. 2008/0188437; and Reich et al. (2003) Mol. Vis. 9:210); VEGF receptor-1 (VEGFR1) (e.g., Sirna-027; see, e.g., Kaiser et al. (2010) *Am. J. Ophthalmol.* 150:33; and Shen et al. (2006) *Gene Ther.* 13:225); or VEGF receptor-2 (VEGFR2) (Kou et al. (2005) *Biochem.* 44:15064). See also, U.S. Pat. Nos. 6,649, 596, 6,399,586, 5,661,135, 5,639,872, and 5,639,736; and 7,947,659 and 7,919,473.

Aptamers

Where the gene product is an aptamer, exemplary aptamers of interest include an aptamer against VEGF. See, e.g., Ng et al. (2006) *Nat. Rev. Drug Discovery* 5:123; and Lee et al. (2005) *Proc. Natl. Acad. Sci. USA* 102:18902. For example, a VEGF aptamer can comprise the nucleotide sequence 5'-cgcaaucagugaaugcuuauacauccg-3' (SEQ ID NO://). Also suitable for use is a platelet-derived growth factor (PDGF)-specific aptamer, e.g., E10030; see, e.g., Ni and Hui (2009) *Ophthalmologica* 223:401; and Akiyama et al. (2006) *J. Cell Physiol.* 207:407).

Polypeptides

Where the gene product is a polypeptide, the polypeptide is generally a polypeptide that enhances function of a retinal cell, e.g., the function of a rod or cone photoreceptor cell, a retinal ganglion cell, a Müller cell, a bipolar cell, an amacrine cell, a horizontal cell, or a retinal pigment epithelial cell. Exemplary polypeptides include neuroprotective polypeptides (e.g., glial cell derived neurotrophic factor (GDNF), ciliary neurotrophic factor (CNTF), neurotrophin-4 (NT4), nerve growth factor (NGF), and neurturin (NTN)); anti-angiogenic polypeptides (e.g., a soluble VEGF receptor; a VEGF-binding antibody; a VEGF-binding antibody fragment (e.g., a single chain anti-VEGF antibody); endostatin; tumstatin; angiostatin; a soluble Flt polypeptide (Lai et al. (2005) *Mol. Ther.* 12:659); an Fc fusion protein comprising a soluble Flt polypeptide (see, e.g., Pechan et al. (2009) *Gene Ther.* 16:10); pigment epithelium-derived factor (PEDF); a soluble Tie-2 receptor; etc.); tissue inhibitor of metalloproteinases-3 (TIMP-3); a light-responsive opsin, e.g., a rhodopsin; anti-apoptotic polypeptides (e.g., Bcl-2, Bcl-X1; XIAP); and the like. Suitable polypeptides include, but are not limited to, glial derived neurotrophic factor (GDNF); fibroblast growth factor; fibroblast growth factor 2; neurturin (NTN); ciliary neurotrophic factor (CNTF); nerve growth factor (NGF); neurotrophin-4 (NT4); brain derived neurotrophic factor (BDNF; e.g., a polypeptide comprising an amino acid sequence having at least about 90%, at least about 95%, at least about 98%, at least about 99%, or 100%, amino acid sequence identity to a contiguous stretch of from about 200 amino acids to 247 amino acids of the amino acid sequence depicted in FIG. 7B (SEQ ID NO:11)); epidermal growth factor; rhodopsin; X-linked inhibitor of apoptosis; and Sonic hedgehog.

Suitable light-responsive opsins include, e.g., a light-responsive opsin as described in U.S. Patent Publication No. 2007/0261127 (e.g., channelrhodopsin-2; ChR2; Chop2); U.S. Patent Publication No. 2001/0086421; U.S. Patent Publication No. 2010/0015095; U.S. Patent Publication No. 2016/0002302; U.S. Patent Publication No. 2013/0347137; U.S. Patent Publication No. 2013/0019325; and Diester et al. (2011) *Nat. Neurosci.* 14:387. See, Thyagarajan et al. (2010) *J Neurosci.* 30(26):8745-8758; Lagali et al. (2008) *Nat Neurosci.* 11(6):667-675; Doroudchi et al. (2011) *Mol Ther.* 19(7):1220-1229; Henriksen et al. (2014) *J. Ophthalmic Vis. Res.* 9:374; Tomita et al. (2014) *Mol. Ther.* 22:1434.

Suitable polypeptides include light-gated ion channel polypeptides. See, e.g., Gaub et al. (2014) *Proc. Natl. Acad. Sci. USA* 111:E5574. For example, a suitable polypeptide is a light-gated ionotropic glutamate receptor (LiGluR). Expression of LiGluR in retinal ganglion cells and ON-bipolar cells, in the presence of a photoisomerizable compound, renders the cells responsive to light. LiGluR comprises a L439C substitution; see, Caporale et al. (2011) *Mol Ther.* 19:1212-1219; Volgraf et al. (2006) *Nat Chem Biol.* 2:47-52; and Gorostiza et al. (2007) *Proc Natl Acad Sci USA.* 104:10865-10870. Photoisomerizable compounds include, e.g., maleimide-azobenzene-glutamate 0 with peak efficiency at 460 nm ($MAG0_{460}$). $MAG0_{460}$ has the following structure:

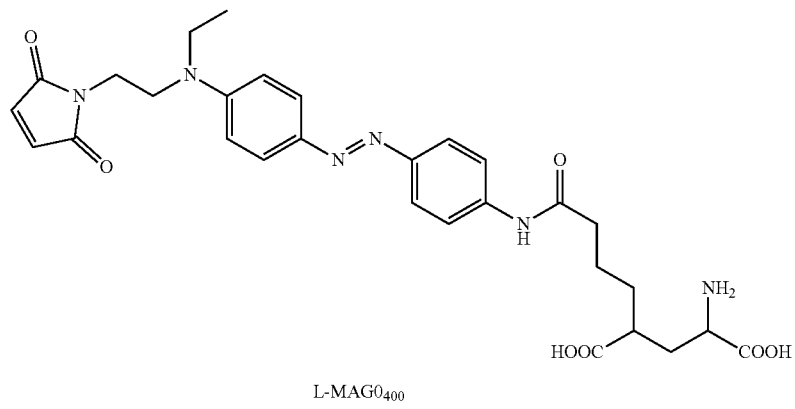 [SMILES: CCN(CCN1C(=O)C=CC1=O)c1ccc(/N=N/c2ccc(NC(=O)CCCC(CC(N)C(=O)O)C(=O)O)cc2)cc1]

L-$MAG0_{400}$

Suitable polypeptides also include retinoschisin (e.g., a polypeptide comprising an amino acid sequence having at least about 90%, at least about 95%, at least about 98%, at least about 99%, or 100%, amino acid sequence identity to a contiguous stretch of from about 200 amino acids to 224 amino acids of the amino acid sequence depicted in FIG. 7A (SEQ ID NO:10). Suitable polypeptides include, e.g., retinitis pigmentosa GTPase regulator (RPGR)-interacting protein-1 (see, e.g., GenBank Accession Nos. Q96KN7, Q9EPQ2, and Q9GLM3) (e.g., a polypeptide comprising an amino acid sequence having at least about 90%, at least about 95%, at least about 98%, at least about 99%, or 100%, amino acid sequence identity to a contiguous stretch of from about 1150 amino acids to about 1200 amino acids, or from about 1200 amino acids to 1286 amino acids, of the amino acid sequence depicted in FIG. 7F (SEQ ID NO:15); peripherin-2 (Prph2) (see, e.g., GenBank Accession No. NP_000313 (e.g., a polypeptide comprising an amino acid sequence having at least about 90%, at least about 95%, at least about 98%, at least about 99%, or 100%, amino acid sequence identity to a contiguous stretch of from about 300 amino acids to 346 amino acids of the amino acid sequence depicted in FIG. 7D (SEQ ID NO:13); and Travis et al. (1991) *Genomics* 10:733); peripherin (e.g., a polypeptide comprising an amino acid sequence having at least about 90%, at least about 95%, at least about 98%, at least about 99%, or 100%, amino acid sequence identity to a contiguous stretch of from about 400 amino acids to about 470 amino acids of the amino acid sequence depicted in FIG. 7E (SEQ ID NO:14); a retinal pigment epithelium-specific protein (RPE65), (e.g., a polypeptide comprising an amino acid sequence having at least about 90%, at least about 95%, at least about 98%, at least about 99%, or 100%, amino acid sequence identity to a contiguous stretch of from about 200 amino acids to 247 amino acids of the amino acid sequence depicted in FIG. 7C (SEQ ID NO:12)) (see, e.g., GenBank AAC39660; and Morimura et al. (1998) Proc. Natl. Acad. Sci. USA 95:3088); rod-derived cone viability factor (RdCVF) (e.g., a polypeptide comprising an amino acid sequence having at least about 90%, at least about 95%, at least about 98%, at least about 99%, or 100%, amino acid sequence identity to the amino acid sequence depicted in any one of FIGS. 7H, 7I, and 7J; choroideremia (e.g., a polypeptide comprising an amino acid sequence having at least about 90%, at least about 95%, at least about 98%, at least about 99%, or 100%, amino acid sequence identity to the amino acid sequence depicted in FIG. 7G); retinitis pigmentosa GTPase regulator (RPGR) (e.g., a polypeptide comprising an amino acid sequence having at least about 90%, at least about 95%, at least about 98%, at least about 99%, or 100%, amino acid sequence identity to the amino acid sequence depicted in one of FIG. 7S-7V); and the like. For example, in some cases, a suitable RPGR polypeptide comprises an amino acid sequence having at least about 90%, at least about 95%, at least about 98%, at least about 99%, or 100%, amino acid sequence identity to the amino acid sequence depicted in FIG. 7S. As another example, in some cases, a suitable RPGR polypeptide comprises an amino acid sequence having at least about 90%, at least about 95%, at least about 98%, at least about 99%, or 100%, amino acid sequence identity to the amino acid sequence depicted in FIG. 7T. example, in some cases, a suitable RPGR polypeptide comprises an amino acid sequence having at least about 90%, at least about 95%, at least about 98%, at least about 99%, or 100%, amino acid sequence identity to the amino acid sequence depicted in FIG. 7U. example, in some cases, a suitable RPGR polypeptide comprises an amino acid sequence having at least about 90%, at least about 95%, at least about 98%, at least about 99%, or 100%, amino acid sequence identity to the amino acid sequence depicted in FIG. 7V.

Suitable polypeptides also include: CHM (choroideremia (Rab escort protein 1 (REP1))), a polypeptide that, when defective or missing, causes choroideremia (see, e.g., Donnelly et al. (1994) Hum. Mol. Genet. 3:1017; and van Bokhoven et al. (1994) Hum. Mol. Genet. 3:1041); and Crumbs homolog 1 (CRB1), a polypeptide that, when defective or missing, causes Leber congenital amaurosis and retinitis pigmentosa (see, e.g., den Hollander et al. (1999) Nat. Genet. 23:217; and GenBank Accession No. CAM23328). For example, a suitable REP1 polypeptide can comprise an amino acid having at least about 90%, at least about 95%, at least about 98%, at least about 99%, or 100%, amino acid sequence identity to the amino acid sequence set depicted in FIG. 7G.

Suitable polypeptides include Rod cGMP-specific 3',5'-cyclic phosphodiesterase subunit alpha (PDE6α), Rod cGMP-specific 3',5'-cyclic phosphodiesterase subunit beta isoform 1 (PDE6β isoform 1), Rod cGMP-specific 3',5'-cyclic phosphodiesterase subunit beta isoform 2 (PDE6β isoform 2), Rod cGMP-specific 3',5'-cyclic phosphodiesterase subunit beta isoform 3 (PDE6β isoform 3). For example, a suitable PDE6a polypeptide can comprise an amino acid having at least about 90%, at least about 95%, at least about 98%, at least about 99%, or 100%, amino acid sequence identity to the amino acid sequence set depicted in FIG. 7K. As another example, a suitable PDE6β6 isoform 1 polypeptide can comprise an amino acid having at least about 90%, at least about 95%, at least about 98%, at least about 99%, or 100%, amino acid sequence identity to the amino acid sequence set depicted in FIG. 7L. As another example, a suitable PDE6β6 isoform 2 polypeptide can comprise an amino acid having at least about 90%, at least about 95%, at least about 98%, at least about 99%, or 100%, amino acid sequence identity to the amino acid sequence set depicted in FIG. 7M. As another example, a suitable PDE6β6 isoform 3 polypeptide can comprise an amino acid having at least about 90%, at least about 95%, at least about 98%, at least about 99%, or 100%, amino acid sequence identity to the amino acid sequence set depicted in FIG. 7N.

Suitable polypeptides also include polypeptides that, when defective or missing, lead to achromotopsia, where such polypeptides include, e.g., cone photoreceptor cGMP-gated channel subunit alpha (CNGA3) (see, e.g., GenBank Accession No. NP_001289; and Booij et al. (2011) Ophthalmology 118:160-167); cone photoreceptor cGMP-gated cation channel beta-subunit (CNGB3) (see, e.g., Kohl et al. (2005) Eur J Hum Genet. 13(3):302); guanine nucleotide binding protein (G protein), alpha transducing activity polypeptide 2 (GNAT2) (ACHM4); and ACHM5; and polypeptides that, when defective or lacking, lead to various forms of color blindness (e.g., L-opsin, M-opsin, and S-opsin). See Mancuso et al. (2009) Nature 461(7265):784-787.

For example, a suitable CNGA3 (also known as ACHM2) isoform 1 polypeptide can comprise an amino acid having at least about 90%, at least about 95%, at least about 98%, at least about 99%, or 100%, amino acid sequence identity to the amino acid sequence set depicted in FIG. 7O. As another example, a suitable CNGA3 (also known as ACHM2) isoform 2 polypeptide can comprise an amino acid having at least about 90%, at least about 95%, at least about 98%, at least about 99%, or 100%, amino acid sequence identity to the amino acid sequence set depicted in FIG. 7P.

As another example, a suitable CNGB3 (also known as ACHM3) polypeptide can comprise an amino acid having at least about 90%, at least about 95%, at least about 98%, at least about 99%, or 100%, amino acid sequence identity to the amino acid sequence set depicted in FIG. 7Q. As another example, GNAT2 (also known as ACHM4) can comprise an amino acid having at least about 90%, at least about 95%, at least about 98%, at least about 99%, or 100%, amino acid sequence identity to the amino acid sequence set depicted in FIG. 7R.

Site-Specific Endonucleases

In some cases, a gene product of interest is a site-specific endonuclease that provide for site-specific knock-down of gene function, e.g., where the endonuclease knocks out an allele associated with a retinal disease. For example, where a dominant allele encodes a defective copy of a gene that, when wild-type, is a retinal structural protein and/or provides for normal retinal function, a site-specific endonuclease can be targeted to the defective allele and knock out the defective allele. In some cases, a site-specific endonuclease is an RNA-guided endonuclease.

In addition to knocking out a defective allele, a site-specific nuclease can also be used to stimulate homologous recombination with a donor DNA that encodes a functional copy of the protein encoded by the defective allele. Thus, e.g., a subject rAAV virion can be used to deliver both a site-specific endonuclease that knocks out a defective allele, and can be used to deliver a functional copy of the defective allele, resulting in repair of the defective allele, thereby providing for production of a functional retinal protein (e.g., functional retinoschisin, functional RPE65, functional peripherin, etc.). See, e.g., Li et al. (2011) *Nature* 475:217. In some embodiments, a subject rAAV virion comprises a heterologous nucleotide sequence that encodes a site-specific endonuclease; and a heterologous nucleotide sequence that encodes a functional copy of a defective allele, where the functional copy encodes a functional retinal protein. Functional retinal proteins include, e.g., retinoschisin, RPE65, retinitis pigmentosa GTPase regulator (RGPR)-interacting protein-1, peripherin, peripherin-2, RdCVF, and the like.

Site-specific endonucleases that are suitable for use include, e.g., zinc finger nucleases (ZFNs); meganucleases; and transcription activator-like effector nucleases (TALENs), where such site-specific endonucleases are non-naturally occurring and are modified to target a specific gene. Such site-specific nucleases can be engineered to cut specific locations within a genome, and non-homologous end joining can then repair the break while inserting or deleting several nucleotides. Such site-specific endonucleases (also referred to as "INDELs") then throw the protein out of frame and effectively knock out the gene. See, e.g., U.S. Patent Publication No. 2011/0301073. Suitable site-specific endonucleases include engineered meganuclease re-engineered homing endonucleases. Suitable endonucleases include an I-TevI nuclease. Suitable meganucleases include I-SceI (see, e.g., Bellaiche et al. (1999) *Genetics* 152:1037); and I-CreI (see, e.g., Heath et al. (1997) *Nature Structural Biology* 4:468).

RNA-Guided Endonucleases

In some cases, the gene product is an RNA-guided endonuclease. In some cases, the gene product is an RNA comprising a nucleotide sequence encoding an RNA-guided endonuclease. In some cases, the gene product is a guide RNA, e.g., a single-guide RNA. In some cases, the gene products are: 1) a guide RNA; and 2) an RNA-guided endonuclease. The guide RNA can comprise: a) a protein-binding region that binds to the RNA-guided endonuclease; and b) a region that binds to a target nucleic acid. An RNA-guided endonuclease is also referred to herein as a "genome editing nuclease."

Examples of suitable genome editing nucleases are CRISPR/Cas endonucleases (e.g., class 2 CRISPR/Cas endonucleases such as a type II, type V, or type VI CRISPR/Cas endonucleases). Thus, a genome targeting composition can include a CRISPR/Cas endonuclease (e.g., a class 2 CRISPR/Cas endonuclease such as a type II, type V, or type VI CRISPR/Cas endonuclease). In some cases, a genome targeting composition includes a class 2 CRISPR/Cas endonuclease. In some cases, a genome targeting composition includes a class 2 type II CRISPR/Cas endonuclease (e.g., a Cas9 protein). In some cases, a genome targeting composition includes a class 2 type V CRISPR/Cas endonuclease (e.g., a Cpf1 protein, a C2cl protein, or a C2c3 protein). In some cases, a genome targeting composition includes a class 2 type VI CRISPR/Cas endonuclease (e.g., a C2c2 protein).

In some cases, a genome editing nuclease is a fusion protein that is fused to a heterologous polypeptide (also referred to as a "fusion partner"). In some cases, a genome editing nuclease is fused to an amino acid sequence (a fusion partner) that provides for subcellular localization, i.e., the fusion partner is a subcellular localization sequence (e.g., one or more nuclear localization signals (NLSs) for targeting to the nucleus, two or more NLSs, three or more NLSs, etc.).

In some cases, the genome-editing endonuclease is a Type II CRISPR/Case endonuclease. In some cases, the genome-editing endonuclease is a Cas9 polypeptide. The Cas9 protein is guided to a target site (e.g., stabilized at a target site) within a target nucleic acid sequence (e.g., a chromosomal sequence or an extrachromosomal sequence, e.g., an episomal sequence, a minicircle sequence, a mitochondrial sequence, a chloroplast sequence, etc.) by virtue of its association with the protein-binding segment of the Cas9 guide RNA. In some cases, a Cas9 polypeptide comprises an amino acid sequence having at least 50%, at least 60%, at least 70%, at least 80%, at least 90%, at least 95%, at least 98%, at least 99%, or more than 99%, amino acid sequence identity to the *Streptococcus pyogenes* Cas9 depicted in FIG. 8A. In some cases, the Cas9 polypeptide used in a composition or method of the present disclosure is a *Staphylococcus aureus* Cas9 (saCas9) polypeptide. In some cases, the saCas9 polypeptide comprises an amino acid sequence having at least 85%, at least 90%, at least 95%, at least 98%, at least 99%, or 100%, amino acid sequence identity to the saCas9 amino acid sequence depicted in FIG. 8B.

In some cases, a suitable Cas9 polypeptide is a high-fidelity (HF) Cas9 polypeptide. Kleinstiver et al. (2016) *Nature* 529:490. For example, amino acids N497, R661, Q695, and Q926 of the amino acid sequence depicted in FIG. 8A are substituted, e.g., with alanine. For example, an HF Cas9 polypeptide can comprise an amino acid sequence having at least 90%, at least 95%, at least 98%, at least 99%, or 100%, amino acid sequence identity to the amino acid sequence depicted in FIG. 8A, where amino acids N497, R661, Q695, and Q926 are substituted, e.g., with alanine.

In some cases, a suitable Cas9 polypeptide exhibits altered PAM specificity. See, e.g., Kleinstiver et al. (2015) *Nature* 523:481.

In some cases, the genome-editing endonuclease is a type V CRISPR/Cas endonuclease. In some cases a type V CRISPR/Cas endonuclease is a Cpf1 protein. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence depicted in FIG. 8C.

A nucleic acid that binds to a class 2 CRISPR/Cas endonuclease (e.g., a Cas9 protein; a type V or type VI CRISPR/Cas protein; a Cpf1 protein; etc.) and targets the complex to a specific location within a target nucleic acid is referred to herein as a "guide RNA" or "CRISPR/Cas guide nucleic acid" or "CRISPR/Cas guide RNA." A guide RNA provides target specificity to the complex (the RNP complex) by including a targeting segment, which includes a guide sequence (also referred to herein as a targeting sequence), which is a nucleotide sequence that is complementary to a sequence of a target nucleic acid.

In some cases, a guide RNA includes two separate nucleic acid molecules: an "activator" and a "targeter" and is referred to herein as a "dual guide RNA", a "double-molecule guide RNA", a "two-molecule guide RNA", or a "dgRNA." In some cases, the guide RNA is one molecule (e.g., for some class 2 CRISPR/Cas proteins, the corresponding guide RNA is a single molecule; and in some cases, an activator and targeter are covalently linked to one another, e.g., via intervening nucleotides), and the guide RNA is referred to as a "single guide RNA", a "single-molecule guide RNA," a "one-molecule guide RNA", or simply "sgRNA."

Where the gene product is an RNA-guided endonuclease, or is both an RNA-guided endonuclease and a guide RNA, the gene product can modify a target nucleic acid. In some cases, e.g., where a target nucleic acid comprises a deleterious mutation in a defective allele (e.g., a deleterious mutation in a retinal cell target nucleic acid), the RNA-guided endonuclease/guide RNA complex, together with a donor nucleic acid comprising a nucleotide sequence that corrects the deleterious mutation (e.g., a donor nucleic acid comprising a nucleotide sequence that encodes a functional copy of the protein encoded by the defective allele), can be used to correct the deleterious mutation, e.g., via homology-directed repair (HDR).

In some cases, the gene products are an RNA-guided endonuclease and 2 separate sgRNAs, where the 2 separate sgRNAs provide for deletion of a target nucleic acid via non-homologous end joining (NHEJ).

The present disclosure provides a method of modifying a target nucleic acid in a retinal cell in an individual, where the target nucleic acid comprises a deleterious mutation, the method comprising administering to the individual (e.g., by intraocular; intravitreal; etc. administration) an rAAV virion of the present disclosure, where the rAAV virion comprises a heterologous nucleic acid comprising: i) a nucleotide sequence encoding an RNA-guided endonuclease (e.g., a Cas9 endonuclease); ii) a nucleotide sequence encoding a sgRNA that comprises a nucleotide sequence that is complementary to the target nucleic acid; and iii) a nucleotide sequence encoding a donor DNA template that comprises a nucleotide sequence that corrects the deleterious mutation. Administration of the rAAV virion results in correction of the deleterious mutation in the target nucleic acid by HDR.

The present disclosure provides a method of modifying a target nucleic acid in a retinal cell in an individual, where the target nucleic acid comprises a deleterious mutation, the method comprising administering to the individual (e.g., by intraocular; intravitreal; etc. administration) an rAAV virion of the present disclosure, where the rAAV virion comprises a heterologous nucleic acid comprising: i) a nucleotide sequence encoding an RNA-guided endonuclease (e.g., a Cas9 endonuclease); ii) a nucleotide sequence encoding a first sgRNA that comprises a nucleotide sequence that is complementary to a first sequence in the target nucleic acid; and iii) a nucleotide sequence encoding a second sgRNA that comprises a nucleotide sequence that is complementary to a second sequence in the target nucleic acid. Administration of the rAAV virion results in excision of the deleterious mutation in the target nucleic acid by NHEJ.

Regulatory Sequences

In some cases, a nucleotide sequence encoding a gene product of interest is operably linked to a transcriptional control element. For example, in some cases, a nucleotide sequence encoding a gene product of interest is operably linked to a constitutive promoter. In other cases, a nucleotide sequence encoding a gene product of interest is operably linked to an inducible promoter. In some instances, a nucleotide sequence encoding a gene product of interest is operably linked to a tissue-specific or cell type-specific regulatory element. For example, in some instances, a nucleotide sequence encoding a gene product of interest is operably linked to a retinal cell-specific promoter. For example, in some instances, a nucleotide sequence encoding a gene product of interest is operably linked to a photoreceptor-specific regulatory element (e.g., a photoreceptor-specific promoter), e.g., a regulatory element that confers selective expression of the operably linked gene in a photoreceptor cell. Suitable photoreceptor-specific regulatory elements include, e.g., a rhodopsin promoter; a rhodopsin kinase promoter (Young et al. (2003) *Ophthalmol. Vis. Sci.* 44:4076); a beta phosphodiesterase gene promoter (Nicoud et al. (2007) *J. Gene Med.* 9:1015); a retinitis pigmentosa gene promoter (Nicoud et al. (2007) supra); an interphotoreceptor retinoid-binding protein (IRBP) gene enhancer (Nicoud et al. (2007) supra); an IRBP gene promoter (Yokoyama et al. (1992) *Exp Eye Res.* 55:225).

PHARMACEUTICAL COMPOSITIONS

The present disclosure provides a pharmaceutical composition comprising: a) a subject rAAV virion, as described above; and b) a pharmaceutically acceptable carrier, diluent, excipient, or buffer. In some embodiments, the pharmaceutically acceptable carrier, diluent, excipient, or buffer is suitable for use in a human.

Such excipients, carriers, diluents, and buffers include any pharmaceutical agent that can be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

Methods of Delivering a Gene Product to a Retinal Cell and Treatment Methods

The present disclosure provides a method of delivering a gene product to a retinal cell in an individual, the method comprising administering to the individual a subject rAAV virion as described above. The gene product can be a polypeptide or an interfering RNA (e.g., an shRNA, an siRNA, and the like), an aptamer, or a site-specific endonuclease (e.g., an RNA-guided endonuclease), as described above. Delivering a gene product to a retinal cell can provide for treatment of a retinal disease. The retinal cell can be a photoreceptor, a retinal ganglion cell, a Müller cell, a bipolar cell, an amacrine cell, a horizontal cell, or a retinal pigmented epithelial cell. In some cases, the retinal cell is a photoreceptor cell, e.g., a rod or cone cell.

The present disclosure provides a method modifying a target nucleic acid in a retinal cell, the method comprising contacting the retinal cell with: 1) an rAAV virion of the present disclosure, wherein the rAAV virion comprises a heterologous nucleic acid comprising a nucleotide sequence encoding an RNA-guided endonuclease that binds a guide RNA; and 2) the guide RNA. The present disclosure provides a method modifying a target nucleic acid in a retinal cell, the method comprising contacting the retinal cell with an rAAV virion of the present disclosure, wherein the rAAV virion comprises a heterologous nucleic acid comprising a nucleotide sequence encoding: i) an RNA-guided endonuclease that binds a guide RNA; and ii) the guide RNA. In some cases, the method comprises contacting the retinal cell with a donor DNA template. In some cases, the RNA-guided endonuclease is a Cas9 polypeptide. In some cases, the guide RNA is a single-guide RNA.

The present disclosure provides a method of treating an ocular disease (e.g., a retinal disease), the method comprising administering to an individual in need thereof an effective amount of a subject rAAV virion as described above. A subject rAAV virion can be administered via intraocular injection, by intravitreal injection, or by any other convenient mode or route of administration. Other convenient modes or routes of administration include, e.g., intravenous, intranasal, etc.

A "therapeutically effective amount" will fall in a relatively broad range that can be determined through experimentation and/or clinical trials. For example, for in vivo injection, i.e., injection directly into the eye, a therapeutically effective dose will be on the order of from about $10^6$ to about $10^{15}$ of the rAAV virions, e.g., from about $10^8$ to $10^{12}$ rAAV virions. For in vitro transduction, an effective amount of rAAV virions to be delivered to cells will be on the order of from about $10^8$ to about $10^{13}$ of the rAAV virions. Other effective dosages can be readily established by one of ordinary skill in the art through routine trials establishing dose response curves.

In some embodiments, more than one administration (e.g., two, three, four or more administrations) may be employed to achieve the desired level of gene expression. In some cases, the more than one administration is administered at various intervals, e.g., daily, weekly, twice monthly, monthly, every 3 months, every 6 months, yearly, etc. In some cases, multiple administrations are administered over a period of time of from 1 month to 2 months, from 2 months to 4 months, from 4 months to 8 months, from 8 months to 12 months, from 1 year to 2 years, from 2 years to 5 years, or more than 5 years.

Ocular diseases that can be treated using a subject method include, but are not limited to, acute macular neuroretinopathy; Behcet's disease; choroidal neovascularization; diabetic uveitis; histoplasmosis; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy; photocoagulation, radiation retinopathy; epiretinal membrane disorders; branch retinal vein occlusion; anterior ischemic optic neuropathy; non-retinopathy diabetic retinal dysfunction; retinoschisis; retinitis pigmentosa; glaucoma; Usher syndrome, cone-rod dystrophy; Stargardt disease (fundus flavimaculatus); inherited macular degeneration; chorioretinal degeneration; Leber congenital amaurosis; congenital stationary night blindness; choroideremia; Bardet-Biedl syndrome; macular telangiectasia; Leber's hereditary optic neuropathy; retinopathy of prematurity; disorders of color vision, including achromatopsia, protanopia, deuteranopia, and tritanopia; and Bietti's crystalline dystrophy.

Nucleic Acids and Host Cells

The present disclosure provides an isolated nucleic acid comprising a nucleotide sequence that encodes a subject variant adeno-associated virus (AAV) capsid protein as described above, where the variant AAV capsid protein comprises an insertion of from about 5 amino acids to about 20 amino acids in the GH loop or loop IV relative to a corresponding parental AAV capsid protein, and where the variant capsid protein, when present in an AAV virion, provides for increased infectivity of a retinal cell compared to the infectivity of the retinal cell by an AAV virion comprising the corresponding parental AAV capsid protein. A subject isolated nucleic acid can be an AAV vector, e.g., a recombinant AAV vector.

Insertion Peptides

A variant AAV capsid protein encoded by a subject nucleic acid has an insertion peptide of from about 5 amino acids to about 20 amino acids in length is inserted into the GH loop of an AAV capsid. The insertion peptide has a length of 5 amino acids, 6 amino acids, 7 amino acids, 8 amino acids, 9 amino acids, 10 amino acids, 11 amino acids, 12 amino acids, 13 amino acids, 14 amino acids, 15 amino acids, 16 amino acids, 17 amino acids, 18 amino acids, 19 amino acids, or 20 amino acids. Suitable insertion peptides are as described above. Suitable insertion peptides include a peptide of any one of Formulas I-X, as described above.

A subject recombinant AAV vector can be used to generate a subject recombinant AAV virion, as described above. Thus, the present disclosure provides a recombinant AAV vector that, when introduced into a suitable cell, can provide for production of a subject recombinant AAV virion.

The present invention further provides host cells, e.g., isolated (genetically modified) host cells, comprising a subject nucleic acid. A subject host cell can be an isolated cell, e.g., a cell in in vitro culture. A subject host cell is useful for producing a subject rAAV virion, as described below. Where a subject host cell is used to produce a subject rAAV virion, it is referred to as a "packaging cell." In some embodiments, a subject host cell is stably genetically modified with a subject nucleic acid. In other embodiments, a subject host cell is transiently genetically modified with a subject nucleic acid.

A subject nucleic acid is introduced stably or transiently into a host cell, using established techniques, including, but not limited to, electroporation, calcium phosphate precipitation, liposome-mediated transfection, and the like. For stable transformation, a subject nucleic acid will generally further include a selectable marker, e.g., any of several well-known selectable markers such as neomycin resistance, and the like.

A subject host cell is generated by introducing a subject nucleic acid into any of a variety of cells, e.g., mammalian cells, including, e.g., murine cells, and primate cells (e.g., human cells). Suitable mammalian cells include, but are not limited to, primary cells and cell lines, where suitable cell lines include, but are not limited to, 293 cells, COS cells, HeLa cells, Vero cells, 3T3 mouse fibroblasts, C3H10T1/2 fibroblasts, CHO cells, and the like. Non-limiting examples of suitable host cells include, e.g., HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like. A subject host cell can also be made using a baculovirus to infect insect cells such as Sf9 cells, which produce AAV (see, e.g., U.S. Pat. No. 7,271,002; U.S. patent application Ser. No. 12/297,958)

In some embodiments, a subject genetically modified host cell includes, in addition to a nucleic acid comprising a nucleotide sequence encoding a variant AAV capsid protein, as described above, a nucleic acid that comprises a nucleotide sequence encoding one or more AAV rep proteins. In other embodiments, a subject host cell further comprises an rAAV vector. An rAAV virion can be generated using a subject host cell. Methods of generating an rAAV virion are described in, e.g., U.S. Patent Publication No. 2005/0053922 and U.S. Patent Publication No. 2009/0202490.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-34 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A recombinant adeno-associated virus (rAAV) virion comprising: a) a variant AAV capsid protein, wherein the variant AAV capsid protein comprises an insertion of a heterologous peptide having a length of from about 5 amino acids to about 20 amino acids in the capsid protein GH loop relative to a corresponding parental AAV capsid protein, and wherein the variant capsid protein confers increased infectivity of a retinal cell compared to the infectivity of the retinal cell by a control AAV virion comprising the corresponding parental AAV capsid protein; and b) a heterologous nucleic acid comprising a nucleotide sequence encoding a heterologous gene product.

Aspect 2. The rAAV virion of aspect 1, wherein the rAAV virion exhibits at least 5-fold increased infectivity of a retinal cell compared to the infectivity of the retinal cell by a control AAV virion comprising the corresponding parental AAV capsid protein.

Aspect 3. The rAAV virion of aspect 1, wherein the rAAV virion exhibits at least 10-fold increased infectivity of a retinal cell compared to the infectivity of the retinal cell by an AAV virion comprising the corresponding parental AAV capsid protein.

Aspect 4. The rAAV virion of any one of aspects 1-3, wherein the rAAV virion exhibits at least 5-fold increased localization to one or more of the inner nuclear layer, the outer nuclear layer, the photoreceptor layer, the ganglion cell layer, and the retinal pigment epithelium, compared to the extent of localization to the inner nuclear layer, the outer nuclear layer, the photoreceptor layer, the ganglion cell layer, or the retinal pigment epithelium, by an AAV virion comprising the corresponding parental AAV capsid protein.

Aspect 5. The rAAV virion of any one of aspects 1-4, wherein the insertion site is between amino acids corresponding to amino acids 570 and 611 of VP1 of AAV2, or the corresponding position in the capsid protein of another AAV serotype.

Aspect 6. The rAAV virion of any one of aspects 1-5, wherein the insertion site is located between amino acids corresponding to amino acids 587 and 588 of VP1 of AAV2, or the corresponding position in the capsid protein of another AAV serotype.

Aspect 7. The rAAV virion of any one of aspects 1-6, wherein gene product is an interfering RNA or an aptamer.

Aspect 8. The rAAV virion of any one of aspects 1-6, wherein the gene product is a polypeptide.

Aspect 9. The rAAV virion of aspect 8, wherein the polypeptide is a neuroprotective polypeptide, an anti-angiogenic polypeptide, or a polypeptide that enhances function of a retinal cell.

Aspect 10. The rAAV virion of aspect 8, wherein the polypeptide is an RNA-guided endonuclease.

Aspect 11. The rAAV virion of aspect 10, wherein the RNA-guided endonuclease is a Cas9 polypeptide.

Aspect 12. The rAAV virion of aspect 10, wherein the gene product is an RNA-guided endonuclease and a guide RNA.

Aspect 13. The rAAV virion of any one of aspects 1-12, wherein the heterologous peptide inserted into the GH loop is of any one of Formulas I-X.

Aspect 14. The rAAV virion of any one of aspects 1-12, wherein the heterologous peptide is a peptide of Formula I: $X_1X_2X_3X_4X_5X_6X_7X_8X_9X_{10}$,
wherein:
$X_1$ is Leu, Ile, Pro, or Gln;
$X_2$ is Ala, Pro, Ser, Asp, Gly, Thr, or Val;
$X_3$ is Lys, His, Thr, Ile, Pro, Val, Arg, Ala, Asp, Glu, Asn, Gln, or Tyr;
$X_4$, if present, is Gln, Asp, Ser, Gly, Thr, Ile, Asn, Glu, Lys, or Arg;
$X_5$ is Asp, Ser, Gln, Val, Thr, Gly, Ala, Asn, Lys, or Tyr;
$X_6$ is Thr, Ala, Gln, Ser, Glu, Pro, or Ile;
$X_7$ is Thr, Ser, Asn, Pro, Leu, Gln, Lys, Ala, or Cys;
$X_8$ is Lys, Ser, Arg, Thr, Ala, Glu, Ile, or Asn;
$X_9$ is Asn, Pro, Ser, Lys, His, Ile, Thr, or Ala; and
$X_{10}$ is Ala, Phe, Asp, Thr, Val, or Met.

Aspect 15. The rAAV virion of aspect 14, wherein the heterologous peptide comprises one of the following amino acid sequences: (1) LAKDATKNA (SEQ ID NO:47); (2) PAHQDTTKNA (SEQ ID NO:48); (3) LAHQDTTKNA (SEQ ID NO:49); (4) LATTSQNKPA (SEQ ID NO:50); (5) LAISDQTKHA (SEQ ID NO:51); (6) IARGVAPSSA (SEQ ID NO:52); (7) LAPDSTTRSA (SEQ ID NO:53); (8) LAKGTELKPA (SEQ ID NO:54); (9) LAIIDATKNA (SEQ ID NO:55); (10) LAVDGAQRSA (SEQ ID NO:56); (11) PAPQDTTKKA (SEQ ID NO:57); (12) LPHQDTTKNA (SEQ ID NO:58); (13) LAKDATKTIA (SEQ ID NO:59); (14) LAKQQSASTA (SEQ ID NO:60); (15) LAKSDQSKPA (SEQ ID NO:61); (16) LSHQDTTKNA (SEQ ID NO:62); (17) LAANQPSKPA (SEQ ID NO:63); (18) LAVSDSTKAA (SEQ ID NO:64); (19) LAAQGTAKKPA (SEQ ID NO:65); (20) LAPDQTTRNA (SEQ ID NO:66); (21) LAASDSTKAA (SEQ ID NO:67); (22) LAPQDTTKNA (SEQ ID NO:68); (23) LAKADETRPA (SEQ ID NO:69); (24) LAHQDTAKNA (SEQ ID NO:70); (25) LAHQDTKKNA (SEQ ID NO:71); (26) LAHQDTTKHA (SEQ ID NO:72); (27) LAHQDTTKKA (SEQ ID NO:73); (28) LAHQDTTRNA (SEQ ID NO:74); (29) LAHQDTTNA (SEQ ID NO:75); (30) LAHQGTTKNA (SEQ ID NO:76); (31) LAHQVTTKNA (SEQ ID NO:77); (32) LAISDQSKPA (SEQ ID NO:78); (33)

LADATKTA (SEQ ID NO:79); (34) LAKDTTKNA (SEQ ID NO:80); (35) LAKSDQSRPA (SEQ ID NO:81); (36) LAPQDTKKNA (SEQ ID NO:82); (37) LATSDSTKAA (SEQ ID NO:83); (38) LAVDGSQRSA (SEQ ID NO:84); (39) LPISDQTKHA (SEQ ID NO:85); (40) LPKDATKTIA (SEQ ID NO:86); (41) LPPQDTTKNA (SEQ ID NO:87); (42) PAPQDTTKNA (SEQ ID NO:88); (43) QAHQDTTKNA (SEQ ID NO:89); (44) LAHETSPRPA (SEQ ID NO:90); (45) LAKSTSTAPA (SEQ ID NO:91); (46) LADQDTTKNA (SEQ ID NO:92); (47) LAESDQSKPA (SEQ ID NO:93); (48) LAHKDTTKNA (SEQ ID NO:94); (49) LAHKTQQKM (SEQ ID NO:95); (50) LAHQDTTENA (SEQ ID NO:96); (51) LAHQDTTINA (SEQ ID NO:97); (52) LAHQDTTKKT (SEQ ID NO:98); (53) LAHQDTTKND (SEQ ID NO:99); (54) LAHQDTTKNT (SEQ ID NO:100); (55) LAHQDTTKNV (SEQ ID NO:101); (56) LAHQDTTKTM (SEQ ID NO:102); (57) LAHQNTTKNA (SEQ ID NO:103); (58) LAHRDTTKNA (SEQ ID NO:104); (59) LAISDQTNHA (SEQ ID NO:105); (60) LAKQKSASTA (SEQ ID NO:106); (61) LAKSDQCKPA (SEQ ID NO:107); (62) LAKSDQSKPD (SEQ ID NO:10⁸); (63) LAKSDQSNPA (SEQ ID NO:109); (64) LAKSYQSKPA (SEQ ID NO:110); (65) LANQDTTKNA (SEQ ID NO:111); (66) LAPQNTTKNA (SEQ ID NO:112); (67) LAPSSIQKPA (SEQ ID NO:113); (68) LAQQDTTKNA (SEQ ID NO:114); (69) LAYQDTTKNA (SEQ ID NO:115); (70) LDHQDTTKNA (SEQ ID NO:116); (71) LDHQDTTKSA (SEQ ID NO:117); (72) LGHQDTTKNA (SEQ ID NO:118); (73) LPHQDTTKND (SEQ ID NO:119); (74) LPHQDTTKNT (SEQ ID NO:120); (75) LPHQDTTNNA (SEQ ID NO:121); (76) LTHQDTTKNA (SEQ ID NO:122); (77) LTKDATKTIA (SEQ ID NO:123); (78) LTPQDTTKNA (SEQ ID NO:124); and (79) LVHQDTTKNA (SEQ ID NO:125).

Aspect 16. The rAAV virion of any one of aspects 1-12, wherein the heterologous peptide is a peptide of Formula II:

$X_1X_2X_3X_4X_5X_6X_7X_8X_9X_{10}$, wherein:

$X_1$ is Leu, Ile, or Pro;
$X_2$ is Ala, Pro, or Ser;
$X_3$ is Lys, His, Thr, Ile, Pro, Val, Arg, or Ala;
$X_4$ (if present) is Gln, Asp, Ser, Gly, Thr, Ile, or Asn;
$X_5$ is Asp, Ser, Gln, Val, Thr, Gly, or Ala;
$X_6$ is Thr, Ala, Gln, Ser, Glu, or Pro;
$X_7$ is Thr, Ser, Asn, Pro, Leu, Gln, Lys, or Ala;
$X_8$ is Lys, Ser, Arg, or Thr;
$X_9$ is Asn, Pro, Ser, Lys, His, Ile, Thr, or Ala; and
$X_{10}$ is Ala.

Aspect 17. The rAAV virion of aspect 16, wherein the peptide comprises one of the following amino acid sequences: (1) LAKDATKNA (SEQ ID NO:47); (2) PAHQDTTKNA (SEQ ID NO:48); (3) LAHQDTTKNA (SEQ ID NO:49); (4) LATTSQNKPA (SEQ ID NO:50); (5) LAISDQTKHA (SEQ ID NO:51); (6) IARGVAPSSA (SEQ ID NO:52); (7) LAPDSTTRSA (SEQ ID NO:53); (8) LAKGTELKPA (SEQ ID NO:54); (9) LAIIDATKNA (SEQ ID NO:55); (10) LAVDGAQRSA (SEQ ID NO:56); (11) PAPQDTTKKA (SEQ ID NO:57); (12) LPHQDTTKNA (SEQ ID NO:58); (13) LAKDATKTIA (SEQ ID NO:59); (14) LAKQQSASTA (SEQ ID NO:60); (15) LAKSDQSKPA (SEQ ID NO:61); (16) LSHQDTTKNA (SEQ ID NO:62); (17) LAANQPSKPA (SEQ ID NO:63); (18) LAVSDSTKAA (SEQ ID NO:64); (19) LAAQGTAKKPA (SEQ ID NO:65); (20) LAPDQTTRNA (SEQ ID NO:66); (21) LAASDSTKAA (SEQ ID NO:67); (22) LAPQDTTKNA (SEQ ID NO:68); (23) LAKADETRPA (SEQ ID NO:69); (24) LAHQDTAKNA (SEQ ID NO:70); (25) LAHQDTKKNA (SEQ ID NO:71); (26) LAHQDTTKHA (SEQ ID NO:72); (27) LAHQDTTKKA (SEQ ID NO:73); (28) LAHQDTTRNA (SEQ ID NO:74); (29) LAHQDTTNA (SEQ ID NO:75); (30) LAHQGTTKNA (SEQ ID NO:76); (31) LAHQVTTKNA (SEQ ID NO:77); (32) LAISDQSKPA (SEQ ID NO:78); (33) LADATKTA (SEQ ID NO:79); (34) LAKDTTKNA (SEQ ID NO:80); (35) LAKSDQSRPA (SEQ ID NO:81); (36) LAPQDTKKNA (SEQ ID NO:82); (37) LATSDSTKAA (SEQ ID NO:83); (38) LAVDGSQRSA (SEQ ID NO:84); (39) LPISDQTKHA (SEQ ID NO:85); (40) LPKDATKTIA (SEQ ID NO:86); (41) LPPQDTTKNA (SEQ ID NO:87); and (42) PAPQDTTKNA (SEQ ID NO:88).

Aspect 18. The rAAV virion of aspect 16, wherein the peptide comprises one of the following amino acid sequences: (1) LAKDATKNA (SEQ ID NO:47); (2) PAHQDTTKNA (SEQ ID NO:48); (3) LAHQDTTKNA (SEQ ID NO:49); (4) LATTSQNKPA (SEQ ID NO:50); (5) LAISDQTKHA (SEQ ID NO:51); (6) IARGVAPSSA (SEQ ID NO:52); (7) LAPDSTTRSA (SEQ ID NO:53); (8) LAKGTELKPA (SEQ ID NO:54); (9) LAIIDATKNA (SEQ ID NO:55); (10) LAVDGAQRSA (SEQ ID NO:56); (11) PAPQDTTKKA (SEQ ID NO:57); (12) LPHQDTTKNA (SEQ ID NO:58); (13) LAKDATKTIA (SEQ ID NO:59); (14) LAKQQSASTA (SEQ ID NO:60); (15) LAKSDQSKPA (SEQ ID NO:61); (16) LSHQDTTKNA (SEQ ID NO:62); (17) LAANQPSKPA (SEQ ID NO:63); and (18) LAVSDSTKAA (SEQ ID NO:64).

Aspect 19. A pharmaceutical composition comprising: a) a recombinant adeno-associated virus virion of any one of aspects 1-18; and b) a pharmaceutically acceptable excipient.

Aspect 20. A method of delivering a gene product to a retinal cell in an individual, the method comprising administering to the individual a recombinant adeno-associated virus (rAAV) virion according any one of aspects 1-18.

Aspect 21. The method of aspect 20, wherein the gene product is a polypeptide.

Aspect 22. The method of aspect 20, wherein the gene product is a short interfering RNA or an aptamer.

Aspect 23. The method of aspect 21, wherein the polypeptide is a neuroprotective factor, an anti-angiogenic polypeptide, an anti-apoptotic factor, or a polypeptide that enhances function of a retinal cell.

Aspect 24. The method of aspect 21, wherein the polypeptide is glial derived neurotrophic factor, fibroblast growth factor 2, neurturin, ciliary neurotrophic factor, nerve growth factor, brain derived neurotrophic factor, epidermal growth factor, rhodopsin, X-linked inhibitor of apoptosis, retinoschisin, RPE65, retinitis pigmentosa GTPase-interacting protein-1, peripherin, peripherin-2, a rhodopsin, RdCVF, retinitis pigmentosa GTPase regulator (RPGR), or Sonic hedgehog.

Aspect 25. The method of aspect 21, wherein the polypeptide is an RNA-guided endonuclease.

Aspect 26. A method of treating an ocular disease, the method comprising administering to an individual in need thereof an effective amount of a recombinant adeno-associated virus (rAAV) virion according to any one of aspects 1-18.

Aspect 27. The method of aspect 26, wherein said administering is by intraocular injection.

Aspect 28. The method of aspect 26, wherein said administering is by intravitreal injection.

Aspect 29. The method of aspect 26, wherein the ocular disease is glaucoma, retinitis pigmentosa, macular degeneration, retinoschisis, Leber's Congenital Amaurosis, diabetic retinopathy, achromotopsia, or color blindness.

Aspect 30. An isolated nucleic acid comprising a nucleotide sequence that encodes a variant adeno-associated virus (AAV) capsid protein, wherein the variant AAV capsid protein comprises an insertion of from about 5 amino acids to about 20 amino acids in the capsid protein GH loop relative to a corresponding parental AAV capsid protein, and wherein the variant capsid protein, when present in an AAV virion, provides for increased infectivity of the AAV virion of a retinal cell, and wherein the amino acid insertion is in the GH loop of a native AAV capsid, wherein the insertion is a peptide of any one of Formulas I-X.

Aspect 31. The isolated nucleic acid of aspect 30, wherein the insertion site is between amino acids 587 and 588 of AAV2, between amino acids 590 and 591 of AAV1, between amino acids 575 and 576 of AAV5, between amino acids 590 and 591 of AAV6, between amino acids 589 and 590 of AAV7, between amino acids 590 and 591 of AAV8, between amino acids 588 and 589 of AAV9, or between amino acids 588 and 589 of AAV10.

Aspect 32. An isolated, genetically modified host cell comprising the nucleic acid of aspect 30 or aspect 31.

Aspect 33. A variant adeno-associated virus (AAV) capsid protein, wherein the variant AAV capsid protein comprises an insertion of from about 5 amino acids to about 20 amino acids wherein the amino acid insertion is in the GH loop of a native AAV capsid, wherein the insertion is a peptide of any one of Formulas I-X.

Aspect 34. In any of aspects 1-33, the heterologous peptide that is inserted into the GH loop can be of one of Formulas I-X, where:

Formula I is $X_1X_2X_3X_4X_5X_6X_7X_8X_9X_{10}$, where:
$X_1$ is Leu, Ile, Pro, or Gln;
$X_2$ is Ala, Pro, Ser, Asp, Gly, Thr, or Val;
$X_3$ is Lys, His, Thr, Ile, Pro, Val, Arg, Ala, Asp, Glu, Asn, Gln, or Tyr;
$X_4$ (if present) is Gln, Asp, Ser, Gly, Thr, Ile, Asn, Glu, Lys, or Arg;
$X_5$ is Asp, Ser, Gln, Val, Thr, Gly, Ala, Asn, Lys, or Tyr;
$X_6$ is Thr, Ala, Gln, Ser, Glu, Pro, or Ile;
$X_7$ is Thr, Ser, Asn, Pro, Leu, Gln, Lys, Ala, or Cys;
$X_8$ is Lys, Ser, Arg, Thr, Ala, Glu, Ile, or Asn;
$X_9$ is Asn, Pro, Ser, Lys, His, Ile, Thr, or Ala; and
$X_{10}$ is Ala, Phe, Asp, Thr, Val, or Met;

Formula II is $X_1X_2X_3X_4X_5X_6X_7X_8X_9X_{10}$, where:
$X_1$ is Leu, Ile, or Pro;
$X_2$ is Ala, Pro, or Ser;
$X_3$ is Lys, His, Thr, Ile, Pro, Val, Arg, or Ala;
$X_4$ (if present) is Gln, Asp, Ser, Gly, Thr, Ile, or Asn;
$X_5$ is Asp, Ser, Gln, Val, Thr, Gly, or Ala;
$X_6$ is Thr, Ala, Gln, Ser, Glu, or Pro;
$X_7$ is Thr, Ser, Asn, Pro, Leu, Gln, Lys, or Ala;
$X_8$ is Lys, Ser, Arg, or Thr;
$X_9$ is Asn, Pro, Ser, Lys, His, Ile, Thr, or Ala; and
$X_{10}$ is Ala;

Formula III is $X_1X_2X_3X_4X_5X_6X_7X_8X_9X_{10}$, where:
$X_1$ is Leu, Ile, or Pro;
$X_2$ is Ala, Pro, or Ser;
$X_3$ is Lys, His, Thr, Ile, Pro, Val, Arg, or Ala;
$X_4$ (if present) is Gln, Asp, Ser, Gly, Thr, Ile, or Asn;
$X_5$ is Asp, Ser, Gln, Val, Thr, Gly, or Ala;
$X_6$ is Thr, Ala, Gln, Ser, Glu, or Pro;
$X_7$ is Thr, Ser, Asn, Pro, Leu, Gln, Lys, or Ala;
$X_8$ is Lys, Ser, Arg, or Thr;
$X_9$ is Asn, Pro, Ser, Lys, His, Ile, Thr, or Ala; and
$X_{10}$ is Ala, Thr, Asp Val, or Met;

Formula IV is $X_1X_2X_3X_4X_5X_6X_7X_8X_9X_{10}$, where:
$X_1$ is Leu;
$X_2$ is Ala;
$X_3$ is Lys, His, Thr, Ile, Pro, or Val;
$X_4$ (if present) is Gln, Asp, Ser, or Gly;
$X_5$ is Asp, Ser, or Gln;
$X_6$ is Thr, Ala, Gln, or Ser;
$X_7$ is Thr or Ser;
$X_8$ is Lys, Ser, or Arg;
$X_9$ is Asn, Pro, or Ser; and
$X_{10}$ is Ala;

Formula V is $X_1X_2X_3X_4X_5X_6X_7X_8X_9X_{10}$, where:
$X_1$ is Leu;
$X_2$ is Ala;
$X_3$ is Lys or His;
$X_4$ (if present) is Gln, Asp, Ser, or Gly;
$X_5$ is Asp, Ser, or Gln;
$X_6$ is Thr, Ala, Gln, or Ser;
$X_7$ is Thr or Ser;
$X_8$ is Lys, Ser, or Arg;
$X_9$ is Asn, Pro, or Ser; and
$X_{10}$ is Ala;

Formula VI is $X_1X_2X_3X_4X_5X_6X_7X_8X_9X_{10}$, where:
$X_1$ is Leu;
$X_2$ is Ala;
$X_3$ is Asn, Lys, Thr, Gln, Ser, Ile, or Leu;
$X_4$ is Ser, Ala, Thr, Glu, Gln, Gly, Lys, or Pro;
$X_5$ is Asp, Pro, Glu, Thr, Asn, or Arg;
$X_6$ is Ile, His, Thr, Gln, Asn, Tyr, Asp, or Glu;
$X_7$ is Gln, Thr, Asn, Ala, or Lys;
$X_8$ is Lys, Thr, Arg, or Asp;
$X_9$ is Pro, Asn, Thr, Arg, Lys, or Ser; and
$X_{10}$ is Ala;

Formula VII is LAHQDTTKX$_1$X$_2$X$_3$(SEQ ID NO:148), where $X_1$ is Lys, Thr, Asn, or His; $X_2$ is Ala, Thr, Val, Ile, Met, or Asp; and $X_3$, if present, is Ala;

Formula VIII is LAX$_1$QX$_2$TX$_3$X$_4$X$_5$X$_6$(SEQ ID NO:149), where $X_1$ is Ala, Pro, Asp, or His; $X_2$ is Gly or Asp; $X_3$ is Ala, Thr, or Lys; $X_4$ is Asn, Glu, Lys, Arg, or Thr; $X_5$ is Leu, Asn, Lys, or Thr; and $X_6$, if present, is Ala, Thr, Asp, Val, or Met;

Formula IX is $X_1AX_2X_3DX_4TKX_5A$ (SEQ ID NO:150), where $X_1$ is Val or Leu; $X_2$ is Ile, Val, His, or Asp; $X_3$ is Glu, Ser, Lys, or Gln; $X_4$ is His, Ser, or Thr; and $X_5$ is Ser, Ala, Asn, His, or Lys; and Formula X is $X_1X_2X_3AX_4QX_5TX_6KNA$ (SEQ ID NO:151), where $X_1$, if present, is Leu; $X_2$, if present, is Ala; $X_3$ is Lys, Leu, or Pro; $X_4$ is Asn, His, Pro, or Tyr; $X_5$ is Asn, Gly, Val, or Asp; and $X_6$ is Pro or Thr.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s);

nt, nucleotide(s); i.m., intramuscular(ly); i.p., intraperitoneal(ly); s.c., subcutaneous(ly); and the like.

Example 1: Generation and Characterization of AAV Virions with AAV Capsid Variants An iterative in vivo screening methodology was used to create AAV with capsid variants able to overcome the significant and complex barriers preventing panretinal AAV infection in a large animal eye. Dogs are an important preclinical model for retinal degenerative disease, with an eye size and structure similar to humans, and many forms of retinal disease are naturally occurring in a variety of dog breeds. The screening method was used to identify 96 AAV variants capable of panretinal infection in the canine retina. Deep sequencing was used to quantify the performance of 18 of these variants from the pool of screened AAV variants in canine retina. Infectivity was quantified based on levels of viral DNA and mRNA in retinal cells following intravitreal injection. These variants can be used for a wide variety of gene delivery strategies in large animal and human eyes.

A peptide display library containing a random 21-nucleotide insert (surrounded by a 5' 6-nucleotide linker and a 3' 3-nucleotide linker) at a surface exposed position on the AAV capsid was created. Virus was packaged such that each viral genome was encapsidated within the capsid protein shell that that genome encoded. Therefore functional improvements identified through selection can be linked to the genome sequence contained within the viral capsid. From this library, an iterative in vivo screening selection process was used to identify variants with the ability to infect the canine retina from the vitreous (FIG. 1). Canine eyes were injected in each round with ~250 L of 10E+13-10E+14 viral genomes/mL (vg/mL) titer virus. Three weeks after injection, eyes were enucleated, and retinal punches were taken from central and peripheral regions of the retina. RPE cells were separated from retinal tissue, and tissue was frozen. DNA was then collected from retinal cells, and cap genes were polymerase chain reaction (PCR) amplified from isolated samples. Cap genes were used for subsequent AAV packaging.

FIG. 1. Illustration of the directed evolution methodology used to develop canine retinal AAV variants. Peptide display libraries were created, packaged into AAV vectors, and injected into the canine eye via intravitreal injections. Iterative round of selection were used to positively select AAV variants from the pool of vectors. Three rounds of selection were followed by a round of error prone PCR, followed by additional selection rounds.

Following 5 rounds of selection, Illumina deep sequencing was used to identify variants that increased over the rounds in relative representation in the library of AAV variants. An increase of representation in the viral library indicates positive selection and ability to infect the canine retina from the vitreous. Out of a library of ~10E+7 variants, the top 96 variants that were selected for in the in vivo screen are provided in Table 1.

TABLE 1

| | Peptide No. | SEQID NO: |
|---|---|---|
| LAKDATKNA | 1 | 47 |
| PAHQDTTKNA | 2 | 48 |
| LAHQDTTKNA | 3 | 49 |
| LATTSQNKPA | 4 | 50 |
| LAISDQTKHA | 5 | 51 |

TABLE 1-continued

| | Peptide No. | SEQID NO: |
|---|---|---|
| IARGVAPSSA | 6 | 52 |
| LAPDSTTRSA | 7 | 53 |
| LAKGTELKPA | 8 | 54 |
| LAHDATKNA | 9 | 55 |
| LAVDGAQRSA | 10 | 56 |
| PAPQDTTKKA | 11 | 57 |
| LPHQDTTKNA | 12 | 58 |
| LAKDATKTIA | 13 | 59 |
| LAKQQSASTA | 14 | 60 |
| LAKSDQ.SKPA | 15 | 61 |
| LSHQDTTKNA | 16 | 62 |
| LAANQPSKPA | 17 | 63 |
| LAVSDSTKAA | 18 | 64 |
| LAAQGTAKPA | 19 | 65 |
| LAPDQTTRNA | 20 | 66 |
| LAASDSTKAA | 21 | 67 |
| LAPQDTTKNA | 22 | 68 |
| LAKADETRPA | 23 | 69 |
| LAHQDTAKNA | 24 | 70 |
| LAHQDTKKNA | 25 | 71 |
| LAHQDTTKHA | 26 | 72 |
| LAHQDTTKKA | 27 | 73 |
| LAHQDTTRNA | 28 | 74 |
| LAHQDTTTNA | 29 | 75 |
| LAHQGTTKNA | 30 | 76 |
| LAHQVTTKNA | 31 | 77 |
| LAISDQSKPA | 32 | 78 |
| LAKDATKTA | 33 | 79 |
| LAKDTTKNA | 34 | 80 |
| LAKSDQSRPA | 35 | 81 |
| LAPQDTKKNA | 36 | 82 |
| LATSDSTKAA | 37 | 83 |
| LAVDGSQRSA | 38 | 84 |
| LPISDQTKHA | 39 | 85 |
| LPKDATKTIA | 40 | 86 |
| LPPQDTTKNA | 41 | 87 |
| PAPQDTTKNA | 42 | 88 |
| QAHQDTTKNA | 43 | 89 |
| LAHETSPRPA | 44 | 90 |
| LAKSTSTAPA | 45 | 91 |
| LADQDTTKNA | 46 | 92 |
| LAESDQSKPA | 47 | 93 |
| LAHKDTTKNA | 48 | 94 |
| LAHKTQQKM | 49 | 95 |
| LAHQDTTENA | 50 | 96 |
| LAHQDTTINA | 51 | 97 |
| LAHQDTTKKT | 52 | 98 |
| LAHQDTTKND | 53 | 99 |
| LAHQDTTKNT | 54 | 100 |
| LAHQDTTKNV | 55 | 101 |
| LAHQDTTKTM | 56 | 102 |
| LAHQNTTKNA | 57 | 103 |
| LAHRDTTKNA | 58 | 104 |
| LAISDQTNHA | 59 | 105 |
| LAKQKSASTA | 60 | 106 |
| LAKSDQCKPA | 61 | 107 |
| LAKSDQSKPD | 62 | 108 |
| LAKSDQSNPA | 63 | 109 |
| LAKSYQSKPA | 64 | 110 |
| LANQDTTKNA | 65 | 111 |
| LAPQNTTKNA | 66 | 112 |
| LAPSSIQKPA | 67 | 113 |
| LAQQDTTKNA | 68 | 114 |
| LAYQDTTKNA | 69 | 115 |
| LDHQDTTKNA | 70 | 116 |
| LDHQDTTKSA | 71 | 117 |
| LGHQDTTKNA | 72 | 118 |
| LPHQDTTKND | 73 | 119 |
| LPHQDTTKNT | 74 | 120 |
| LPHQDTTNNA | 75 | 121 |
| LTHQDTTKNA | 76 | 122 |
| LTKDATKTIA | 77 | 123 |
| LTPQDTTKNA | 78 | 124 |
| LVHQDTTKNA | 79 | 125 |
| LAKANQNTPA | 80 | 126 |
| LATTPITKPA | 81 | 127 |
| LATTPIAKPA | 82 | 128 |
| LAIEDHTKSA | 83 | 129 |

TABLE 1-continued

| | Peptide No. | SEQ ID NO: |
|---|---|---|
| LAQSEHQRPA | 84 | 130 |
| LAKSPNKDNA | 85 | 131 |
| LANQDYTKTA | 86 | 132 |
| LANSTDQTRA | 87 | 133 |
| LALGETTRPA | 88 | 134 |
| LANSTEQTRA | 89 | 135 |
| LAQADTTKNA | 90 | 136 |
| LASKDITKTA | 91 | 137 |
| LASPRHNKKC | 92 | 138 |
| LAHQDTTKTIA | 93 | 139 |
| LAAQGTANL | 94 | 140 |
| VAIEDHTKSA | 95 | 141 |
| LAKANQNTPKNA | 96 | 142 |

The ability of the top 18 variants of the 96 variants depicted in Table 1 to infect the canine retina was further quantified using high throughput sequencing. Table 2 depicts the top 18 variants chosen for further quantification.

TABLE 2

| | |
|---|---|
| LAKDATKNA | (SEQ ID NO: 47) |
| PAHQDTTKNA | (SEQ ID NO: 48) |
| LAHQDTTKNA | (SEQ ID NO: 49) |
| LATTSQNKPA | (SEQ ID NO: 50) |
| LAISDQTKHA | (SEQ ID NO: 51) |
| IARGVAPSSA | (SEQ ID NO: 52) |
| LAPDSTTRSA | (SEQ ID NO: 53) |
| LAKGTELKPA | (SEQ ID NO: 54) |
| LAIIDATKNA | (SEQ ID NO: 55) |
| LAVDGAQRSA | (SEQ ID NO: 56) |
| PAPQDTTKKA | (SEQ ID NO: 57) |
| LPHQDTTKNA | (SEQ ID NO: 58) |
| LAKDATKTIA | (SEQ ID NO: 59) |
| LAKQQSASTA | (SEQ ID NO: 60) |
| LAKSDQSKPA | (SEQ ID NO: 61) |

TABLE 2-continued

| | |
|---|---|
| LSHQDTTKNA | (SEQ ID NO: 62) |
| LAANQPSKPA | (SEQ ID NO: 63) |
| LAVSDSTKAA | (SEQ ID NO: 64) |

Eighteen variants were packaged with a ubiquitous CAG promoter driving expression of GFP. The GFP cDNA was fused to a unique 25 base-pair bar code identifier. Each of the 18 variants was packaged with a unique GFP barcode. Packaged variants were mixed in equal ratios and injected into the retina, along with control AAV2-based vectors (negative controls representing the naturally occurring parental serotype). After injection, DNA and mRNA were collected from photoreceptor and RPE cells. DNA and mRNA levels were quantified to determine the ability of the canine-derived vectors to deliver DNA to the retina and lead to transgene expression (FIG. 2).

Figure 2:
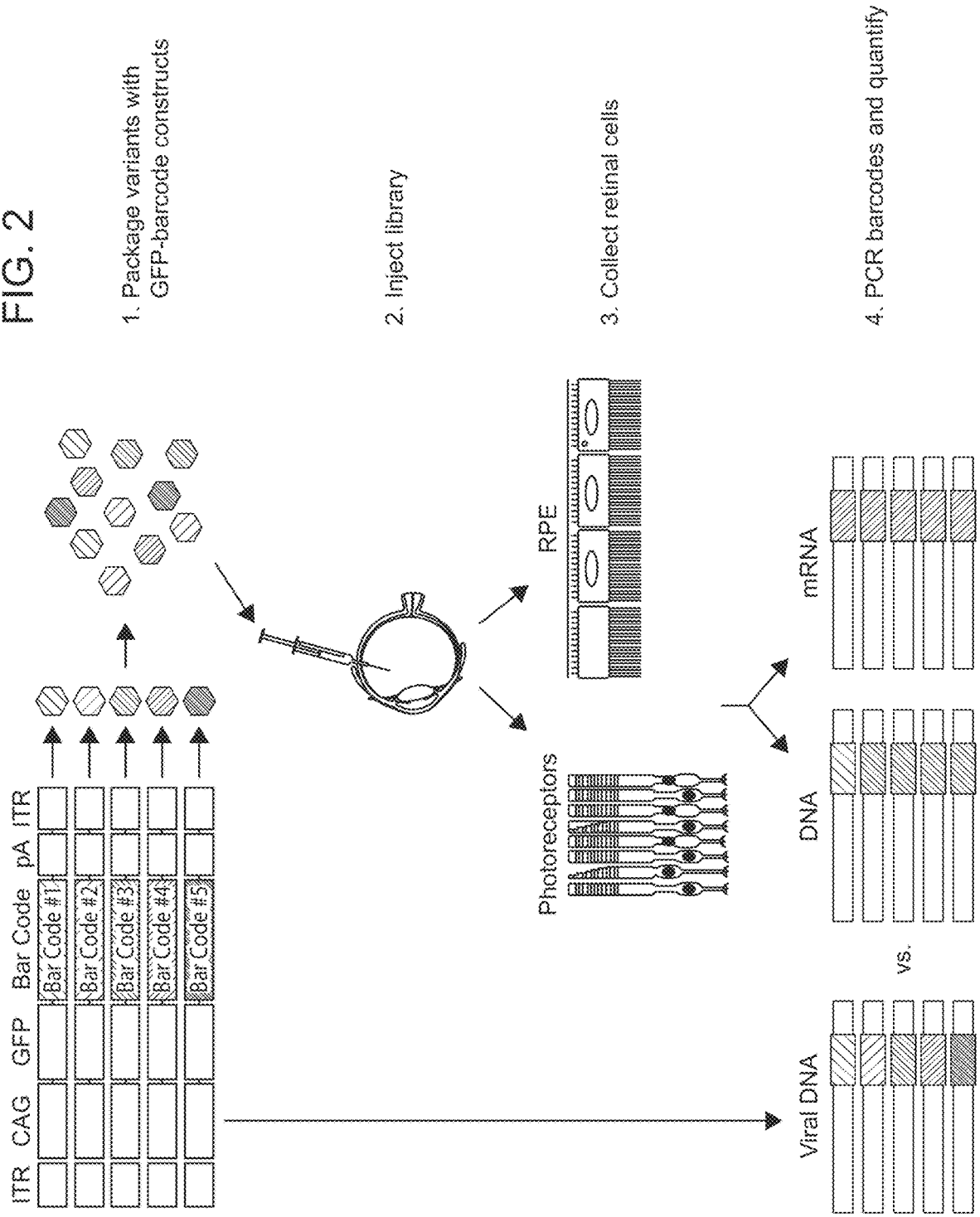
FIG. 2 is a schematic depiction of deep sequencing of AAV variants containing green fluorescent protein (GFP)-barcode constructs.

FIG. 2. Deep sequencing of variants containing GFP-barcode constructs. Infection of the canine retina by the canine-derived variants was quantified by deep sequencing of tagged GFP cDNA and mRNA.

Expression of the 18-member library was imaged using confocal microscopy of frozen retinal sections. GFP expression showed that retinal cells in the inner retina, and photoreceptors in the outer retina were targeted with the 18-member library (FIG. 3).

Figure 3:
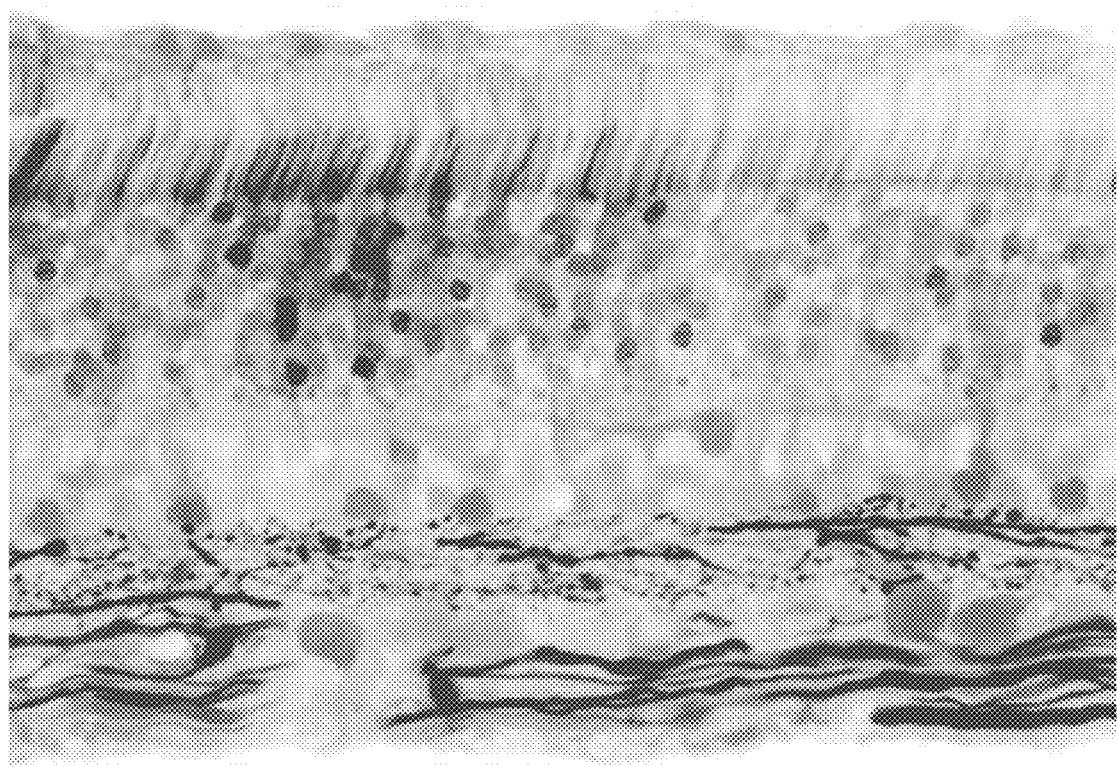
FIG. 3 depicts infection of cells in the ganglion cell layer, the inner nuclear layer, the photoreceptor layer, and the retinal pigment epithelium (RPE) layer, by an 18-member AAV variant library.

FIG. 3. The 18-member canine-derived AAV variant library infects cells in the ganglion cell layer, the inner nuclear layer, the photoreceptor layer, and the RPE layer.

Of the top 18 variants tested, 2 variants led to highest level of DNA and mRNA recovery. The variant leading to the highest level of DNA recovery had the insertion sequence ~588-PAPQDTTKKA (SEQ ID NO:57). The variant leading to the highest level of mRNA expression had the insertion sequence ~588-LAPDSTTRSA (SEQ ID NO:53).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A recombinant adeno-associated virus (rAAV) virion comprising:
   a) a variant AAV capsid protein, wherein the variant AAV capsid protein comprises an insertion of a heterologous peptide having a length of from 10 amino acids to 20 amino acids in the capsid protein GH loop relative to a corresponding parental AAV capsid protein, wherein the variant capsid protein confers increased infectivity of a retinal cell compared to the infectivity of the retinal cell by a control AAV virion comprising the corresponding parental AAV capsid protein, and
   wherein the heterologous peptide comprises the amino acid sequence LATTSQNKPA (SEQ ID NO:50); and
   b) a heterologous nucleic acid comprising a nucleotide sequence encoding a heterologous gene product.

2. The rAAV virion of claim 1, wherein the insertion site is between amino acids corresponding to amino acids 570 and 611 of VP1 of AAV2, or the corresponding position in the capsid protein of another AAV serotype.

3. The rAAV virion of claim 2, wherein the insertion site is located between amino acids corresponding to amino acids 587 and 588 of VP1 of AAV2, or the corresponding position in the capsid protein of another AAV serotype.

4. The rAAV virion of claim 1, wherein the gene product is:
   a) an interfering RNA or an aptamer;
   b) a polypeptide; or
   c) an RNA-guided endonuclease and a guide RNA.

5. The rAAV virion of claim 4, wherein the gene product is a polypeptide, and wherein the polypeptide is a neuroprotective polypeptide, an anti-angiogenic polypeptide, or a polypeptide that enhances function of a retinal cell, or an RNA-guided endonuclease.

6. The rAAV virion of claim 4, wherein the gene product is a polypeptide, and wherein the polypeptide is glial derived neurotrophic factor, fibroblast growth factor 2, neurturin, ciliary neurotrophic factor, nerve growth factor, brain derived neurotrophic factor, epidermal growth factor, rhodopsin, X-linked inhibitor of apoptosis, retinoschisin, RPE65, retinitis pigmentosa GTPase-interacting protein-1, peripherin, peripherin-2, a rhodopsin, RdCVF, retinitis pigmentosa GTPase regulator (RPGR), Sonic hedgehog, or an RNA-guided endonuclease.

7. A pharmaceutical composition comprising:
   a) a recombinant adeno-associated virus virion of claim 1; and
   b) a pharmaceutically acceptable excipient.

8. A method of delivering a gene product to a retinal cell in an individual, the method comprising administering to the individual a recombinant adeno-associated virus (rAAV) virion according to claim 1.

9. A method of treating an ocular disease, the method comprising administering to an individual in need thereof an effective amount of a recombinant adeno-associated virus (rAAV) virion according to claim 1.

10. An isolated nucleic acid comprising a nucleotide sequence that encodes a variant adeno-associated virus (AAV) capsid protein, wherein the variant AAV capsid protein comprises an insertion of a heterologous peptide having a length of from 10 amino acids to 20 amino acids in the capsid protein GH loop relative to a corresponding parental AAV capsid protein, and wherein the variant capsid protein, when present in an AAV virion, provides for increased infectivity of the AAV virion of a retinal cell, wherein the insertion is in the GH loop of a native AAV capsid, and
   wherein the heterologous peptide comprises the amino acid sequence LATTSQNKPA (SEQ ID NO:50).

11. The isolated nucleic acid of claim 10, wherein the insertion site is between amino acids corresponding to amino acids 570 and 611 of VP1 of AAV2, or the corresponding position in the capsid protein of another AAV serotype.

12. The isolated nucleic acid of claim 10, wherein the insertion site is between amino acids 587 and 588 of AAV2, between amino acids 590 and 591 of AAV1, between amino acids 575 and 576 of AAV5, between amino acids 590 and 591 of AAV6, between amino acids 589 and 590 of AAV7, between amino acids 590 and 591 of AAV8, between amino acids 588 and 589 of AAV9, or between amino acids 588 and 589 of AAV10.

13. A variant adeno-associated virus (AAV) capsid protein, wherein the variant AAV capsid protein comprises an insertion of a heterologous peptide having a length of from 10 amino acids to 20 amino acids wherein the insertion is in the GH loop of a native AAV capsid, and wherein the heterologous peptide comprises the amino acid sequence LATTSQNKPA (SEQ ID NO:50).

14. The variant AAV capsid protein of claim 13, wherein the insertion site is between amino acids corresponding to amino acids 570 and 611 of VP1 of AAV2, or the corresponding position in the capsid protein of another AAV serotype.

15. The variant AAV capsid protein of claim 13, wherein the insertion site is between amino acids 587 and 588 of AAV2, between amino acids 590 and 591 of AAV1, between amino acids 575 and 576 of AAV5, between amino acids 590 and 591 of AAV6, between amino acids 589 and 590 of AAV7, between amino acids 590 and 591 of AAV8, between amino acids 588 and 589 of AAV9, or between amino acids 588 and 589 of AAV10.

* * * * *

SEQUENCE LISTING

```
<160> NUMBER OF SEQ ID NOS: 152

<210> SEQ ID NO 1
<211> LENGTH: 733
<212> TYPE: PRT
<213> ORGANISM: Adeno-associated virus-2

<400> SEQUENCE: 1

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
```

-continued

```
                50                  55                  60
Val Asn Glu Ala Asp Ala Ala Leu Glu His Asp Lys Ala Tyr Asp
 65                  70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Pro Val Lys Thr Ala Pro Gly Lys Lys Arg
        130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480
```

```
Pro Cys Tyr Arg Gln Gln Arg Val Ser Lys Thr Ser Ala Asp Asn Asn
            485                 490                 495

Asn Ser Glu Tyr Ser Trp Thr Gly Ala Thr Lys Tyr His Leu Asn Gly
        500                 505                 510

Arg Asp Ser Leu Val Asn Pro Gly Pro Ala Met Ala Ser His Lys Asp
    515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg
                725                 730

<210> SEQ ID NO 2
<211> LENGTH: 42
<212> TYPE: PRT
<213> ORGANISM: Adeno-associated virus-2

<400> SEQUENCE: 2

Pro Val Ala Thr Glu Gln Tyr Gly Ser Val Ser Thr Asn Leu Gln Arg
1               5                   10                  15

Gly Asn Arg Gln Ala Ala Thr Ala Asp Val Asn Thr Gln Gly Val Leu
            20                  25                  30

Pro Gly Met Val Trp Gln Asp Arg Asp Val
        35                  40

<210> SEQ ID NO 3
<211> LENGTH: 42
<212> TYPE: PRT
<213> ORGANISM: Adeno-associated virus-1

<400> SEQUENCE: 3

Pro Val Ala Thr Glu Arg Phe Gly Thr Val Ala Val Asn Phe Gln Ser
1               5                   10                  15

Ser Ser Thr Asp Pro Ala Thr Gly Asp Val His Ala Met Gly Ala Leu
            20                  25                  30
```

-continued

Pro Gly Met Val Trp Gln Asp Arg Asp Val
        35                  40

<210> SEQ ID NO 4
<211> LENGTH: 42
<212> TYPE: PRT
<213> ORGANISM: Adeno-associated virus-5

<400> SEQUENCE: 4

Arg Val Ala Tyr Asn Val Gly Gly Gln Met Ala Thr Asn Asn Gln Ser
1               5                   10                  15

Ser Thr Thr Ala Pro Ala Thr Gly Thr Tyr Asn Leu Gln Glu Ile Val
            20                  25                  30

Pro Gly Ser Val Trp Met Glu Arg Asp Val
        35                  40

<210> SEQ ID NO 5
<211> LENGTH: 42
<212> TYPE: PRT
<213> ORGANISM: Adeno-associated virus-6

<400> SEQUENCE: 5

Pro Val Ala Thr Glu Arg Phe Gly Thr Val Ala Val Asn Leu Gln Ser
1               5                   10                  15

Ser Ser Thr Asp Pro Ala Thr Gly Asp Val His Val Met Gly Ala Leu
            20                  25                  30

Pro Gly Met Val Trp Gln Asp Arg Asp Val
        35                  40

<210> SEQ ID NO 6
<211> LENGTH: 42
<212> TYPE: PRT
<213> ORGANISM: Adeno-associated virus-7

<400> SEQUENCE: 6

Pro Val Ala Thr Glu Glu Tyr Gly Ile Val Ser Ser Asn Leu Gln Ala
1               5                   10                  15

Ala Asn Thr Ala Ala Gln Thr Gln Val Val Asn Asn Gln Gly Ala Leu
            20                  25                  30

Pro Gly Met Val Trp Gln Asn Arg Asp Val
        35                  40

<210> SEQ ID NO 7
<211> LENGTH: 42
<212> TYPE: PRT
<213> ORGANISM: Adeno-associated virus-8

<400> SEQUENCE: 7

Pro Val Ala Thr Glu Glu Tyr Gly Ile Val Ala Asp Asn Leu Gln Gln
1               5                   10                  15

Gln Asn Thr Ala Pro Gln Ile Gly Thr Val Asn Ser Gln Gly Ala Leu
            20                  25                  30

Pro Gly Met Val Trp Gln Asn Arg Asp Val
        35                  40

<210> SEQ ID NO 8
<211> LENGTH: 42
<212> TYPE: PRT
<213> ORGANISM: Adeno-associated virus-9

<400> SEQUENCE: 8

```
Pro Val Thr Glu Ser Tyr Gly Gln Val Ala Thr Asn His Gln Ser
1               5                   10                  15

Ala Gln Ala Gln Ala Gln Thr Gly Trp Val Gln Asn Gln Gly Ile Leu
            20                  25                  30

Pro Gly Met Val Trp Gln Asp Arg Asp Val
            35                  40

<210> SEQ ID NO 9
<211> LENGTH: 42
<212> TYPE: PRT
<213> ORGANISM: Adeno-associated virus-10

<400> SEQUENCE: 9

Pro Val Thr Glu Gln Tyr Gly Val Val Ala Asp Asn Leu Gln Gln
1               5                   10                  15

Ala Asn Thr Gly Pro Ile Val Gly Asn Val Asn Ser Gln Gly Ala Leu
            20                  25                  30

Pro Gly Met Val Trp Gln Asn Arg Asp Val
            35                  40

<210> SEQ ID NO 10
<211> LENGTH: 224
<212> TYPE: PRT
<213> ORGANISM: Homo sapiens

<400> SEQUENCE: 10

Met Ser Arg Lys Ile Glu Gly Phe Leu Leu Leu Leu Leu Phe Gly Tyr
1               5                   10                  15

Glu Ala Thr Leu Gly Leu Ser Ser Thr Glu Asp Glu Gly Glu Asp Pro
            20                  25                  30

Trp Tyr Gln Lys Ala Cys Lys Cys Asp Cys Gln Gly Gly Pro Asn Ala
            35                  40                  45

Leu Trp Ser Ala Gly Ala Thr Ser Leu Asp Cys Ile Pro Glu Cys Pro
50                  55                  60

Tyr His Lys Pro Leu Gly Phe Glu Ser Gly Glu Val Thr Pro Asp Gln
65                  70                  75                  80

Ile Thr Cys Ser Asn Pro Glu Gln Tyr Val Gly Trp Tyr Ser Ser Trp
                85                  90                  95

Thr Ala Asn Lys Ala Arg Leu Asn Ser Gln Gly Phe Gly Cys Ala Trp
            100                 105                 110

Leu Ser Lys Phe Gln Asp Ser Ser Gln Trp Leu Gln Ile Asp Leu Lys
        115                 120                 125

Glu Ile Lys Val Ile Ser Gly Ile Leu Thr Gln Gly Arg Cys Asp Ile
130                 135                 140

Asp Glu Trp Met Thr Lys Tyr Ser Val Gln Tyr Arg Thr Asp Glu Arg
145                 150                 155                 160

Leu Asn Trp Ile Tyr Tyr Lys Asp Gln Thr Gly Asn Asn Arg Val Phe
                165                 170                 175

Tyr Gly Asn Ser Asp Arg Thr Ser Thr Val Gln Asn Leu Leu Arg Pro
            180                 185                 190

Pro Ile Ile Ser Arg Phe Ile Arg Leu Ile Pro Leu Gly Trp His Val
        195                 200                 205

Arg Ile Ala Ile Arg Met Glu Leu Leu Glu Cys Val Ser Lys Cys Ala
    210                 215                 220

<210> SEQ ID NO 11
```

```
<211> LENGTH: 247
<212> TYPE: PRT
<213> ORGANISM: Homo sapiens

<400> SEQUENCE: 11

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
50                  55                  60

His Val Ile Glu Glu Leu Leu Asp Glu Asp His Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Met Val Leu Arg
        115                 120                 125

His Ser Asp Pro Ala Arg Arg Gly Glu Leu Ser Val Cys Asp Ser Ile
130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Arg Gly Arg
                245

<210> SEQ ID NO 12
<211> LENGTH: 533
<212> TYPE: PRT
<213> ORGANISM: Homo sapiens

<400> SEQUENCE: 12

Met Ser Ile Gln Val Glu His Pro Ala Gly Gly Tyr Lys Lys Leu Phe
1               5                   10                  15

Glu Thr Val Glu Glu Leu Ser Ser Pro Leu Thr Ala His Val Thr Gly
            20                  25                  30

Arg Ile Pro Leu Trp Leu Thr Gly Ser Leu Leu Arg Cys Gly Pro Gly
        35                  40                  45

Leu Phe Glu Val Gly Ser Glu Pro Phe Tyr His Leu Phe Asp Gly Gln
50                  55                  60

Ala Leu Leu His Lys Phe Asp Phe Lys Glu Gly His Val Thr Tyr His
65                  70                  75                  80

Arg Arg Phe Ile Arg Thr Asp Ala Tyr Val Arg Ala Met Thr Glu Lys
                85                  90                  95
```

```
Arg Ile Val Ile Thr Glu Phe Gly Thr Cys Ala Phe Pro Asp Pro Cys
            100                 105                 110
Lys Asn Ile Phe Ser Arg Phe Ser Tyr Phe Arg Gly Val Glu Val
            115                 120             125
Thr Asp Asn Ala Leu Val Asn Val Tyr Pro Val Gly Glu Asp Tyr Tyr
            130                 135                 140
Ala Cys Thr Glu Thr Asn Phe Ile Thr Lys Ile Asn Pro Glu Thr Leu
145                 150                 155                 160
Glu Thr Ile Lys Gln Val Asp Leu Cys Asn Tyr Val Ser Val Asn Gly
                165                 170                 175
Ala Thr Ala His Pro His Ile Glu Asn Asp Gly Thr Val Tyr Asn Ile
            180                 185                 190
Gly Asn Cys Phe Gly Lys Asn Phe Ser Ile Ala Tyr Asn Ile Val Lys
            195                 200                 205
Ile Pro Pro Leu Gln Ala Asp Lys Glu Asp Pro Ile Ser Lys Ser Glu
            210                 215                 220
Ile Val Val Gln Phe Pro Cys Ser Asp Arg Phe Lys Pro Ser Tyr Val
225                 230                 235                 240
His Ser Phe Gly Leu Thr Pro Asn Tyr Ile Val Phe Val Glu Thr Pro
                245                 250                 255
Val Lys Ile Asn Leu Phe Lys Phe Leu Ser Ser Trp Ser Leu Trp Gly
            260                 265                 270
Ala Asn Tyr Met Asp Cys Phe Glu Ser Asn Glu Thr Met Gly Val Trp
            275                 280                 285
Leu His Ile Ala Asp Lys Lys Arg Lys Lys Tyr Leu Asn Asn Lys Tyr
            290                 295                 300
Arg Thr Ser Pro Phe Asn Leu Phe His His Ile Asn Thr Tyr Glu Asp
305                 310                 315                 320
Asn Gly Phe Leu Ile Val Asp Leu Cys Cys Trp Lys Gly Phe Glu Phe
                325                 330                 335
Val Tyr Asn Tyr Leu Tyr Leu Ala Asn Leu Arg Glu Asn Trp Glu Glu
            340                 345                 350
Val Lys Lys Asn Ala Arg Lys Ala Pro Gln Pro Glu Val Arg Arg Tyr
            355                 360                 365
Val Leu Pro Leu Asn Ile Asp Lys Ala Asp Thr Gly Lys Asn Leu Val
            370                 375                 380
Thr Leu Pro Asn Thr Thr Ala Thr Ala Ile Leu Cys Ser Asp Glu Thr
385                 390                 395                 400
Ile Trp Leu Glu Pro Glu Val Leu Phe Ser Gly Pro Arg Gln Ala Phe
                405                 410                 415
Glu Phe Pro Gln Ile Asn Tyr Gln Lys Tyr Cys Gly Lys Pro Tyr Thr
            420                 425                 430
Tyr Ala Tyr Gly Leu Gly Leu Asn His Phe Val Pro Asp Arg Leu Cys
            435                 440                 445
Lys Leu Asn Val Lys Thr Lys Glu Thr Trp Val Trp Gln Glu Pro Asp
            450                 455                 460
Ser Tyr Pro Ser Glu Pro Ile Phe Val Ser His Pro Asp Ala Leu Glu
465                 470                 475                 480
Glu Asp Asp Gly Val Val Leu Ser Val Val Ser Pro Gly Ala Gly
                485                 490                 495
Gln Lys Pro Ala Tyr Leu Leu Ile Leu Asn Ala Lys Asp Leu Ser Glu
            500                 505                 510
```

```
Val Ala Arg Ala Glu Val Glu Ile Asn Ile Pro Val Thr Phe His Gly
            515                 520                 525

Leu Phe Lys Lys Ser
            530

<210> SEQ ID NO 13
<211> LENGTH: 346
<212> TYPE: PRT
<213> ORGANISM: Homo sapiens

<400> SEQUENCE: 13

Met Ala Leu Leu Lys Val Lys Phe Asp Gln Lys Lys Arg Val Lys Leu
1               5                   10                  15

Ala Gln Gly Leu Trp Leu Met Asn Trp Phe Ser Val Leu Ala Gly Ile
            20                  25                  30

Ile Ile Phe Ser Leu Gly Leu Phe Leu Lys Ile Glu Leu Arg Lys Arg
            35                  40                  45

Ser Asp Val Met Asn Asn Ser Glu Ser His Phe Val Pro Asn Ser Leu
        50                  55                  60

Ile Gly Met Gly Val Leu Ser Cys Val Phe Asn Ser Leu Ala Gly Lys
65                  70                  75                  80

Ile Cys Tyr Asp Ala Leu Asp Pro Ala Lys Tyr Ala Arg Trp Lys Pro
                85                  90                  95

Trp Leu Lys Pro Tyr Leu Ala Ile Cys Val Leu Phe Asn Ile Ile Leu
            100                 105                 110

Phe Leu Val Ala Leu Cys Cys Phe Leu Leu Arg Gly Ser Leu Glu Asn
            115                 120                 125

Thr Leu Gly Gln Gly Leu Lys Asn Gly Met Lys Tyr Tyr Arg Asp Thr
        130                 135                 140

Asp Thr Pro Gly Arg Cys Phe Met Lys Lys Thr Ile Asp Met Leu Gln
145                 150                 155                 160

Ile Glu Phe Lys Cys Cys Gly Asn Asn Gly Phe Arg Asp Trp Phe Glu
                165                 170                 175

Ile Gln Trp Ile Ser Asn Arg Tyr Leu Asp Phe Ser Ser Lys Glu Val
            180                 185                 190

Lys Asp Arg Ile Lys Ser Asn Val Asp Gly Arg Tyr Leu Val Asp Gly
            195                 200                 205

Val Pro Phe Ser Cys Cys Asn Pro Ser Ser Pro Arg Pro Cys Ile Gln
        210                 215                 220

Tyr Gln Ile Thr Asn Asn Ser Ala His Tyr Ser Tyr Asp His Gln Thr
225                 230                 235                 240

Glu Glu Leu Asn Leu Trp Val Arg Gly Cys Arg Ala Ala Leu Leu Ser
                245                 250                 255

Tyr Tyr Ser Ser Leu Met Asn Ser Met Gly Val Val Thr Leu Leu Ile
            260                 265                 270

Trp Leu Phe Glu Val Thr Ile Thr Ile Gly Leu Arg Tyr Leu Gln Thr
            275                 280                 285

Ser Leu Asp Gly Val Ser Asn Pro Glu Glu Ser Glu Ser Glu Ser Gln
        290                 295                 300

Gly Trp Leu Leu Glu Arg Ser Val Pro Glu Thr Trp Lys Ala Phe Leu
305                 310                 315                 320

Glu Ser Val Lys Lys Leu Gly Lys Gly Asn Gln Val Glu Ala Glu Gly
                325                 330                 335

Ala Asp Ala Gly Gln Ala Pro Glu Ala Gly
            340                 345
```

<210> SEQ ID NO 14
<211> LENGTH: 470
<212> TYPE: PRT
<213> ORGANISM: Homo sapiens

<400> SEQUENCE: 14

```
Met Ser His His Pro Ser Gly Leu Arg Ala Gly Phe Ser Thr Ser
1               5                   10                  15

Tyr Arg Arg Thr Phe Gly Pro Pro Ser Leu Ser Pro Gly Ala Phe
                20                  25                  30

Ser Tyr Ser Ser Ser Ser Arg Phe Ser Ser Arg Leu Leu Gly Ser
                35                  40                  45

Ala Ser Pro Ser Ser Ser Val Arg Leu Gly Ser Phe Arg Ser Pro Arg
    50                  55                  60

Ala Gly Ala Gly Ala Leu Leu Arg Leu Pro Ser Glu Arg Leu Asp Phe
65                  70                  75                  80

Ser Met Ala Glu Ala Leu Asn Gln Glu Phe Leu Ala Thr Arg Ser Asn
                85                  90                  95

Glu Lys Gln Glu Leu Gln Glu Leu Asn Asp Arg Phe Ala Asn Phe Ile
                100                 105                 110

Glu Lys Val Arg Phe Leu Glu Gln Gln Asn Ala Ala Leu Arg Gly Glu
                115                 120                 125

Leu Ser Gln Ala Arg Gly Gln Glu Pro Ala Arg Ala Asp Gln Leu Cys
130                 135                 140

Gln Gln Glu Leu Arg Glu Leu Arg Arg Glu Leu Glu Leu Leu Gly Arg
145                 150                 155                 160

Glu Arg Asp Arg Val Gln Val Glu Arg Asp Gly Leu Ala Glu Asp Leu
                165                 170                 175

Ala Ala Leu Lys Gln Arg Leu Glu Glu Glu Thr Arg Lys Arg Glu Asp
                180                 185                 190

Ala Glu His Asn Leu Val Leu Phe Arg Lys Asp Val Asp Asp Ala Thr
                195                 200                 205

Leu Ser Arg Leu Glu Leu Glu Arg Lys Ile Glu Ser Leu Met Asp Glu
210                 215                 220

Ile Glu Phe Leu Lys Lys Leu His Glu Glu Glu Leu Arg Asp Leu Gln
225                 230                 235                 240

Val Ser Val Glu Ser Gln Gln Val Gln Gln Val Glu Val Glu Ala Thr
                245                 250                 255

Val Lys Pro Glu Leu Thr Ala Ala Leu Arg Asp Ile Arg Ala Gln Tyr
                260                 265                 270

Glu Ser Ile Ala Ala Lys Asn Leu Gln Glu Ala Glu Glu Trp Tyr Lys
                275                 280                 285

Ser Lys Tyr Ala Asp Leu Ser Asp Ala Ala Asn Arg Asn His Glu Ala
290                 295                 300

Leu Arg Gln Ala Lys Gln Glu Met Asn Glu Ser Arg Arg Gln Ile Gln
305                 310                 315                 320

Ser Leu Thr Cys Glu Val Asp Gly Leu Arg Gly Thr Asn Glu Ala Leu
                325                 330                 335

Leu Arg Gln Leu Arg Glu Leu Glu Glu Gln Phe Ala Leu Glu Ala Gly
                340                 345                 350

Gly Tyr Gln Ala Gly Ala Ala Arg Leu Glu Glu Glu Leu Arg Gln Leu
                355                 360                 365

Lys Glu Glu Met Ala Arg His Leu Arg Glu Tyr Gln Glu Leu Leu Asn
```

-continued

```
                    370                 375                 380
Val Lys Met Ala Leu Asp Ile Glu Ile Ala Thr Tyr Arg Lys Leu Leu
385                 390                 395                 400

Glu Gly Glu Glu Ser Arg Ile Ser Val Pro Val His Ser Phe Ala Ser
                    405                 410                 415

Leu Asn Ile Lys Thr Thr Val Pro Glu Val Pro Pro Gln Asp Ser
                420                 425                 430

His Ser Arg Lys Thr Val Leu Ile Lys Thr Ile Glu Thr Arg Asn Gly
                435                 440                 445

Glu Val Val Thr Glu Ser Gln Lys Glu Gln Arg Ser Glu Leu Asp Lys
450                 455                 460

Ser Ser Ala His Ser Tyr
465                 470

<210> SEQ ID NO 15
<211> LENGTH: 1286
<212> TYPE: PRT
<213> ORGANISM: Homo sapiens

<400> SEQUENCE: 15

Met Ser His Leu Val Asp Pro Thr Ser Gly Asp Leu Pro Val Arg Asp
1               5                   10                  15

Ile Asp Ala Ile Pro Leu Val Leu Pro Ala Ser Lys Gly Lys Asn Met
                20                  25                  30

Lys Thr Gln Pro Pro Leu Ser Arg Met Asn Arg Glu Glu Leu Glu Asp
            35                  40                  45

Ser Phe Phe Arg Leu Arg Glu Asp His Met Leu Val Lys Glu Leu Ser
    50                  55                  60

Trp Lys Gln Gln Asp Glu Ile Lys Arg Leu Arg Thr Thr Leu Leu Arg
65                  70                  75                  80

Leu Thr Ala Ala Gly Arg Asp Leu Arg Val Ala Glu Glu Ala Ala Pro
                85                  90                  95

Leu Ser Glu Thr Ala Arg Arg Gly Gln Lys Ala Gly Trp Arg Gln Arg
                100                 105                 110

Leu Ser Met His Gln Arg Pro Gln Met His Arg Leu Gly His Phe
            115                 120                 125

His Cys Val Gly Pro Ala Ser Pro Arg Arg Ala Gln Pro Arg Val Gln
    130                 135                 140

Val Gly His Arg Gln Leu His Thr Ala Gly Ala Pro Val Pro Glu Lys
145                 150                 155                 160

Pro Lys Arg Gly Pro Arg Asp Arg Leu Ser Tyr Thr Ala Pro Ser
                165                 170                 175

Phe Lys Glu His Ala Thr Asn Glu Asn Arg Gly Glu Val Ala Ser Lys
                180                 185                 190

Pro Ser Glu Leu Val Ser Gly Ser Asn Ser Ile Ile Ser Phe Ser Ser
            195                 200                 205

Val Ile Ser Met Ala Lys Pro Ile Gly Leu Cys Met Pro Asn Ser Ala
    210                 215                 220

His Ile Met Ala Ser Asn Thr Met Gln Val Glu Glu Pro Pro Lys Ser
225                 230                 235                 240

Pro Glu Lys Met Trp Pro Lys Asp Glu Asn Phe Glu Gln Arg Ser Ser
                245                 250                 255

Leu Glu Cys Ala Gln Lys Ala Ala Glu Leu Arg Ala Ser Ile Lys Glu
                260                 265                 270
```

```
Lys Val Glu Leu Ile Arg Leu Lys Lys Leu Leu His Glu Arg Asn Ala
            275                 280                 285

Ser Leu Val Met Thr Lys Ala Gln Leu Thr Glu Val Gln Glu Ala Tyr
        290                 295                 300

Glu Thr Leu Leu Gln Lys Asn Gln Gly Ile Leu Ser Ala Ala His Glu
305                 310                 315                 320

Ala Leu Leu Lys Gln Val Asn Glu Leu Arg Ala Glu Leu Lys Glu Glu
                325                 330                 335

Ser Lys Lys Ala Val Ser Leu Lys Ser Gln Leu Glu Asp Val Ser Ile
            340                 345                 350

Leu Gln Met Thr Leu Lys Glu Phe Gln Glu Arg Val Glu Asp Leu Glu
        355                 360                 365

Lys Glu Arg Lys Leu Leu Asn Asp Asn Tyr Asp Lys Leu Leu Glu Ser
    370                 375                 380

Met Leu Asp Ser Ser Asp Ser Ser Ser Gln Pro His Trp Ser Asn Glu
385                 390                 395                 400

Leu Ile Ala Glu Gln Leu Gln Gln Gln Val Ser Gln Leu Gln Asp Gln
                405                 410                 415

Leu Asp Ala Glu Leu Glu Asp Lys Arg Lys Val Leu Leu Glu Leu Ser
            420                 425                 430

Arg Glu Lys Ala Gln Asn Glu Asp Leu Lys Leu Glu Val Thr Asn Ile
        435                 440                 445

Leu Gln Lys His Lys Gln Glu Val Glu Leu Leu Gln Asn Ala Ala Thr
    450                 455                 460

Ile Ser Gln Pro Pro Asp Arg Gln Ser Glu Pro Ala Thr His Pro Ala
465                 470                 475                 480

Val Leu Gln Glu Asn Thr Gln Ile Glu Pro Ser Glu Pro Lys Asn Gln
                485                 490                 495

Glu Glu Lys Lys Leu Ser Gln Val Leu Asn Glu Leu Gln Val Ser His
            500                 505                 510

Ala Glu Thr Thr Leu Glu Leu Glu Lys Thr Arg Asp Met Leu Ile Leu
        515                 520                 525

Gln Arg Lys Ile Asn Val Cys Tyr Gln Glu Glu Leu Glu Ala Met Met
    530                 535                 540

Thr Lys Ala Asp Asn Asp Asn Arg Asp His Lys Glu Lys Leu Glu Arg
545                 550                 555                 560

Leu Thr Arg Leu Leu Asp Leu Lys Asn Asn Arg Ile Lys Gln Leu Glu
                565                 570                 575

Gly Ile Leu Arg Ser His Asp Leu Pro Thr Ser Glu Gln Leu Lys Asp
            580                 585                 590

Val Ala Tyr Gly Thr Arg Pro Leu Ser Leu Cys Leu Glu Thr Leu Pro
        595                 600                 605

Ala His Gly Asp Glu Asp Lys Val Asp Ile Ser Leu Leu His Gln Gly
    610                 615                 620

Glu Asn Leu Phe Glu Leu His Ile His Gln Ala Phe Leu Thr Ser Ala
625                 630                 635                 640

Ala Leu Ala Gln Ala Gly Asp Thr Gln Pro Thr Thr Phe Cys Thr Tyr
                645                 650                 655

Ser Phe Tyr Asp Phe Glu Thr His Cys Thr Pro Leu Ser Val Gly Pro
            660                 665                 670

Gln Pro Leu Tyr Asp Phe Thr Ser Gln Tyr Val Met Glu Thr Asp Ser
        675                 680                 685

Leu Phe Leu His Tyr Leu Gln Glu Ala Ser Ala Arg Leu Asp Ile His
```

```
            690             695             700
Gln Ala Met Ala Ser Glu His Ser Thr Leu Ala Ala Gly Trp Ile Cys
705             710             715             720

Phe Asp Arg Val Leu Glu Thr Val Glu Lys Val His Gly Leu Ala Thr
            725             730             735

Leu Ile Gly Ala Gly Gly Glu Glu Phe Gly Val Leu Glu Tyr Trp Met
            740             745             750

Arg Leu Arg Phe Pro Ile Lys Pro Ser Leu Gln Ala Cys Asn Lys Arg
            755             760             765

Lys Lys Ala Gln Val Tyr Leu Ser Thr Asp Val Leu Gly Gly Arg Lys
            770             775             780

Ala Gln Glu Glu Glu Phe Arg Ser Glu Ser Trp Glu Pro Gln Asn Glu
785             790             795             800

Leu Trp Ile Glu Ile Thr Lys Cys Cys Gly Leu Arg Ser Arg Trp Leu
            805             810             815

Gly Thr Gln Pro Ser Pro Tyr Ala Val Tyr Arg Phe Phe Thr Phe Ser
            820             825             830

Asp His Asp Thr Ala Ile Ile Pro Ala Ser Asn Asn Pro Tyr Phe Arg
            835             840             845

Asp Gln Ala Arg Phe Pro Val Leu Val Thr Ser Asp Leu Asp His Tyr
            850             855             860

Leu Arg Arg Glu Ala Leu Ser Ile His Val Phe Asp Asp Glu Asp Leu
865             870             875             880

Glu Pro Gly Ser Tyr Leu Gly Arg Ala Arg Val Pro Leu Leu Pro Leu
            885             890             895

Ala Lys Asn Glu Ser Ile Lys Gly Asp Phe Asn Leu Thr Asp Pro Ala
            900             905             910

Glu Lys Pro Asn Gly Ser Ile Gln Val Gln Leu Asp Trp Lys Phe Pro
            915             920             925

Tyr Ile Pro Pro Glu Ser Phe Leu Lys Pro Glu Ala Gln Thr Lys Gly
            930             935             940

Lys Asp Thr Lys Asp Ser Ser Lys Ile Ser Ser Glu Glu Lys Ala
945             950             955             960

Ser Phe Pro Ser Gln Asp Gln Met Ala Ser Pro Glu Val Pro Ile Glu
            965             970             975

Ala Gly Gln Tyr Arg Ser Lys Arg Lys Pro Pro His Gly Gly Glu Arg
            980             985             990

Lys Glu Lys Glu His Gln Val Val Ser Tyr Ser Arg Arg Lys His Gly
            995             1000            1005

Lys Arg Ile Gly Val Gln Gly Lys Asn Arg Met Glu Tyr Leu Ser
    1010            1015            1020

Leu Asn Ile Leu Asn Gly Asn Thr Pro Glu Gln Val Asn Tyr Thr
    1025            1030            1035

Glu Trp Lys Phe Ser Glu Thr Asn Ser Phe Ile Gly Asp Gly Phe
    1040            1045            1050

Lys Asn Gln His Glu Glu Glu Met Thr Leu Ser His Ser Ala
    1055            1060            1065

Leu Lys Gln Lys Glu Pro Leu His Pro Val Asn Asp Lys Glu Ser
    1070            1075            1080

Ser Glu Gln Gly Ser Glu Val Ser Glu Ala Gln Thr Thr Asp Ser
    1085            1090            1095

Asp Asp Val Ile Val Pro Pro Met Ser Gln Lys Tyr Pro Lys Ala
    1100            1105            1110
```

Asp Ser Glu Lys Met Cys Ile Glu Ile Val Ser Leu Ala Phe Tyr
1115                 1120                1125

Pro Glu Ala Glu Val Met Ser Asp Glu Asn Ile Lys Gln Val Tyr
1130                 1135                1140

Val Glu Tyr Lys Phe Tyr Asp Leu Pro Leu Ser Glu Thr Glu Thr
1145                 1150                1155

Pro Val Ser Leu Arg Lys Pro Arg Ala Gly Glu Glu Ile His Phe
1160                 1165                1170

His Phe Ser Lys Val Ile Asp Leu Asp Pro Gln Glu Gln Gln Gly
1175                 1180                1185

Arg Arg Arg Phe Leu Phe Asp Met Leu Asn Gly Gln Asp Pro Asp
1190                 1195                1200

Gln Gly His Leu Lys Phe Thr Val Val Ser Asp Pro Leu Asp Glu
1205                 1210                1215

Glu Lys Lys Glu Cys Glu Glu Val Gly Tyr Ala Tyr Leu Gln Leu
1220                 1225                1230

Trp Gln Ile Leu Glu Ser Gly Arg Asp Ile Leu Glu Gln Glu Leu
1235                 1240                1245

Asp Ile Val Ser Pro Glu Asp Leu Ala Thr Pro Ile Gly Arg Leu
1250                 1255                1260

Lys Val Ser Leu Gln Ala Ala Ala Val Leu His Ala Ile Tyr Lys
1265                 1270                1275

Glu Met Thr Glu Asp Leu Phe Ser
1280                 1285

<210> SEQ ID NO 16
<211> LENGTH: 653
<212> TYPE: PRT
<213> ORGANISM: Homo sapiens

<400> SEQUENCE: 16

Met Ala Asp Thr Leu Pro Ser Glu Phe Asp Val Ile Val Ile Gly Thr
1               5                   10                  15

Gly Leu Pro Glu Ser Ile Ile Ala Ala Ala Cys Ser Arg Ser Gly Arg
                20                  25                  30

Arg Val Leu His Val Asp Ser Arg Ser Tyr Tyr Gly Gly Asn Trp Ala
            35                  40                  45

Ser Phe Ser Phe Ser Gly Leu Leu Ser Trp Leu Lys Glu Tyr Gln Glu
        50                  55                  60

Asn Ser Asp Ile Val Ser Asp Ser Pro Val Trp Gln Asp Gln Ile Leu
65                  70                  75                  80

Glu Asn Glu Glu Ala Ile Ala Leu Ser Arg Lys Asp Lys Thr Ile Gln
                85                  90                  95

His Val Glu Val Phe Cys Tyr Ala Ser Gln Asp Leu His Glu Asp Val
            100                 105                 110

Glu Glu Ala Gly Ala Leu Gln Lys Asn His Ala Leu Val Thr Ser Ala
        115                 120                 125

Asn Ser Thr Glu Ala Ala Asp Ser Ala Phe Leu Pro Thr Glu Asp Glu
    130                 135                 140

Ser Leu Ser Thr Met Ser Cys Glu Met Leu Thr Glu Gln Thr Pro Ser
145                 150                 155                 160

Ser Asp Pro Glu Asn Ala Leu Glu Val Asn Gly Ala Glu Val Thr Gly
                165                 170                 175

Glu Lys Glu Asn His Cys Asp Asp Lys Thr Cys Val Pro Ser Thr Ser

-continued

```
                180                 185                 190
Ala Glu Asp Met Ser Glu Asn Val Pro Ile Ala Glu Asp Thr Thr Glu
                    195                 200                 205

Gln Pro Lys Lys Asn Arg Ile Thr Tyr Ser Gln Ile Ile Lys Glu Gly
        210                 215                 220

Arg Arg Phe Asn Ile Asp Leu Val Ser Lys Leu Leu Tyr Ser Arg Gly
225                 230                 235                 240

Leu Leu Ile Asp Leu Leu Ile Lys Ser Asn Val Ser Arg Tyr Ala Glu
                245                 250                 255

Phe Lys Asn Ile Thr Arg Ile Leu Ala Phe Arg Glu Gly Arg Val Glu
            260                 265                 270

Gln Val Pro Cys Ser Arg Ala Asp Val Phe Asn Ser Lys Gln Leu Thr
        275                 280                 285

Met Val Glu Lys Arg Met Leu Met Lys Phe Leu Thr Phe Cys Met Glu
    290                 295                 300

Tyr Glu Lys Tyr Pro Asp Glu Tyr Lys Gly Tyr Glu Glu Ile Thr Phe
305                 310                 315                 320

Tyr Glu Tyr Leu Lys Thr Gln Lys Leu Thr Pro Asn Leu Gln Tyr Ile
                325                 330                 335

Val Met His Ser Ile Ala Met Thr Ser Glu Thr Ala Ser Ser Thr Ile
            340                 345                 350

Asp Gly Leu Lys Ala Thr Lys Asn Phe Leu His Cys Leu Gly Arg Tyr
        355                 360                 365

Gly Asn Thr Pro Phe Leu Phe Pro Leu Tyr Gly Gln Gly Glu Leu Pro
    370                 375                 380

Gln Cys Phe Cys Arg Met Cys Ala Val Phe Gly Gly Ile Tyr Cys Leu
385                 390                 395                 400

Arg His Ser Val Gln Cys Leu Val Val Asp Lys Glu Ser Arg Lys Cys
                405                 410                 415

Lys Ala Ile Ile Asp Gln Phe Gly Gln Arg Ile Ile Ser Glu His Phe
            420                 425                 430

Leu Val Glu Asp Ser Tyr Phe Pro Glu Asn Met Cys Ser Arg Val Gln
        435                 440                 445

Tyr Arg Gln Ile Ser Arg Ala Val Leu Ile Thr Asp Arg Ser Val Leu
    450                 455                 460

Lys Thr Asp Ser Asp Gln Gln Ile Ser Ile Leu Thr Val Pro Ala Glu
465                 470                 475                 480

Glu Pro Gly Thr Phe Ala Val Arg Val Ile Glu Leu Cys Ser Ser Thr
                485                 490                 495

Met Thr Cys Met Lys Gly Thr Tyr Leu Val His Leu Thr Cys Thr Ser
            500                 505                 510

Ser Lys Thr Ala Arg Glu Asp Leu Glu Ser Val Val Gln Lys Leu Phe
        515                 520                 525

Val Pro Tyr Thr Glu Met Glu Ile Glu Asn Glu Gln Val Glu Lys Pro
    530                 535                 540

Arg Ile Leu Trp Ala Leu Tyr Phe Asn Met Arg Asp Ser Ser Asp Ile
545                 550                 555                 560

Ser Arg Ser Cys Tyr Asn Asp Leu Pro Ser Asn Val Tyr Val Cys Ser
                565                 570                 575

Gly Pro Asp Cys Gly Leu Gly Asn Asp Asn Ala Val Lys Gln Ala Glu
            580                 585                 590

Thr Leu Phe Gln Glu Ile Cys Pro Asn Glu Asp Phe Cys Pro Pro Pro
        595                 600                 605
```

Pro Asn Pro Glu Asp Ile Ile Leu Asp Gly Asp Ser Leu Gln Pro Glu
        610                 615                 620

Ala Ser Glu Ser Ser Ala Ile Pro Glu Ala Asn Ser Glu Thr Phe Lys
625                 630                 635                 640

Glu Ser Thr Asn Leu Gly Asn Leu Glu Glu Ser Ser Glu
                645                 650

<210> SEQ ID NO 17
<211> LENGTH: 212
<212> TYPE: PRT
<213> ORGANISM: Homo sapiens

<400> SEQUENCE: 17

Met Ala Ser Leu Phe Ser Gly Arg Ile Leu Ile Arg Asn Asn Ser Asp
1               5                   10                  15

Gln Asp Glu Leu Asp Thr Glu Ala Glu Val Ser Arg Arg Leu Glu Asn
            20                  25                  30

Arg Leu Val Leu Leu Phe Phe Gly Ala Gly Ala Cys Pro Gln Cys Gln
        35                  40                  45

Ala Phe Val Pro Ile Leu Lys Asp Phe Phe Val Arg Leu Thr Asp Glu
50                  55                  60

Phe Tyr Val Leu Arg Ala Ala Gln Leu Ala Leu Val Tyr Val Ser Gln
65                  70                  75                  80

Asp Ser Thr Glu Glu Gln Gln Asp Leu Phe Leu Lys Asp Met Pro Lys
                85                  90                  95

Lys Trp Leu Phe Leu Pro Phe Glu Asp Asp Leu Arg Arg Asp Leu Gly
            100                 105                 110

Arg Gln Phe Ser Val Glu Arg Leu Pro Ala Val Val Val Leu Lys Pro
        115                 120                 125

Asp Gly Asp Val Leu Thr Arg Asp Gly Ala Asp Glu Ile Gln Arg Leu
130                 135                 140

Gly Thr Ala Cys Phe Ala Asn Trp Gln Glu Ala Ala Glu Val Leu Asp
145                 150                 155                 160

Arg Asn Phe Gln Leu Pro Glu Asp Leu Glu Asp Gln Glu Pro Arg Ser
                165                 170                 175

Leu Thr Glu Cys Leu Arg Arg His Lys Tyr Arg Val Glu Lys Ala Ala
            180                 185                 190

Arg Gly Gly Arg Asp Pro Gly Gly Gly Glu Gly Gly Ala
        195                 200                 205

Gly Gly Leu Phe
    210

<210> SEQ ID NO 18
<211> LENGTH: 156
<212> TYPE: PRT
<213> ORGANISM: Homo sapiens

<400> SEQUENCE: 18

Met Val Asp Ile Leu Gly Glu Arg His Leu Val Thr Cys Lys Gly Ala
1               5                   10                  15

Thr Val Glu Ala Glu Ala Leu Gln Asn Lys Val Val Ala Leu Tyr
            20                  25                  30

Phe Ala Ala Ala Arg Cys Ala Pro Ser Arg Asp Phe Thr Pro Leu Leu
        35                  40                  45

Cys Asp Phe Tyr Thr Ala Leu Val Ala Glu Ala Arg Arg Pro Ala Pro
50                  55                  60

Phe Glu Val Val Phe Val Ser Ala Asp Gly Ser Gln Glu Met Leu
65                  70                  75                  80

Asp Phe Met Arg Glu Leu His Gly Ala Trp Leu Ala Leu Pro Phe His
                85                  90                  95

Asp Pro Tyr Arg His Glu Leu Arg Lys Arg Tyr Asn Val Thr Ala Ile
            100                 105                 110

Pro Lys Leu Val Ile Val Lys Gln Asn Gly Glu Val Ile Thr Asn Lys
        115                 120                 125

Gly Arg Lys Gln Ile Arg Glu Arg Gly Leu Ala Cys Phe Gln Asp Trp
    130                 135                 140

Val Glu Ala Ala Asp Ile Phe Gln Asn Phe Ser Val
145                 150                 155

<210> SEQ ID NO 19
<211> LENGTH: 135
<212> TYPE: PRT
<213> ORGANISM: Homo sapiens

<400> SEQUENCE: 19

Met Val Asp Ile Leu Gly Glu Arg His Leu Val Thr Cys Lys Gly Ala
1               5                   10                  15

Thr Val Glu Ala Glu Ala Leu Gln Asn Lys Val Val Ala Leu Tyr
            20                  25                  30

Phe Ala Ala Ala Arg Cys Ala Pro Ser Arg Asp Phe Thr Pro Leu Leu
            35                  40                  45

Cys Asp Phe Tyr Thr Ala Leu Val Ala Glu Ala Arg Arg Pro Ala Pro
50                  55                  60

Phe Glu Val Val Phe Val Ser Ala Asp Gly Ser Ser Gln Glu Met Leu
65                  70                  75                  80

Asp Phe Met Arg Glu Leu His Gly Ala Trp Leu Ala Leu Pro Phe His
                85                  90                  95

Asp Pro Tyr Arg Gln Arg Ser Leu Ala Leu Leu Pro Arg Leu Glu Cys
            100                 105                 110

Ser Gly Val Ile Leu Ala His Cys Asn Leu Cys Leu Leu Gly Ser Ser
        115                 120                 125

Asp Ser Leu Ala Leu Ala Ser
    130                 135

<210> SEQ ID NO 20
<211> LENGTH: 860
<212> TYPE: PRT
<213> ORGANISM: Homo sapiens

<400> SEQUENCE: 20

Met Gly Glu Val Thr Ala Glu Glu Val Glu Lys Phe Leu Asp Ser Asn
1               5                   10                  15

Ile Gly Phe Ala Lys Gln Tyr Tyr Asn Leu His Tyr Arg Ala Lys Leu
            20                  25                  30

Ile Ser Asp Leu Leu Gly Ala Lys Glu Ala Ala Val Asp Phe Ser Asn
        35                  40                  45

Tyr His Ser Pro Ser Ser Met Glu Glu Ser Glu Ile Ile Phe Asp Leu
    50                  55                  60

Leu Arg Asp Phe Gln Glu Asn Leu Gln Thr Glu Lys Cys Ile Phe Asn
65                  70                  75                  80

Val Met Lys Lys Leu Cys Phe Leu Leu Gln Ala Asp Arg Met Ser Leu
                85                  90                  95

-continued

Phe Met Tyr Arg Thr Arg Asn Gly Ile Ala Glu Leu Ala Thr Arg Leu
            100                 105                 110

Phe Asn Val His Lys Asp Ala Val Leu Glu Asp Cys Leu Val Met Pro
            115                 120                 125

Asp Gln Glu Ile Val Phe Pro Leu Asp Met Gly Ile Val Gly His Val
        130                 135                 140

Ala His Ser Lys Lys Ile Ala Asn Val Pro Asn Thr Glu Glu Asp Glu
145                 150                 155                 160

His Phe Cys Asp Phe Val Asp Ile Leu Thr Glu Tyr Lys Thr Lys Asn
                165                 170                 175

Ile Leu Ala Ser Pro Ile Met Asn Gly Lys Asp Val Val Ala Ile Ile
            180                 185                 190

Met Ala Val Asn Lys Val Asp Gly Ser His Phe Thr Lys Arg Asp Glu
        195                 200                 205

Glu Ile Leu Leu Lys Tyr Leu Asn Phe Ala Asn Leu Ile Met Lys Val
    210                 215                 220

Tyr His Leu Ser Tyr Leu His Asn Cys Glu Thr Arg Arg Gly Gln Ile
225                 230                 235                 240

Leu Leu Trp Ser Gly Ser Lys Val Phe Glu Glu Leu Thr Asp Ile Glu
                245                 250                 255

Arg Gln Phe His Lys Ala Leu Tyr Thr Val Arg Ala Phe Leu Asn Cys
            260                 265                 270

Asp Arg Tyr Ser Val Gly Leu Leu Asp Met Thr Lys Gln Lys Glu Phe
        275                 280                 285

Phe Asp Val Trp Pro Val Leu Met Gly Glu Val Pro Pro Tyr Ser Gly
    290                 295                 300

Pro Arg Thr Pro Asp Gly Arg Glu Ile Asn Phe Tyr Lys Val Ile Asp
305                 310                 315                 320

Tyr Ile Leu His Gly Lys Glu Asp Ile Lys Val Ile Pro Asn Pro Pro
                325                 330                 335

Pro Asp His Trp Ala Leu Val Ser Gly Leu Pro Ala Tyr Val Ala Gln
            340                 345                 350

Asn Gly Leu Ile Cys Asn Ile Met Asn Ala Pro Ala Glu Asp Phe Phe
        355                 360                 365

Ala Phe Gln Lys Glu Pro Leu Asp Glu Ser Gly Trp Met Ile Lys Asn
    370                 375                 380

Val Leu Ser Met Pro Ile Val Asn Lys Lys Glu Glu Ile Val Gly Val
385                 390                 395                 400

Ala Thr Phe Tyr Asn Arg Lys Asp Gly Lys Pro Phe Asp Glu Met Asp
                405                 410                 415

Glu Thr Leu Met Glu Ser Leu Thr Gln Phe Leu Gly Trp Ser Val Leu
            420                 425                 430

Asn Pro Asp Thr Tyr Glu Ser Met Asn Lys Leu Glu Asn Arg Lys Asp
        435                 440                 445

Ile Phe Gln Asp Ile Val Lys Tyr His Val Lys Cys Asp Asn Glu Glu
    450                 455                 460

Ile Gln Lys Ile Leu Lys Thr Arg Glu Val Tyr Gly Lys Glu Pro Trp
465                 470                 475                 480

Glu Cys Glu Glu Glu Glu Leu Ala Glu Ile Leu Gln Ala Glu Leu Pro
                485                 490                 495

Asp Ala Asp Lys Tyr Glu Ile Asn Lys Phe His Phe Ser Asp Leu Pro
            500                 505                 510

```
Leu Thr Glu Leu Glu Leu Val Lys Cys Gly Ile Gln Met Tyr Tyr Glu
            515                 520                 525

Leu Lys Val Val Asp Lys Phe His Ile Pro Gln Glu Ala Leu Val Arg
        530                 535                 540

Phe Met Tyr Ser Leu Ser Lys Gly Tyr Arg Lys Ile Thr Tyr His Asn
545                 550                 555                 560

Trp Arg His Gly Phe Asn Val Gly Gln Thr Met Phe Ser Leu Leu Val
                565                 570                 575

Thr Gly Lys Leu Lys Arg Tyr Phe Thr Asp Leu Glu Ala Leu Ala Met
            580                 585                 590

Val Thr Ala Ala Phe Cys His Asp Ile Asp His Arg Gly Thr Asn Asn
        595                 600                 605

Leu Tyr Gln Met Lys Ser Gln Asn Pro Leu Ala Lys Leu His Gly Ser
610                 615                 620

Ser Ile Leu Glu Arg His His Leu Glu Phe Gly Lys Thr Leu Leu Arg
625                 630                 635                 640

Asp Glu Ser Leu Asn Ile Phe Gln Asn Leu Asn Arg Arg Gln His Glu
                645                 650                 655

His Ala Ile His Met Met Asp Ile Ala Ile Ile Ala Thr Asp Leu Ala
            660                 665                 670

Leu Tyr Phe Lys Lys Arg Thr Met Phe Gln Lys Ile Val Asp Gln Ser
        675                 680                 685

Lys Thr Tyr Glu Ser Glu Gln Glu Trp Thr Gln Tyr Met Met Leu Glu
690                 695                 700

Gln Thr Arg Lys Glu Ile Val Met Ala Met Met Thr Ala Cys Asp
705                 710                 715                 720

Leu Ser Ala Ile Thr Lys Pro Trp Glu Val Gln Ser Gln Val Ala Leu
                725                 730                 735

Leu Val Ala Ala Glu Phe Trp Glu Gln Gly Asp Leu Glu Arg Thr Val
            740                 745                 750

Leu Gln Gln Asn Pro Ile Pro Met Met Asp Arg Asn Lys Ala Asp Glu
        755                 760                 765

Leu Pro Lys Leu Gln Val Gly Phe Ile Asp Phe Val Cys Thr Phe Val
770                 775                 780

Tyr Lys Glu Phe Ser Arg Phe His Glu Glu Ile Thr Pro Met Leu Asp
785                 790                 795                 800

Gly Ile Thr Asn Asn Arg Lys Glu Trp Lys Ala Leu Ala Asp Glu Tyr
                805                 810                 815

Asp Ala Lys Met Lys Val Gln Glu Glu Lys Lys Gln Lys Gln Gln Ser
            820                 825                 830

Ala Lys Ser Ala Ala Gly Asn Gln Pro Gly Gly Asn Pro Ser Pro
        835                 840                 845

Gly Gly Ala Thr Thr Ser Lys Ser Cys Cys Ile Gln
850                 855                 860

<210> SEQ ID NO 21
<211> LENGTH: 854
<212> TYPE: PRT
<213> ORGANISM: Homo sapiens

<400> SEQUENCE: 21

Met Ser Leu Ser Glu Glu Gln Ala Arg Ser Phe Leu Asp Gln Asn Pro
1               5                   10                  15

Asp Phe Ala Arg Gln Tyr Phe Gly Lys Lys Leu Ser Pro Glu Asn Val
            20                  25                  30
```

Ala Ala Ala Cys Glu Asp Gly Cys Pro Pro Asp Cys Asp Ser Leu Arg
            35                  40                  45

Asp Leu Cys Gln Val Glu Glu Ser Thr Ala Leu Leu Glu Leu Val Gln
     50                  55                  60

Asp Met Gln Glu Ser Ile Asn Met Glu Arg Val Val Phe Lys Val Leu
65                   70                  75                  80

Arg Arg Leu Cys Thr Leu Leu Gln Ala Asp Arg Cys Ser Leu Phe Met
                85                  90                  95

Tyr Arg Gln Arg Asn Gly Val Ala Glu Leu Ala Thr Arg Leu Phe Ser
            100                 105                 110

Val Gln Pro Asp Ser Val Leu Glu Asp Cys Leu Val Pro Pro Asp Ser
        115                 120                 125

Glu Ile Val Phe Pro Leu Asp Ile Gly Val Val Gly His Val Ala Gln
    130                 135                 140

Thr Lys Lys Met Val Asn Val Glu Asp Val Ala Glu Cys Pro His Phe
145                 150                 155                 160

Ser Ser Phe Ala Asp Glu Leu Thr Asp Tyr Lys Thr Lys Asn Met Leu
                165                 170                 175

Ala Thr Pro Ile Met Asn Gly Lys Asp Val Val Ala Val Ile Met Ala
            180                 185                 190

Val Asn Lys Leu Asn Gly Pro Phe Phe Thr Ser Glu Asp Glu Asp Val
        195                 200                 205

Phe Leu Lys Tyr Leu Asn Phe Ala Thr Leu Tyr Leu Lys Ile Tyr His
    210                 215                 220

Leu Ser Tyr Leu His Asn Cys Glu Thr Arg Arg Gly Gln Val Leu Leu
225                 230                 235                 240

Trp Ser Ala Asn Lys Val Phe Glu Glu Leu Thr Asp Ile Glu Arg Gln
                245                 250                 255

Phe His Lys Ala Phe Tyr Thr Val Arg Ala Tyr Leu Asn Cys Glu Arg
            260                 265                 270

Tyr Ser Val Gly Leu Leu Asp Met Thr Lys Glu Lys Glu Phe Phe Asp
        275                 280                 285

Val Trp Ser Val Leu Met Gly Glu Ser Gln Pro Tyr Ser Gly Pro Arg
    290                 295                 300

Thr Pro Asp Gly Arg Glu Ile Val Phe Tyr Lys Val Ile Asp Tyr Ile
305                 310                 315                 320

Leu His Gly Lys Glu Glu Ile Lys Val Ile Pro Thr Pro Ser Ala Asp
                325                 330                 335

His Trp Ala Leu Ala Ser Gly Leu Pro Ser Tyr Val Ala Glu Ser Gly
            340                 345                 350

Phe Ile Cys Asn Ile Met Asn Ala Ser Ala Asp Glu Met Phe Lys Phe
        355                 360                 365

Gln Glu Gly Ala Leu Asp Asp Ser Gly Trp Leu Ile Lys Asn Val Leu
    370                 375                 380

Ser Met Pro Ile Val Asn Lys Lys Glu Glu Ile Val Gly Val Ala Thr
385                 390                 395                 400

Phe Tyr Asn Arg Lys Asp Gly Lys Pro Phe Asp Glu Gln Asp Glu Val
                405                 410                 415

Leu Met Glu Ser Leu Thr Gln Phe Leu Gly Trp Ser Val Met Asn Thr
            420                 425                 430

Asp Thr Tyr Asp Lys Met Asn Lys Leu Glu Asn Arg Lys Asp Ile Ala
        435                 440                 445

-continued

```
Gln Asp Met Val Leu Tyr His Val Lys Cys Asp Arg Asp Glu Ile Gln
450                 455                 460

Leu Ile Leu Pro Thr Arg Ala Arg Leu Gly Lys Glu Pro Ala Asp Cys
465                 470                 475                 480

Asp Glu Asp Glu Leu Gly Glu Ile Leu Lys Glu Glu Leu Pro Gly Pro
                485                 490                 495

Thr Thr Phe Asp Ile Tyr Glu Phe His Phe Ser Asp Leu Glu Cys Thr
            500                 505                 510

Glu Leu Asp Leu Val Lys Cys Gly Ile Gln Met Tyr Tyr Glu Leu Gly
            515                 520                 525

Val Val Arg Lys Phe Gln Ile Pro Gln Glu Val Leu Val Arg Phe Leu
530                 535                 540

Phe Ser Ile Ser Lys Gly Tyr Arg Arg Ile Thr Tyr His Asn Trp Arg
545                 550                 555                 560

His Gly Phe Asn Val Ala Gln Thr Met Phe Thr Leu Leu Met Thr Gly
                565                 570                 575

Lys Leu Lys Ser Tyr Tyr Thr Asp Leu Glu Ala Phe Ala Met Val Thr
            580                 585                 590

Ala Gly Leu Cys His Asp Ile Asp His Arg Gly Thr Asn Asn Leu Tyr
            595                 600                 605

Gln Met Lys Ser Gln Asn Pro Leu Ala Lys Leu His Gly Ser Ser Ile
610                 615                 620

Leu Glu Arg His His Leu Glu Phe Gly Lys Phe Leu Leu Ser Glu Glu
625                 630                 635                 640

Thr Leu Asn Ile Tyr Gln Asn Leu Asn Arg Arg Gln His Glu His Val
                645                 650                 655

Ile His Leu Met Asp Ile Ala Ile Ala Thr Asp Leu Ala Leu Tyr
            660                 665                 670

Phe Lys Lys Arg Ala Met Phe Gln Lys Ile Val Asp Glu Ser Lys Asn
            675                 680                 685

Tyr Gln Asp Lys Lys Ser Trp Val Glu Tyr Leu Ser Leu Glu Thr Thr
690                 695                 700

Arg Lys Glu Ile Val Met Ala Met Met Met Thr Ala Cys Asp Leu Ser
705                 710                 715                 720

Ala Ile Thr Lys Pro Trp Glu Val Gln Ser Lys Val Ala Leu Leu Val
                725                 730                 735

Ala Ala Glu Phe Trp Glu Gln Gly Asp Leu Glu Arg Thr Val Leu Asp
            740                 745                 750

Gln Gln Pro Ile Pro Met Met Asp Arg Asn Lys Ala Ala Glu Leu Pro
            755                 760                 765

Lys Leu Gln Val Gly Phe Ile Asp Phe Val Cys Thr Phe Val Tyr Lys
770                 775                 780

Glu Phe Ser Arg Phe His Glu Glu Ile Leu Pro Met Phe Asp Arg Leu
785                 790                 795                 800

Gln Asn Asn Arg Lys Glu Trp Lys Ala Leu Ala Asp Glu Tyr Glu Ala
                805                 810                 815

Lys Val Lys Ala Leu Glu Glu Lys Glu Glu Glu Arg Val Ala Ala
            820                 825                 830

Lys Lys Val Gly Thr Glu Ile Cys Asn Gly Gly Pro Ala Pro Lys Ser
            835                 840                 845

Ser Thr Cys Cys Ile Leu
850
```

<210> SEQ ID NO 22
<211> LENGTH: 853
<212> TYPE: PRT
<213> ORGANISM: Homo sapiens

<400> SEQUENCE: 22

```
Met Ser Leu Ser Glu Glu Gln Ala Arg Ser Phe Leu Asp Gln Asn Pro
1               5                   10                  15

Asp Phe Ala Arg Gln Tyr Phe Gly Lys Lys Leu Ser Pro Glu Asn Val
            20                  25                  30

Ala Ala Ala Cys Glu Asp Gly Cys Pro Pro Asp Cys Asp Ser Leu Arg
        35                  40                  45

Asp Leu Cys Gln Val Glu Ser Thr Ala Leu Leu Glu Leu Val Gln
    50                  55                  60

Asp Met Gln Glu Ser Ile Asn Met Glu Arg Val Val Phe Lys Val Leu
65                  70                  75                  80

Arg Arg Leu Cys Thr Leu Leu Gln Ala Asp Arg Cys Ser Leu Phe Met
                85                  90                  95

Tyr Arg Gln Arg Asn Gly Val Ala Glu Leu Ala Thr Arg Leu Phe Ser
            100                 105                 110

Val Gln Pro Asp Ser Val Leu Glu Asp Cys Leu Val Pro Pro Asp Ser
        115                 120                 125

Glu Ile Val Phe Pro Leu Asp Ile Gly Val Val Gly His Val Ala Gln
130                 135                 140

Thr Lys Lys Met Val Asn Val Glu Asp Val Ala Glu Cys Pro His Phe
145                 150                 155                 160

Ser Ser Phe Ala Asp Glu Leu Thr Asp Tyr Lys Thr Lys Asn Met Leu
                165                 170                 175

Ala Thr Pro Ile Met Asn Gly Lys Asp Val Val Ala Val Ile Met Ala
            180                 185                 190

Val Asn Lys Leu Asn Gly Pro Phe Phe Thr Ser Glu Asp Glu Asp Val
        195                 200                 205

Phe Leu Lys Tyr Leu Asn Phe Ala Thr Leu Tyr Leu Lys Ile Tyr His
210                 215                 220

Leu Ser Tyr Leu His Asn Cys Glu Thr Arg Arg Gly Gln Val Leu Leu
225                 230                 235                 240

Trp Ser Ala Asn Lys Val Phe Glu Glu Leu Thr Asp Ile Glu Arg Gln
                245                 250                 255

Phe His Lys Ala Phe Tyr Thr Val Arg Ala Tyr Leu Asn Cys Glu Arg
            260                 265                 270

Tyr Ser Val Gly Leu Leu Asp Met Thr Lys Glu Lys Glu Phe Phe Asp
        275                 280                 285

Val Trp Ser Val Leu Met Gly Glu Ser Gln Pro Tyr Ser Gly Pro Arg
290                 295                 300

Thr Pro Asp Gly Arg Glu Ile Val Phe Tyr Lys Val Ile Asp Tyr Ile
305                 310                 315                 320

Leu His Gly Lys Glu Glu Ile Lys Val Ile Pro Thr Pro Ser Ala Asp
                325                 330                 335

His Trp Ala Leu Ala Ser Gly Leu Pro Ser Tyr Val Ala Glu Ser Gly
            340                 345                 350

Phe Ile Cys Asn Ile Met Asn Ala Ser Ala Asp Glu Met Phe Lys Phe
        355                 360                 365

Gln Glu Gly Ala Leu Asp Asp Ser Gly Trp Leu Ile Lys Asn Val Leu
370                 375                 380
```

-continued

```
Ser Met Pro Ile Val Asn Lys Lys Glu Glu Ile Val Gly Val Ala Thr
385                 390                 395                 400

Phe Tyr Asn Arg Lys Asp Gly Lys Pro Phe Asp Glu Gln Asp Glu Val
            405                 410                 415

Leu Met Glu Ser Leu Thr Gln Phe Leu Gly Trp Ser Val Met Asn Thr
        420                 425                 430

Asp Thr Tyr Asp Lys Met Asn Lys Leu Glu Asn Arg Lys Asp Ile Ala
    435                 440                 445

Gln Asp Met Val Leu Tyr His Val Lys Cys Asp Arg Asp Glu Ile Gln
450                 455                 460

Leu Ile Leu Pro Thr Arg Ala Arg Leu Gly Lys Glu Pro Ala Asp Cys
465                 470                 475                 480

Asp Glu Asp Glu Leu Gly Glu Ile Leu Lys Glu Leu Pro Gly Pro
            485                 490                 495

Thr Thr Phe Asp Ile Tyr Glu Phe His Phe Ser Asp Leu Glu Cys Thr
            500                 505                 510

Glu Leu Asp Leu Val Lys Cys Gly Ile Gln Met Tyr Tyr Glu Leu Gly
        515                 520                 525

Val Val Arg Lys Phe Gln Ile Pro Gln Glu Val Leu Val Arg Phe Leu
    530                 535                 540

Phe Ser Ile Ser Lys Gly Tyr Arg Arg Ile Thr Tyr His Asn Trp Arg
545                 550                 555                 560

His Gly Phe Asn Val Ala Gln Thr Met Phe Thr Leu Leu Met Thr Gly
            565                 570                 575

Lys Leu Lys Ser Tyr Tyr Thr Asp Leu Glu Ala Phe Ala Met Val Thr
            580                 585                 590

Ala Gly Leu Cys His Asp Ile Asp His Arg Gly Thr Asn Asn Leu Tyr
        595                 600                 605

Gln Met Lys Ser Gln Asn Pro Leu Ala Lys Leu His Gly Ser Ser Ile
    610                 615                 620

Leu Glu Arg His His Leu Glu Phe Gly Lys Phe Leu Leu Ser Glu Glu
625                 630                 635                 640

Thr Leu Asn Ile Tyr Gln Asn Leu Asn Arg Arg Gln His Glu His Val
            645                 650                 655

Ile His Leu Met Asp Ile Ala Ile Ala Thr Asp Leu Ala Leu Tyr
            660                 665                 670

Phe Lys Lys Arg Ala Met Phe Gln Lys Ile Val Asp Glu Ser Lys Asn
        675                 680                 685

Tyr Gln Asp Lys Lys Ser Trp Val Glu Tyr Leu Ser Leu Glu Thr Thr
    690                 695                 700

Arg Lys Glu Ile Val Met Ala Met Met Met Thr Ala Cys Asp Leu Ser
705                 710                 715                 720

Ala Ile Thr Lys Pro Trp Glu Val Gln Ser Lys Val Ala Leu Leu Val
            725                 730                 735

Ala Ala Glu Phe Trp Glu Gln Gly Asp Leu Glu Arg Thr Val Leu Asp
            740                 745                 750

Gln Gln Pro Ile Pro Met Met Asp Arg Asn Lys Ala Ala Glu Leu Pro
        755                 760                 765

Lys Leu Gln Val Gly Phe Ile Asp Phe Val Cys Thr Phe Val Tyr Lys
    770                 775                 780

Glu Phe Ser Arg Phe His Glu Glu Ile Leu Pro Met Phe Asp Arg Leu
785                 790                 795                 800

Gln Asn Asn Arg Lys Glu Trp Lys Ala Leu Ala Asp Glu Tyr Glu Ala
```

-continued

```
                805                 810                 815
Lys Val Lys Ala Leu Glu Glu Lys Glu Glu Glu Arg Val Ala Ala
            820                 825                 830
Lys Lys Gly Thr Glu Ile Cys Asn Gly Gly Pro Ala Pro Lys Ser Ser
            835                 840                 845
Thr Cys Cys Ile Leu
        850

<210> SEQ ID NO 23
<211> LENGTH: 575
<212> TYPE: PRT
<213> ORGANISM: Homo sapiens

<400> SEQUENCE: 23

Met Thr Lys Glu Lys Glu Phe Phe Asp Val Trp Ser Val Leu Met Gly
1               5                   10                  15
Glu Ser Gln Pro Tyr Ser Gly Pro Arg Thr Pro Asp Gly Arg Glu Ile
            20                  25                  30
Val Phe Tyr Lys Val Ile Asp Tyr Ile Leu His Gly Lys Glu Glu Ile
            35                  40                  45
Lys Val Ile Pro Thr Pro Ser Ala Asp His Trp Ala Leu Ala Ser Gly
        50                  55                  60
Leu Pro Ser Tyr Val Ala Glu Ser Gly Phe Ile Cys Asn Ile Met Asn
65                  70                  75                  80
Ala Ser Ala Asp Glu Met Phe Lys Phe Gln Glu Gly Ala Leu Asp Asp
                85                  90                  95
Ser Gly Trp Leu Ile Lys Asn Val Leu Ser Met Pro Ile Val Asn Lys
            100                 105                 110
Lys Glu Glu Ile Val Gly Val Ala Thr Phe Tyr Asn Arg Lys Asp Gly
            115                 120                 125
Lys Pro Phe Asp Glu Gln Asp Glu Val Leu Met Glu Ser Leu Thr Gln
        130                 135                 140
Phe Leu Gly Trp Ser Val Met Asn Thr Asp Thr Tyr Asp Lys Met Asn
145                 150                 155                 160
Lys Leu Glu Asn Arg Lys Asp Ile Ala Gln Asp Met Val Leu Tyr His
                165                 170                 175
Val Lys Cys Asp Arg Asp Glu Ile Gln Leu Ile Leu Pro Thr Arg Ala
            180                 185                 190
Arg Leu Gly Lys Glu Pro Ala Asp Cys Asp Glu Asp Glu Leu Gly Glu
            195                 200                 205
Ile Leu Lys Glu Glu Leu Pro Gly Pro Thr Thr Phe Asp Ile Tyr Glu
        210                 215                 220
Phe His Phe Ser Asp Leu Glu Cys Thr Glu Leu Asp Leu Val Lys Cys
225                 230                 235                 240
Gly Ile Gln Met Tyr Tyr Glu Leu Gly Val Val Arg Lys Phe Gln Ile
                245                 250                 255
Pro Gln Glu Val Leu Val Arg Phe Leu Phe Ser Ile Ser Lys Gly Tyr
            260                 265                 270
Arg Arg Ile Thr Tyr His Asn Trp Arg His Gly Phe Asn Val Ala Gln
            275                 280                 285
Thr Met Phe Thr Leu Leu Met Thr Gly Lys Leu Lys Ser Tyr Tyr Thr
        290                 295                 300
Asp Leu Glu Ala Phe Ala Met Val Thr Ala Gly Leu Cys His Asp Ile
305                 310                 315                 320
```

Asp His Arg Gly Thr Asn Asn Leu Tyr Gln Met Lys Ser Gln Asn Pro
              325                 330                 335

Leu Ala Lys Leu His Gly Ser Ser Ile Leu Glu Arg His His Leu Glu
          340                 345                 350

Phe Gly Lys Phe Leu Leu Ser Glu Glu Thr Leu Asn Ile Tyr Gln Asn
      355                 360                 365

Leu Asn Arg Arg Gln His Glu His Val Ile His Leu Met Asp Ile Ala
  370                 375                 380

Ile Ile Ala Thr Asp Leu Ala Leu Tyr Phe Lys Lys Arg Ala Met Phe
385                 390                 395                 400

Gln Lys Ile Val Asp Glu Ser Lys Asn Tyr Gln Asp Lys Lys Ser Trp
              405                 410                 415

Val Glu Tyr Leu Ser Leu Glu Thr Thr Arg Lys Glu Ile Val Met Ala
          420                 425                 430

Met Met Met Thr Ala Cys Asp Leu Ser Ala Ile Thr Lys Pro Trp Glu
      435                 440                 445

Val Gln Ser Lys Val Ala Leu Leu Val Ala Ala Glu Phe Trp Glu Gln
  450                 455                 460

Gly Asp Leu Glu Arg Thr Val Leu Asp Gln Gln Pro Ile Pro Met Met
465                 470                 475                 480

Asp Arg Asn Lys Ala Ala Glu Leu Pro Lys Leu Gln Val Gly Phe Ile
              485                 490                 495

Asp Phe Val Cys Thr Phe Val Tyr Lys Glu Phe Ser Arg Phe His Glu
          500                 505                 510

Glu Ile Leu Pro Met Phe Asp Arg Leu Gln Asn Asn Arg Lys Glu Trp
      515                 520                 525

Lys Ala Leu Ala Asp Glu Tyr Glu Ala Lys Val Lys Ala Leu Glu Glu
  530                 535                 540

Lys Glu Glu Glu Glu Arg Val Ala Ala Lys Lys Val Gly Thr Glu Ile
545                 550                 555                 560

Cys Asn Gly Gly Pro Ala Pro Lys Ser Ser Thr Cys Cys Ile Leu
              565                 570                 575

<210> SEQ ID NO 24
<211> LENGTH: 694
<212> TYPE: PRT
<213> ORGANISM: Homo sapiens

<400> SEQUENCE: 24

Met Ala Lys Ile Asn Thr Gln Tyr Ser His Pro Ser Arg Thr His Leu
1               5                   10                  15

Lys Val Lys Thr Ser Asp Arg Asp Leu Asn Arg Ala Glu Asn Gly Leu
              20                  25                  30

Ser Arg Ala His Ser Ser Ser Glu Thr Ser Ser Val Leu Gln Pro
          35                  40                  45

Gly Ile Ala Met Glu Thr Arg Gly Leu Ala Asp Ser Gly Gln Gly Ser
      50                  55                  60

Phe Thr Gly Gln Gly Ile Ala Arg Leu Ser Arg Leu Ile Phe Leu Leu
65                  70                  75                  80

Arg Arg Trp Ala Ala Arg His Val His His Gln Asp Gln Gly Pro Asp
              85                  90                  95

Ser Phe Pro Asp Arg Phe Arg Gly Ala Glu Leu Lys Glu Val Ser Ser
          100                 105                 110

Gln Glu Ser Asn Ala Gln Ala Asn Val Gly Ser Gln Glu Pro Ala Asp
      115                 120                 125

-continued

```
Arg Gly Arg Ser Ala Trp Pro Leu Ala Lys Cys Asn Thr Asn Thr Ser
        130                 135                 140
Asn Asn Thr Glu Glu Glu Lys Lys Thr Lys Lys Lys Asp Ala Ile Val
145                 150                 155                 160
Val Asp Pro Ser Ser Asn Leu Tyr Tyr Arg Trp Leu Thr Ala Ile Ala
                165                 170                 175
Leu Pro Val Phe Tyr Asn Trp Tyr Leu Leu Ile Cys Arg Ala Cys Phe
            180                 185                 190
Asp Glu Leu Gln Ser Glu Tyr Leu Met Leu Trp Leu Val Leu Asp Tyr
        195                 200                 205
Ser Ala Asp Val Leu Tyr Val Leu Asp Val Leu Val Arg Ala Arg Thr
210                 215                 220
Gly Phe Leu Glu Gln Gly Leu Met Val Ser Asp Thr Asn Arg Leu Trp
225                 230                 235                 240
Gln His Tyr Lys Thr Thr Thr Gln Phe Lys Leu Asp Val Leu Ser Leu
                245                 250                 255
Val Pro Thr Asp Leu Ala Tyr Leu Lys Val Gly Thr Asn Tyr Pro Glu
            260                 265                 270
Val Arg Phe Asn Arg Leu Leu Lys Phe Ser Arg Leu Phe Glu Phe Phe
        275                 280                 285
Asp Arg Thr Glu Thr Arg Thr Asn Tyr Pro Asn Met Phe Arg Ile Gly
        290                 295                 300
Asn Leu Val Leu Tyr Ile Leu Ile Ile His Trp Asn Ala Cys Ile
305                 310                 315                 320
Tyr Phe Ala Ile Ser Lys Phe Ile Gly Phe Gly Thr Asp Ser Trp Val
                325                 330                 335
Tyr Pro Asn Ile Ser Ile Pro Glu His Gly Arg Leu Ser Arg Lys Tyr
            340                 345                 350
Ile Tyr Ser Leu Tyr Trp Ser Thr Leu Thr Leu Thr Thr Ile Gly Glu
        355                 360                 365
Thr Pro Pro Pro Val Lys Asp Glu Glu Tyr Leu Phe Val Val Val Asp
        370                 375                 380
Phe Leu Val Gly Val Leu Ile Phe Ala Thr Ile Val Gly Asn Val Gly
385                 390                 395                 400
Ser Met Ile Ser Asn Met Asn Ala Ser Arg Ala Glu Phe Gln Ala Lys
                405                 410                 415
Ile Asp Ser Ile Lys Gln Tyr Met Gln Phe Arg Lys Val Thr Lys Asp
            420                 425                 430
Leu Glu Thr Arg Val Ile Arg Trp Phe Asp Tyr Leu Trp Ala Asn Lys
        435                 440                 445
Lys Thr Val Asp Glu Lys Glu Val Leu Lys Ser Leu Pro Asp Lys Leu
        450                 455                 460
Lys Ala Glu Ile Ala Ile Asn Val His Leu Asp Thr Leu Lys Lys Val
465                 470                 475                 480
Arg Ile Phe Gln Asp Cys Glu Ala Gly Leu Leu Val Glu Leu Val Leu
                485                 490                 495
Lys Leu Arg Pro Thr Val Phe Ser Pro Gly Asp Tyr Ile Cys Lys Lys
            500                 505                 510
Gly Asp Ile Gly Lys Glu Met Tyr Ile Ile Asn Glu Gly Lys Leu Ala
        515                 520                 525
Val Val Ala Asp Asp Gly Val Thr Gln Phe Val Val Leu Ser Asp Gly
530                 535                 540
```

```
Ser Tyr Phe Gly Glu Ile Ser Ile Leu Asn Ile Lys Gly Ser Lys Ser
545                 550                 555                 560

Gly Asn Arg Arg Thr Ala Asn Ile Arg Ser Ile Gly Tyr Ser Asp Leu
                565                 570                 575

Phe Cys Leu Ser Lys Asp Asp Leu Met Glu Ala Leu Thr Glu Tyr Pro
                580                 585                 590

Glu Ala Lys Lys Ala Leu Glu Glu Lys Gly Arg Gln Ile Leu Met Lys
                595                 600                 605

Asp Asn Leu Ile Asp Glu Glu Leu Ala Arg Ala Gly Ala Asp Pro Lys
                610                 615                 620

Asp Leu Glu Glu Lys Val Glu Gln Leu Gly Ser Ser Leu Asp Thr Leu
625                 630                 635                 640

Gln Thr Arg Phe Ala Arg Leu Leu Ala Glu Tyr Asn Ala Thr Gln Met
                645                 650                 655

Lys Met Lys Gln Arg Leu Ser Gln Leu Glu Ser Gln Val Lys Gly Gly
                660                 665                 670

Gly Asp Lys Pro Leu Ala Asp Gly Glu Val Pro Gly Asp Ala Thr Lys
                675                 680                 685

Thr Glu Asp Lys Gln Gln
                690

<210> SEQ ID NO 25
<211> LENGTH: 676
<212> TYPE: PRT
<213> ORGANISM: Homo sapiens

<400> SEQUENCE: 25

Met Ala Lys Ile Asn Thr Gln Tyr Ser His Pro Ser Arg Thr His Leu
1               5                   10                  15

Lys Val Lys Thr Ser Asp Arg Asp Leu Asn Arg Ala Glu Asn Gly Leu
                20                  25                  30

Ser Arg Ala His Ser Ser Ser Glu Glu Thr Ser Ser Val Leu Gln Pro
                35                  40                  45

Gly Ile Ala Met Glu Thr Arg Gly Leu Ala Asp Ser Gly Gln Gly Ser
            50                  55                  60

Phe Thr Gly Gln Gly Ile Ala Arg Leu Ser Arg Leu Ile Phe Leu Leu
65                  70                  75                  80

Arg Arg Trp Ala Ala Arg His Val His His Gln Asp Gln Gly Pro Asp
                85                  90                  95

Ser Phe Pro Asp Arg Phe Arg Gly Ala Glu Leu Lys Glu Val Ser Ser
                100                 105                 110

Gln Glu Ser Asn Ala Gln Ala Asn Val Gly Ser Gln Glu Pro Ala Asp
                115                 120                 125

Arg Gly Arg Lys Lys Thr Lys Lys Asp Ala Ile Val Val Asp
            130                 135                 140

Pro Ser Ser Asn Leu Tyr Tyr Arg Trp Leu Thr Ala Ile Ala Leu Pro
145                 150                 155                 160

Val Phe Tyr Asn Trp Tyr Leu Leu Ile Cys Arg Ala Cys Phe Asp Glu
                165                 170                 175

Leu Gln Ser Glu Tyr Leu Met Leu Trp Leu Val Leu Asp Tyr Ser Ala
                180                 185                 190

Asp Val Leu Tyr Val Leu Asp Val Leu Val Arg Ala Arg Thr Gly Phe
                195                 200                 205

Leu Glu Gln Gly Leu Met Val Ser Asp Thr Asn Arg Leu Trp Gln His
                210                 215                 220
```

-continued

```
Tyr Lys Thr Thr Thr Gln Phe Lys Leu Asp Val Leu Ser Leu Val Pro
225                 230                 235                 240

Thr Asp Leu Ala Tyr Leu Lys Val Gly Thr Asn Tyr Pro Glu Val Arg
            245                 250                 255

Phe Asn Arg Leu Leu Lys Phe Ser Arg Leu Phe Glu Phe Phe Asp Arg
        260                 265                 270

Thr Glu Thr Arg Thr Asn Tyr Pro Asn Met Phe Arg Ile Gly Asn Leu
    275                 280                 285

Val Leu Tyr Ile Leu Ile Ile His Trp Asn Ala Cys Ile Tyr Phe
290                 295                 300

Ala Ile Ser Lys Phe Ile Gly Phe Gly Thr Asp Ser Trp Val Tyr Pro
305                 310                 315                 320

Asn Ile Ser Ile Pro Glu His Gly Arg Leu Ser Arg Lys Tyr Ile Tyr
            325                 330                 335

Ser Leu Tyr Trp Ser Thr Leu Thr Leu Thr Thr Ile Gly Glu Thr Pro
        340                 345                 350

Pro Pro Val Lys Asp Glu Glu Tyr Leu Phe Val Val Asp Phe Leu
    355                 360                 365

Val Gly Val Leu Ile Phe Ala Thr Ile Val Gly Asn Val Gly Ser Met
370                 375                 380

Ile Ser Asn Met Asn Ala Ser Arg Ala Glu Phe Gln Ala Lys Ile Asp
385                 390                 395                 400

Ser Ile Lys Gln Tyr Met Gln Phe Arg Lys Val Thr Lys Asp Leu Glu
            405                 410                 415

Thr Arg Val Ile Arg Trp Phe Asp Tyr Leu Trp Ala Asn Lys Lys Thr
        420                 425                 430

Val Asp Glu Lys Glu Val Leu Lys Ser Leu Pro Asp Lys Leu Lys Ala
    435                 440                 445

Glu Ile Ala Ile Asn Val His Leu Asp Thr Leu Lys Lys Val Arg Ile
450                 455                 460

Phe Gln Asp Cys Glu Ala Gly Leu Leu Val Glu Leu Val Leu Lys Leu
465                 470                 475                 480

Arg Pro Thr Val Phe Ser Pro Gly Asp Tyr Ile Cys Lys Lys Gly Asp
            485                 490                 495

Ile Gly Lys Glu Met Tyr Ile Ile Asn Glu Gly Lys Leu Ala Val Val
        500                 505                 510

Ala Asp Asp Gly Val Thr Gln Phe Val Val Leu Ser Asp Gly Ser Tyr
    515                 520                 525

Phe Gly Glu Ile Ser Ile Leu Asn Ile Lys Gly Ser Lys Ser Gly Asn
530                 535                 540

Arg Arg Thr Ala Asn Ile Arg Ser Ile Gly Tyr Ser Asp Leu Phe Cys
545                 550                 555                 560

Leu Ser Lys Asp Asp Leu Met Glu Ala Leu Thr Glu Tyr Pro Glu Ala
            565                 570                 575

Lys Lys Ala Leu Glu Glu Lys Gly Arg Gln Ile Leu Met Lys Asp Asn
        580                 585                 590

Leu Ile Asp Glu Glu Leu Ala Arg Ala Gly Ala Asp Pro Lys Asp Leu
    595                 600                 605

Glu Glu Lys Val Glu Gln Leu Gly Ser Ser Leu Asp Thr Leu Gln Thr
610                 615                 620

Arg Phe Ala Arg Leu Leu Ala Glu Tyr Asn Ala Thr Gln Met Lys Met
625                 630                 635                 640
```

```
Lys Gln Arg Leu Ser Gln Leu Glu Ser Gln Val Lys Gly Gly Asp
            645                 650                 655

Lys Pro Leu Ala Asp Gly Glu Val Pro Gly Asp Ala Thr Lys Thr Glu
        660                 665                 670

Asp Lys Gln Gln
        675

<210> SEQ ID NO 26
<211> LENGTH: 809
<212> TYPE: PRT
<213> ORGANISM: Homo sapiens

<400> SEQUENCE: 26

Met Phe Lys Ser Leu Thr Lys Val Asn Lys Val Lys Pro Ile Gly Glu
1               5                   10                  15

Asn Asn Glu Asn Glu Gln Ser Ser Arg Arg Asn Glu Glu Gly Ser His
            20                  25                  30

Pro Ser Asn Gln Ser Gln Gln Thr Thr Ala Gln Glu Glu Asn Lys Gly
        35                  40                  45

Glu Glu Lys Ser Leu Lys Thr Lys Ser Thr Pro Val Thr Ser Glu Glu
    50                  55                  60

Pro His Thr Asn Ile Gln Asp Lys Leu Ser Lys Lys Asn Ser Ser Gly
65                  70                  75                  80

Asp Leu Thr Thr Asn Pro Asp Pro Gln Asn Ala Ala Glu Pro Thr Gly
                85                  90                  95

Thr Val Pro Glu Gln Lys Glu Met Asp Pro Gly Lys Glu Gly Pro Asn
            100                 105                 110

Ser Pro Gln Asn Lys Pro Pro Ala Ala Pro Val Ile Asn Glu Tyr Ala
        115                 120                 125

Asp Ala Gln Leu His Asn Leu Val Lys Arg Met Arg Gln Arg Thr Ala
    130                 135                 140

Leu Tyr Lys Lys Lys Leu Val Glu Gly Asp Leu Ser Ser Pro Glu Ala
145                 150                 155                 160

Ser Pro Gln Thr Ala Lys Pro Thr Ala Val Pro Pro Val Lys Glu Ser
                165                 170                 175

Asp Asp Lys Pro Thr Glu His Tyr Tyr Arg Leu Leu Trp Phe Lys Val
            180                 185                 190

Lys Lys Met Pro Leu Thr Glu Tyr Leu Lys Arg Ile Lys Leu Pro Asn
        195                 200                 205

Ser Ile Asp Ser Tyr Thr Asp Arg Leu Tyr Leu Leu Trp Leu Leu Leu
    210                 215                 220

Val Thr Leu Ala Tyr Asn Trp Asn Cys Cys Phe Ile Pro Leu Arg Leu
225                 230                 235                 240

Val Phe Pro Tyr Gln Thr Ala Asp Asn Ile His Tyr Trp Leu Ile Ala
                245                 250                 255

Asp Ile Ile Cys Asp Ile Ile Tyr Leu Tyr Asp Met Leu Phe Ile Gln
            260                 265                 270

Pro Arg Leu Gln Phe Val Arg Gly Gly Asp Ile Ile Val Asp Ser Asn
        275                 280                 285

Glu Leu Arg Lys His Tyr Arg Thr Ser Thr Lys Phe Gln Leu Asp Val
    290                 295                 300

Ala Ser Ile Ile Pro Phe Asp Ile Cys Tyr Leu Phe Gly Phe Asn
305                 310                 315                 320

Pro Met Phe Arg Ala Asn Arg Met Leu Lys Tyr Thr Ser Phe Phe Glu
                325                 330                 335
```

```
Phe Asn His His Leu Glu Ser Ile Met Asp Lys Ala Tyr Ile Tyr Arg
                340                 345                 350

Val Ile Arg Thr Thr Gly Tyr Leu Phe Ile Leu His Ile Asn Ala
            355                 360                 365

Cys Val Tyr Tyr Trp Ala Ser Asn Tyr Glu Gly Ile Gly Thr Thr Arg
370                 375                 380

Trp Val Tyr Asp Gly Gly Asn Glu Tyr Leu Arg Cys Tyr Tyr Trp
385                 390                 395                 400

Ala Val Arg Thr Leu Ile Thr Ile Gly Gly Leu Pro Glu Pro Gln Thr
                405                 410                 415

Leu Phe Glu Ile Val Phe Gln Leu Leu Asn Phe Ser Gly Val Phe
                420                 425                 430

Val Phe Ser Ser Leu Ile Gly Gln Met Arg Asp Val Ile Gly Ala Ala
                435                 440                 445

Thr Ala Asn Gln Asn Tyr Phe Arg Ala Cys Met Asp Asp Thr Ile Ala
                450                 455                 460

Tyr Met Asn Asn Tyr Ser Ile Pro Lys Leu Val Gln Lys Arg Val Arg
465                 470                 475                 480

Thr Trp Tyr Glu Tyr Thr Trp Asp Ser Gln Arg Met Leu Asp Glu Ser
                485                 490                 495

Asp Leu Leu Lys Thr Leu Pro Thr Thr Val Gln Leu Ala Leu Ala Ile
                500                 505                 510

Asp Val Asn Phe Ser Ile Ile Ser Lys Val Asp Leu Phe Lys Gly Cys
                515                 520                 525

Asp Thr Gln Met Ile Tyr Asp Met Leu Leu Arg Leu Lys Ser Val Leu
                530                 535                 540

Tyr Leu Pro Gly Asp Phe Val Cys Lys Lys Gly Glu Ile Gly Lys Glu
545                 550                 555                 560

Met Tyr Ile Ile Lys His Gly Glu Val Gln Val Leu Gly Gly Pro Asp
                565                 570                 575

Gly Thr Lys Val Leu Val Thr Leu Lys Ala Gly Ser Val Phe Gly Glu
                580                 585                 590

Ile Ser Leu Leu Ala Ala Gly Gly Gly Asn Arg Arg Thr Ala Asn Val
            595                 600                 605

Val Ala His Gly Phe Ala Asn Leu Leu Thr Leu Asp Lys Lys Thr Leu
                610                 615                 620

Gln Glu Ile Leu Val His Tyr Pro Asp Ser Glu Arg Ile Leu Met Lys
625                 630                 635                 640

Lys Ala Arg Val Leu Leu Lys Gln Lys Ala Lys Thr Ala Glu Ala Thr
                645                 650                 655

Pro Pro Arg Lys Asp Leu Ala Leu Leu Phe Pro Pro Lys Glu Glu Thr
                660                 665                 670

Pro Lys Leu Phe Lys Thr Leu Leu Gly Gly Thr Gly Lys Ala Ser Leu
                675                 680                 685

Ala Arg Leu Leu Lys Leu Lys Arg Glu Gln Ala Ala Gln Lys Lys Glu
                690                 695                 700

Asn Ser Glu Gly Gly Glu Glu Gly Lys Glu Asn Glu Asp Lys Gln
705                 710                 715                 720

Lys Glu Asn Glu Asp Lys Gln Lys Asn Glu Asp Lys Gly Lys Glu
                725                 730                 735

Asn Glu Asp Lys Asp Lys Gly Arg Glu Pro Glu Glu Lys Pro Leu Asp
                740                 745                 750
```

```
Arg Pro Glu Cys Thr Ala Ser Pro Ile Ala Val Glu Glu Pro His
        755                 760                 765

Ser Val Arg Arg Thr Val Leu Pro Arg Gly Thr Ser Arg Gln Ser Leu
770                 775                 780

Ile Ile Ser Met Ala Pro Ser Ala Glu Gly Gly Glu Glu Val Leu Thr
785                 790                 795                 800

Ile Glu Val Lys Glu Lys Ala Lys Gln
                805

<210> SEQ ID NO 27
<211> LENGTH: 354
<212> TYPE: PRT
<213> ORGANISM: Homo sapiens

<400> SEQUENCE: 27

Met Gly Ser Gly Ala Ser Ala Glu Asp Lys Glu Leu Ala Lys Arg Ser
1               5                   10                  15

Lys Glu Leu Glu Lys Lys Leu Gln Glu Asp Ala Asp Lys Glu Ala Lys
            20                  25                  30

Thr Val Lys Leu Leu Leu Gly Ala Gly Glu Ser Gly Lys Ser Thr
        35                  40                  45

Ile Val Lys Gln Met Lys Ile Ile His Gln Asp Gly Tyr Ser Pro Glu
50                  55                  60

Glu Cys Leu Glu Phe Lys Ala Ile Ile Tyr Gly Asn Val Leu Gln Ser
65                  70                  75                  80

Ile Leu Ala Ile Ile Arg Ala Met Thr Thr Leu Gly Ile Asp Tyr Ala
                85                  90                  95

Glu Pro Ser Cys Ala Asp Asp Gly Arg Gln Leu Asn Asn Leu Ala Asp
            100                 105                 110

Ser Ile Glu Glu Gly Thr Met Pro Pro Glu Leu Val Glu Val Ile Arg
        115                 120                 125

Arg Leu Trp Lys Asp Gly Gly Val Gln Ala Cys Phe Glu Arg Ala Ala
    130                 135                 140

Glu Tyr Gln Leu Asn Asp Ser Ala Ser Tyr Tyr Leu Asn Gln Leu Glu
145                 150                 155                 160

Arg Ile Thr Asp Pro Glu Tyr Leu Pro Ser Glu Gln Asp Val Leu Arg
                165                 170                 175

Ser Arg Val Lys Thr Thr Gly Ile Ile Glu Thr Lys Phe Ser Val Lys
            180                 185                 190

Asp Leu Asn Phe Arg Met Phe Asp Val Gly Gly Gln Arg Ser Glu Arg
        195                 200                 205

Lys Lys Trp Ile His Cys Phe Glu Gly Val Thr Cys Ile Ile Phe Cys
    210                 215                 220

Ala Ala Leu Ser Ala Tyr Asp Met Val Leu Val Glu Asp Asp Glu Val
225                 230                 235                 240

Asn Arg Met His Glu Ser Leu His Leu Phe Asn Ser Ile Cys Asn His
                245                 250                 255

Lys Phe Phe Ala Ala Thr Ser Ile Val Leu Phe Leu Asn Lys Lys Asp
            260                 265                 270

Leu Phe Glu Glu Lys Ile Lys Lys Val His Leu Ser Ile Cys Phe Pro
        275                 280                 285

Glu Tyr Asp Gly Asn Asn Ser Tyr Asp Ala Gly Asn Tyr Ile Lys
    290                 295                 300

Ser Gln Phe Leu Asp Leu Asn Met Arg Lys Asp Val Lys Glu Ile Tyr
305                 310                 315                 320
```

```
Ser His Met Thr Cys Ala Thr Asp Thr Gln Asn Val Lys Phe Val Phe
                325                 330                 335

Asp Ala Val Thr Asp Ile Ile Ile Lys Glu Asn Leu Lys Asp Cys Gly
            340                 345                 350

Leu Phe

<210> SEQ ID NO 28
<211> LENGTH: 815
<212> TYPE: PRT
<213> ORGANISM: Homo sapiens

<400> SEQUENCE: 28

Met Arg Glu Pro Glu Leu Met Pro Asp Ser Gly Ala Val Phe Thr
1               5                   10                  15

Phe Gly Lys Ser Lys Phe Ala Glu Asn Asn Pro Gly Lys Phe Trp Phe
                20                  25                  30

Lys Asn Asp Val Pro Val His Leu Ser Cys Gly Asp Glu His Ser Ala
                35                  40                  45

Val Val Thr Gly Asn Asn Lys Leu Tyr Met Phe Gly Ser Asn Asn Trp
50                  55                  60

Gly Gln Leu Gly Leu Gly Ser Lys Ser Ala Ile Ser Lys Pro Thr Cys
65                  70                  75                  80

Val Lys Ala Leu Lys Pro Glu Lys Val Lys Leu Ala Ala Cys Gly Arg
                85                  90                  95

Asn His Thr Leu Val Ser Thr Glu Gly Gly Asn Val Tyr Ala Thr Gly
                100                 105                 110

Gly Asn Asn Glu Gly Gln Leu Gly Leu Gly Asp Thr Glu Glu Arg Asn
            115                 120                 125

Thr Phe His Val Ile Ser Phe Phe Thr Ser Glu His Lys Ile Lys Gln
            130                 135                 140

Leu Ser Ala Gly Ser Asn Thr Ser Ala Ala Leu Thr Glu Asp Gly Arg
145                 150                 155                 160

Leu Phe Met Trp Gly Asp Asn Ser Glu Gly Gln Ile Gly Leu Lys Asn
                165                 170                 175

Val Ser Asn Val Cys Val Pro Gln Gln Val Thr Ile Gly Lys Pro Val
                180                 185                 190

Ser Trp Ile Ser Cys Gly Tyr Tyr His Ser Ala Phe Val Thr Thr Asp
            195                 200                 205

Gly Glu Leu Tyr Val Phe Gly Glu Pro Glu Asn Gly Lys Leu Gly Leu
            210                 215                 220

Pro Asn Gln Leu Leu Gly Asn His Arg Thr Pro Gln Leu Val Ser Glu
225                 230                 235                 240

Ile Pro Glu Lys Val Ile Gln Val Ala Cys Gly Gly Glu His Thr Val
                245                 250                 255

Val Leu Thr Glu Asn Ala Val Tyr Thr Phe Gly Leu Gly Gln Phe Gly
                260                 265                 270

Gln Leu Gly Leu Gly Thr Phe Leu Phe Glu Thr Ser Glu Pro Lys Val
            275                 280                 285

Ile Glu Asn Ile Arg Asp Gln Thr Ile Ser Tyr Ile Ser Cys Gly Glu
            290                 295                 300

Asn His Thr Ala Leu Ile Thr Asp Ile Gly Leu Met Tyr Thr Phe Gly
305                 310                 315                 320

Asp Gly Arg His Gly Lys Leu Gly Leu Gly Leu Glu Asn Phe Thr Asn
                325                 330                 335
```

-continued

His Phe Ile Pro Thr Leu Cys Ser Asn Phe Leu Arg Phe Ile Val Lys
                340                 345                 350

Leu Val Ala Cys Gly Gly Cys His Met Val Val Phe Ala Ala Pro His
            355                 360                 365

Arg Gly Val Ala Lys Glu Ile Glu Phe Asp Glu Ile Asn Asp Thr Cys
    370                 375                 380

Leu Ser Val Ala Thr Phe Leu Pro Tyr Ser Ser Leu Thr Ser Gly Asn
385                 390                 395                 400

Val Leu Gln Arg Thr Leu Ser Ala Arg Met Arg Arg Glu Arg Glu
                405                 410                 415

Arg Ser Pro Asp Ser Phe Ser Met Arg Arg Thr Leu Pro Pro Ile Glu
            420                 425                 430

Gly Thr Leu Gly Leu Ser Ala Cys Phe Leu Pro Asn Ser Val Phe Pro
            435                 440                 445

Arg Cys Ser Glu Arg Asn Leu Gln Glu Ser Val Leu Ser Glu Gln Asp
    450                 455                 460

Leu Met Gln Pro Glu Glu Pro Asp Tyr Leu Leu Asp Glu Met Thr Lys
465                 470                 475                 480

Glu Ala Glu Ile Asp Asn Ser Ser Thr Val Glu Ser Leu Gly Glu Thr
                485                 490                 495

Thr Asp Ile Leu Asn Met Thr His Ile Met Ser Leu Asn Ser Asn Glu
            500                 505                 510

Lys Ser Leu Lys Leu Ser Pro Val Gln Lys Gln Lys Gln Gln Thr
    515                 520                 525

Ile Gly Glu Leu Thr Gln Asp Thr Ala Leu Thr Glu Asn Asp Asp Ser
            530                 535                 540

Asp Glu Tyr Glu Glu Met Ser Glu Met Lys Glu Gly Lys Ala Cys Lys
545                 550                 555                 560

Gln His Val Ser Gln Gly Ile Phe Met Thr Gln Pro Ala Thr Thr Ile
                565                 570                 575

Glu Ala Phe Ser Asp Glu Glu Val Glu Ile Pro Glu Glu Lys Glu Gly
            580                 585                 590

Ala Glu Asp Ser Lys Gly Asn Gly Ile Glu Glu Gln Glu Val Glu Ala
    595                 600                 605

Asn Glu Glu Asn Val Lys Val His Gly Gly Arg Lys Glu Lys Thr Glu
    610                 615                 620

Ile Leu Ser Asp Asp Leu Thr Asp Lys Ala Glu Asp His Glu Phe Ser
625                 630                 635                 640

Lys Thr Glu Glu Leu Lys Leu Glu Asp Val Asp Glu Glu Ile Asn Ala
                645                 650                 655

Glu Asn Val Glu Ser Lys Lys Lys Thr Val Gly Asp Asp Glu Ser Val
            660                 665                 670

Pro Thr Gly Tyr His Ser Lys Thr Glu Gly Ala Glu Arg Thr Asn Asp
    675                 680                 685

Asp Ser Ser Ala Glu Thr Ile Glu Lys Lys Glu Lys Ala Asn Leu Glu
    690                 695                 700

Glu Arg Ala Ile Cys Glu Tyr Asn Glu Asn Pro Lys Gly Tyr Met Leu
705                 710                 715                 720

Asp Asp Ala Asp Ser Ser Ser Leu Glu Ile Leu Glu Asn Ser Glu Thr
                725                 730                 735

Thr Pro Ser Lys Asp Met Lys Lys Thr Lys Lys Ile Phe Leu Phe Lys
            740                 745                 750

```
Arg Val Pro Ser Ile Asn Gln Lys Ile Val Lys Asn Asn Glu Pro
            755                 760                 765

Leu Pro Glu Ile Lys Ser Ile Gly Asp Gln Ile Leu Lys Ser Asp
        770                 775                 780

Asn Lys Asp Ala Asp Gln Asn His Met Ser Gln Asn His Gln Asn Ile
785             790                 795                 800

Pro Pro Thr Asn Thr Glu Arg Arg Ser Lys Ser Cys Thr Ile Leu
                805                 810                 815

<210> SEQ ID NO 29
<211> LENGTH: 646
<212> TYPE: PRT
<213> ORGANISM: Homo sapiens

<400> SEQUENCE: 29

Met Arg Glu Pro Glu Glu Leu Met Pro Asp Ser Gly Ala Val Phe Thr
1               5                   10                  15

Phe Gly Lys Ser Lys Phe Ala Glu Asn Asn Pro Gly Lys Phe Trp Phe
                20                  25                  30

Lys Asn Asp Val Pro Val His Leu Ser Cys Gly Asp Glu His Ser Ala
                35                  40                  45

Val Val Thr Gly Asn Asn Lys Leu Tyr Met Phe Gly Ser Asn Asn Trp
    50                  55                  60

Gly Gln Leu Gly Leu Gly Ser Lys Ser Ala Ile Ser Lys Pro Thr Cys
65              70                  75                  80

Val Lys Ala Leu Lys Pro Glu Lys Val Lys Leu Ala Ala Cys Gly Arg
                85                  90                  95

Asn His Thr Leu Val Ser Thr Glu Gly Gly Asn Val Tyr Ala Thr Gly
                100                 105                 110

Gly Asn Asn Glu Gly Gln Leu Gly Leu Gly Asp Thr Glu Glu Arg Asn
                115                 120                 125

Thr Phe His Val Ile Ser Phe Phe Thr Ser Glu His Lys Ile Lys Gln
                130                 135                 140

Leu Ser Ala Gly Ser Asn Thr Ser Ala Ala Leu Thr Glu Asp Gly Arg
145             150                 155                 160

Leu Phe Met Trp Gly Asp Asn Ser Glu Gly Gln Ile Gly Leu Lys Asn
                165                 170                 175

Val Ser Asn Val Cys Val Pro Gln Gln Val Thr Ile Gly Lys Pro Val
                180                 185                 190

Ser Trp Ile Ser Cys Gly Tyr Tyr His Ser Ala Phe Val Thr Thr Asp
                195                 200                 205

Gly Glu Leu Tyr Val Phe Gly Glu Pro Glu Asn Gly Lys Leu Gly Leu
                210                 215                 220

Pro Asn Gln Leu Leu Gly Asn His Arg Thr Pro Gln Leu Val Ser Glu
225             230                 235                 240

Ile Pro Glu Lys Val Ile Gln Val Ala Cys Gly Gly Glu His Thr Val
                245                 250                 255

Val Leu Thr Glu Asn Ala Val Tyr Thr Phe Gly Leu Gly Gln Phe Gly
                260                 265                 270

Gln Leu Gly Leu Gly Thr Phe Leu Phe Glu Thr Ser Glu Pro Lys Val
                275                 280                 285

Ile Glu Asn Ile Arg Asp Gln Thr Ile Ser Tyr Ile Ser Cys Gly Glu
                290                 295                 300

Asn His Thr Ala Leu Ile Thr Asp Ile Gly Leu Met Tyr Thr Phe Gly
305             310                 315                 320
```

```
Asp Gly Arg His Gly Lys Leu Gly Leu Gly Leu Glu Asn Phe Thr Asn
            325                 330                 335

His Phe Ile Pro Thr Leu Cys Ser Asn Phe Leu Arg Phe Ile Val Lys
            340                 345                 350

Leu Val Ala Cys Gly Gly Cys His Met Val Val Phe Ala Ala Pro His
            355                 360                 365

Arg Gly Val Ala Lys Glu Ile Glu Phe Asp Glu Ile Asn Asp Thr Cys
            370                 375                 380

Leu Ser Val Ala Thr Phe Leu Pro Tyr Ser Ser Leu Thr Ser Gly Asn
385                 390                 395                 400

Val Leu Gln Arg Thr Leu Ser Ala Arg Met Arg Arg Glu Arg Glu
            405                 410                 415

Arg Ser Pro Asp Ser Phe Ser Met Arg Arg Thr Leu Pro Pro Ile Glu
            420                 425                 430

Gly Thr Leu Gly Leu Ser Ala Cys Phe Leu Pro Asn Ser Val Phe Pro
            435                 440                 445

Arg Cys Ser Glu Arg Asn Leu Gln Glu Ser Val Leu Ser Glu Gln Asp
            450                 455                 460

Leu Met Gln Pro Glu Glu Pro Asp Tyr Leu Leu Asp Glu Met Thr Lys
465                 470                 475                 480

Glu Ala Glu Ile Asp Asn Ser Ser Thr Val Glu Ser Leu Gly Glu Thr
            485                 490                 495

Thr Asp Ile Leu Asn Met Thr His Ile Met Ser Leu Asn Ser Asn Glu
            500                 505                 510

Lys Ser Leu Lys Leu Ser Pro Val Gln Lys Gln Lys Gln Gln Thr
            515                 520                 525

Ile Gly Glu Leu Thr Gln Asp Thr Ala Leu Thr Glu Asn Asp Asp Ser
            530                 535                 540

Asp Glu Tyr Glu Glu Met Ser Glu Met Lys Glu Gly Lys Ala Cys Lys
545                 550                 555                 560

Gln His Val Ser Gln Gly Ile Phe Met Thr Gln Pro Ala Thr Thr Ile
            565                 570                 575

Glu Ala Phe Ser Asp Glu Glu Val Glu Ile Pro Glu Glu Lys Glu Gly
            580                 585                 590

Ala Glu Asp Ser Lys Gly Asn Gly Ile Glu Glu Gln Glu Val Glu Ala
            595                 600                 605

Asn Glu Glu Asn Val Lys Val His Gly Gly Arg Lys Glu Lys Thr Glu
            610                 615                 620

Ile Leu Ser Asp Asp Leu Thr Asp Lys Ala Glu Tyr Ser Ala Ser His
625                 630                 635                 640

Ser Gln Ile Val Ser Val
            645

<210> SEQ ID NO 30
<211> LENGTH: 1152
<212> TYPE: PRT
<213> ORGANISM: Homo sapiens

<400> SEQUENCE: 30

Met Arg Glu Pro Glu Glu Leu Met Pro Asp Ser Gly Ala Val Phe Thr
1               5                   10                  15

Phe Gly Lys Ser Lys Phe Ala Glu Asn Asn Pro Gly Lys Phe Trp Phe
            20                  25                  30

Lys Asn Asp Val Pro Val His Leu Ser Cys Gly Asp Glu His Ser Ala
```

-continued

```
                35                  40                  45
Val Val Thr Gly Asn Asn Lys Leu Tyr Met Phe Gly Ser Asn Asn Trp
 50                  55                  60

Gly Gln Leu Gly Leu Gly Ser Lys Ser Ala Ile Ser Lys Pro Thr Cys
 65                  70                  75                  80

Val Lys Ala Leu Lys Pro Glu Lys Val Lys Leu Ala Ala Cys Gly Arg
                 85                  90                  95

Asn His Thr Leu Val Ser Thr Glu Gly Gly Asn Val Tyr Ala Thr Gly
                100                 105                 110

Gly Asn Asn Glu Gly Gln Leu Gly Leu Gly Asp Thr Glu Glu Arg Asn
                115                 120                 125

Thr Phe His Val Ile Ser Phe Phe Thr Ser Glu His Lys Ile Lys Gln
130                 135                 140

Leu Ser Ala Gly Ser Asn Thr Ser Ala Ala Leu Thr Glu Asp Gly Arg
145                 150                 155                 160

Leu Phe Met Trp Gly Asp Asn Ser Glu Gly Gln Ile Gly Leu Lys Asn
                165                 170                 175

Val Ser Asn Val Cys Val Pro Gln Gln Val Thr Ile Gly Lys Pro Val
                180                 185                 190

Ser Trp Ile Ser Cys Gly Tyr Tyr His Ser Ala Phe Val Thr Thr Asp
                195                 200                 205

Gly Glu Leu Tyr Val Phe Gly Glu Pro Glu Asn Gly Lys Leu Gly Leu
210                 215                 220

Pro Asn Gln Leu Leu Gly Asn His Arg Thr Pro Gln Leu Val Ser Glu
225                 230                 235                 240

Ile Pro Glu Lys Val Ile Gln Val Ala Cys Gly Gly Glu His Thr Val
                245                 250                 255

Val Leu Thr Glu Asn Ala Val Tyr Thr Phe Gly Leu Gly Gln Phe Gly
                260                 265                 270

Gln Leu Gly Leu Gly Thr Phe Leu Phe Glu Thr Ser Glu Pro Lys Val
                275                 280                 285

Ile Glu Asn Ile Arg Asp Gln Thr Ile Ser Tyr Ile Ser Cys Gly Glu
290                 295                 300

Asn His Thr Ala Leu Ile Thr Asp Ile Gly Leu Met Tyr Thr Phe Gly
305                 310                 315                 320

Asp Gly Arg His Gly Lys Leu Gly Leu Gly Leu Glu Asn Phe Thr Asn
                325                 330                 335

His Phe Ile Pro Thr Leu Cys Ser Asn Phe Leu Arg Phe Ile Val Lys
                340                 345                 350

Leu Val Ala Cys Gly Gly Cys His Met Val Val Phe Ala Ala Pro His
                355                 360                 365

Arg Gly Val Ala Lys Glu Ile Glu Phe Asp Glu Ile Asn Asp Thr Cys
                370                 375                 380

Leu Ser Val Ala Thr Phe Leu Pro Tyr Ser Ser Leu Thr Ser Gly Asn
385                 390                 395                 400

Val Leu Gln Arg Thr Leu Ser Ala Arg Met Arg Arg Arg Glu Arg Glu
                405                 410                 415

Arg Ser Pro Asp Ser Phe Ser Met Arg Arg Thr Leu Pro Pro Ile Glu
                420                 425                 430

Gly Thr Leu Gly Leu Ser Ala Cys Phe Leu Pro Asn Ser Val Phe Pro
                435                 440                 445

Arg Cys Ser Glu Arg Asn Leu Gln Glu Ser Val Leu Ser Glu Gln Asp
450                 455                 460
```

```
Leu Met Gln Pro Glu Glu Pro Asp Tyr Leu Leu Asp Glu Met Thr Lys
465                 470                 475                 480

Glu Ala Glu Ile Asp Asn Ser Ser Thr Val Glu Ser Leu Gly Glu Thr
                485                 490                 495

Thr Asp Ile Leu Asn Met Thr His Ile Met Ser Leu Asn Ser Asn Glu
            500                 505                 510

Lys Ser Leu Lys Leu Ser Pro Val Gln Lys Gln Lys Gln Gln Thr
        515                 520                 525

Ile Gly Glu Leu Thr Gln Asp Thr Ala Leu Thr Glu Asn Asp Asp Ser
    530                 535                 540

Asp Glu Tyr Glu Glu Met Ser Glu Met Lys Glu Gly Lys Ala Cys Lys
545                 550                 555                 560

Gln His Val Ser Gln Gly Ile Phe Met Thr Gln Pro Ala Thr Thr Ile
                565                 570                 575

Glu Ala Phe Ser Asp Glu Glu Val Glu Ile Pro Glu Glu Lys Glu Gly
                580                 585                 590

Ala Glu Asp Ser Lys Gly Asn Gly Ile Glu Glu Gln Glu Val Glu Ala
            595                 600                 605

Asn Glu Glu Asn Val Lys Val His Gly Gly Arg Lys Glu Lys Thr Glu
610                 615                 620

Ile Leu Ser Asp Asp Leu Thr Asp Lys Ala Glu Val Ser Glu Gly Lys
625                 630                 635                 640

Ala Lys Ser Val Gly Glu Ala Glu Asp Gly Pro Glu Gly Arg Gly Asp
                645                 650                 655

Gly Thr Cys Glu Glu Gly Ser Ser Gly Ala Glu His Trp Gln Asp Glu
                660                 665                 670

Glu Arg Glu Lys Gly Glu Lys Asp Lys Gly Arg Gly Glu Met Glu Arg
                675                 680                 685

Pro Gly Glu Gly Glu Lys Glu Leu Ala Glu Lys Glu Glu Trp Lys Lys
            690                 695                 700

Arg Asp Gly Glu Glu Gln Glu Gln Lys Glu Arg Glu Gln Gly His Gln
705                 710                 715                 720

Lys Glu Arg Asn Gln Glu Met Glu Glu Gly Gly Glu Glu Glu His Gly
                725                 730                 735

Glu Gly Glu Glu Glu Glu Gly Asp Arg Glu Glu Glu Glu Glu Lys Glu
                740                 745                 750

Gly Glu Gly Lys Glu Glu Gly Glu Glu Glu Val Glu Gly Glu Arg
            755                 760                 765

Glu Lys Glu Glu Gly Glu Arg Lys Lys Glu Glu Arg Ala Gly Lys Glu
        770                 775                 780

Glu Lys Gly Glu Glu Gly Asp Gln Gly Glu Gly Glu Glu Glu Glu
785                 790                 795                 800

Thr Glu Gly Arg Gly Glu Glu Lys Glu Glu Gly Gly Glu Val Glu Gly
                805                 810                 815

Gly Glu Val Glu Glu Gly Lys Gly Glu Arg Glu Glu Glu Glu Glu
        820                 825                 830

Gly Glu Gly Glu Glu Glu Glu Gly Glu Gly Glu Glu Glu Glu Gly Glu
            835                 840                 845

Gly Glu Glu Glu Glu Gly Glu Gly Lys Gly Glu Glu Glu Gly Glu Glu
            850                 855                 860

Gly Glu Gly Glu Glu Glu Gly Glu Glu Gly Glu Gly Glu Gly Glu Glu
            865                 870                 875                 880
```

```
Glu Glu Gly Glu Gly Glu Gly Glu Gly Glu Gly Glu Gly Glu
            885                 890                 895

Glu Glu Glu Gly Glu Gly Glu Gly Glu Glu Gly Glu Gly Glu Gly
            900                 905                 910

Glu Glu Glu Glu Gly Glu Gly Lys Gly Glu Glu Gly Glu Glu Gly
            915                 920                 925

Glu Gly Glu Gly Glu Glu Glu Glu Gly Glu Gly Glu Asp Gly
            930                 935                 940

Glu Gly Glu Gly Glu Glu Glu Gly Glu Trp Glu Gly Glu Glu Glu
945                 950                 955                 960

Glu Gly Glu Gly Glu Gly Glu Glu Gly Glu Gly Glu Gly Glu Glu
            965                 970                 975

Gly Glu Gly Glu Gly Glu Glu Glu Gly Glu Gly Glu Gly Glu Glu
            980                 985                 990

Glu Glu Gly Glu Gly Glu Gly Glu Glu Glu Gly Glu Gly Glu Glu Glu
            995                 1000                1005

Gly Glu  Gly Glu Gly Glu Glu  Glu Glu Glu Gly Glu  Val Glu Gly
            1010                1015                1020

Glu Val  Glu Gly Glu Glu Gly  Glu Gly Glu Gly Glu  Glu Glu Glu
            1025                1030                1035

Gly Glu  Glu Glu Gly Glu Glu  Arg Glu Lys Glu Gly  Glu Gly Glu
            1040                1045                1050

Glu Asn  Arg Arg Asn Arg Glu  Glu Glu Glu Glu Glu  Glu Gly Lys
            1055                1060                1065

Tyr Gln  Glu Thr Gly Glu Glu  Glu Asn Glu Arg Gln  Asp Gly Glu
            1070                1075                1080

Glu Tyr  Lys Lys Val Ser Lys  Ile Lys Gly Ser Val  Lys Tyr Gly
            1085                1090                1095

Lys His  Lys Thr Tyr Gln Lys  Lys Ser Val Thr Asn  Thr Gln Gly
            1100                1105                1110

Asn Gly  Lys Glu Gln Arg Ser  Lys Met Pro Val Gln  Ser Lys Arg
            1115                1120                1125

Leu Leu  Lys Asn Gly Pro Ser  Gly Ser Lys Lys Phe  Trp Asn Asn
            1130                1135                1140

Val Leu  Pro His Tyr Leu Glu  Leu Lys
            1145                1150

<210> SEQ ID NO 31
<211> LENGTH: 1020
<212> TYPE: PRT
<213> ORGANISM: Homo sapiens

<400> SEQUENCE: 31

Met Arg Glu Pro Glu Glu Leu Met Pro Asp Ser Gly Ala Val Phe Thr
1               5                   10                  15

Phe Gly Lys Ser Lys Phe Ala Glu Asn Asn Pro Gly Lys Phe Trp Phe
                20                  25                  30

Lys Asn Asp Val Pro Val His Leu Ser Cys Gly Asp Glu His Ser Ala
            35                  40                  45

Val Val Thr Gly Asn Asn Lys Leu Tyr Met Phe Gly Ser Asn Asn Trp
        50                  55                  60

Gly Gln Leu Gly Leu Gly Ser Lys Ser Ala Ile Ser Lys Pro Thr Cys
65                  70                  75                  80

Val Lys Ala Leu Lys Pro Glu Lys Val Lys Leu Ala Ala Cys Gly Arg
                85                  90                  95
```

```
Asn His Thr Leu Val Ser Thr Glu Gly Gly Asn Val Tyr Ala Thr Gly
            100                 105                 110

Gly Asn Asn Glu Gly Gln Leu Gly Leu Gly Asp Thr Glu Glu Arg Asn
            115                 120                 125

Thr Phe His Val Ile Ser Phe Phe Thr Ser Glu His Lys Ile Lys Gln
            130                 135                 140

Leu Ser Ala Gly Ser Asn Thr Ser Ala Ala Leu Thr Glu Asp Gly Arg
145                 150                 155                 160

Leu Phe Met Trp Gly Asp Asn Ser Glu Gly Gln Ile Gly Leu Lys Asn
                165                 170                 175

Val Ser Asn Val Cys Val Pro Gln Gln Val Thr Ile Gly Lys Pro Val
            180                 185                 190

Ser Trp Ile Ser Cys Gly Tyr Tyr His Ser Ala Phe Val Thr Thr Asp
            195                 200                 205

Gly Glu Leu Tyr Val Phe Gly Glu Pro Glu Asn Gly Lys Leu Gly Leu
            210                 215                 220

Pro Asn Gln Leu Leu Gly Asn His Arg Thr Pro Gln Leu Val Ser Glu
225                 230                 235                 240

Ile Pro Glu Lys Val Ile Gln Val Ala Cys Gly Gly Glu His Thr Val
                245                 250                 255

Val Leu Thr Glu Asn Ala Val Tyr Thr Phe Gly Leu Gly Gln Phe Gly
            260                 265                 270

Gln Leu Gly Leu Gly Thr Phe Leu Phe Glu Thr Ser Glu Pro Lys Val
            275                 280                 285

Ile Glu Asn Ile Arg Asp Gln Thr Ile Ser Tyr Ile Ser Cys Gly Glu
            290                 295                 300

Asn His Thr Ala Leu Ile Thr Asp Ile Gly Leu Met Tyr Thr Phe Gly
305                 310                 315                 320

Asp Gly Arg His Gly Lys Leu Gly Leu Gly Leu Glu Asn Phe Thr Asn
                325                 330                 335

His Phe Ile Pro Thr Leu Cys Ser Asn Phe Leu Arg Phe Ile Val Lys
            340                 345                 350

Leu Val Ala Cys Gly Gly Cys His Met Val Val Phe Ala Ala Pro His
            355                 360                 365

Arg Gly Val Ala Lys Glu Ile Glu Phe Asp Glu Ile Asn Asp Thr Cys
            370                 375                 380

Leu Ser Val Ala Thr Phe Leu Pro Tyr Ser Ser Leu Thr Ser Gly Asn
385                 390                 395                 400

Val Leu Gln Arg Thr Leu Ser Ala Arg Met Arg Arg Arg Glu Arg Glu
                405                 410                 415

Arg Ser Pro Asp Ser Phe Ser Met Arg Arg Thr Leu Pro Pro Ile Glu
            420                 425                 430

Gly Thr Leu Gly Leu Ser Ala Cys Phe Leu Pro Asn Ser Val Phe Pro
            435                 440                 445

Arg Cys Ser Glu Arg Asn Leu Gln Glu Ser Val Leu Ser Glu Gln Asp
            450                 455                 460

Leu Met Gln Pro Glu Glu Pro Asp Tyr Leu Leu Asp Glu Met Thr Lys
465                 470                 475                 480

Glu Ala Glu Ile Asp Asn Ser Ser Thr Val Glu Ser Leu Gly Glu Thr
                485                 490                 495

Thr Asp Ile Leu Asn Met Thr His Ile Met Ser Leu Asn Ser Asn Glu
            500                 505                 510
```

-continued

```
Lys Ser Leu Lys Leu Ser Pro Val Gln Lys Gln Lys Gln Gln Thr
        515                 520                 525

Ile Gly Glu Leu Thr Gln Asp Thr Ala Leu Thr Glu Asn Asp Asp Ser
530                     535                 540

Asp Glu Tyr Glu Glu Met Ser Glu Met Lys Glu Gly Lys Ala Cys Lys
545                 550                 555                 560

Gln His Val Ser Gln Gly Ile Phe Met Thr Gln Pro Ala Thr Thr Ile
                565                 570                 575

Glu Ala Phe Ser Asp Glu Glu Val Gly Asn Asp Thr Gly Gln Val Gly
            580                 585                 590

Pro Gln Ala Asp Thr Asp Gly Glu Gly Leu Gln Lys Glu Val Tyr Arg
        595                 600                 605

His Glu Asn Asn Asn Gly Val Asp Gln Leu Asp Ala Lys Glu Ile Glu
    610                 615                 620

Lys Glu Ser Asp Gly Gly His Ser Gln Lys Glu Ser Glu Ala Glu Glu
625                 630                 635                 640

Ile Asp Ser Glu Lys Glu Thr Lys Leu Ala Glu Ile Ala Gly Met Lys
                645                 650                 655

Asp Leu Arg Glu Arg Glu Lys Ser Thr Lys Lys Met Ser Pro Phe Phe
            660                 665                 670

Gly Asn Leu Pro Asp Arg Gly Met Asn Thr Glu Ser Glu Glu Asn Lys
        675                 680                 685

Asp Phe Val Lys Lys Arg Glu Ser Cys Lys Gln Asp Val Ile Phe Asp
    690                 695                 700

Ser Glu Arg Glu Ser Val Glu Lys Pro Asp Ser Tyr Met Glu Gly Ala
705                 710                 715                 720

Ser Glu Ser Gln Gln Gly Ile Ala Asp Gly Phe Gln Gln Pro Glu Ala
                725                 730                 735

Ile Glu Phe Ser Ser Gly Glu Lys Glu Asp Asp Glu Val Glu Thr Asp
            740                 745                 750

Gln Asn Ile Arg Tyr Gly Arg Lys Leu Ile Glu Gln Gly Asn Glu Lys
        755                 760                 765

Glu Thr Lys Pro Ile Ile Ser Lys Ser Met Ala Lys Tyr Asp Phe Lys
    770                 775                 780

Cys Asp Arg Leu Ser Glu Ile Pro Glu Glu Lys Glu Gly Ala Glu Asp
785                 790                 795                 800

Ser Lys Gly Asn Gly Ile Glu Glu Gln Glu Val Glu Ala Asn Glu Glu
                805                 810                 815

Asn Val Lys Val His Gly Gly Arg Lys Glu Lys Thr Glu Ile Leu Ser
            820                 825                 830

Asp Asp Leu Thr Asp Lys Ala Glu Asp His Glu Phe Ser Lys Thr Glu
        835                 840                 845

Glu Leu Lys Leu Glu Asp Val Asp Glu Glu Ile Asn Ala Glu Asn Val
    850                 855                 860

Glu Ser Lys Lys Lys Thr Val Gly Asp Asp Ser Val Pro Thr Gly
865                 870                 875                 880

Tyr His Ser Lys Thr Glu Gly Ala Glu Arg Thr Asn Asp Ser Ser
                885                 890                 895

Ala Glu Thr Ile Glu Lys Lys Glu Lys Ala Asn Leu Glu Glu Arg Ala
            900                 905                 910

Ile Cys Glu Tyr Asn Glu Asn Pro Lys Gly Tyr Met Leu Asp Asp Ala
        915                 920                 925

Asp Ser Ser Ser Leu Glu Ile Leu Glu Asn Ser Glu Thr Thr Pro Ser
```

```
                    930               935              940
Lys Asp Met Lys Thr Lys Lys Ile Phe Leu Phe Lys Arg Val Pro
945                 950              955              960

Ser Ile Asn Gln Lys Ile Val Lys Asn Asn Asn Glu Pro Leu Pro Glu
                    965              970              975

Ile Lys Ser Ile Gly Asp Gln Ile Ile Leu Lys Ser Asp Asn Lys Asp
                980              985              990

Ala Asp Gln Asn His Met Ser Gln Asn His Gln Asn Ile Pro Pro Thr
            995              1000             1005

Asn Thr Glu Arg Arg Ser Lys Ser Cys Thr Ile Leu
        1010             1015             1020

<210> SEQ ID NO 32
<211> LENGTH: 1368
<212> TYPE: PRT
<213> ORGANISM: Streptococcus pyogenes

<400> SEQUENCE: 32

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285
```

```
Leu Phe Leu Ala Ala Lys Asn Leu Ser Asp Ala Ile Leu Leu Ser Asp
    290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
        355                 360                 365
Gln Glu Glu Phe Tyr Lys Phe Ile Lys Pro Ile Leu Glu Lys Met Asp
370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
        435                 440                 445
Pro Tyr Tyr Val Gly Pro Leu Ala Arg Gly Asn Ser Arg Phe Ala Trp
    450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
        515                 520                 525
Tyr Val Thr Glu Gly Met Arg Lys Pro Ala Phe Leu Ser Gly Glu Gln
    530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
            580                 585                 590
Thr Tyr His Asp Leu Leu Lys Ile Ile Lys Asp Lys Asp Phe Leu Asp
        595                 600                 605
Asn Glu Glu Asn Glu Asp Ile Leu Glu Asp Ile Val Leu Thr Leu Thr
    610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
            660                 665                 670
Lys Gln Ser Gly Lys Thr Ile Leu Asp Phe Leu Lys Ser Asp Gly Phe
        675                 680                 685
Ala Asn Arg Asn Phe Met Gln Leu Ile His Asp Asp Ser Leu Thr Phe
    690                 695                 700
Lys Glu Asp Ile Gln Lys Ala Gln Val Ser Gly Gln Gly Asp Ser Leu
```

```
            705                 710                 715                 720
His Glu His Ile Ala Asn Leu Ala Gly Ser Pro Ala Ile Lys Lys Gly
                    725                 730                 735
Ile Leu Gln Thr Val Lys Val Val Asp Glu Leu Val Lys Val Met Gly
                    740                 745                 750
Arg His Lys Pro Glu Asn Ile Val Ile Glu Met Ala Arg Glu Asn Gln
                    755                 760                 765
Thr Thr Gln Lys Gly Gln Lys Asn Ser Arg Glu Arg Met Lys Arg Ile
            770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                    805                 810                 815
Gln Asn Gly Arg Asp Met Tyr Val Asp Gln Glu Leu Asp Ile Asn Arg
                    820                 825                 830
Leu Ser Asp Tyr Asp Val Asp His Ile Val Pro Gln Ser Phe Leu Lys
                    835                 840                 845
Asp Asp Ser Ile Asp Asn Lys Val Leu Thr Arg Ser Asp Lys Asn Arg
            850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                    885                 890                 895
Phe Asp Asn Leu Thr Lys Ala Glu Arg Gly Gly Leu Ser Glu Leu Asp
                    900                 905                 910
Lys Ala Gly Phe Ile Lys Arg Gln Leu Val Glu Thr Arg Gln Ile Thr
                    915                 920                 925
Lys His Val Ala Gln Ile Leu Asp Ser Arg Met Asn Thr Lys Tyr Asp
            930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                    965                 970                 975
Glu Ile Asn Asn Tyr His His Ala His Asp Ala Tyr Leu Asn Ala Val
                    980                 985                 990
Val Gly Thr Ala Leu Ile Lys Lys Tyr Pro Lys Leu Glu Ser Glu Phe
                    995                 1000                1005
Val Tyr Gly Asp Tyr Lys Val Tyr Asp Val Arg Lys Met Ile Ala
                    1010                1015                1020
Lys Ser Glu Gln Glu Ile Gly Lys Ala Thr Ala Lys Tyr Phe Phe
                    1025                1030                1035
Tyr Ser Asn Ile Met Asn Phe Phe Lys Thr Glu Ile Thr Leu Ala
                    1040                1045                1050
Asn Gly Glu Ile Arg Lys Arg Pro Leu Ile Glu Thr Asn Gly Glu
                    1055                1060                1065
Thr Gly Glu Ile Val Trp Asp Lys Gly Arg Asp Phe Ala Thr Val
                    1070                1075                1080
Arg Lys Val Leu Ser Met Pro Gln Val Asn Ile Val Lys Lys Thr
                    1085                1090                1095
Glu Val Gln Thr Gly Gly Phe Ser Lys Glu Ser Ile Leu Pro Lys
                    1100                1105                1110
Arg Asn Ser Asp Lys Leu Ile Ala Arg Lys Lys Asp Trp Asp Pro
                    1115                1120                1125
```

```
Lys Lys Tyr Gly Gly Phe Asp Ser Pro Thr Val Ala Tyr Ser Val
1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
1340                1345                1350

Gly Leu Tyr Glu Thr Arg Ile Asp Leu Ser Gln Leu Gly Gly Asp
    1355                1360                1365

<210> SEQ ID NO 33
<211> LENGTH: 1053
<212> TYPE: PRT
<213> ORGANISM: Staphylococcus aureus

<400> SEQUENCE: 33

Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
                20                  25                  30

Val Arg Leu Phe Lys Glu Ala Asn Val Glu Asn Asn Glu Gly Arg Arg
            35                  40                  45

Ser Lys Arg Gly Ala Arg Arg Leu Lys Arg Arg Arg His Arg Ile
        50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
```

```
            115                 120                 125
Gly Asn Glu Leu Ser Thr Lys Glu Gln Ile Ser Arg Asn Ser Lys Ala
        130                 135                 140
Leu Glu Glu Lys Tyr Val Ala Glu Leu Gln Leu Glu Arg Leu Lys Lys
145                 150                 155                 160
Asp Gly Glu Val Arg Gly Ser Ile Asn Arg Phe Lys Thr Ser Asp Tyr
                165                 170                 175
Val Lys Glu Ala Lys Gln Leu Leu Lys Val Gln Lys Ala Tyr His Gln
            180                 185                 190
Leu Asp Gln Ser Phe Ile Asp Thr Tyr Ile Asp Leu Leu Glu Thr Arg
        195                 200                 205
Arg Thr Tyr Tyr Glu Gly Pro Gly Glu Gly Ser Pro Phe Gly Trp Lys
210                 215                 220
Asp Ile Lys Glu Trp Tyr Glu Met Leu Met Gly His Cys Thr Tyr Phe
225                 230                 235                 240
Pro Glu Glu Leu Arg Ser Val Lys Tyr Ala Tyr Asn Ala Asp Leu Tyr
                245                 250                 255
Asn Ala Leu Asn Asp Leu Asn Asn Leu Val Ile Thr Arg Asp Glu Asn
            260                 265                 270
Glu Lys Leu Glu Tyr Tyr Glu Lys Phe Gln Ile Ile Glu Asn Val Phe
        275                 280                 285
Lys Gln Lys Lys Lys Pro Thr Leu Lys Gln Ile Ala Lys Glu Ile Leu
290                 295                 300
Val Asn Glu Glu Asp Ile Lys Gly Tyr Arg Val Thr Ser Thr Gly Lys
305                 310                 315                 320
Pro Glu Phe Thr Asn Leu Lys Val Tyr His Asp Ile Lys Asp Ile Thr
                325                 330                 335
Ala Arg Lys Glu Ile Ile Glu Asn Ala Glu Leu Leu Asp Gln Ile Ala
            340                 345                 350
Lys Ile Leu Thr Ile Tyr Gln Ser Ser Glu Asp Ile Gln Glu Glu Leu
        355                 360                 365
Thr Asn Leu Asn Ser Glu Leu Thr Gln Glu Glu Ile Glu Gln Ile Ser
        370                 375                 380
Asn Leu Lys Gly Tyr Thr Gly Thr His Asn Leu Ser Leu Lys Ala Ile
385                 390                 395                 400
Asn Leu Ile Leu Asp Glu Leu Trp His Thr Asn Asp Asn Gln Ile Ala
                405                 410                 415
Ile Phe Asn Arg Leu Lys Leu Val Pro Lys Lys Val Asp Leu Ser Gln
            420                 425                 430
Gln Lys Glu Ile Pro Thr Thr Leu Val Asp Asp Phe Ile Leu Ser Pro
        435                 440                 445
Val Val Lys Arg Ser Phe Ile Gln Ser Ile Lys Val Ile Asn Ala Ile
450                 455                 460
Ile Lys Lys Tyr Gly Leu Pro Asn Asp Ile Ile Ile Glu Leu Ala Arg
465                 470                 475                 480
Glu Lys Asn Ser Lys Asp Ala Gln Lys Met Ile Asn Glu Met Gln Lys
                485                 490                 495
Arg Asn Arg Gln Thr Asn Glu Arg Ile Glu Glu Ile Ile Arg Thr Thr
            500                 505                 510
Gly Lys Glu Asn Ala Lys Tyr Leu Ile Glu Lys Ile Lys Leu His Asp
        515                 520                 525
Met Gln Glu Gly Lys Cys Leu Tyr Ser Leu Glu Ala Ile Pro Leu Glu
        530                 535                 540
```

```
Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
        595                 600                 605

Leu Asn Leu Ala Lys Gly Lys Gly Arg Ile Ser Lys Thr Lys Lys Glu
    610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
            660                 665                 670

Val Lys Ser Ile Asn Gly Gly Phe Thr Ser Phe Leu Arg Arg Lys Trp
        675                 680                 685

Lys Phe Lys Lys Glu Arg Asn Lys Gly Tyr Lys His His Ala Glu Asp
    690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
            740                 745                 750

Ile Phe Ile Thr Pro His Gln Ile Lys His Ile Lys Asp Phe Lys Asp
        755                 760                 765

Tyr Lys Tyr Ser His Arg Val Asp Lys Lys Pro Asn Arg Glu Leu Ile
    770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
        835                 840                 845

Asp Glu Lys Asn Pro Leu Tyr Lys Tyr Tyr Glu Glu Thr Gly Asn Tyr
    850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
            900                 905                 910

Arg Phe Asp Val Tyr Leu Asp Asn Gly Val Tyr Lys Phe Val Thr Val
        915                 920                 925

Lys Asn Leu Asp Val Ile Lys Lys Glu Asn Tyr Tyr Glu Val Asn Ser
    930                 935                 940

Lys Cys Tyr Glu Glu Ala Lys Lys Leu Lys Lys Ile Ser Asn Gln Ala
945                 950                 955                 960
```

```
Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
            980                 985                 990

Glu Val Asn Met Ile Asp Ile Thr Tyr Arg Glu Tyr Leu Glu Asn Met
        995                 1000                1005

Asn Asp Lys Arg Pro Pro Arg Ile Ile Lys Thr Ile Ala Ser Lys
    1010                1015                1020

Thr Gln Ser Ile Lys Lys Tyr Ser Thr Asp Ile Leu Gly Asn Leu
    1025                1030                1035

Tyr Glu Val Lys Ser Lys Lys His Pro Gln Ile Ile Lys Lys Gly
    1040                1045                1050

<210> SEQ ID NO 34
<211> LENGTH: 1300
<212> TYPE: PRT
<213> ORGANISM: Francisella tularensis

<400> SEQUENCE: 34

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285
```

```
Phe Val Asn Gly Glu Asn Thr Lys Arg Lys Gly Ile Asn Glu Tyr Ile
    290                 295                 300
Asn Leu Tyr Ser Gln Gln Ile Asn Asp Lys Thr Leu Lys Lys Tyr Lys
305                 310                 315                 320
Met Ser Val Leu Phe Lys Gln Ile Leu Ser Asp Thr Glu Ser Lys Ser
                325                 330                 335
Phe Val Ile Asp Lys Leu Glu Asp Asp Ser Asp Val Val Thr Thr Met
            340                 345                 350
Gln Ser Phe Tyr Glu Gln Ile Ala Ala Phe Lys Thr Val Glu Glu Lys
        355                 360                 365
Ser Ile Lys Glu Thr Leu Ser Leu Leu Phe Asp Asp Leu Lys Ala Gln
370                 375                 380
Lys Leu Asp Leu Ser Lys Ile Tyr Phe Lys Asn Asp Lys Ser Leu Thr
385                 390                 395                 400
Asp Leu Ser Gln Gln Val Phe Asp Asp Tyr Ser Val Ile Gly Thr Ala
                405                 410                 415
Val Leu Glu Tyr Ile Thr Gln Gln Ile Ala Pro Lys Asn Leu Asp Asn
            420                 425                 430
Pro Ser Lys Lys Glu Gln Glu Leu Ile Ala Lys Lys Thr Glu Lys Ala
        435                 440                 445
Lys Tyr Leu Ser Leu Glu Thr Ile Lys Leu Ala Leu Glu Glu Phe Asn
450                 455                 460
Lys His Arg Asp Ile Asp Lys Gln Cys Arg Phe Glu Glu Ile Leu Ala
465                 470                 475                 480
Asn Phe Ala Ala Ile Pro Met Ile Phe Asp Glu Ile Ala Gln Asn Lys
                485                 490                 495
Asp Asn Leu Ala Gln Ile Ser Ile Lys Tyr Gln Asn Gln Gly Lys Lys
            500                 505                 510
Asp Leu Leu Gln Ala Ser Ala Glu Asp Val Lys Ala Ile Lys Asp
        515                 520                 525
Leu Leu Asp Gln Thr Asn Asn Leu Leu His Lys Leu Lys Ile Phe His
530                 535                 540
Ile Ser Gln Ser Glu Asp Lys Ala Asn Ile Leu Asp Lys Asp Glu His
545                 550                 555                 560
Phe Tyr Leu Val Phe Glu Glu Cys Tyr Phe Glu Leu Ala Asn Ile Val
                565                 570                 575
Pro Leu Tyr Asn Lys Ile Arg Asn Tyr Ile Thr Gln Lys Pro Tyr Ser
            580                 585                 590
Asp Glu Lys Phe Lys Leu Asn Phe Glu Asn Ser Thr Leu Ala Asn Gly
        595                 600                 605
Trp Asp Lys Asn Lys Glu Pro Asp Asn Thr Ala Ile Leu Phe Ile Lys
610                 615                 620
Asp Asp Lys Tyr Tyr Leu Gly Val Met Asn Lys Lys Asn Asn Lys Ile
625                 630                 635                 640
Phe Asp Asp Lys Ala Ile Lys Glu Asn Lys Gly Glu Gly Tyr Lys Lys
                645                 650                 655
Ile Val Tyr Lys Leu Leu Pro Gly Ala Asn Lys Met Leu Pro Lys Val
            660                 665                 670
Phe Phe Ser Ala Lys Ser Ile Lys Phe Tyr Asn Pro Ser Glu Asp Ile
        675                 680                 685
Leu Arg Ile Arg Asn His Ser Thr His Thr Lys Asn Gly Ser Pro Gln
690                 695                 700
```

```
Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
            725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
        770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
            805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
            835                 840                 845

Ile Ala Asn Lys Asn Lys Asp Asn Pro Lys Lys Glu Ser Val Phe Glu
850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
            885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
            915                 920                 925

Val Asp Gly Lys Gly Asn Ile Ile Lys Gln Asp Thr Phe Asn Ile Ile
930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
            965                 970                 975

Ile Lys Glu Met Lys Glu Gly Tyr Leu Ser Gln Val Val His Glu Ile
            980                 985                 990

Ala Lys Leu Val Ile Glu Tyr Asn Ala Ile Val Val Phe Glu Asp Leu
            995                 1000                1005

Asn Phe Gly Phe Lys Arg Gly Arg Phe Lys Val Glu Lys Gln Val
    1010            1015            1020

Tyr Gln Lys Leu Glu Lys Met Leu Ile Glu Lys Leu Asn Tyr Leu
    1025            1030            1035

Val Phe Lys Asp Asn Glu Phe Asp Lys Thr Gly Gly Val Leu Arg
    1040            1045            1050

Ala Tyr Gln Leu Thr Ala Pro Phe Glu Thr Phe Lys Lys Met Gly
    1055            1060            1065

Lys Gln Thr Gly Ile Ile Tyr Tyr Val Pro Ala Gly Phe Thr Ser
    1070            1075            1080

Lys Ile Cys Pro Val Thr Gly Phe Val Asn Gln Leu Tyr Pro Lys
    1085            1090            1095

Tyr Glu Ser Val Ser Lys Ser Gln Glu Phe Phe Ser Lys Phe Asp
    1100            1105            1110

Lys Ile Cys Tyr Asn Leu Asp Lys Gly Tyr Phe Glu Phe Ser Phe
```

-continued

```
            1115                1120                1125

Asp Tyr Lys Asn Phe Gly Asp Lys Ala Ala Lys Gly Lys Trp Thr
        1130                1135                1140

Ile Ala Ser Phe Gly Ser Arg Leu Ile Asn Phe Arg Asn Ser Asp
        1145                1150                1155

Lys Asn His Asn Trp Asp Thr Arg Glu Val Tyr Pro Thr Lys Glu
        1160                1165                1170

Leu Glu Lys Leu Leu Lys Asp Tyr Ser Ile Glu Tyr Gly His Gly
        1175                1180                1185

Glu Cys Ile Lys Ala Ala Ile Cys Gly Glu Ser Asp Lys Lys Phe
        1190                1195                1200

Phe Ala Lys Leu Thr Ser Val Leu Asn Thr Ile Leu Gln Met Arg
        1205                1210                1215

Asn Ser Lys Thr Gly Thr Glu Leu Asp Tyr Leu Ile Ser Pro Val
        1220                1225                1230

Ala Asp Val Asn Gly Asn Phe Phe Asp Ser Arg Gln Ala Pro Lys
        1235                1240                1245

Asn Met Pro Gln Asp Ala Asp Ala Asn Gly Ala Tyr His Ile Gly
        1250                1255                1260

Leu Lys Gly Leu Met Leu Leu Gly Arg Ile Lys Asn Asn Gln Glu
        1265                1270                1275

Gly Lys Lys Leu Asn Leu Val Ile Lys Asn Glu Glu Tyr Phe Glu
        1280                1285                1290

Phe Val Gln Asn Arg Asn Asn
        1295                1300

<210> SEQ ID NO 35
<211> LENGTH: 297
<212> TYPE: PRT
<213> ORGANISM: Adeno-associated virus-1

<400> SEQUENCE: 35

Thr Phe Ser Tyr Thr Phe Glu Glu Val Pro Phe His Ser Ser Tyr Ala
1               5                   10                  15

His Ser Gln Ser Leu Asp Arg Leu Met Asn Pro Leu Ile Asp Gln Tyr
            20                  25                  30

Leu Tyr Tyr Leu Asn Arg Thr Gln Asn Gln Ser Gly Ser Ala Gln Asn
        35                  40                  45

Lys Asp Leu Leu Phe Ser Arg Gly Ser Pro Ala Gly Met Ser Val Gln
50                  55                  60

Pro Lys Asn Trp Leu Pro Gly Pro Cys Tyr Arg Gln Gln Arg Val Ser
65                  70                  75                  80

Lys Thr Lys Thr Asp Asn Asn Asn Ser Asn Phe Thr Trp Thr Gly Ala
                85                  90                  95

Ser Lys Tyr Asn Leu Asn Gly Arg Glu Ser Ile Ile Asn Pro Gly Thr
            100                 105                 110

Ala Met Ala Ser His Lys Asp Asp Glu Asp Lys Phe Phe Pro Met Ser
        115                 120                 125

Gly Val Met Ile Phe Gly Lys Glu Ser Ala Gly Ala Ser Asn Thr Ala
    130                 135                 140

Leu Asp Asn Val Met Ile Thr Asp Glu Glu Glu Ile Lys Ala Thr Asn
145                 150                 155                 160

Pro Val Ala Thr Glu Arg Phe Gly Thr Val Ala Val Asn Phe Lys Asp
                165                 170                 175
```

```
Asp Glu Asp Lys Phe Pro Met Ser Gly Val Met Ile Phe Gly Lys
            180                 185                 190

Glu Ser Ala Gly Ala Ser Asn Thr Ala Leu Asp Asn Val Met Ile Thr
        195                 200                 205

Asp Glu Glu Ile Lys Ala Thr Asn Pro Val Ala Thr Glu Arg Phe
    210                 215                 220

Gly Thr Val Ala Val Asn Phe Gln Ser Ser Thr Asp Pro Ala Thr
225                 230                 235                 240

Gly Asp Val His Ala Met Gly Ala Leu Pro Gly Met Val Trp Gln Asp
                245                 250                 255

Arg Asp Val Tyr Leu Gln Gly Pro Ile Trp Ala Lys Ile Pro His Thr
            260                 265                 270

Asp Gly His Phe His Pro Ser Pro Leu Met Gly Gly Phe Gly Leu Lys
        275                 280                 285

Asn Pro Pro Gln Ile Leu Ile Lys
    290                 295

<210> SEQ ID NO 36
<211> LENGTH: 240
<212> TYPE: PRT
<213> ORGANISM: Adeno-associated virus-6

<400> SEQUENCE: 36

Thr Phe Ser Tyr Thr Phe Glu Asp Val Pro Phe His Ser Ser Tyr Ala
1               5                   10                  15

His Ser Gln Ser Leu Asp Arg Leu Met Asn Pro Leu Ile Asp Gln Tyr
            20                  25                  30

Leu Tyr Tyr Leu Asn Arg Thr Gln Asn Gln Ser Gly Ser Ala Gln Asn
        35                  40                  45

Lys Asp Leu Leu Phe Ser Arg Gly Ser Pro Ala Gly Met Ser Val Gln
    50                  55                  60

Pro Lys Asn Trp Leu Pro Gly Pro Cys Tyr Arg Gln Gln Arg Val Ser
65                  70                  75                  80

Lys Thr Lys Thr Asp Asn Asn Asn Ser Asn Phe Thr Trp Thr Gly Ala
                85                  90                  95

Ser Lys Tyr Asn Leu Asn Gly Arg Glu Ser Ile Ile Asn Pro Gly Thr
            100                 105                 110

Ala Met Ala Ser His Lys Asp Asp Lys Asp Lys Phe Phe Pro Met Ser
        115                 120                 125

Gly Val Met Ile Phe Gly Lys Glu Ser Ala Gly Ala Ser Asn Thr Ala
130                 135                 140

Leu Asp Asn Val Met Ile Thr Asp Glu Glu Glu Ile Lys Ala Thr Asn
145                 150                 155                 160

Pro Val Ala Thr Glu Arg Phe Gly Thr Val Ala Val Asn Leu Gln Ser
                165                 170                 175

Ser Ser Thr Asp Pro Ala Thr Gly Asp Val His Val Met Gly Ala Leu
            180                 185                 190

Pro Gly Met Val Trp Gln Asp Arg Asp Val Tyr Leu Gln Gly Pro Ile
        195                 200                 205

Trp Ala Lys Ile Pro His Thr Asp Gly His Phe His Pro Ser Pro Leu
    210                 215                 220

Met Gly Gly Phe Gly Leu Lys His Pro Pro Pro Gln Ile Leu Ile Lys
225                 230                 235                 240

<210> SEQ ID NO 37
```

<211> LENGTH: 240
<212> TYPE: PRT
<213> ORGANISM: Adeno-associated virus-3

<400> SEQUENCE: 37

```
Phe Ser Tyr Thr Phe Glu Asp Val Pro Phe His Ser Ser Tyr Ala His
1               5                   10                  15

Ser Gln Ser Leu Asp Arg Leu Met Asn Pro Leu Ile Asp Gln Tyr Leu
            20                  25                  30

Tyr Tyr Leu Asn Arg Thr Gln Gly Thr Thr Ser Gly Thr Thr Asn Gln
        35                  40                  45

Ser Arg Leu Leu Phe Ser Gln Ala Gly Pro Gln Ser Met Ser Leu Gln
50                  55                  60

Ala Arg Asn Trp Leu Pro Gly Pro Cys Tyr Arg Gln Gln Arg Leu Ser
65                  70                  75                  80

Lys Thr Ala Asn Asp Asn Asn Ser Asn Phe Pro Trp Thr Ala Ala
                85                  90                  95

Ser Lys Tyr His Leu Asn Gly Arg Asp Ser Leu Val Asn Pro Gly Pro
            100                 105                 110

Ala Met Ala Ser His Lys Asp Asp Glu Glu Lys Phe Phe Pro Met His
        115                 120                 125

Gly Asn Leu Ile Phe Gly Lys Glu Gly Thr Thr Ala Ser Asn Ala Glu
    130                 135                 140

Leu Asp Asn Val Met Ile Thr Asp Glu Glu Glu Ile Arg Thr Thr Asn
145                 150                 155                 160

Pro Val Ala Thr Glu Gln Tyr Gly Thr Val Ala Asn Asn Leu Gln Ser
                165                 170                 175

Ser Asn Thr Ala Pro Thr Thr Gly Thr Val Asn His Gln Gly Ala Leu
            180                 185                 190

Pro Gly Met Val Trp Gln Asp Arg Asp Val Tyr Leu Gln Gly Pro Ile
        195                 200                 205

Trp Ala Lys Ile Pro His Thr Asp Gly His Phe His Pro Ser Pro Leu
    210                 215                 220

Met Gly Gly Phe Gly Leu Lys His Pro Pro Pro Gln Ile Met Ile Lys
225                 230                 235                 240
```

<210> SEQ ID NO 38
<211> LENGTH: 240
<212> TYPE: PRT
<213> ORGANISM: Adeno-associated virus-2

<400> SEQUENCE: 38

```
Phe Ser Tyr Thr Phe Glu Asp Val Pro Phe His Ser Ser Tyr Ala His
1               5                   10                  15

Ser Gln Ser Leu Asp Arg Leu Met Asn Pro Leu Ile Asp Gln Tyr Leu
            20                  25                  30

Tyr Tyr Leu Ser Arg Thr Asn Thr Pro Ser Gly Thr Thr Thr Gln Ser
        35                  40                  45

Arg Leu Gln Phe Ser Gln Ala Gly Ala Ser Asp Ile Arg Asp Gln Ser
50                  55                  60

Arg Asn Trp Leu Pro Gly Pro Cys Tyr Arg Gln Gln Arg Val Ser Lys
65                  70                  75                  80

Thr Ser Ala Asp Asn Asn Asn Ser Glu Tyr Ser Trp Thr Gly Ala Thr
                85                  90                  95

Lys Tyr His Leu Asn Gly Arg Asp Ser Leu Val Asn Pro Gly Pro Ala
            100                 105                 110
```

```
Met Ala Ser His Lys Asp Asp Glu Glu Lys Phe Phe Pro Gln Ser Gly
            115                 120                 125

Val Leu Ile Phe Gly Lys Gln Gly Ser Glu Lys Thr Asn Val Asp Ile
        130                 135                 140

Glu Lys Val Met Ile Thr Asp Glu Glu Ile Arg Thr Thr Asn Pro
145                 150                 155                 160

Val Ala Thr Glu Gln Tyr Gly Ser Val Ser Thr Asn Leu Gln Arg Gly
            165                 170                 175

Asn Arg Gln Ala Ala Thr Ala Asp Val Asn Thr Gln Gly Val Leu Pro
            180                 185                 190

Gly Met Val Trp Gln Asp Arg Asp Val Tyr Leu Gln Gly Pro Ile Trp
            195                 200                 205

Ala Lys Ile Pro His Thr Asp Gly His Phe His Pro Ser Pro Leu Met
            210                 215                 220

Gly Gly Phe Gly Leu Lys His Pro Pro Gln Ile Leu Ile Lys Asn
225                 230                 235                 240

<210> SEQ ID NO 39
<211> LENGTH: 243
<212> TYPE: PRT
<213> ORGANISM: Adeno-associated virus-8

<400> SEQUENCE: 39

Asn Phe Gln Phe Thr Tyr Thr Phe Glu Asp Val Pro Phe His Ser Ser
1               5                   10                  15

Tyr Ala His Ser Gln Ser Leu Asp Arg Leu Met Asn Pro Leu Ile Asp
            20                  25                  30

Gln Tyr Leu Tyr Tyr Leu Ser Arg Thr Gln Thr Thr Gly Gly Thr Ala
        35                  40                  45

Asn Thr Gln Thr Leu Gly Phe Ser Gln Gly Gly Pro Asn Thr Met Ala
    50                  55                  60

Asn Gln Ala Lys Asn Trp Leu Pro Gly Pro Cys Tyr Arg Gln Gln Arg
65                  70                  75                  80

Val Ser Thr Thr Thr Gly Gln Asn Asn Asn Ser Asn Phe Ala Trp Thr
                85                  90                  95

Ala Gly Thr Lys Tyr His Leu Asn Gly Arg Asn Ser Leu Ala Asn Pro
            100                 105                 110

Gly Ile Ala Met Ala Thr His Lys Asp Asp Glu Glu Arg Phe Phe Pro
        115                 120                 125

Ser Asn Gly Ile Leu Ile Phe Gly Lys Gln Asn Ala Ala Arg Asp Asn
    130                 135                 140

Ala Asp Tyr Ser Asp Val Met Leu Thr Ser Glu Glu Glu Ile Lys Thr
145                 150                 155                 160

Thr Asn Pro Val Ala Thr Glu Glu Tyr Gly Ile Val Ala Asp Asn Leu
                165                 170                 175

Gln Gln Gln Asn Thr Ala Pro Gln Ile Gly Thr Val Asn Ser Gln Gly
            180                 185                 190

Ala Leu Pro Gly Met Val Trp Gln Asn Arg Asp Val Tyr Leu Gln Gly
        195                 200                 205

Pro Ile Trp Ala Lys Ile Pro His Thr Asp Gly Asn Phe His Pro Ser
    210                 215                 220

Pro Leu Met Gly Gly Phe Gly Leu Lys His Pro Pro Pro Gln Ile Leu
225                 230                 235                 240

Ile Lys Asn
```

-continued

```
<210> SEQ ID NO 40
<211> LENGTH: 243
<212> TYPE: PRT
<213> ORGANISM: Adeno-associated virus-8.1

<400> SEQUENCE: 40
```

| | | | | | | | | | | | | | | | |
|---|---|---|---|---|---|---|---|---|---|---|---|---|---|---|---|
| Asn | Phe | Gln | Phe | Thr | Tyr | Thr | Phe | Glu | Asp | Val | Pro | Phe | His | Ser | Ser |
| 1 | | | | 5 | | | | | 10 | | | | | 15 | |
| Tyr | Ala | His | Ser | Gln | Ser | Leu | Asp | Arg | Leu | Met | Asn | Pro | Leu | Ile | Asp |
| | | | 20 | | | | | 25 | | | | | 30 | | |
| Gln | Tyr | Leu | Tyr | Tyr | Leu | Ser | Arg | Thr | Gln | Thr | Thr | Gly | Gly | Thr | Ala |
| | | 35 | | | | | 40 | | | | | 45 | | | |
| Asn | Thr | Gln | Thr | Leu | Gly | Phe | Ser | Gln | Gly | Gly | Pro | Asn | Thr | Met | Ala |
| 50 | | | | | 55 | | | | | 60 | | | | | |
| Asn | Gln | Ala | Lys | Asn | Trp | Leu | Pro | Gly | Pro | Cys | Tyr | Arg | Gln | Gln | Arg |
| 65 | | | | | 70 | | | | | 75 | | | | | 80 |
| Val | Ser | Thr | Thr | Thr | Gly | Gln | Asn | Asn | Asn | Ser | Asn | Phe | Ala | Trp | Thr |
| | | | | 85 | | | | | 90 | | | | | 95 | |
| Ala | Gly | Thr | Lys | Tyr | His | Leu | Asn | Gly | Arg | Asn | Ser | Leu | Ala | Asn | Pro |
| | | | 100 | | | | | 105 | | | | | 110 | | |
| Gly | Ile | Ala | Met | Ala | Thr | His | Lys | Asp | Asp | Glu | Glu | Arg | Phe | Phe | Pro |
| | | 115 | | | | | 120 | | | | | 125 | | | |
| Ser | Asn | Gly | Ile | Leu | Ile | Phe | Gly | Lys | Gln | Asn | Ala | Ala | Arg | Asp | Asn |
| | 130 | | | | | 135 | | | | | 140 | | | | |
| Ala | Asp | Tyr | Ser | Asp | Val | Met | Leu | Thr | Ser | Glu | Glu | Ile | Lys | Thr |
| 145 | | | | | 150 | | | | | 155 | | | | | 160 |
| Thr | Asn | Pro | Val | Ala | Thr | Glu | Glu | Tyr | Gly | Ile | Val | Ala | Asp | Asn | Leu |
| | | | | 165 | | | | | 170 | | | | | 175 | |
| Gln | Gly | Gln | Arg | Gln | Ala | Ala | Gln | Ile | Gly | Thr | Val | Asn | Ser | Gln | Gly |
| | | | 180 | | | | | 185 | | | | | 190 | | |
| Ala | Leu | Pro | Gly | Met | Val | Trp | Gln | Asn | Arg | Asp | Val | Tyr | Leu | Gln | Gly |
| | | 195 | | | | | 200 | | | | | 205 | | | |
| Pro | Ile | Trp | Ala | Lys | Ile | Pro | His | Thr | Asp | Gly | Asn | Phe | His | Pro | Ser |
| | 210 | | | | | 215 | | | | | 220 | | | | |
| Pro | Leu | Met | Gly | Gly | Phe | Gly | Leu | Lys | His | Pro | Pro | Gln | Ile | Leu |
| 225 | | | | | 230 | | | | | 235 | | | | | 240 |
| Ile | Lys | Asn | | | | | | | | | | | | | |

```
<210> SEQ ID NO 41
<211> LENGTH: 241
<212> TYPE: PRT
<213> ORGANISM: Adeno-associated virus-8 Rh8

<400> SEQUENCE: 41
```

| | | | | | | | | | | | | | | | |
|---|---|---|---|---|---|---|---|---|---|---|---|---|---|---|---|
| Phe | Gln | Phe | Ser | Tyr | Thr | Phe | Glu | Asp | Val | Pro | Phe | His | Ser | Ser | Tyr |
| 1 | | | | 5 | | | | | 10 | | | | | 15 | |
| Ala | His | Ser | Gln | Ser | Leu | Asp | Arg | Leu | Met | Asn | Pro | Leu | Ile | Asp | Gln |
| | | | 20 | | | | | 25 | | | | | 30 | | |
| Tyr | Leu | Tyr | Tyr | Leu | Val | Arg | Thr | Gln | Thr | Thr | Gly | Thr | Gly | Gly | Thr |
| | | 35 | | | | | 40 | | | | | 45 | | | |
| Gln | Thr | Leu | Ala | Phe | Ser | Gln | Ala | Gly | Pro | Ser | Ser | Met | Ala | Asn | Gln |
| | 50 | | | | | 55 | | | | | 60 | | | | |
| Ala | Arg | Asn | Trp | Val | Pro | Gly | Pro | Cys | Tyr | Arg | Gln | Gln | Arg | Val | Ser |
| 65 | | | | | 70 | | | | | 75 | | | | | 80 |

```
Thr Thr Thr Asn Gln Asn Asn Asn Ser Asn Phe Ala Trp Thr Gly Ala
            85                  90                  95

Ala Lys Phe Lys Leu Asn Gly Arg Asp Ser Leu Met Asn Pro Gly Val
        100                 105                 110

Ala Met Ala Ser His Lys Asp Asp Asp Arg Phe Phe Pro Ser Ser
        115                 120                 125

Gly Val Leu Ile Phe Gly Lys Gln Gly Ala Gly Asn Asp Gly Val Asp
        130                 135                 140

Tyr Ser Gln Val Leu Ile Thr Asp Glu Glu Glu Ile Lys Ala Thr Asn
145                 150                 155                 160

Pro Val Ala Thr Glu Glu Tyr Gly Ala Val Ala Ile Asn Asn Gln Ala
                165                 170                 175

Ala Asn Thr Gln Ala Gln Thr Gly Leu Val His Asn Gln Gly Val Ile
                180                 185                 190

Pro Gly Met Val Trp Gln Asn Arg Asp Val Tyr Leu Gln Gly Pro Ile
        195                 200                 205

Trp Ala Lys Ile Pro His Thr Asp Gly Asn Phe His Pro Ser Pro Leu
        210                 215                 220

Met Gly Gly Phe Gly Leu Lys His Pro Pro Pro Gln Ile Leu Ile Lys
225                 230                 235                 240

Asn

<210> SEQ ID NO 42
<211> LENGTH: 243
<212> TYPE: PRT
<213> ORGANISM: Adeno-associated virus-10

<400> SEQUENCE: 42

Asn Phe Glu Phe Ser Tyr Thr Phe Glu Asp Val Pro Phe His Ser Ser
1               5                   10                  15

Tyr Ala His Ser Gln Ser Leu Asp Arg Leu Met Asn Pro Leu Ile Asp
            20                  25                  30

Gln Tyr Leu Tyr Tyr Leu Ser Arg Thr Gln Ser Thr Gly Gly Thr Gln
        35                  40                  45

Gly Thr Gln Gln Leu Leu Phe Ser Gln Ala Gly Pro Ala Asn Met Ser
    50                  55                  60

Ala Gln Ala Lys Asn Trp Leu Pro Gly Pro Cys Tyr Arg Gln Gln Arg
65                  70                  75                  80

Val Ser Thr Thr Leu Ser Gln Asn Asn Asn Ser Asn Phe Ala Trp Thr
            85                  90                  95

Gly Ala Thr Lys Tyr His Leu Asn Gly Arg Asp Ser Leu Val Asn Pro
        100                 105                 110

Gly Val Ala Met Ala Thr His Lys Asp Asp Glu Glu Arg Phe Phe Pro
        115                 120                 125

Ser Ser Gly Val Leu Met Phe Gly Lys Gln Gly Ala Gly Arg Asp Asn
    130                 135                 140

Val Asp Tyr Ser Ser Val Met Leu Thr Ser Glu Glu Glu Ile Lys Thr
145                 150                 155                 160

Thr Asn Pro Val Ala Thr Glu Gln Tyr Gly Val Val Ala Asp Asn Leu
                165                 170                 175

Gln Gln Ala Asn Thr Gly Pro Ile Val Gly Asn Val Asn Ser Gln Gly
            180                 185                 190

Ala Leu Pro Gly Met Val Trp Gln Asn Arg Asp Val Tyr Leu Gln Gly
        195                 200                 205
```

-continued

Pro Ile Trp Ala Lys Ile Pro His Thr Asp Gly Asn Phe His Pro Ser
210                 215                 220

Pro Leu Met Gly Gly Phe Gly Leu Lys His Pro Pro Gln Ile Leu
225                 230                 235                 240

Ile Lys Asn

<210> SEQ ID NO 43
<211> LENGTH: 242
<212> TYPE: PRT
<213> ORGANISM: Adeno-associated virus-7

<400> SEQUENCE: 43

Phe Glu Phe Ser Tyr Ser Phe Glu Asp Val Pro Phe His Ser Ser Tyr
1               5                   10                  15

Ala His Ser Gln Ser Leu Asp Arg Leu Met Asn Pro Leu Ile Asp Gln
                20                  25                  30

Tyr Leu Tyr Tyr Leu Ala Arg Thr Gln Ser Asn Pro Gly Gly Thr Ala
            35                  40                  45

Gly Asn Arg Glu Leu Gln Phe Tyr Gln Gly Gly Pro Ser Thr Met Ala
50                  55                  60

Glu Gln Ala Lys Asn Trp Leu Pro Gly Pro Cys Phe Arg Gln Gln Arg
65                  70                  75                  80

Val Ser Lys Thr Leu Asp Gln Asn Asn Asn Ser Asn Phe Ala Trp Thr
                85                  90                  95

Gly Ala Thr Lys Tyr His Leu Asn Gly Arg Asn Ser Leu Val Asn Pro
            100                 105                 110

Gly Val Ala Met Ala Thr His Lys Asp Asp Glu Asp Arg Phe Phe Pro
        115                 120                 125

Ser Ser Gly Val Leu Ile Phe Gly Lys Thr Gly Ala Thr Asn Lys Thr
130                 135                 140

Thr Leu Glu Asn Val Leu Met Thr Asn Glu Glu Glu Ile Arg Pro Thr
145                 150                 155                 160

Asn Pro Val Ala Thr Glu Glu Tyr Gly Ile Val Ser Ser Asn Leu Gln
                165                 170                 175

Ala Ala Asn Thr Ala Ala Gln Thr Gln Val Val Asn Asn Gln Gly Ala
            180                 185                 190

Leu Pro Gly Met Val Trp Gln Asn Arg Asp Val Tyr Leu Gln Gly Pro
        195                 200                 205

Ile Trp Ala Lys Ile Pro His Thr Asp Gly Asn Phe His Pro Ser Pro
210                 215                 220

Leu Met Gly Gly Phe Gly Leu Lys His Pro Pro Gln Ile Leu Ile
225                 230                 235                 240

Lys Asn

<210> SEQ ID NO 44
<211> LENGTH: 240
<212> TYPE: PRT
<213> ORGANISM: Adeno-associated virus-9

<400> SEQUENCE: 44

Phe Gln Phe Ser Tyr Glu Phe Glu Asn Val Pro Phe His Ser Ser Tyr
1               5                   10                  15

Ala His Ser Gln Ser Leu Asp Arg Leu Met Asn Pro Leu Ile Asp Gln
                20                  25                  30

Tyr Leu Tyr Tyr Leu Ser Lys Thr Ile Asn Gly Ser Gly Gln Asn Gln
            35                  40                  45

-continued

```
Gln Thr Leu Lys Phe Ser Val Ala Gly Pro Ser Asn Met Ala Val Gln
 50                  55                  60

Gly Arg Asn Tyr Ile Pro Gly Pro Ser Tyr Arg Gln Gln Arg Val Ser
 65                  70                  75                  80

Thr Thr Val Thr Gln Asn Asn Ser Glu Phe Ala Trp Pro Gly Ala
                 85                  90                  95

Ser Ser Trp Ala Leu Asn Gly Arg Asn Ser Leu Met Asn Pro Gly Pro
                100                 105                 110

Ala Met Ala Ser His Lys Glu Gly Glu Asp Arg Phe Phe Pro Leu Ser
                115                 120                 125

Gly Ser Leu Ile Phe Gly Lys Gln Gly Thr Gly Arg Asp Asn Val Asp
            130                 135                 140

Ala Asp Lys Val Met Ile Thr Asn Glu Glu Ile Lys Thr Thr Asn
145                 150                 155                 160

Pro Val Ala Thr Glu Ser Tyr Gly Gln Val Ala Thr Asn His Gln Ser
                165                 170                 175

Ala Gln Ala Gln Ala Gln Thr Gly Trp Val Gln Asn Gln Gly Ile Leu
                180                 185                 190

Pro Gly Met Val Trp Gln Asp Arg Asp Val Tyr Leu Gln Gly Pro Ile
            195                 200                 205

Trp Ala Lys Ile Pro His Thr Asp Gly Asn Phe His Pro Ser Pro Leu
210                 215                 220

Met Gly Gly Phe Gly Met Lys His Pro Pro Gln Ile Leu Ile Lys
225                 230                 235                 240
```

<210> SEQ ID NO 45
<211> LENGTH: 240
<212> TYPE: PRT
<213> ORGANISM: Adeno-associated virus-9.1

<400> SEQUENCE: 45

```
Phe Gln Phe Ser Tyr Glu Phe Glu Asn Val Pro Phe His Ser Ser Tyr
 1               5                  10                  15

Ala His Ser Gln Ser Leu Asp Arg Leu Met Asn Pro Leu Ile Asp Gln
                 20                  25                  30

Tyr Leu Tyr Tyr Leu Ser Lys Thr Ile Asn Gly Ser Gly Gln Asn Gln
             35                  40                  45

Gln Thr Leu Lys Phe Ser Val Ala Gly Pro Ser Asn Met Ala Val Gln
 50                  55                  60

Gly Arg Asn Tyr Ile Pro Gly Pro Ser Tyr Arg Gln Gln Arg Val Ser
 65                  70                  75                  80

Thr Thr Val Thr Gln Asn Asn Ser Glu Phe Ala Trp Pro Gly Ala
                 85                  90                  95

Ser Ser Trp Ala Leu Asn Gly Arg Asn Ser Leu Met Asn Pro Gly Pro
                100                 105                 110

Ala Met Ala Ser His Lys Glu Gly Glu Asp Arg Phe Phe Pro Leu Ser
                115                 120                 125

Gly Ser Leu Ile Phe Gly Lys Gln Gly Thr Gly Arg Asp Asn Val Asp
            130                 135                 140

Ala Asp Lys Val Met Ile Thr Asn Glu Glu Ile Lys Thr Thr Asn
145                 150                 155                 160

Pro Val Ala Thr Glu Ser Tyr Gly Gln Val Ala Thr Asn His Gln Ser
                165                 170                 175

Gly Gln Ala Gln Ala Ala Thr Gly Trp Val Gln Asn Gln Gly Ile Leu
```

```
            180                 185                 190
Pro Gly Met Val Trp Gln Asp Arg Asp Val Tyr Leu Gln Gly Pro Ile
        195                 200                 205
Trp Ala Lys Ile Pro His Thr Asp Gly Asn Phe His Pro Ser Pro Leu
    210                 215                 220
Met Gly Gly Phe Gly Met Lys His Pro Pro Gln Ile Leu Ile Lys
225                 230                 235                 240

<210> SEQ ID NO 46
<211> LENGTH: 240
<212> TYPE: PRT
<213> ORGANISM: Adeno-associated virus-5

<400> SEQUENCE: 46

Asn Phe Glu Phe Thr Tyr Asn Phe Glu Val Pro Phe His Ser Ser
1               5                   10                  15
Phe Ala Pro Ser Gln Asn Leu Phe Lys Leu Ala Asn Pro Leu Val Asp
                20                  25                  30
Gln Tyr Leu Tyr Arg Phe Val Ser Thr Asn Asn Thr Gly Gly Val Gln
            35                  40                  45
Phe Asn Lys Asn Leu Ala Gly Arg Tyr Ala Asn Thr Tyr Lys Asn Trp
50                  55                  60
Phe Pro Gly Pro Met Gly Arg Thr Gln Gly Trp Asn Leu Gly Ser Gly
65                  70                  75                  80
Val Asn Arg Ala Ser Val Ser Ala Phe Ala Thr Thr Asn Arg Met Glu
                85                  90                  95
Leu Glu Gly Ala Ser Tyr Gln Val Pro Pro Gln Pro Asn Gly Met Thr
            100                 105                 110
Asn Asn Leu Gln Gly Ser Asn Thr Tyr Ala Leu Glu Asn Thr Met Ile
        115                 120                 125
Phe Asn Ser Gln Pro Ala Asn Pro Gly Thr Thr Ala Thr Tyr Leu Glu
    130                 135                 140
Gly Asn Met Leu Ile Thr Ser Glu Ser Glu Thr Gln Pro Val Asn Arg
145                 150                 155                 160
Val Ala Tyr Asn Val Gly Gly Gln Met Ala Thr Asn Asn Gln Ser Ser
                165                 170                 175
Thr Thr Ala Pro Ala Thr Gly Thr Tyr Asn Leu Gln Glu Ile Val Pro
            180                 185                 190
Gly Ser Val Trp Met Glu Arg Asp Val Tyr Leu Gln Gly Pro Ile Trp
        195                 200                 205
Ala Lys Ile Pro Glu Thr Gly Ala His Phe His Pro Ser Pro Ala Met
    210                 215                 220
Gly Gly Phe Gly Leu Lys His Pro Pro Met Met Leu Ile Lys Asn
225                 230                 235                 240

<210> SEQ ID NO 47
<211> LENGTH: 9
<212> TYPE: PRT
<213> ORGANISM: Artificial Sequence
<220> FEATURE:
<223> OTHER INFORMATION: Synthetic peptide

<400> SEQUENCE: 47

Leu Ala Lys Asp Ala Thr Lys Asn Ala
1               5

<210> SEQ ID NO 48
```

```
<211> LENGTH: 10
<212> TYPE: PRT
<213> ORGANISM: Artificial Sequence
<220> FEATURE:
<223> OTHER INFORMATION: Synthetic peptide

<400> SEQUENCE: 48

Pro Ala His Gln Asp Thr Thr Lys Asn Ala
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Synthetic peptide

<400> SEQUENCE: 49

Leu Ala His Gln Asp Thr Thr Lys Asn Ala
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Synthetic peptide

<400> SEQUENCE: 50

Leu Ala Thr Thr Ser Gln Asn Lys Pro Ala
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Synthetic peptide

<400> SEQUENCE: 51

Leu Ala Ile Ser Asp Gln Thr Lys His Ala
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Synthetic peptide

<400> SEQUENCE: 52

Ile Ala Arg Gly Val Ala Pro Ser Ser Ala
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Synthetic peptide

<400> SEQUENCE: 53

Leu Ala Pro Asp Ser Thr Thr Arg Ser Ala
1               5                   10

<210> SEQ ID NO 54
<211> LENGTH: 10
```

<212> TYPE: PRT
<213> ORGANISM: Artificial Sequence
<220> FEATURE:
<223> OTHER INFORMATION: Synthetic peptide

<400> SEQUENCE: 54

Leu Ala Lys Gly Thr Glu Leu Lys Pro Ala
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Synthetic peptide

<400> SEQUENCE: 55

Leu Ala Ile Ile Asp Ala Thr Lys Asn Ala
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Synthetic peptide

<400> SEQUENCE: 56

Leu Ala Val Asp Gly Ala Gln Arg Ser Ala
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Synthetic peptide

<400> SEQUENCE: 57

Pro Ala Pro Gln Asp Thr Thr Lys Lys Ala
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Synthetic peptide

<400> SEQUENCE: 58

Leu Pro His Gln Asp Thr Thr Lys Asn Ala
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Synthetic peptide

<400> SEQUENCE: 59

Leu Ala Lys Asp Ala Thr Lys Thr Ile Ala
1               5                   10

<210> SEQ ID NO 60
<211> LENGTH: 10
<212> TYPE: PRT

```
<213> ORGANISM: Artificial Sequence
<220> FEATURE:
<223> OTHER INFORMATION: Synthetic peptide

<400> SEQUENCE: 60

Leu Ala Lys Gln Gln Ser Ala Ser Thr Ala
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Synthetic peptide

<400> SEQUENCE: 61

Leu Ala Lys Ser Asp Gln Ser Lys Pro Ala
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Synthetic peptide

<400> SEQUENCE: 62

Leu Ser His Gln Asp Thr Thr Lys Asn Ala
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Synthetic peptide

<400> SEQUENCE: 63

Leu Ala Ala Asn Gln Pro Ser Lys Pro Ala
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Synthetic peptide

<400> SEQUENCE: 64

Leu Ala Val Ser Asp Ser Thr Lys Ala Ala
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Synthetic peptide

<400> SEQUENCE: 65

Leu Ala Ala Gln Gly Thr Ala Lys Pro Ala
1               5                   10

<210> SEQ ID NO 66
<211> LENGTH: 10
<212> TYPE: PRT
<213> ORGANISM: Artificial Sequence
```

```
<220> FEATURE:
<223> OTHER INFORMATION: Synthetic peptide

<400> SEQUENCE: 66

Leu Ala Pro Asp Gln Thr Thr Arg Asn Ala
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Synthetic peptide

<400> SEQUENCE: 67

Leu Ala Ala Ser Asp Ser Thr Lys Ala Ala
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Synthetic peptide

<400> SEQUENCE: 68

Leu Ala Pro Gln Asp Thr Thr Lys Asn Ala
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Synthetic peptide

<400> SEQUENCE: 69

Leu Ala Lys Ala Asp Glu Thr Arg Pro Ala
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Synthetic peptide

<400> SEQUENCE: 70

Leu Ala His Gln Asp Thr Ala Lys Asn Ala
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Synthetic peptide

<400> SEQUENCE: 71

Leu Ala His Gln Asp Thr Lys Lys Asn Ala
1               5                   10

<210> SEQ ID NO 72
<211> LENGTH: 10
<212> TYPE: PRT
<213> ORGANISM: Artificial Sequence
<220> FEATURE:
```

<223> OTHER INFORMATION: Synthetic peptide

<400> SEQUENCE: 72

Leu Ala His Gln Asp Thr Thr Lys His Ala
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Synthetic peptide

<400> SEQUENCE: 73

Leu Ala His Gln Asp Thr Thr Lys Lys Ala
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Synthetic peptide

<400> SEQUENCE: 74

Leu Ala His Gln Asp Thr Thr Arg Asn Ala
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Synthetic peptide

<400> SEQUENCE: 75

Leu Ala His Gln Asp Thr Thr Thr Asn Ala
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Synthetic peptide

<400> SEQUENCE: 76

Leu Ala His Gln Gly Thr Thr Lys Asn Ala
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Synthetic peptide

<400> SEQUENCE: 77

Leu Ala His Gln Val Thr Thr Lys Asn Ala
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Synthetic peptide

<400> SEQUENCE: 78

Leu Ala Ile Ser Asp Gln Ser Lys Pro Ala
1               5                   10

<210> SEQ ID NO 79
<211> LENGTH: 9
<212> TYPE: PRT
<213> ORGANISM: Artificial Sequence
<220> FEATURE:
<223> OTHER INFORMATION: Synthetic peptide

<400> SEQUENCE: 79

Leu Ala Lys Asp Ala Thr Lys Thr Ala
1               5

<210> SEQ ID NO 80
<211> LENGTH: 9
<212> TYPE: PRT
<213> ORGANISM: Artificial Sequence
<220> FEATURE:
<223> OTHER INFORMATION: Synthetic peptide

<400> SEQUENCE: 80

Leu Ala Lys Asp Thr Thr Lys Asn Ala
1               5

<210> SEQ ID NO 81
<211> LENGTH: 10
<212> TYPE: PRT
<213> ORGANISM: Artificial Sequence
<220> FEATURE:
<223> OTHER INFORMATION: Synthetic peptide

<400> SEQUENCE: 81

Leu Ala Lys Ser Asp Gln Ser Arg Pro Ala
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Synthetic peptide

<400> SEQUENCE: 82

Leu Ala Pro Gln Asp Thr Lys Lys Asn Ala
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Synthetic peptide

<400> SEQUENCE: 83

Leu Ala Thr Ser Asp Ser Thr Lys Ala Ala
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Synthetic peptide

<400> SEQUENCE: 84

Leu Ala Val Asp Gly Ser Gln Arg Ser Ala
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Synthetic peptide

<400> SEQUENCE: 85

Leu Pro Ile Ser Asp Gln Thr Lys His Ala
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Synthetic peptide

<400> SEQUENCE: 86

Leu Pro Lys Asp Ala Thr Lys Thr Ile Ala
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Synthetic peptide

<400> SEQUENCE: 87

Leu Pro Pro Gln Asp Thr Thr Lys Asn Ala
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Synthetic peptide

<400> SEQUENCE: 88

Pro Ala Pro Gln Asp Thr Thr Lys Asn Ala
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Synthetic peptide

<400> SEQUENCE: 89

Gln Ala His Gln Asp Thr Thr Lys Asn Ala
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Synthetic peptide

<400> SEQUENCE: 90

```
Leu Ala His Glu Thr Ser Pro Arg Pro Ala
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Synthetic peptide

<400> SEQUENCE: 91

Leu Ala Lys Ser Thr Ser Thr Ala Pro Ala
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Synthetic peptide

<400> SEQUENCE: 92

Leu Ala Asp Gln Asp Thr Thr Lys Asn Ala
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Synthetic peptide

<400> SEQUENCE: 93

Leu Ala Glu Ser Asp Gln Ser Lys Pro Ala
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Synthetic peptide

<400> SEQUENCE: 94

Leu Ala His Lys Asp Thr Thr Lys Asn Ala
1               5                   10

<210> SEQ ID NO 95
<211> LENGTH: 9
<212> TYPE: PRT
<213> ORGANISM: Artificial Sequence
<220> FEATURE:
<223> OTHER INFORMATION: Synthetic peptide

<400> SEQUENCE: 95

Leu Ala His Lys Thr Gln Gln Lys Met
1               5

<210> SEQ ID NO 96
<211> LENGTH: 10
<212> TYPE: PRT
<213> ORGANISM: Artificial Sequence
<220> FEATURE:
<223> OTHER INFORMATION: Synthetic peptide

<400> SEQUENCE: 96
```

```
Leu Ala His Gln Asp Thr Thr Glu Asn Ala
1               5                   10

<210> SEQ ID NO 97
<211> LENGTH: 10
<212> TYPE: PRT
<213> ORGANISM: Artificial Sequence
<220> FEATURE:
<223> OTHER INFORMATION: Synthetic peptide

<400> SEQUENCE: 97

Leu Ala His Gln Asp Thr Thr Ile Asn Ala
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Synthetic peptide

<400> SEQUENCE: 98

Leu Ala His Gln Asp Thr Thr Lys Lys Thr
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Synthetic peptide

<400> SEQUENCE: 99

Leu Ala His Gln Asp Thr Thr Lys Asn Asp
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Synthetic peptide

<400> SEQUENCE: 100

Leu Ala His Gln Asp Thr Thr Lys Asn Thr
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Synthetic peptide

<400> SEQUENCE: 101

Leu Ala His Gln Asp Thr Thr Lys Asn Val
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Synthetic peptide

<400> SEQUENCE: 102

Leu Ala His Gln Asp Thr Thr Lys Thr Met
```

```
1               5                   10

<210> SEQ ID NO 103
<211> LENGTH: 10
<212> TYPE: PRT
<213> ORGANISM: Artificial Sequence
<220> FEATURE:
<223> OTHER INFORMATION: Synthetic peptide

<400> SEQUENCE: 103

Leu Ala His Gln Asn Thr Thr Lys Asn Ala
1               5                   10

<210> SEQ ID NO 104
<211> LENGTH: 10
<212> TYPE: PRT
<213> ORGANISM: Artificial Sequence
<220> FEATURE:
<223> OTHER INFORMATION: Synthetic peptide

<400> SEQUENCE: 104

Leu Ala His Arg Asp Thr Thr Lys Asn Ala
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Synthetic peptide

<400> SEQUENCE: 105

Leu Ala Ile Ser Asp Gln Thr Asn His Ala
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Synthetic peptide

<400> SEQUENCE: 106

Leu Ala Lys Gln Lys Ser Ala Ser Thr Ala
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Synthetic peptide

<400> SEQUENCE: 107

Leu Ala Lys Ser Asp Gln Cys Lys Pro Ala
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Synthetic peptide

<400> SEQUENCE: 108

Leu Ala Lys Ser Asp Gln Ser Lys Pro Asp
1               5                   10
```

```
<210> SEQ ID NO 109
<211> LENGTH: 10
<212> TYPE: PRT
<213> ORGANISM: Artificial Sequence
<220> FEATURE:
<223> OTHER INFORMATION: Synthetic peptide

<400> SEQUENCE: 109

Leu Ala Lys Ser Asp Gln Ser Asn Pro Ala
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Synthetic peptide

<400> SEQUENCE: 110

Leu Ala Lys Ser Tyr Gln Ser Lys Pro Ala
1               5                   10

<210> SEQ ID NO 111
<211> LENGTH: 10
<212> TYPE: PRT
<213> ORGANISM: Artificial Sequence
<220> FEATURE:
<223> OTHER INFORMATION: Synthetic peptide

<400> SEQUENCE: 111

Leu Ala Asn Gln Asp Thr Thr Lys Asn Ala
1               5                   10

<210> SEQ ID NO 112
<211> LENGTH: 10
<212> TYPE: PRT
<213> ORGANISM: Artificial Sequence
<220> FEATURE:
<223> OTHER INFORMATION: Synthetic peptide

<400> SEQUENCE: 112

Leu Ala Pro Gln Asn Thr Thr Lys Asn Ala
1               5                   10

<210> SEQ ID NO 113
<211> LENGTH: 10
<212> TYPE: PRT
<213> ORGANISM: Artificial Sequence
<220> FEATURE:
<223> OTHER INFORMATION: Synthetic peptide

<400> SEQUENCE: 113

Leu Ala Pro Ser Ser Ile Gln Lys Pro Ala
1               5                   10

<210> SEQ ID NO 114
<211> LENGTH: 10
<212> TYPE: PRT
<213> ORGANISM: Artificial Sequence
<220> FEATURE:
<223> OTHER INFORMATION: Synthetic peptide

<400> SEQUENCE: 114

Leu Ala Gln Gln Asp Thr Thr Lys Asn Ala
1               5                   10
```

<210> SEQ ID NO 115
<211> LENGTH: 10
<212> TYPE: PRT
<213> ORGANISM: Artificial Sequence
<220> FEATURE:
<223> OTHER INFORMATION: Synthetic peptide

<400> SEQUENCE: 115

Leu Ala Tyr Gln Asp Thr Thr Lys Asn Ala
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Synthetic peptide

<400> SEQUENCE: 116

Leu Asp His Gln Asp Thr Thr Lys Asn Ala
1               5                   10

<210> SEQ ID NO 117
<211> LENGTH: 10
<212> TYPE: PRT
<213> ORGANISM: Artificial Sequence
<220> FEATURE:
<223> OTHER INFORMATION: Synthetic peptide

<400> SEQUENCE: 117

Leu Asp His Gln Asp Thr Thr Lys Ser Ala
1               5                   10

<210> SEQ ID NO 118
<211> LENGTH: 10
<212> TYPE: PRT
<213> ORGANISM: Artificial Sequence
<220> FEATURE:
<223> OTHER INFORMATION: Synthetic peptide

<400> SEQUENCE: 118

Leu Gly His Gln Asp Thr Thr Lys Asn Ala
1               5                   10

<210> SEQ ID NO 119
<211> LENGTH: 10
<212> TYPE: PRT
<213> ORGANISM: Artificial Sequence
<220> FEATURE:
<223> OTHER INFORMATION: Synthetic peptide

<400> SEQUENCE: 119

Leu Pro His Gln Asp Thr Thr Lys Asn Asp
1               5                   10

<210> SEQ ID NO 120
<211> LENGTH: 10
<212> TYPE: PRT
<213> ORGANISM: Artificial Sequence
<220> FEATURE:
<223> OTHER INFORMATION: Synthetic peptide

<400> SEQUENCE: 120

Leu Pro His Gln Asp Thr Thr Lys Asn Thr
1               5                   10

```
<210> SEQ ID NO 121
<211> LENGTH: 10
<212> TYPE: PRT
<213> ORGANISM: Artificial Sequence
<220> FEATURE:
<223> OTHER INFORMATION: Synthetic peptide

<400> SEQUENCE: 121

Leu Pro His Gln Asp Thr Thr Asn Asn Ala
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Synthetic peptide

<400> SEQUENCE: 122

Leu Thr His Gln Asp Thr Thr Lys Asn Ala
1               5                   10

<210> SEQ ID NO 123
<211> LENGTH: 10
<212> TYPE: PRT
<213> ORGANISM: Artificial Sequence
<220> FEATURE:
<223> OTHER INFORMATION: Synthetic peptide

<400> SEQUENCE: 123

Leu Thr Lys Asp Ala Thr Lys Thr Ile Ala
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Synthetic peptide

<400> SEQUENCE: 124

Leu Thr Pro Gln Asp Thr Thr Lys Asn Ala
1               5                   10

<210> SEQ ID NO 125
<211> LENGTH: 10
<212> TYPE: PRT
<213> ORGANISM: Artificial Sequence
<220> FEATURE:
<223> OTHER INFORMATION: Synthetic peptide

<400> SEQUENCE: 125

Leu Val His Gln Asp Thr Thr Lys Asn Ala
1               5                   10

<210> SEQ ID NO 126
<211> LENGTH: 10
<212> TYPE: PRT
<213> ORGANISM: Artificial Sequence
<220> FEATURE:
<223> OTHER INFORMATION: Synthetic peptide

<400> SEQUENCE: 126

Leu Ala Lys Ala Asn Gln Asn Thr Pro Ala
1               5                   10

<210> SEQ ID NO 127
```

```
<211> LENGTH: 10
<212> TYPE: PRT
<213> ORGANISM: Artificial Sequence
<220> FEATURE:
<223> OTHER INFORMATION: Synthetic peptide

<400> SEQUENCE: 127

Leu Ala Thr Thr Pro Ile Thr Lys Pro Ala
1               5                   10

<210> SEQ ID NO 128
<211> LENGTH: 10
<212> TYPE: PRT
<213> ORGANISM: Artificial Sequence
<220> FEATURE:
<223> OTHER INFORMATION: Synthetic peptide

<400> SEQUENCE: 128

Leu Ala Thr Thr Pro Ile Ala Lys Pro Ala
1               5                   10

<210> SEQ ID NO 129
<211> LENGTH: 10
<212> TYPE: PRT
<213> ORGANISM: Artificial Sequence
<220> FEATURE:
<223> OTHER INFORMATION: Synthetic peptide

<400> SEQUENCE: 129

Leu Ala Ile Glu Asp His Thr Lys Ser Ala
1               5                   10

<210> SEQ ID NO 130
<211> LENGTH: 10
<212> TYPE: PRT
<213> ORGANISM: Artificial Sequence
<220> FEATURE:
<223> OTHER INFORMATION: Synthetic peptide

<400> SEQUENCE: 130

Leu Ala Gln Ser Glu His Gln Arg Pro Ala
1               5                   10

<210> SEQ ID NO 131
<211> LENGTH: 10
<212> TYPE: PRT
<213> ORGANISM: Artificial Sequence
<220> FEATURE:
<223> OTHER INFORMATION: Synthetic peptide

<400> SEQUENCE: 131

Leu Ala Lys Ser Pro Asn Lys Asp Asn Ala
1               5                   10

<210> SEQ ID NO 132
<211> LENGTH: 10
<212> TYPE: PRT
<213> ORGANISM: Artificial Sequence
<220> FEATURE:
<223> OTHER INFORMATION: Synthetic peptide

<400> SEQUENCE: 132

Leu Ala Asn Gln Asp Tyr Thr Lys Thr Ala
1               5                   10

<210> SEQ ID NO 133
<211> LENGTH: 10
```

```
<212> TYPE: PRT
<213> ORGANISM: Artificial Sequence
<220> FEATURE:
<223> OTHER INFORMATION: Synthetic peptide

<400> SEQUENCE: 133

Leu Ala Asn Ser Thr Asp Gln Thr Arg Ala
1               5                   10

<210> SEQ ID NO 134
<211> LENGTH: 10
<212> TYPE: PRT
<213> ORGANISM: Artificial Sequence
<220> FEATURE:
<223> OTHER INFORMATION: Synthetic peptide

<400> SEQUENCE: 134

Leu Ala Leu Gly Glu Thr Thr Arg Pro Ala
1               5                   10

<210> SEQ ID NO 135
<211> LENGTH: 10
<212> TYPE: PRT
<213> ORGANISM: Artificial Sequence
<220> FEATURE:
<223> OTHER INFORMATION: Synthetic peptide

<400> SEQUENCE: 135

Leu Ala Asn Ser Thr Glu Gln Thr Arg Ala
1               5                   10

<210> SEQ ID NO 136
<211> LENGTH: 10
<212> TYPE: PRT
<213> ORGANISM: Artificial Sequence
<220> FEATURE:
<223> OTHER INFORMATION: Synthetic peptide

<400> SEQUENCE: 136

Leu Ala Gln Ala Asp Thr Thr Lys Asn Ala
1               5                   10

<210> SEQ ID NO 137
<211> LENGTH: 10
<212> TYPE: PRT
<213> ORGANISM: Artificial Sequence
<220> FEATURE:
<223> OTHER INFORMATION: Synthetic peptide

<400> SEQUENCE: 137

Leu Ala Ser Lys Asp Ile Thr Lys Thr Ala
1               5                   10

<210> SEQ ID NO 138
<211> LENGTH: 10
<212> TYPE: PRT
<213> ORGANISM: Artificial Sequence
<220> FEATURE:
<223> OTHER INFORMATION: Synthetic peptide

<400> SEQUENCE: 138

Leu Ala Ser Pro Arg His Asn Lys Lys Cys
1               5                   10

<210> SEQ ID NO 139
<211> LENGTH: 11
<212> TYPE: PRT
```

```
<213> ORGANISM: Artificial Sequence
<220> FEATURE:
<223> OTHER INFORMATION: Synthetic peptide

<400> SEQUENCE: 139

Leu Ala His Gln Asp Thr Thr Lys Thr Ile Ala
1               5                   10

<210> SEQ ID NO 140
<211> LENGTH: 9
<212> TYPE: PRT
<213> ORGANISM: Artificial Sequence
<220> FEATURE:
<223> OTHER INFORMATION: Synthetic peptide

<400> SEQUENCE: 140

Leu Ala Ala Gln Gly Thr Ala Asn Leu
1               5

<210> SEQ ID NO 141
<211> LENGTH: 10
<212> TYPE: PRT
<213> ORGANISM: Artificial Sequence
<220> FEATURE:
<223> OTHER INFORMATION: Synthetic peptide

<400> SEQUENCE: 141

Val Ala Ile Glu Asp His Thr Lys Ser Ala
1               5                   10

<210> SEQ ID NO 142
<211> LENGTH: 12
<212> TYPE: PRT
<213> ORGANISM: Artificial Sequence
<220> FEATURE:
<223> OTHER INFORMATION: Synthetic peptide

<400> SEQUENCE: 142

Leu Ala Lys Ala Asn Gln Asn Thr Pro Lys Asn Ala
1               5                   10

<210> SEQ ID NO 143
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: Misc_feature
<222> LOCATION: (10)..(10)
<223> OTHER INFORMATION: Xaa is any amino acid

<400> SEQUENCE: 143

Leu Ala His Gln Asp Thr Thr Lys Lys Xaa
1               5                   10

<210> SEQ ID NO 144
<211> LENGTH: 10
<212> TYPE: PRT
<213> ORGANISM: Artificial Sequence
<220> FEATURE:
<223> OTHER INFORMATION: Synthetic peptide

<400> SEQUENCE: 144

Leu Ala His Gln Asp Thr Thr Lys Lys Asp
1               5                   10
```

```
<210> SEQ ID NO 145
<211> LENGTH: 10
<212> TYPE: PRT
<213> ORGANISM: Artificial Sequence
<220> FEATURE:
<223> OTHER INFORMATION: Synthetic peptide

<400> SEQUENCE: 145

Leu Ala His Gln Asp Thr Thr Lys Lys Val
1               5                   10

<210> SEQ ID NO 146
<211> LENGTH: 10
<212> TYPE: PRT
<213> ORGANISM: Artificial Sequence
<220> FEATURE:
<223> OTHER INFORMATION: Synthetic peptide

<400> SEQUENCE: 146

Leu Ala His Gln Asp Thr Thr Lys Lys Met
1               5                   10

<210> SEQ ID NO 147
<211> LENGTH: 7
<212> TYPE: PRT
<213> ORGANISM: Artificial Sequence
<220> FEATURE:
<223> OTHER INFORMATION: Synthetic peptide

<400> SEQUENCE: 147

Leu Gly Glu Thr Thr Arg Pro
1               5

<210> SEQ ID NO 148
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: Misc_feature
<222> LOCATION: (9)..(9)
<223> OTHER INFORMATION: Xaa is Lys, Thr, Asn, or His
<220> FEATURE:
<221> NAME/KEY: Misc_feature
<222> LOCATION: (10)..(10)
<223> OTHER INFORMATION: Xaa is Ala, Thr, Val, Ile, Met, or Asp
<220> FEATURE:
<221> NAME/KEY: Misc_feature
<222> LOCATION: (11)..(11)
<223> OTHER INFORMATION: Xaa is Ala

<400> SEQUENCE: 148

Leu Ala His Gln Asp Thr Thr Lys Xaa Xaa Xaa
1               5                   10

<210> SEQ ID NO 149
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: Misc_feature
<222> LOCATION: (3)..(3)
<223> OTHER INFORMATION: Xaa is Ala, Pro, Asp, or His
<220> FEATURE:
<221> NAME/KEY: Misc_feature
<222> LOCATION: (5)..(5)
<223> OTHER INFORMATION: Xaa is Gly or Asp
<220> FEATURE:
```

```
<221> NAME/KEY: Misc_feature
<222> LOCATION: (7)..(7)
<223> OTHER INFORMATION: Xaa is Ala, Thr, or Lys
<220> FEATURE:
<221> NAME/KEY: Misc_feature
<222> LOCATION: (8)..(8)
<223> OTHER INFORMATION: Xaa is Asn, Glu, Lys, Arg, or Thr
<220> FEATURE:
<221> NAME/KEY: Misc_feature
<222> LOCATION: (9)..(9)
<223> OTHER INFORMATION: Xaa is Leu, Asn, Lys, or Thr
<220> FEATURE:
<221> NAME/KEY: Misc_feature
<222> LOCATION: (10)..(10)
<223> OTHER INFORMATION: Xaa is Ala, Thr, Asp, Val, or Met

<400> SEQUENCE: 149

Leu Ala Xaa Gln Xaa Thr Xaa Xaa Xaa Xaa
1               5                   10

<210> SEQ ID NO 150
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: Misc_feature
<222> LOCATION: (1)..(1)
<223> OTHER INFORMATION: Xaa is Val or Leu
<220> FEATURE:
<221> NAME/KEY: Misc_feature
<222> LOCATION: (3)..(3)
<223> OTHER INFORMATION: Xaa is Ile, Val, His, or Asp
<220> FEATURE:
<221> NAME/KEY: Misc_feature
<222> LOCATION: (4)..(4)
<223> OTHER INFORMATION: Xaa is Glu, Ser, Lys, or Gln
<220> FEATURE:
<221> NAME/KEY: Misc_feature
<222> LOCATION: (6)..(6)
<223> OTHER INFORMATION: Xaa is His, Ser, or Thr
<220> FEATURE:
<221> NAME/KEY: Misc_feature
<222> LOCATION: (9)..(9)
<223> OTHER INFORMATION: Xaa is Ser, Ala, Asn, His, or Lys

<400> SEQUENCE: 150

Xaa Ala Xaa Xaa Asp Xaa Thr Lys Xaa Ala
1               5                   10

<210> SEQ ID NO 151
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: Misc_feature
<222> LOCATION: (1)..(1)
<223> OTHER INFORMATION: Xaa is Leu
<220> FEATURE:
<221> NAME/KEY: Misc_feature
<222> LOCATION: (2)..(2)
<223> OTHER INFORMATION: Xaa is Ala
<220> FEATURE:
<221> NAME/KEY: Misc_feature
<222> LOCATION: (3)..(3)
<223> OTHER INFORMATION: Xaa is  Lys, Leu, or Pro
<220> FEATURE:
<221> NAME/KEY: Misc_feature
<222> LOCATION: (5)..(5)
<223> OTHER INFORMATION: Xaa is  Asn, His, Pro, or Tyr
<220> FEATURE:
<221> NAME/KEY: Misc_feature
```

```
<222> LOCATION: (7)..(7)
<223> OTHER INFORMATION: Xaa is  Asn, Gly, Val, or Asp
<220> FEATURE:
<221> NAME/KEY: Misc_feature
<222> LOCATION: (9)..(9)
<223> OTHER INFORMATION: Xaa is  Pro or Thr

<400> SEQUENCE: 151

Xaa Xaa Xaa Ala Xaa Gln Xaa Thr Xaa Lys Asn Ala
1               5                   10

<210> SEQ ID NO 152
<211> LENGTH: 27
<212> TYPE: RNA
<213> ORGANISM: Artificial Sequence
<220> FEATURE:
<223> OTHER INFORMATION: Synthetic sequence

<400> SEQUENCE: 152
cgcaaucagu gaaugcuuau acauccg                                         27
```